(12) United States Patent
Keller et al.

(10) Patent No.: US 12,225,643 B2
(45) Date of Patent: Feb. 11, 2025

(54) LIGHTING FIXTURE AND METHODS

(71) Applicant: Cree Lighting USA LLC, Racine, WI (US)

(72) Inventors: Bernd P. Keller, Santa Barbara, CA (US); Michael Leung, Ventura, CA (US); Benjamin A. Jacobson, Santa Barbara, CA (US); Eric Tarsa, Goleta, CA (US); James Ibbetson, Goleta, CA (US); Claudio Girotto, Santa Barbara, CA (US); Amruteshwar Hiremath, Cary, NC (US)

(73) Assignee: Cree Lighting USA LLC, Racine, WI (US)

( * ) Notice: Subject to any disclaimer, the term of this patent is extended or adjusted under 35 U.S.C. 154(b) by 0 days.

(21) Appl. No.: 18/449,228

(22) Filed: Aug. 14, 2023

(65) Prior Publication Data
US 2024/0074013 A1 Feb. 29, 2024

Related U.S. Application Data

(63) Continuation-in-part of application No. 17/499,405, filed on Oct. 12, 2021, now Pat. No. 11,729,877, (Continued)

(51) Int. Cl.
*H05B 45/20* (2020.01)
*A61N 5/06* (2006.01)
(Continued)

(52) U.S. Cl.
CPC ............... *H05B 45/20* (2020.01); *F21K 9/61* (2016.08); *F21S 8/006* (2013.01); *F21S 8/026* (2013.01);
(Continued)

(58) Field of Classification Search
CPC ........ H05B 45/20; H05B 45/22; H05B 45/28; F21K 9/61; F21S 8/006; F21S 8/026;
(Continued)

(56) References Cited

U.S. PATENT DOCUMENTS

| | | | |
|---|---|---|---|
| 5,823,652 | A | 10/1998 | Vann |
| 7,246,932 | B2 | 7/2007 | Burtsev et al. |

(Continued)

FOREIGN PATENT DOCUMENTS

| | | |
|---|---|---|
| EP | 2918901 A1 | 9/2015 |
| JP | 2011138731 A | 7/2011 |

(Continued)

OTHER PUBLICATIONS

Non-Final Office Action for U.S. Appl. No. 15/972,199, mailed Jun. 28, 2019, 8 pages.
(Continued)

*Primary Examiner* — Alan B Cariaso
(74) *Attorney, Agent, or Firm* — Withrow & Terranova, P.L.L.C.; Vincent K. Gustafson

(57) ABSTRACT

A lighting fixture appears as a skylight and is referred to as a skylight fixture. First and second light engines of the fixture provide different color points, peak light intensity angles, far-field light distribution characteristics, and/or circadian stimulus values. A skylight fixture may include a sky-resembling assembly and a plurality of sun-resembling assemblies, with dedicated optical assemblies and/or light sources. A lighting fixture may include multiple waveguides that different extraction feature patterns and/or may be sequentially arranged.

26 Claims, 78 Drawing Sheets

Related U.S. Application Data which is a continuation-in-part of application No. 17/120,802, filed on Dec. 14, 2020, now Pat. No. 11,638,339, and a continuation-in-part of application No. 17/113,768, filed on Dec. 7, 2020, now Pat. No. 11,156,760, and a continuation-in-part of application No. 16/990,230, filed on Aug. 11, 2020, now Pat. No. 11,209,138, said application No. 17/120,802 is a continuation of application No. 16/667,239, filed on Oct. 29, 2019, now Pat. No. 10,900,621, said application No. 16/990,230 is a continuation of application No. 16/657,254, filed on Oct. 18, 2019, now Pat. No. 10,781,984, which is a continuation of application No. 15/972,176, filed on May 6, 2018, now Pat. No. 10,465,869, said application No. 17/113,768 is a continuation of application No. 15/972,199, filed on May 6, 2018, now Pat. No. 10,859,753, said application No. 16/667,239 is a continuation of application No. 15/419,538, filed on Jan. 30, 2017, now Pat. No. 10,502,374, said application No. 15/972,176 is a continuation-in-part of application No. 15/419,538, filed on Jan. 30, 2017, now Pat. No. 10,502,374.

(60) Provisional application No. 62/628,131, filed on Feb. 8, 2018.

(51) Int. Cl.

| | |
|---|---|
| *F21K 9/61* | (2016.01) |
| *F21S 8/00* | (2006.01) |
| *F21S 8/02* | (2006.01) |
| *F21S 19/00* | (2006.01) |
| *F21V 7/04* | (2006.01) |
| *F21V 8/00* | (2006.01) |
| *F21V 14/02* | (2006.01) |
| *F21V 33/00* | (2006.01) |
| *F21Y 113/13* | (2016.01) |
| *F21Y 113/17* | (2016.01) |
| *F21Y 115/10* | (2016.01) |

(52) U.S. Cl.
CPC .............. *F21V 7/04* (2013.01); *F21V 33/006* (2013.01); *A61N 2005/0663* (2013.01); *F21S 19/005* (2013.01); *F21V 14/02* (2013.01); *F21Y 2113/13* (2016.08); *F21Y 2113/17* (2016.08); *F21Y 2115/10* (2016.08); *G02B 6/0035* (2013.01); *G02B 6/0051* (2013.01); *G02B 6/0058* (2013.01); *Y02B 20/40* (2013.01)

(58) Field of Classification Search
CPC ........ F21S 19/005; F21V 7/04; F21V 33/006; F21V 14/02; A61N 2005/0663; F21Y 2113/13; F21Y 2113/17; F21Y 2115/10; G02B 6/0035; G02B 6/0051; G02B 6/0058; Y02B 20/40
See application file for complete search history.

(56) References Cited

U.S. PATENT DOCUMENTS

| | | |
|---|---|---|
| 7,802,908 B2 | 9/2010 | Lin et al. |
| 7,872,705 B2 | 1/2011 | Medendorp, Jr. et al. |
| 7,914,195 B2 | 3/2011 | Sawada et al. |
| 8,541,795 B2 | 9/2013 | Keller et al. |
| 8,564,737 B2 | 10/2013 | Medendorp, Jr. et al. |
| 8,564,739 B2 | 10/2013 | Medendorp, Jr. et al. |
| 8,564,742 B2 | 10/2013 | Medendorp, Jr. et al. |
| 8,975,827 B2 | 3/2015 | Chobot et al. |
| 9,195,095 B2 | 11/2015 | Medendorp, Jr. et al. |
| 9,442,243 B2 | 9/2016 | Tarsa |
| 9,488,327 B2 | 11/2016 | Van Gheluwe et al. |
| 9,656,598 B1 | 5/2017 | Salter et al. |
| 9,690,029 B2 | 6/2017 | Keller et al. |
| 9,706,617 B2 | 7/2017 | Carrigan et al. |
| 9,818,919 B2 | 11/2017 | Lowes et al. |
| 9,869,432 B2 | 1/2018 | Keller et al. |
| 10,278,250 B2 | 4/2019 | McBryde et al. |
| 10,451,229 B2 | 10/2019 | Keller et al. |
| 10,465,869 B2 | 11/2019 | Keller et al. |
| 10,502,374 B2 | 12/2019 | Leung et al. |
| 10,582,596 B2* | 3/2020 | Sooch ................... H05B 47/19 |
| 10,859,753 B2 | 12/2020 | Lowes et al. |
| 2005/0072032 A1 | 4/2005 | McCollum et al. |
| 2007/0124970 A1 | 6/2007 | Ijaltason |
| 2010/0027293 A1 | 2/2010 | Li |
| 2010/0046219 A1 | 2/2010 | Pijlman et al. |
| 2010/0174345 A1* | 7/2010 | Ashdown ............... H05B 45/22 |
| | | 607/88 |
| 2011/0164405 A1 | 7/2011 | Boonekamp et al. |
| 2012/0320626 A1 | 12/2012 | Quilici et al. |
| 2013/0121001 A1 | 5/2013 | Shani et al. |
| 2014/0043856 A1 | 2/2014 | Thompson et al. |
| 2014/0070724 A1 | 3/2014 | Gould et al. |
| 2014/0103833 A1 | 4/2014 | Ho et al. |
| 2014/0140091 A1 | 5/2014 | Vasylyev |
| 2014/0185281 A1 | 7/2014 | Lee et al. |
| 2014/0321136 A1 | 10/2014 | Reuschel et al. |
| 2014/0347885 A1 | 11/2014 | Wilcox et al. |
| 2015/0264779 A1 | 9/2015 | Olsen et al. |
| 2016/0003445 A1 | 1/2016 | Hu |
| 2016/0186968 A1 | 6/2016 | Edwards |
| 2016/0227618 A1 | 8/2016 | Meerbeek et al. |
| 2016/0273723 A1 | 9/2016 | Van Gheluwe et al. |
| 2016/0363710 A1 | 12/2016 | Van Boven et al. |
| 2017/0336563 A1 | 11/2017 | Tarsa et al. |
| 2018/0052272 A1 | 2/2018 | Cornelissen et al. |
| 2018/0074250 A1 | 3/2018 | Boonekamp |
| 2018/0246270 A1 | 8/2018 | Di Trapani et al. |
| 2018/0252858 A1 | 9/2018 | Lowes et al. |
| 2018/0279454 A1* | 9/2018 | Takeshita ................ F21V 3/049 |
| 2019/0242539 A1 | 8/2019 | Roberts |

FOREIGN PATENT DOCUMENTS

| | | |
|---|---|---|
| JP | 2016051608 A | 4/2016 |
| JP | 2016514340 A | 5/2016 |
| KR | 20230041314 A | 3/2023 |

OTHER PUBLICATIONS

Final Office Action for U.S. Appl. No. 15/972,199, mailed Jan. 3, 2020, 15 pages.
Notice of Allowance, Examiner-Initiated Interview Summary, and AFCP 2.0 Decision for U.S. Appl. No. 15/972,199, mailed Apr. 29, 2020, 18 pages.
Notice of Allowance for U.S. Appl. No. 15/972,199, mailed Aug. 10, 2020, 15 pages.
Notice of Allowance for U.S. Appl. No. 17/113,768, mailed Jun. 24, 2021, 10 pages.
Applicant-Initiated Interview Summary for U.S. Appl. No. 17/113,768, mailed Jul. 27, 2021, 10 pages.
International Search Report and Written Opinion for International Patent Application No. PCT/US2019/016592, mailed Apr. 17, 2019, 15 pages.
Non-Final Office Action for U.S. Appl. No. 17/499,405, mailed Nov. 10, 2022, 13 pages.
Notice of Allowance for U.S. Appl. No. 17/499,405, mailed Mar. 20, 2023, 9 pages.
International Search Report and Written Opinion for International Patent Application No. PCT/US2024/042211, mailed Nov. 27, 2024, 9 pages.

* cited by examiner (DISPLAY)

(EDGE LIT)

(BACK LIT)

(SIDE LIT)

| ccx | ccy |
|---|---|
| 0.37 | 0.34 |
| 0.35 | 0.38 |
| 0.15 | 0.20 |
| 0.20 | 0.14 |
| 0.37 | 0.34 |

| ccx | ccy |
|---|---|
| 0.29 | 0.32 |
| 0.32 | 0.29 |
| 0.41 | 0.36 |
| 0.48 | 0.39 |
| 0.48 | 0.43 |
| 0.40 | 0.41 |
| 0.35 | 0.38 |
| 0.29 | 0.32 |

| ccx | ccy |
|---|---|
| 0.32 | 0.31 |
| 0.30 | 0.33 |
| 0.15 | 0.17 |
| 0.17 | 0.14 |
| 0.32 | 0.31 |

| ccx | ccy |
|---|---|
| 0.30 | 0.34 |
| 0.30 | 0.30 |
| 0.39 | 0.36 |
| 0.45 | 0.39 |
| 0.47 | 0.43 |
| 0.40 | 0.41 |
| 0.35 | 0.38 |
| 0.30 | 0.34 |

| ccx | ccy |
|---|---|
| 0.39 | 0.31 |
| 0.34 | 0.40 |
| 0.10 | 0.20 |
| 0.16 | 0.06 |
| 0.39 | 0.31 |

| ccx | ccy |
|---|---|
| 0.28 | 0.36 |
| 0.35 | 0.26 |
| 0.44 | 0.33 |
| 0.62 | 0.34 |
| 0.50 | 0.46 |
| 0.43 | 0.45 |
| 0.36 | 0.43 |
| 0.28 | 0.36 |

| ccx | ccy |
|---|---|
| 0.10 | 0.20 |
| 0.36 | 0.43 |
| 0.43 | 0.45 |
| 0.50 | 0.46 |
| 0.62 | 0.34 |
| 0.44 | 0.33 |
| 0.16 | 0.06 |
| 0.10 | 0.20 |

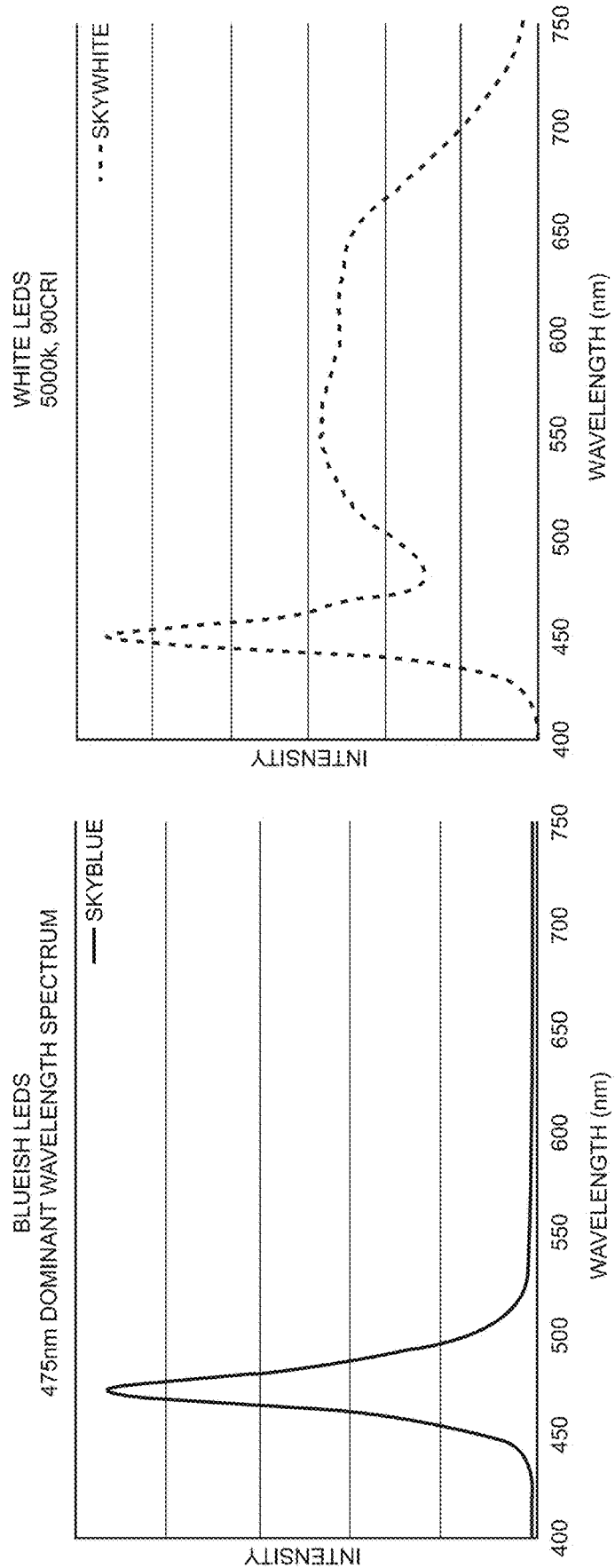

| x | y |
|---|---|
| 0.37 | 0.34 |
| 0.35 | 0.38 |
| 0.15 | 0.20 |
| 0.20 | 0.14 |

| x | y |
|---|---|
| 0.35 | 0.38 |
| 0.105 | 0.195 |
| 0.12 | 0.135 |
| 0.17 | 0.10 |
| 0.20 | 0.14 |
| 0.15 | 0.20 |

| x | y |
|---|---|
| 0.37 | 0.34 |
| 0.35 | 0.38 |
| 0.105 | 0.195 |
| 0.12 | 0.135 |
| 0.17 | 0.10 |
| 0.20 | 0.14 |

| x | y | u' | v' |
|---|---|---|---|
| 0.35 | 0.38 | 0.204082 | 0.498542 |
| 0.105 | 0.195 | 0.081871 | 0.342105 |
| 0.12 | 0.135 | 0.109589 | 0.277397 |
| 0.17 | 0.1 | 0.176166 | 0.233161 |
| 0.2 | 0.14 | 0.186916 | 0.294393 |
| 0.15 | 0.2 | 0.117647 | 0.352941 |

| Greenish polygon | | | |
|---|---|---|---|
| x | y | u' | v' |
| 0.05 | 0.58 | 0.020283976 | 0.529411765 |
| 0.06 | 0.65 | 0.02247191 | 0.547752809 |
| 0.14 | 0.65 | 0.053231939 | 0.55608365 |
| 0.14 | 0.55 | 0.060085837 | 0.53111588 |
| 0.13 | 0.48 | 0.061176471 | 0.508235294 |
| 0.05 | 0.48 | 0.023094688 | 0.498845266 |
| 0.05 | 0.58 | 0.020283976 | 0.529411765 |

FIG. 93B

| Bluish polygon | | | |
|---|---|---|---|
| x | y | u' | v' |
| 0.137 | 0.037 | 0.172870662 | 0.105047319 |
| 0.124 | 0.058 | 0.143851508 | 0.151392111 |
| 0.11 | 0.087 | 0.115062762 | 0.204759414 |
| 0.132 | 0.112 | 0.129411765 | 0.247058824 |
| 0.142 | 0.081 | 0.154013015 | 0.197668113 |
| 0.151 | 0.058 | 0.177961108 | 0.153800825 |
| 0.137 | 0.037 | 0.172870662 | 0.105047319 |

FIG. 93C

| White polygon | | | |
|---|---|---|---|
| x | y | u' | v' |
| 0.3028 | 0.3304 | 0.190464209 | 0.467605988 |
| 0.3213 | 0.3371 | 0.200730953 | 0.473854372 |
| 0.3221 | 0.3261 | 0.205519222 | 0.468160791 |
| 0.3048 | 0.3209 | 0.195347049 | 0.462747549 |
| 0.3028 | 0.3304 | 0.190464209 | 0.467605988 |

FIG. 93D

TIME DEPENDENT DAILY FADING/SEQUENCED PRESETS

| | SUN-EAST | | | SUN-WEST | | | SKY POST LOWER SIDE BRIGHTNESS TRIM | | | PRESET NAME |
|---|---|---|---|---|---|---|---|---|---|---|
| | CCT | LIGHT LEVEL | FADE | CCT | LIGHT LEVEL | FADE | PSEUDO CCT | LIGHT LEVEL | FADE | |
| 5:00:00 AM | 5000K | 35% | | 5000K | 35% | | 3000K | 0% | | NIGHT |
| 6:00:00 AM | 3000K | 25% | | 3100K | 60% | | 2925K | 25% | | DAWN |
| 7:00:00 AM | | | | | | FADING | | | | |
| 8:00:00 AM | 4125K | 48% | | 4125K | 77% | | 3800K | 59% | | MORNING |
| 9:00:00 AM | | | | | | FADING | | | | |
| 10:00:00 AM | | | | | | FADING | | | | |
| 11:00:00 AM | | | | | | FADING | | | | |
| 12:00:00 PM | 4500K | 80% | | 4500K | 80% | | 4500K | 100% | | NOON/MIDDAY |
| 1:00:00 PM | | | | | | FADING | | | | |
| 2:00:00 PM | | | | | | FADING | | | | |
| 3:00:00 PM | | | | | | FADING | | | | |
| 4:00:00 PM | | | | | | FADING | | | | |
| 5:00:00 PM | 4125K | 77% | | 4125K | 48% | | 3800K | 59% | | AFTERNOON |
| 6:00:00 PM | 3100K | 60% | | 3000K | 25% | | 2925K | 25% | | DUSK |
| 7:00:00 PM | 5000K | 35% | | 5000K | 35% | | 3000K | 0% | | NIGHT |
| 8:00:00 PM | | | | | | STATIC | | | | |
| 9:00:00 PM | | | | | | STATIC | | | | |
| 10:00:00 PM | | | | | | STATIC | | | | |
| 11:00:00 PM | | | | | | STATIC | | | | |
| 12:00:00 AM | | | | | | STATIC | | | | |
| 1:00:00 AM | | | | | | STATIC | | | | |
| 2:00:00 AM | | | | | | STATIC | | | | |
| 3:00:00 AM | | | | | | STATIC | | | | |
| 4:00:00 AM | | | | | | STATIC | | | | |

DRIVER : 1%-100%  DRIVER : 1%-100%  DRIVER : 1%-100%
FADE CONTINUOUSLY FROM DEFINED POINT IN TIME TO NEXT DEFINED POINT IN TIME.

FIG. 102A

| ADDITIONAL STATIC PRESETS, NOT PART OF DAILY TIME DRIVEN SEQUENCING | | | | | | | | | |
|---|---|---|---|---|---|---|---|---|---|
| SUN-EAST | | | SUN-WEST | | | SKY | | | |
| CCT | LIGHT LEVEL | FADE | CCT | LIGHT LEVEL | FADE | PSEUDO CCT | LIGHT LEVEL | FADE | PRESET NAME |
| 4125K | 0% | | 3244K | 100% | | 4450K | 60% | | BRIGHT SUNRISE |
| 4550K | 26% | | 4550K | 26% | | 4450K | 0% | | CLOUDY DAY |
| 4660K | 0% | | 4660K | 0% | | 3800K | 59% | | MOONLIGHT |

FIG. 102B

LIGHTING FIXTURE AND METHODS

CROSS-REFERENCE TO RELATED APPLICATIONS

This application is a continuation-in part of U.S. patent application Ser. No. 17/499,405 filed on Oct. 12, 2021 (issuing as U.S. Pat. No. 11,729,877 on Aug. 15, 2023), which is a continuation-in-part of U.S. patent application Ser. No. 17/120,802 filed on Dec. 14, 2020 (now U.S. Pat. No. 11,638,339), which is a continuation of U.S. patent application Ser. No. 16/667,239, filed on Oct. 29, 2019 (now U.S. Pat. No. 10,900,621), which is a continuation of U.S. patent application Ser. No. 15/419,538, filed on Jan. 30, 2017 (now U.S. Pat. No. 10,502,374), wherein the entire disclosures of the foregoing applications and patents are hereby incorporated by reference herein.

U.S. patent application Ser. No. 17/499,405 filed on Oct. 12, 2021 (issuing as U.S. Pat. No. 11,729,877 on Aug. 15, 2023) is also a continuation-in-part of U.S. patent application Ser. No. 16/990,230 filed on Aug. 11, 2020 (now U.S. Pat. No. 11,209,138), which is a continuation of U.S. patent application Ser. No. 16/657,254 filed on Oct. 18, 2019 (now U.S. Pat. No. 10,781,984), which is a continuation of U.S. patent application Ser. No. 15/972,176 filed on May 6, 2018 (now U.S. Pat. No. 10,465,869), which is a continuation-in-part of U.S. patent application Ser. No. 15/419,538 filed on Jan. 30, 2017 (now U.S. Pat. No. 10,502,374), and claims the benefit of U.S. Provisional Patent Application No. 62/628,131 filed on Feb. 8, 2018, wherein the entire disclosures of the foregoing applications and patents are hereby incorporated reference herein.

U.S. patent application Ser. No. 17/499,405 filed on Oct. 12, 2021 (issuing as U.S. Pat. No. 11,729,877 on Aug. 15, 2023) is also a continuation-in-part of U.S. patent application Ser. No. 17/113,768 filed on Dec. 7, 2020 (now U.S. Pat. No. 11,156,760), which is a continuation of U.S. patent application Ser. No. 15/972,199 filed on May 6, 2018 (now U.S. Pat. No. 10,859,753), and claims the benefit of U.S. Provisional Patent Application No. 62/628,131, filed Feb. 8, 2018, wherein the entire disclosures of the foregoing applications and patents are hereby incorporated by reference herein.

FIELD OF THE DISCLOSURE

The present disclosure relates to lighting fixtures and methods of lighting. In some aspects, the disclosure relates to light fixtures (comprising one or more light sources and/or one or more light engines) that mimic or emulate the appearance and/or effects of a skylight, and/or that give an 'outdoor' feel to an indoor space, in some cases even with no exterior light from any windows or doors.

BACKGROUND

Skylights are used to provide natural light (i.e., daylight) in residential, commercial and other buildings, as well as in other structures. A skylight is a window that is generally installed in a roof or ceiling. Skylights are excellent sources of natural light and highly desirable in many residential and commercial buildings. Providing natural light to an area is known to enhance moods, increase productivity, and improve ambiance among many other benefits. Skylights are often used to supplement the natural light in spaces with windows, and are often the only way to provide natural light to interior spaces that are not abutting exterior walls.

Conventional skylights can pose numerous problems, including water leakage, heat loss, lack of light on overcast or stormy days, and installation difficulty or impracticability in certain situations. In addition, conventional skylights (like windows) typically get dirty, streaked and/or smeared, and as a result there is often a frequent desire (or need) to clean them. In addition, direct sunlight can sometimes produce a great deal of glare on work surfaces and other items, e.g., computer screens, and such glare is typically counterproductive and/or annoying (for example, glare can make it difficult or impossible for a worker to see his or her computer screen). Also, direct sunlight (and/or resulting glare) can increase eye strain (even after a short period of time, and more so during prolonged exposure, including continuous exposure as well as intermittent exposure over periods of time).

Additionally, providing skylights in many spaces is impractical or impossible. The lower floors of a building will not have direct access to the roof of the building. In many cases, even the top floor of the building will have structural or mechanical components that prevent the installation of skylights, limit the functionality of skylights, or would cause installation of the skylights to be too expensive.

Accordingly, there is a need to provide the benefits of skylights to those spaces where installation of skylights would be impractical or impossible. It may also be beneficial to provide the benefits of skylights that would overcome the problems associated with conventional skylights, and/or that would enable control over light being provided to an interior space.

Large areas of open indoor space, such as an office or warehouse spaces, require sufficient lighting to allow for safe and comfortable activities by persons occupying or visiting the space at all times including periods when natural lighting, such as that provided by windows, is unavailable or reduced during nighttime, rainy or foggy weather conditions, and/or in the absence of windows. An indoor luminaire for large indoor spaces or smaller indoor spaces, such as hallways or individual office spaces, must illuminate spaces varying in size, floor plan, and intended use. It may be useful for such a luminaire to provide customizable illumination patterns in order to effectively match the light produced by the luminaire with the characteristics of the space to be illuminated. Still further, such a luminaire should be customizable such that desired illumination patterns may be achieved. Additionally, such a luminaire should be aesthetically pleasing, and further, versatile enough to provide illumination patterns suitable for the varied environments mentioned hereinabove.

Advances in light emitting diode (LED) technology have resulted in wide adoption of luminaires that incorporate such devices. While LEDs can be used alone to produce light without the need for supplementary optical devices, it has been found that optical modifiers, such as lenses, reflectors, optical waveguides, and combinations thereof, can significantly improve illumination distribution for particular applications.

An optical waveguide mixes and directs light emitted by one or more light sources, such as one or more LEDs. A typical optical waveguide includes three main components: one or more coupling elements, one or more distribution elements, and one or more extraction elements. The coupling component(s) direct light into the distribution element(s), and condition the light to interact with the subsequent components. The one or more distribution elements control how light flows through the waveguide and is dependent on the waveguide geometry and material. The extraction element(s) determine how light is removed by controlling where and in what direction the light exits the waveguide.

When designing a coupling optic, the primary considerations are: maximizing the efficiency of light transfer from the source into the waveguide; controlling the location of light injected into the waveguide; and controlling the angular distribution of the light in the coupling optic. One way of controlling the spatial and angular spread of injected light is by fitting each source with a dedicated lens. These lenses can be disposed with an air gap between the lens and the coupling optic, or may be manufactured from the same piece of material that defines the waveguide's distribution element(s). Discrete coupling optics allow numerous advantages such as higher efficiency coupling, controlled overlap of light flux from the sources, and angular control of how the injected light interacts with the remaining elements of the waveguide. Discrete coupling optics use refraction, total internal reflection, and surface or volume scattering to control the distribution of light injected into the waveguide.

After light has been coupled into the waveguide, it must be guided and conditioned to the locations of extraction. The simplest example is a fiber-optic cable, which is designed to transport light from one end of the cable to another with minimal loss in between. To achieve this, fiber optic cables are only gradually curved and sharp bends in the waveguide are avoided. In accordance with well-known principles of total internal reflectance light traveling through a waveguide is reflected back into the waveguide from an outer surface thereof, provided that the incident light does not exceed a critical angle with respect to the surface. Specifically, the light rays continue to travel through the waveguide until such rays strike an index interface surface at a particular angle less than an angle measured with respect to a line normal to the surface point at which the light rays are incident (or, equivalently, until the light rays exceed an angle measured with respect to a line tangent to the surface point at which the light rays are incident) and the light rays escape.

In order for an extraction element to remove light from the waveguide, the light must first contact the feature comprising the element. By appropriately shaping the waveguide surfaces, one can control the flow of light across the extraction feature(s). Specifically, selecting the spacing, shape, and other characteristic(s) of the extraction features affects the appearance of the waveguide, its resulting distribution, and efficiency.

Low-profile LED-based luminaires have recently been developed that utilize a string of LED components directed into the edge of a waveguiding element (an "edge-lit" or "edge-coupled" approach). However, such luminaires typically suffer from low efficiency due to losses inherent in coupling light emitted from a predominantly Lambertian emitting source such as a LED component into the narrow edge of a waveguide plane.

SUMMARY

In a first aspect, the present disclosure relates to light fixtures (artificial skylights) that avoid problems with conventional skylights and that provide benefits that are provided by conventional skylights.

Conventional skylights provide a number of benefits including:
  Light that is full spectrum (high quality or color rendering);
  Light that is visually complex due to the combination of diffuse light from the sky and directional light from the sun, which generally have different colors;
  Light that naturally varies with time (i.e., circadian, seasonal) and weather;
  Thus, generally providing a visual connection with the outdoors that is pleasing, and that can improve mood and health.

In accordance with the first aspect of the present disclosure, at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

In some light fixtures in accordance with the first aspect of the present inventive subject matter, many advantages are provided, including the ability to supply light (in residential buildings, commercial buildings, other buildings and other structures) while avoiding or reducing (in comparison to other devices, such as conventional skylights) water leakage, providing lower heat loss, providing light on overcast or stormy days, simplifying installation, providing the ability for installation (e.g., in locations where installation of a skylight would be problematic or impossible, e.g., in the first story of a multi-story structure, or in a building in which the roof is spaced a large distance from a ceiling), providing the ability to control light exiting from the device into an office, a room or any other space (e.g., controlling the brightness and/or the color of light exiting from the light fixture). In addition, light fixtures in accordance with the first aspect of the present inventive subject matter can simplify cleaning (e.g., devices can be more easily accessed, and/or can be removed from a structure on which they are mounted).

In a second aspect, the present disclosure relates to light fixtures that comprise first and second light engines, in which the second light engine comprises a sidewall from which light exits.

In a third aspect, the present disclosure matter relates to light fixtures that output light having specific characteristics. For example, some embodiments provide for light emission that can achieve specific biological effects, such as adjusting a person's biological melatonin levels in a desired way (e.g., during twenty-four-hour periods), for instance to adjust a person's circadian rhythm, to ameliorate a person's circadian rhythm disorders, and/or to adjust a person's alertness (e.g., to increase the person's alertness during some daily time periods and/or to increase the person's drowsiness during other daily time periods).

The present disclosure further includes methods that comprise supplying electricity to any light fixture as described herein. In some of such embodiments, color and brightness of light exiting the light fixture are controlled independently to provide the illusion of natural daylight passing through a conventional skylight.

The present disclosure further includes methods that comprise moving at least one light engine relative to another light engine in any light fixture as described herein.

In accordance with another aspect, the disclosure relates to a lighting fixture that appears as a skylight and is referred to as a skylight fixture. The skylight fixture has a sky-resembling light assembly and a plurality of sun-resembling light assemblies. The sky-resembling light assembly has a specific optical assembly and a specific light source, wherein light from the light source exits a planar interior surface of the optical assembly as sky resembling light. The plurality of sun-resembling light assemblies are arranged adjacent one another and extend downward from a periphery of the sky-resembling light assembly. Each of the plurality of sun-resembling light assemblies has a specific optical assembly and a specific light source, wherein light from the light source exits a planar interior surface of the optical assembly as sun resembling light. The planar interior surfaces of the sky-resembling optical assembly and the plurality of sun-resembling optical assemblies define a cavity. One or more control modules alone or in a collective are configured to, in a first mode, drive the sky-specific light source and each sun-specific light sources such that the sky-resembling assembly has a light emission with a first color point and the at least one of the sun-resembling assemblies has light emission with a second color point that is different from the first color point. The skylight assembly may be configured to emulate a window of a traditional skylight. Each of the plurality of sunlight assemblies may be configured to emulate sunlight passing through and/or reflecting off of sidewalls of the traditional skylight. The interior surfaces need not be planar for either assembly for dome or other shaped skylight fixtures.

In one embodiment, one or both of the sky-specific light source and the sun-specific light source comprise first LEDs that emit light having a third color point, second LEDs that emit light having a fourth color point, and third LEDs that emit light having a fifth color point. In this embodiment or an independent embodiment, an interior angle formed between the planar interior surface of the sky-resembling optical assembly and the planar surface of each of the sun-resembling optical assembly is an obtuse angle. In various embodiments, the interior angle is greater than 90 degrees and less than or equal to 135 degrees; greater than or equal to 95 degrees and less than or equal to 130 degrees; or greater than or equal to 100 degrees and less than or equal to 125 degrees.

In one embodiment, the x coordinate value of the first color point and the x coordinate value of the second color point on the 1931 CIE Chromaticity Diagram differ by at least 0.1. The first color point falls within a first color space defined by x, y coordinates on the 1931 CIE Chromaticity Diagram: (0.37, 0.34), (0.35, 0.38), (0.15, 0.20), and (0.20, 0.14). The second color point falls within a second color space defined by x, y coordinates on the 1931 CIE Chromaticity Diagram: (0.29, 0.32), (0.32, 0.29), (0.41, 0.36), (0.48, 0.39), (0.48, 0.43), (0.40, 0.41), and (0.35, 0.38).

In one embodiment, the x coordinate value of the first color point and the x coordinate value of the second color point on the 1931 CIE Chromaticity Diagram differ by at least 0.1. The first color point falls within a first color space defined by x, y coordinates on the 1931 CIE Chromaticity Diagram: (0.32, 0.31), (0.30, 0.33), (0.15, 0.17), and (0.17, 0.14). The second color point falls within a second color space defined by x, y coordinates on the 1931 CIE Chromaticity Diagram: (0.30, 0.34), (0.30, 0.30), (0.39, 0.36), (0.45, 0.39), (0.47, 0.43), (0.40, 0.41), and (0.35, 0.38).

In one embodiment, the x coordinate value of the first color point and the x coordinate value of the second color point on the 1931 CIE Chromaticity Diagram differ by at least 0.1. The first color point falls within a first color space defined by x, y coordinates on the 1931 CIE Chromaticity Diagram: (0.39, 0.31), (0.34, 0.40), (0.10, 0.20), and (0.16, 0.06). The second color point falls within a second color space defined by x, y coordinates on the 1931 CIE Chromaticity Diagram: (0.28, 0.36), (0.35, 0.26), (0.44, 0.33), (0.62, 0.34), (0.50, 0.46), (0.43, 0.45), (0.36, 0.43).

In one embodiment, the x coordinate value of the first color point and the x coordinate value of the second color point on the 1931 CIE Chromaticity Diagram differ by at least 0.1. The first color point falls within a first color space defined by x, y coordinates on the 1931 CIE Chromaticity Diagram: (0.10, 0.20), (0.36, 0.43), (0.43, 0.45), (0.50, 0.46), (0.62, 0.34), (0.44, 0.33), (0.16, 0.06). The second color point falls within a second color space defined by x, y coordinates on the 1931 CIE Chromaticity Diagram: (0.10, 0.20), (0.36, 0.43), (0.43, 0.45), (0.50, 0.46), (0.62, 0.34), (0.44, 0.33), (0.16, 0.06).

In one embodiment, the x coordinate value of the first color point and the x coordinate value of the second color point on the 1931 CIE Chromaticity Diagram differ by at least 0.15. In another embodiment, the x coordinate value of the first color point and the x coordinate value of the second color point on the 1931 CIE Chromaticity Diagram differ by at least 0.2.

In one embodiment, the x coordinate value of the first color point is less than the x coordinate value of the second color point on the 1931 CIE Chromaticity Diagram. In another embodiment, the y coordinate value of the first color point is less than the y coordinate value of the second color point on the 1931 CIE Chromaticity Diagram. In yet another embodiment, both the x coordinate value of the first color point is less than the x coordinate value of the second color point on the 1931 CIE Chromaticity Diagram and the y coordinate value of the first color point is less than the y coordinate value of the second color point on the 1931 CIE Chromaticity Diagram. The x coordinate value of the first color point and the x coordinate value of the second color point on the 1931 CIE Chromaticity Diagram may differ by at least 0.15, 0.2, and 0.25.

In one embodiment, the sky-specific light source comprises first LEDs that emit light having a third color point, second LEDs that emit light having a fourth color point, and third LEDs that emit light having a fifth color point. The third color point, the fourth color point, and the fifth color point are spaced apart from one another on the 1931 CIE Chromaticity Diagram by at least 0.05 in at least one of x and y directions. The first LEDs may emit white light, and the third color point may be within three, five, seven, or ten MacAdam Ellipses (a/k/a MacAdam step ellipses) of a blackbody curve. The second LEDs may emit bluish light, the third LEDs may emit greenish light, and the y coordinate value of the fourth color point and the y coordinate value of the fifth color point on the 1931 CIE Chromaticity Diagram may differ by at least 0.1, 0.15, or 0.2.

In one embodiment, at least two of the sun-specific light sources may have fourth LEDs that emit light having a sixth color point, fifth LEDs that emit light having a seventh color point, and sixth LEDs that emit light having an eighth color point. The sixth color point, the seventh color point, and the eighth color point may be spaced apart from one another on the 1931 CIE Chromaticity Diagram by at least 0.05, 0.1, or 0.15 in at least one of x and y directions.

In one embodiment, at least two of the sun-specific light sources have first LEDs that emit light having a third color point, second LEDs that emit light having a fourth color point, and third LEDs that emit light having a fifth color point. The third color point, the fourth color point, and the fifth color point spaced may be apart from one another on the 1931 CIE Chromaticity Diagram by at least 0.05, 0.1, or 0.15 in at least one of x and y directions.

In one embodiment, the sky-resembling light assembly and the sun-resembling light assembly may provide a composite light output that has a color rendering index of greater than 90.

In one embodiment, the one or more control modules may be further configured to independently and variably drive the sky-specific light source and each sun-specific source such that the first color point and the second color point are independently variable.

In one embodiment, the one or more control modules may be further configured to drive the sky-specific light source and each sun-specific light source such that the first color point and the second color point change temporally.

In one embodiment, the one or more control modules may be further configured to drive the sky-specific light source and each sun-specific light source such that the first color point and the second color point are selected based on a time of day.

In one embodiment, the one or more control modules may be further configured to drive the sky-specific light source and each sun-specific light source such that the first color point and the second color point are selected based on information received from a remote device.

In one embodiment, the one or more control modules may be further configured to drive the sky-specific light source and each sun-specific light source such that the first color point and the second color point are selected based on sensor information provided by at least one sensor.

In one embodiment, the one or more control modules may be further configured to drive the sky-specific light source and each sun-specific light source such that the first color point and the second color point are selected based on outdoor lighting conditions.

In one embodiment, the one or more control modules may be further configured to drive the sky-specific light source and each sun-specific light source such that the first color point and the second color point are selected based on outdoor weather conditions.

In one embodiment, the one or more control modules may be further configured to drive the sky-specific light source and each sun-specific light source such that the first color point and the second color point are selected based on outdoor environmental conditions.

In one embodiment, the one or more control modules may be further configured to, in a second mode, drive the sky-specific light source and each sun-specific light source to change the first and second color point to provide a circadian stimulus.

In one embodiment, the one or more control modules may be further configured to, in a second mode, drive each sunlight light source to change the second color point of the sunlight light provided by each sunlight source to have additional red spectral content.

In one embodiment, the one or more control modules may be further configured to communicate with other skylight fixtures and drive the sky-specific light source and each sun-specific light source such that the sky-specific emission and sun-specific emission is coordinated with that from the other skylight fixtures.

While the above features of various embodiments are listed separately for clarity, each of the features above may be implemented together in any combination as long as functionality is not destroyed.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

Figure 4:
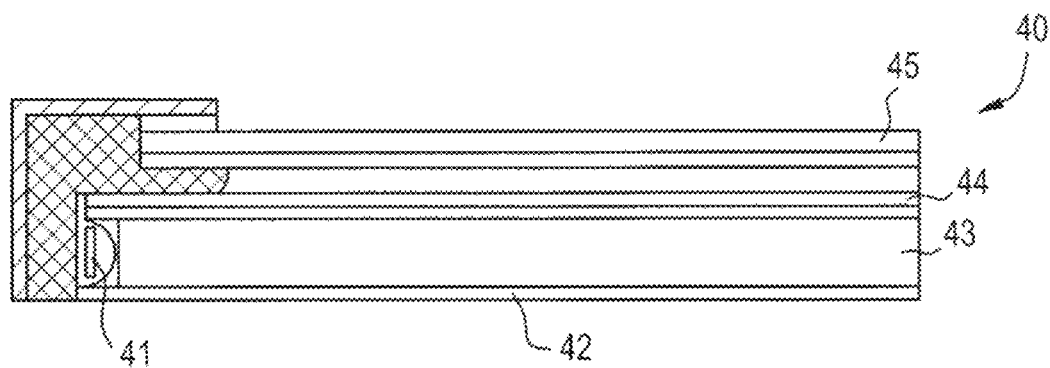

FIG. 4 schematically depicts a representative example of an edge-lit panel that can be used as a component in a light fixture in accordance with the present inventive subject matter.

Figure 5:
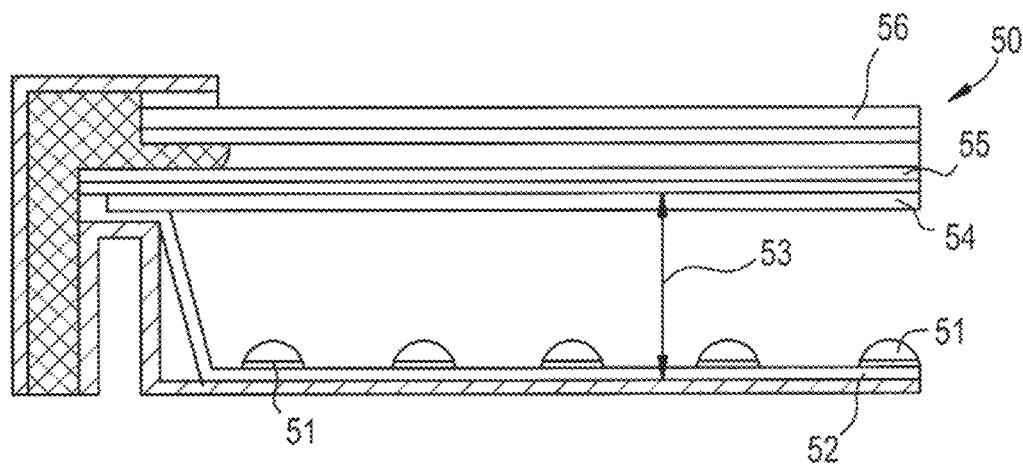

FIG. 5 schematically depicts a representative example of a back-lit panel that can be used as a component in a light fixture in accordance with the present inventive subject matter.

Figure 6:
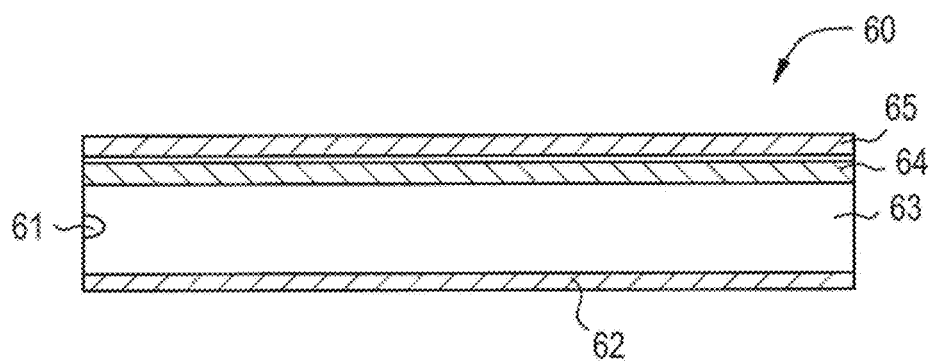

FIG. 6 schematically depicts a representative example of a side-lit panel that can be used as a component in a light fixture in accordance with the present inventive subject matter.

Figure 7:
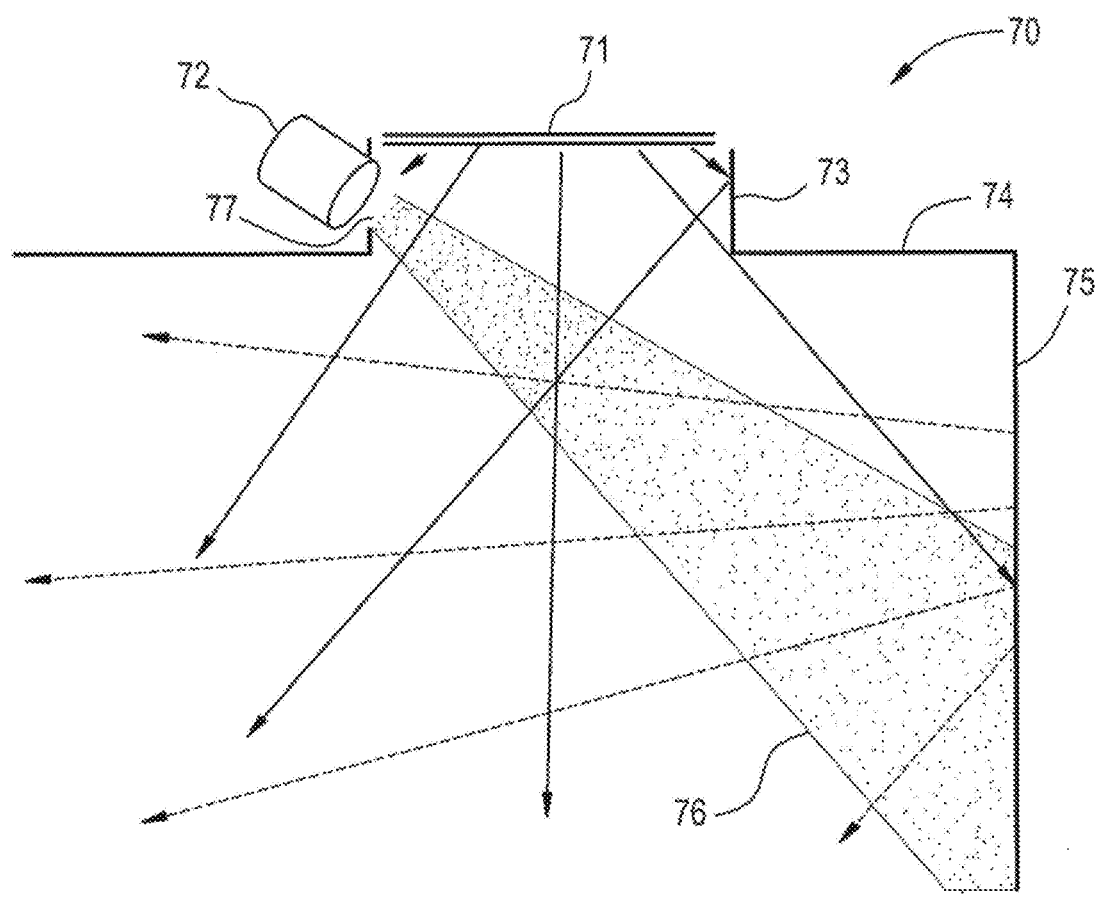

FIG. 7 is a schematic cross-sectional view of an embodiment of a light fixture in accordance with the present inventive subject matter, mounted in a ceiling.

Figure 8:
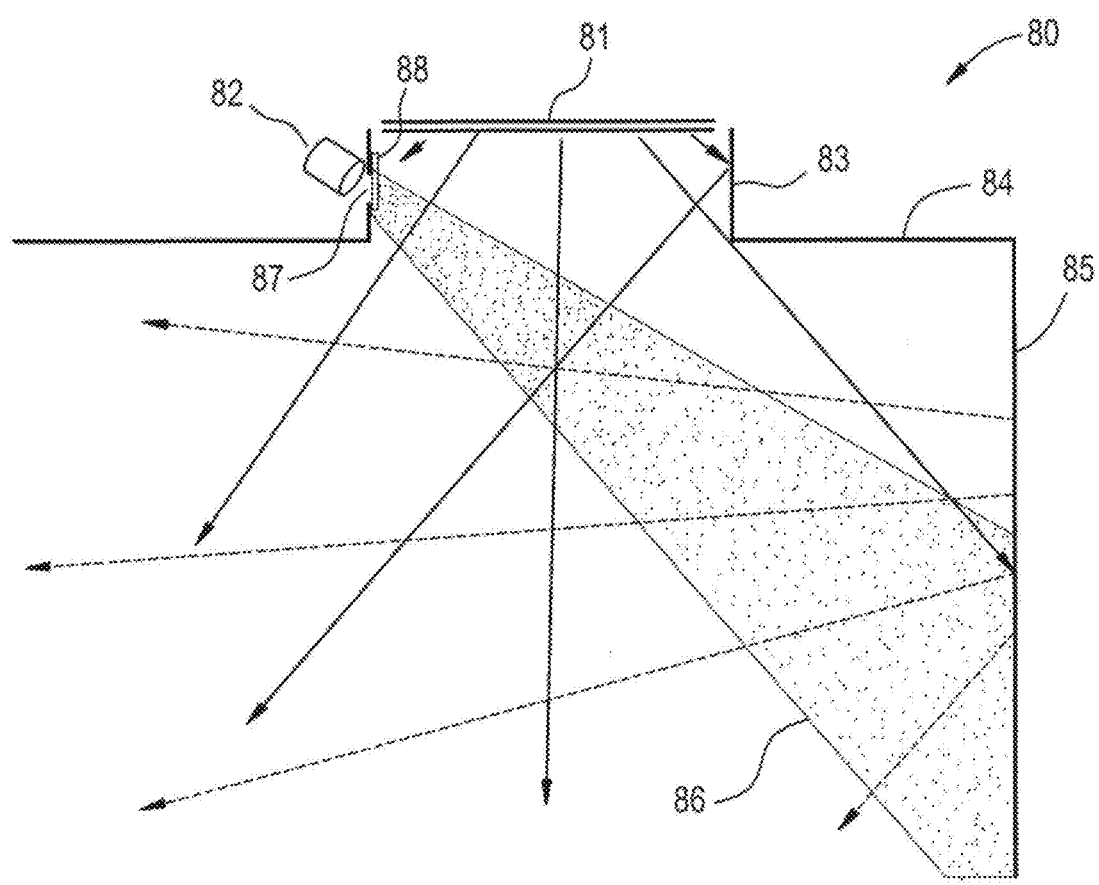

FIG. 8 is a schematic cross-sectional view of an embodiment of a light fixture in accordance with the present inventive subject matter, mounted in a ceiling.

Figure 9A:
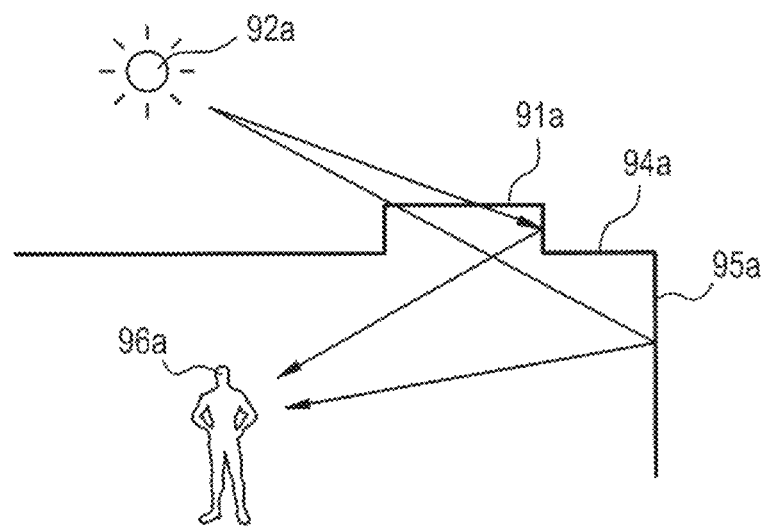
Figure 9B:
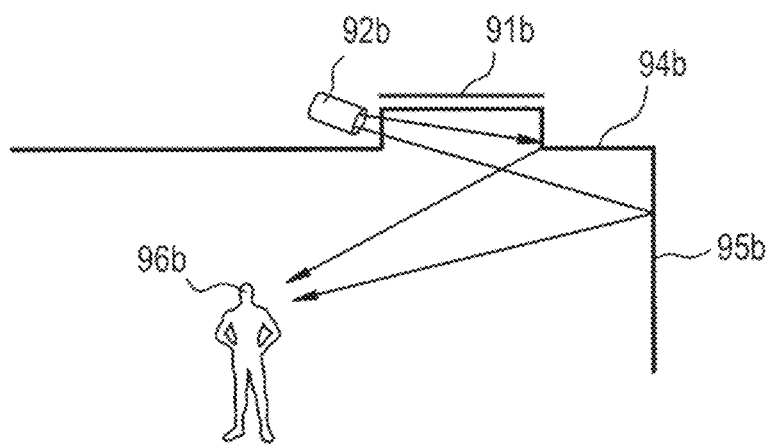
Figure 9C:
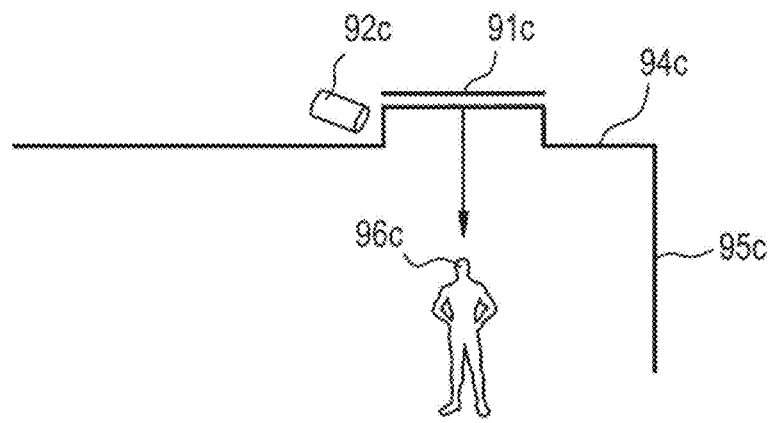

FIG. 9A schematically depicts the visual impression created by a conventional skylight, and FIGS. 9B and 9C depict the visual impression created by representative embodiments of light fixtures in accordance with the present inventive subject matter.

Figure 10:
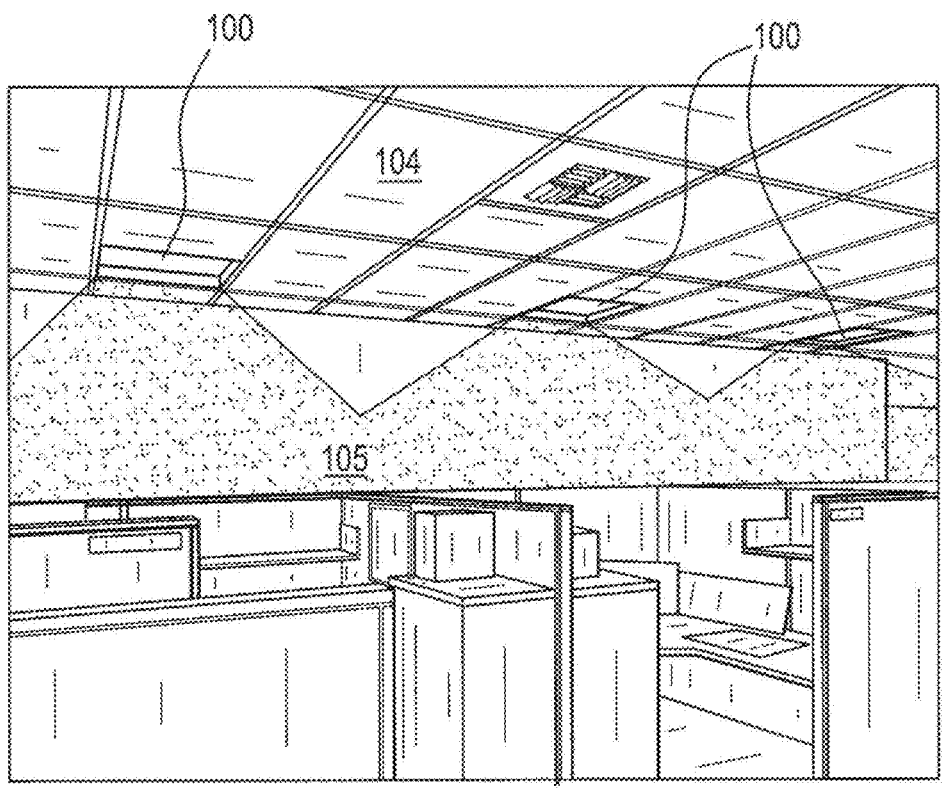

FIG. 10 depicts a room in which three light fixtures (each similar to the light fixture depicted in FIG. 7) are mounted in a ceiling.

Figure 11:
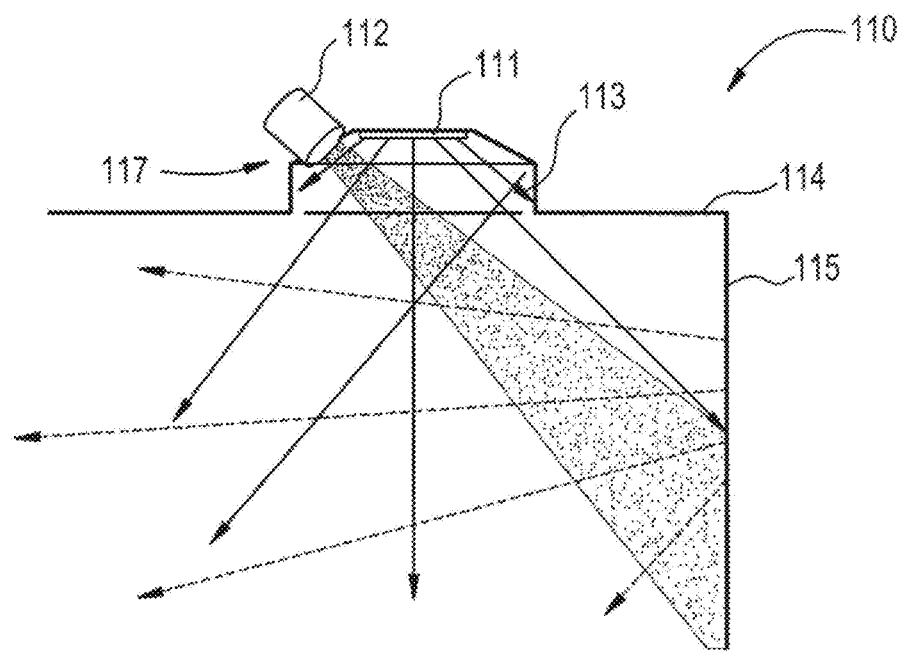

FIG. 11 is a schematic cross-sectional view of an embodiment of a light fixture in accordance with the present inventive subject matter, mounted in a ceiling.

Figure 12:
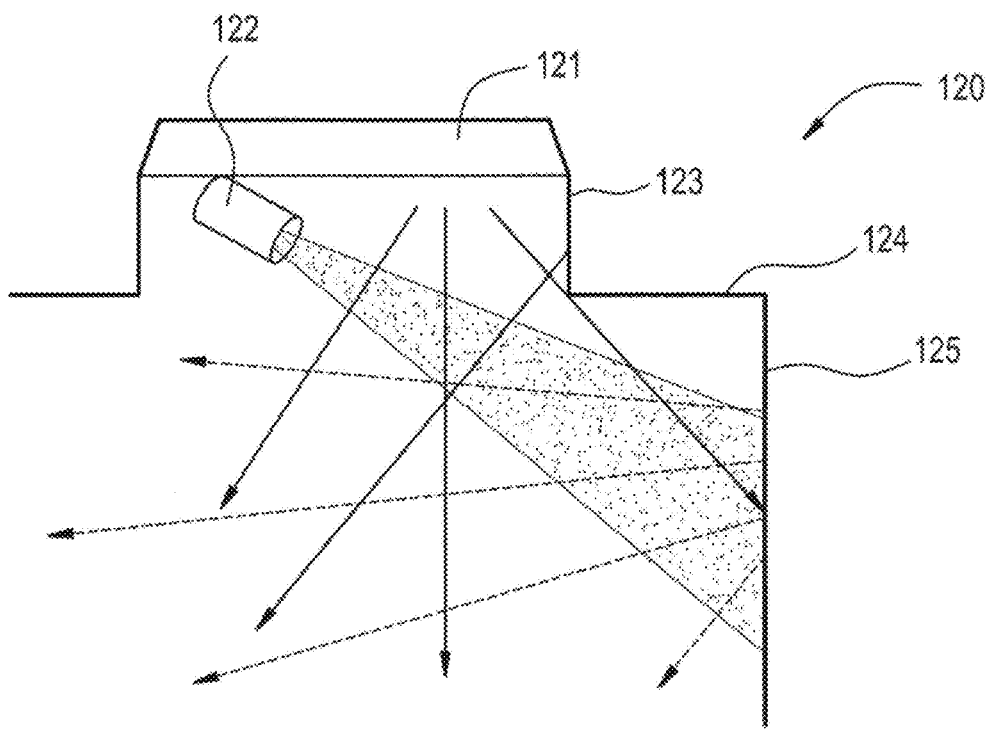

FIG. 12 is a schematic cross-sectional view of an embodiment of a light fixture in accordance with the present inventive subject matter, mounted in a ceiling.

Figure 13:
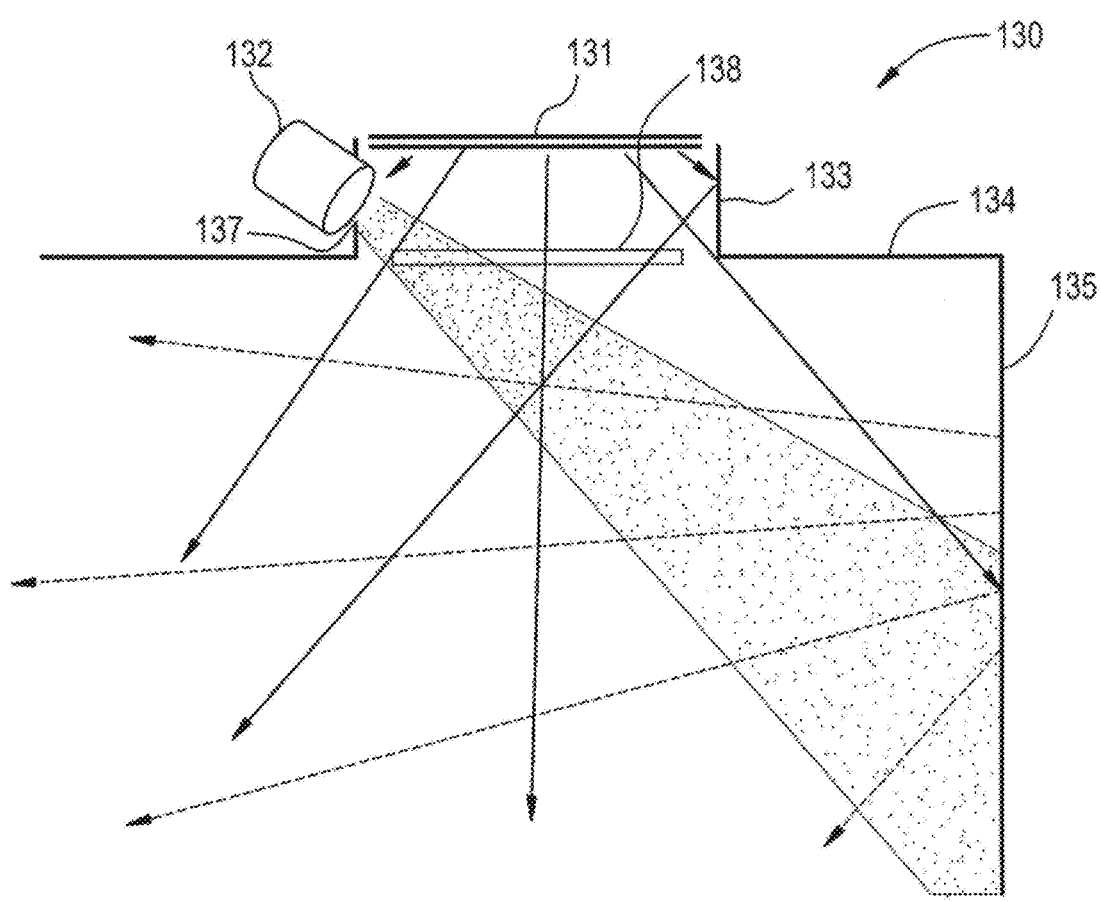

FIG. 13 is a schematic cross-sectional view of an embodiment of a light fixture in accordance with the present inventive subject matter, mounted in a ceiling.

Figure 14:
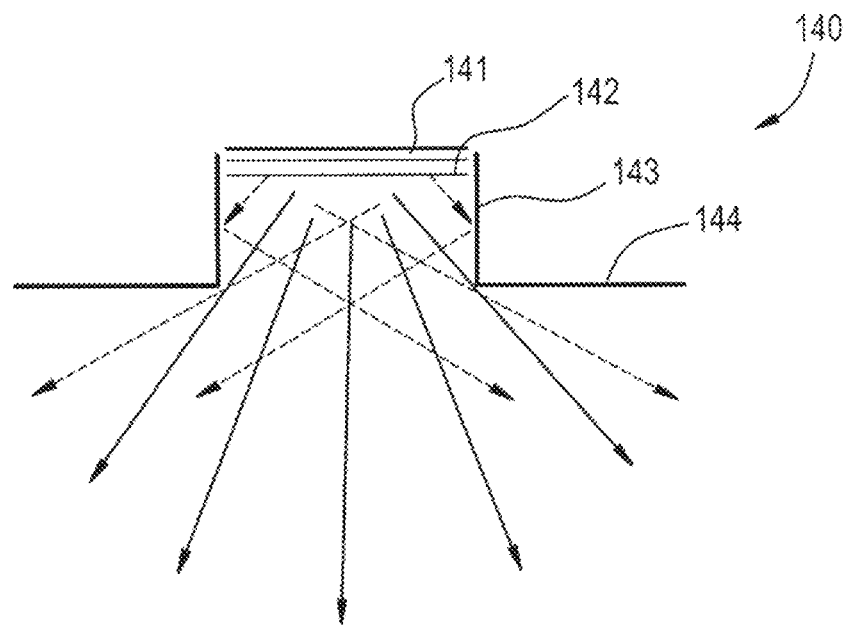

FIG. 14 is a schematic cross-sectional view of an embodiment of a light fixture in accordance with the present inventive subject matter, mounted in a ceiling.

Figure 15:
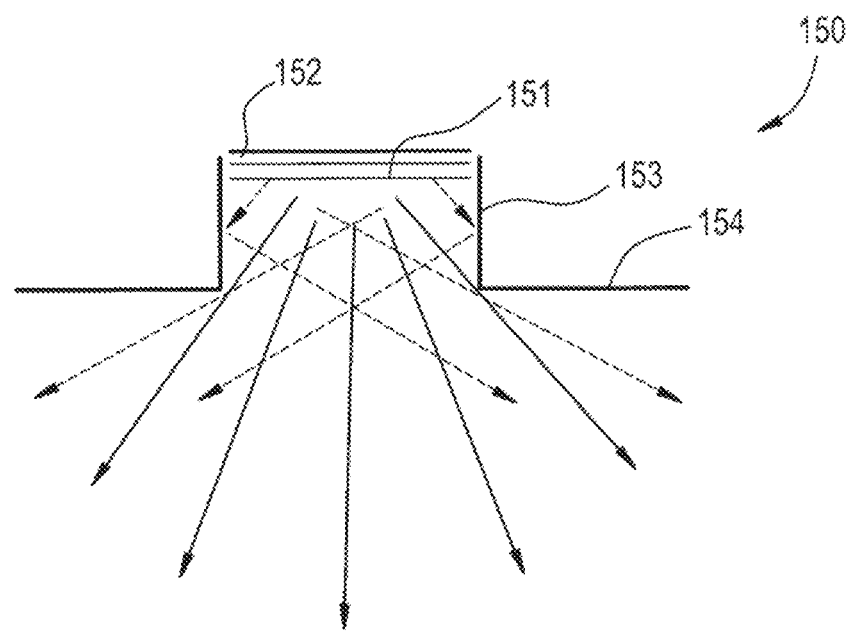

FIG. 15 is a schematic cross-sectional view of an embodiment of a light fixture in accordance with the present inventive subject matter, mounted in a ceiling.

Figure 16:
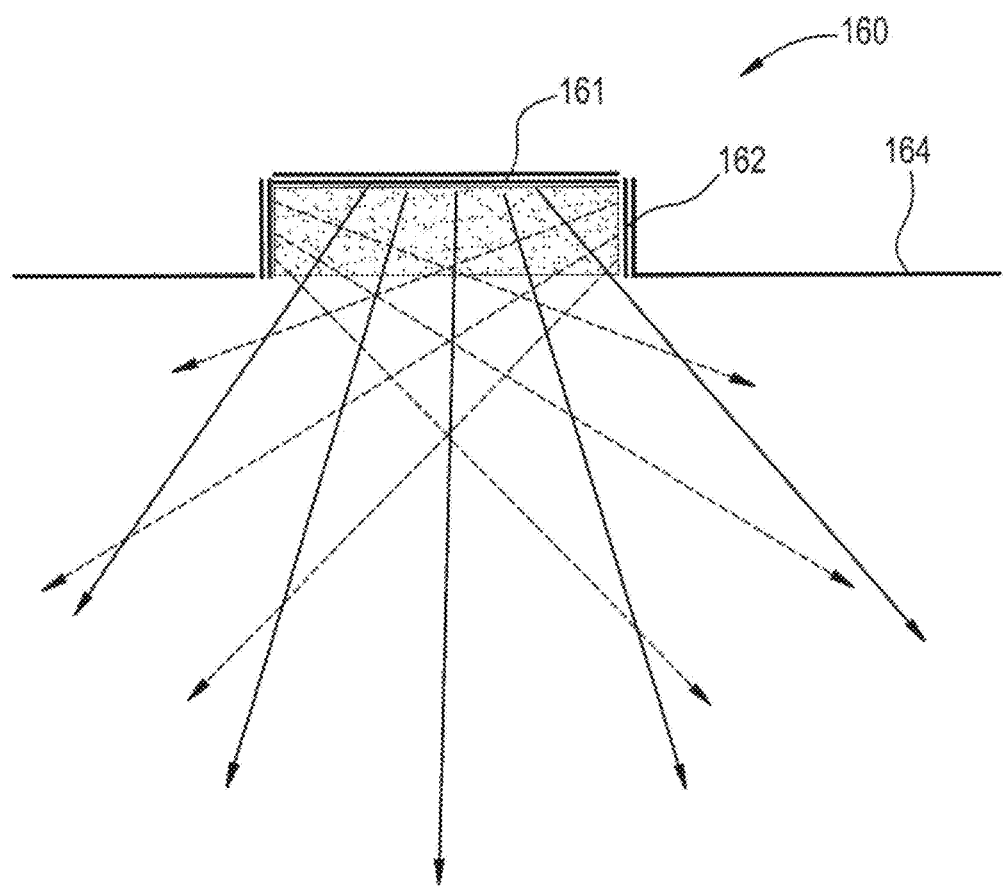

FIG. 16 is a schematic cross-sectional view of an embodiment of a light fixture in accordance with the present inventive subject matter, mounted in a ceiling.

Figure 17:
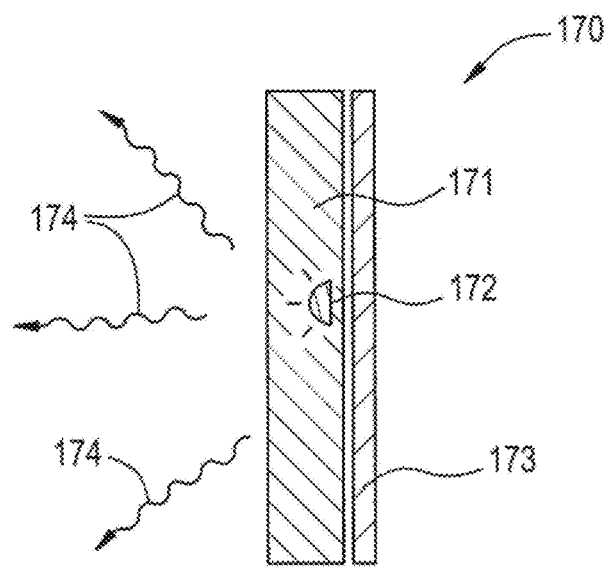

FIG. 17 schematically depicts a cross-sectional view of a portion of a sidewall that can be used as a component in a light fixture in accordance with the present inventive subject matter.

Figure 18:
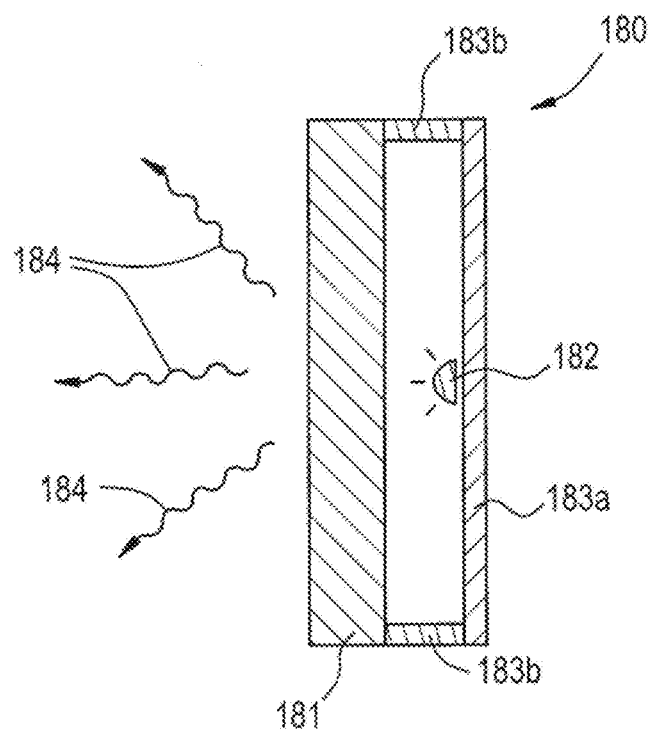

FIG. 18 schematically depicts a cross-sectional view of a portion of a sidewall that can be used as a component in a light fixture in accordance with the present inventive subject matter.

Figure 19:
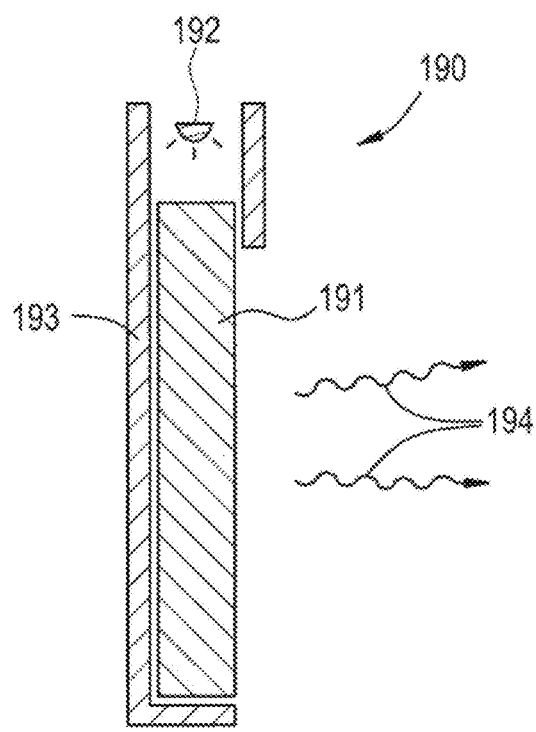

FIG. 19 schematically depicts a cross-sectional view of a portion of a sidewall that can be used as a component in a light fixture in accordance with the present inventive subject matter.

Figure 20:
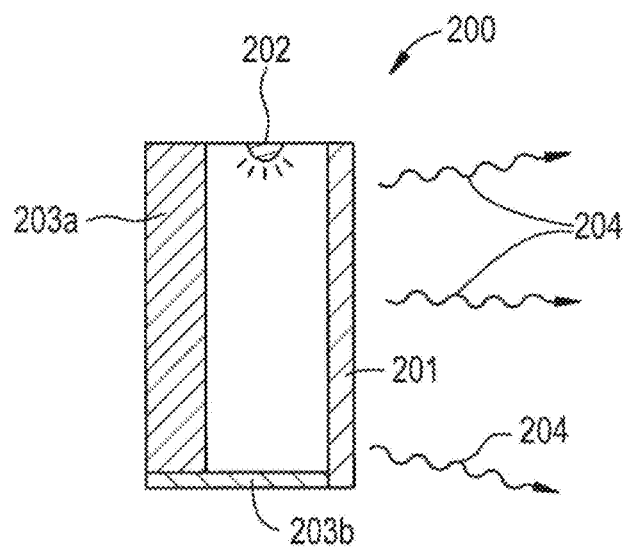

FIG. 20 schematically depicts a cross-sectional view of a portion of a sidewall that can be used as a component in a light fixture in accordance with the present inventive subject matter.

Figure 21:
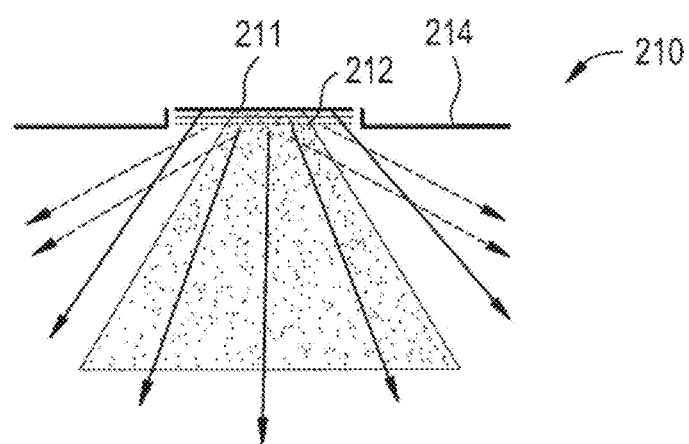

FIG. 21 is a schematic cross-sectional view of an embodiment of a light fixture in accordance with the present inventive subject matter, mounted in a ceiling.

Figure 22:
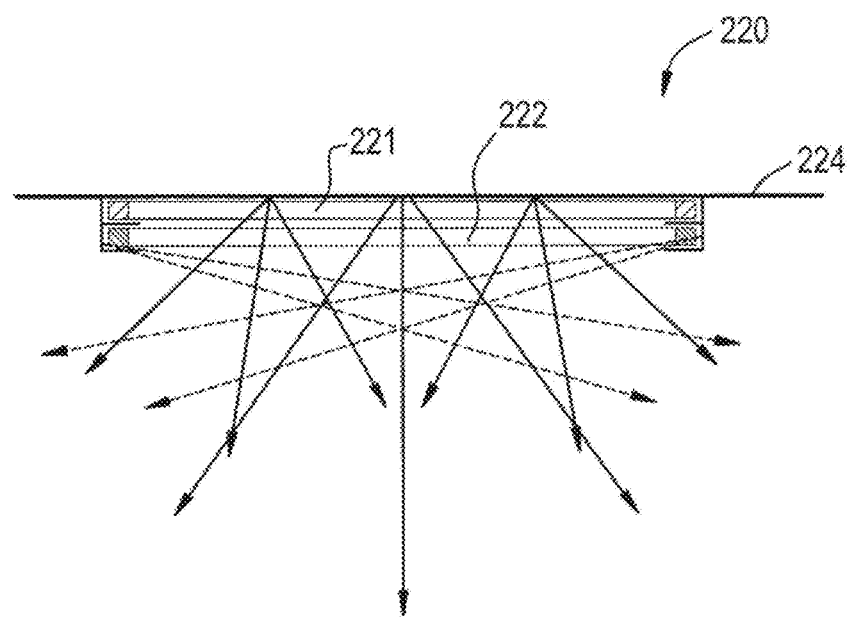

FIG. 22 is a schematic cross-sectional view of an embodiment of a light fixture in accordance with the present inventive subject matter, mounted on a ceiling.

Figure 23:
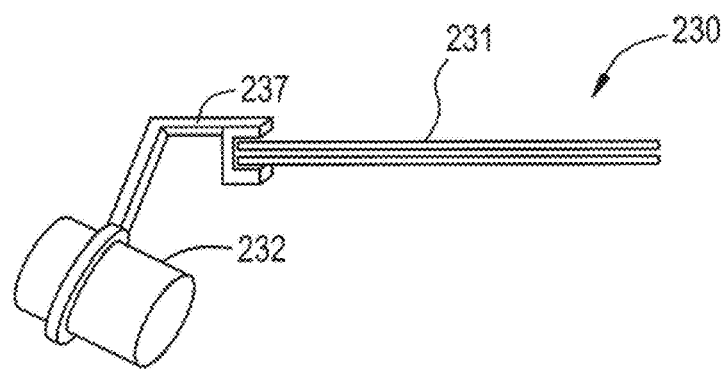

FIG. 23 is a schematic cross-sectional view of an embodiment of a light fixture in accordance with the present inventive subject matter.

Figure 24A:
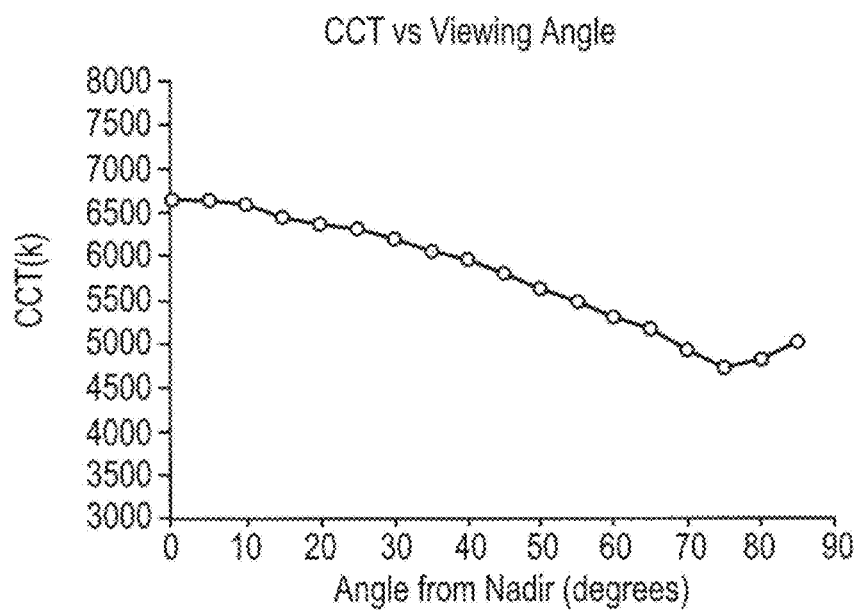

FIG. 24A shows a plot of CCT over viewing angle measured using a light fixture similar to the embodiment of a light fixture depicted in FIG. 16.

Figure 24B:
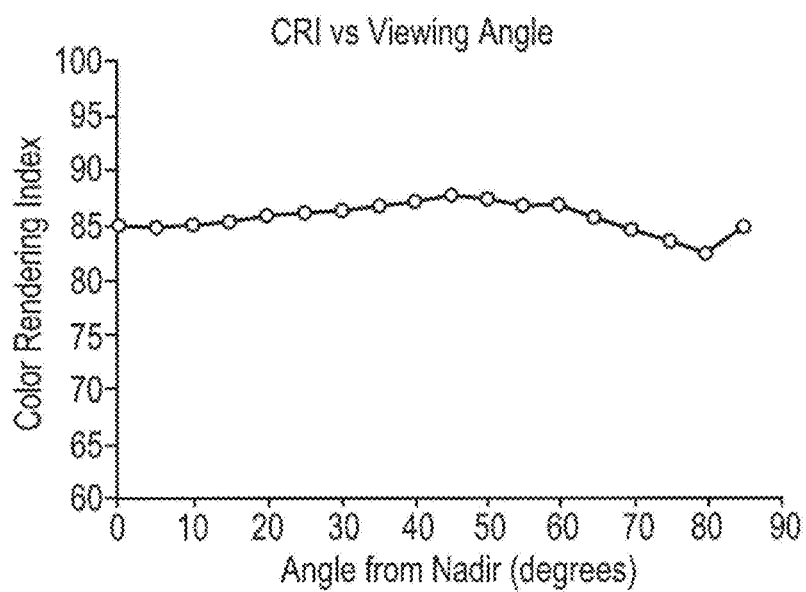

FIG. 24B shows a plot of measured CRI over viewing angle measured using a light fixture similar to the embodiment of a light fixture depicted in FIG. 16.

Figure 25:
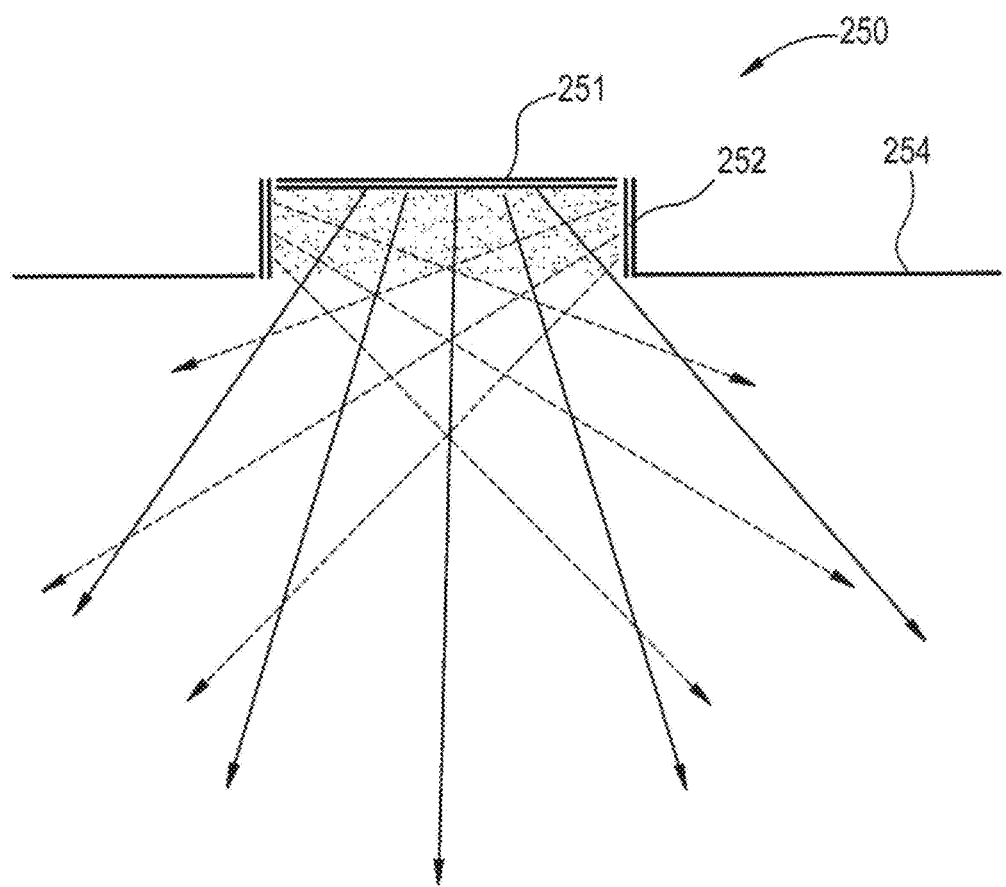

FIG. 25 is a schematic cross-sectional view of an embodiment of a light fixture in accordance with the present inventive subject matter, mounted in a ceiling.

Figure 26:
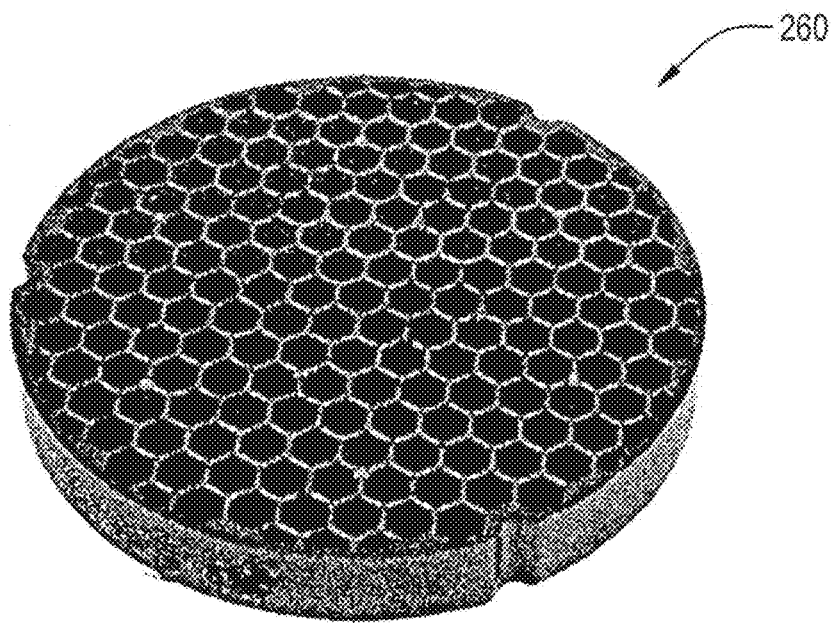

FIG. 26 schematically depicts a representative example of a baffle element 260 suitable for use in accordance with the present inventive subject matter.

Figure 27:
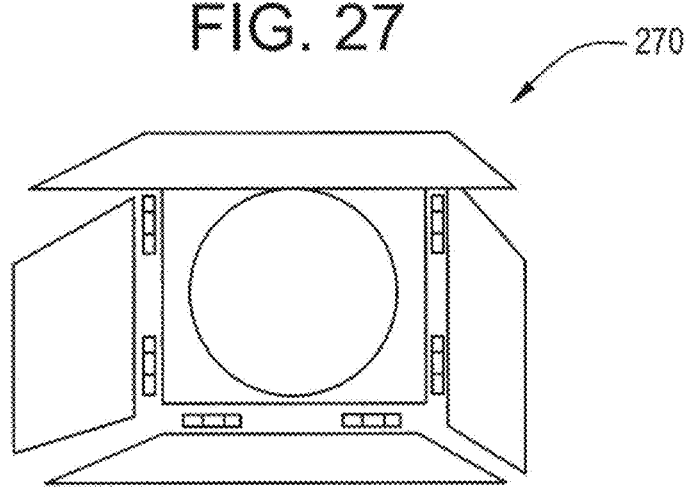

FIG. 27 schematically depicts a representative example of a baffle element 270 suitable for use in accordance with the present inventive subject matter.

Figure 28:
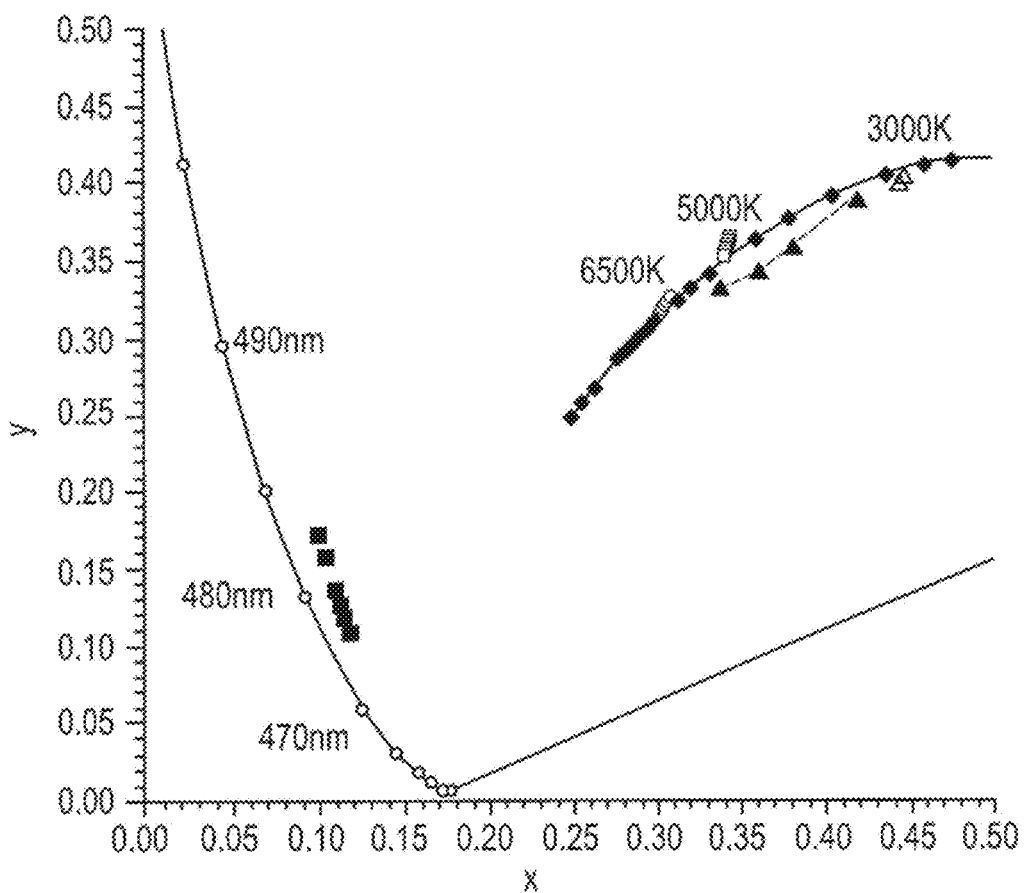

FIG. 28 shows the color points of light emitted by representative examples of the two types of LEDs used in the fabrication of the first light engine (the "sky"), and light emitted by the two types of LEDs used in the fabrication of the second light engine (the "sun") plotted on a portion of the CIE 1931 Chromaticity Diagram.

Figure 29:
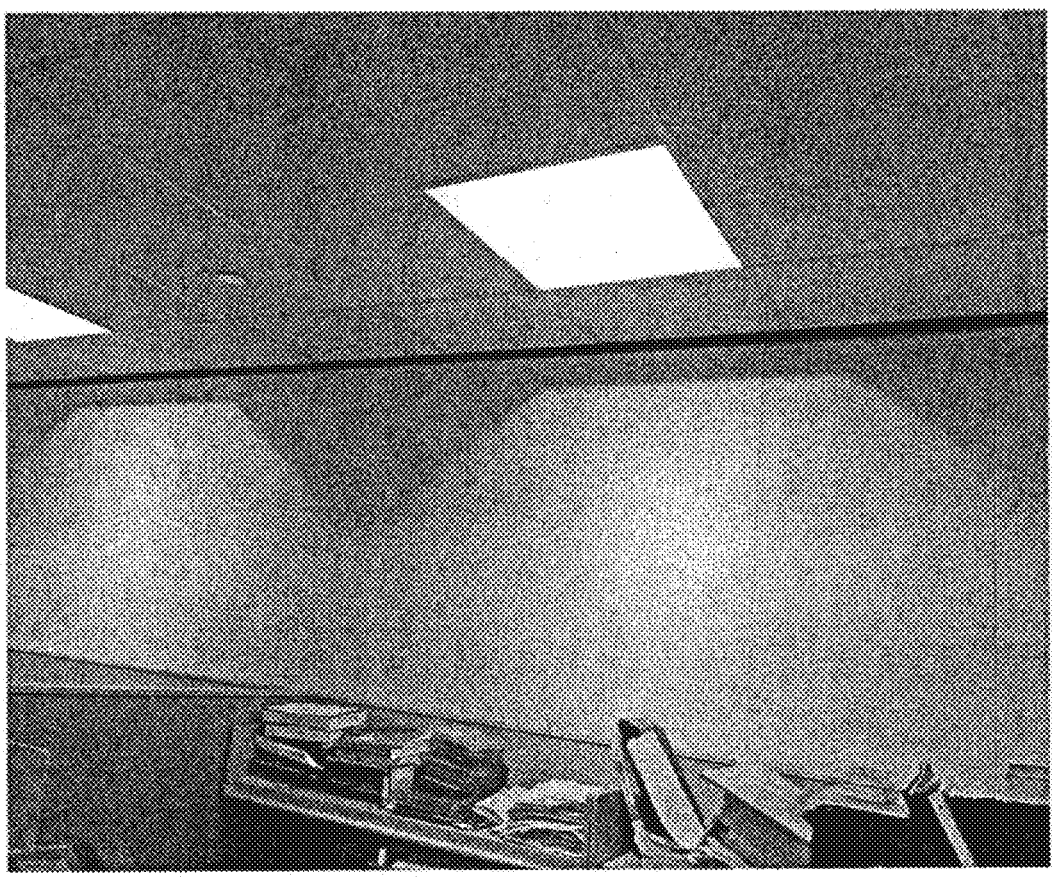

FIG. 29 is a photo of an embodiment of an artificial skylight in accordance with the present inventive subject matter, where the sky ("first light engine") has a color point of (0.3135, 0.3237), and the sun ("second light engine") has a color point of (0.3451, 0.3516).

Figure 30:

FIG. 30 is a photo of an embodiment of an artificial skylight in accordance with the present inventive subject matter, where the sky ("first light engine") has a color point of (0.2383, 0.2472), and the sun ("second light engine") has a color point of (0.3451, 0.3516)

Figure 31:
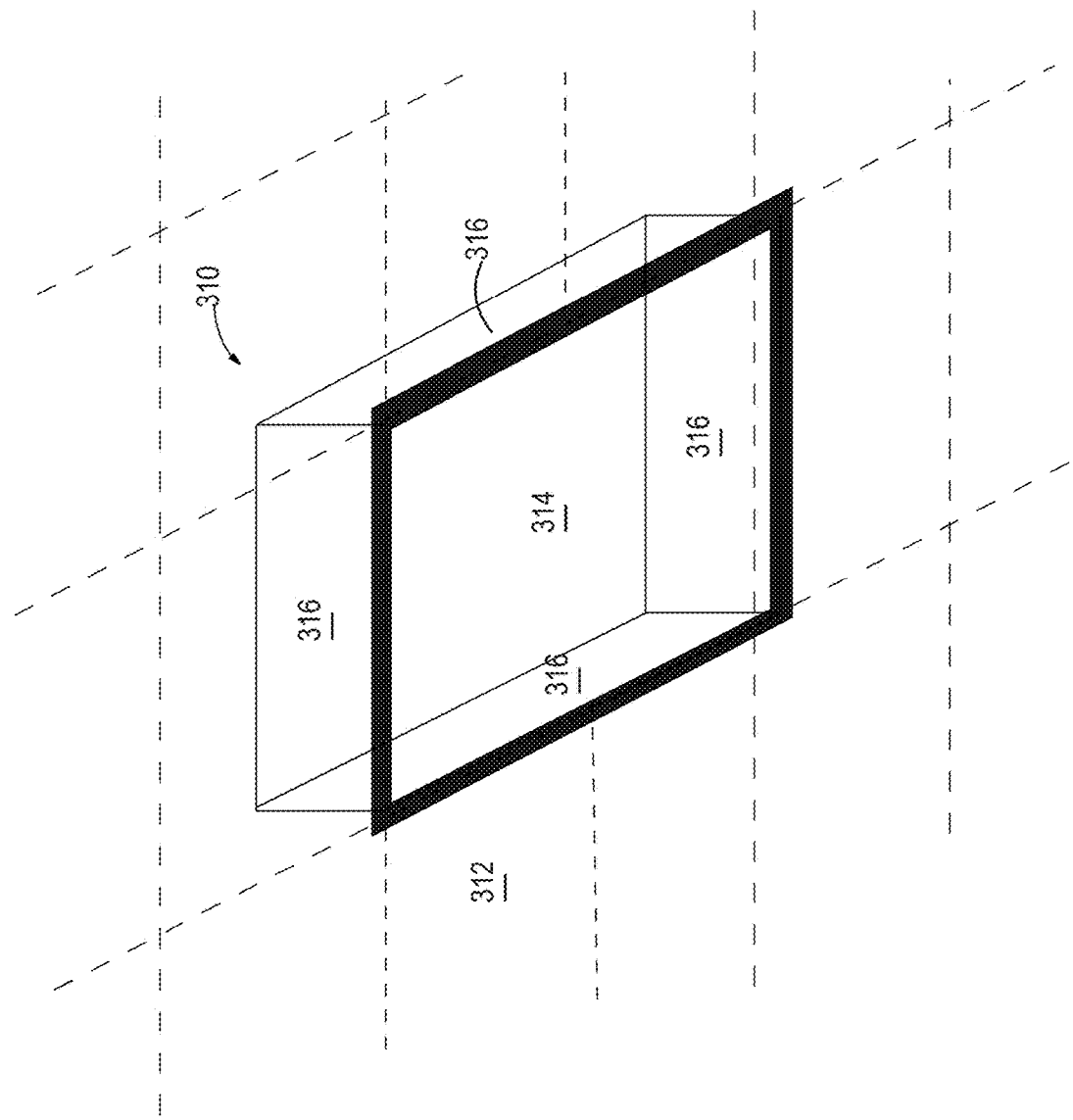

FIG. 31 illustrates a skylight fixture mounted in a ceiling according to one embodiment.

Figure 32A:
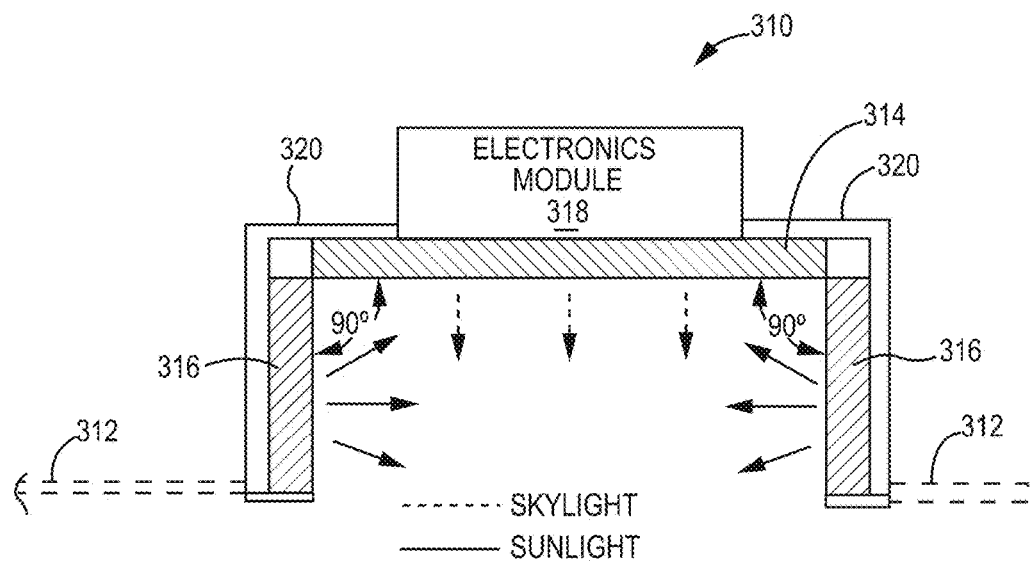

FIG. 32A is a cross-section of a skylight fixture according to a first embodiment.

Figure 32B:
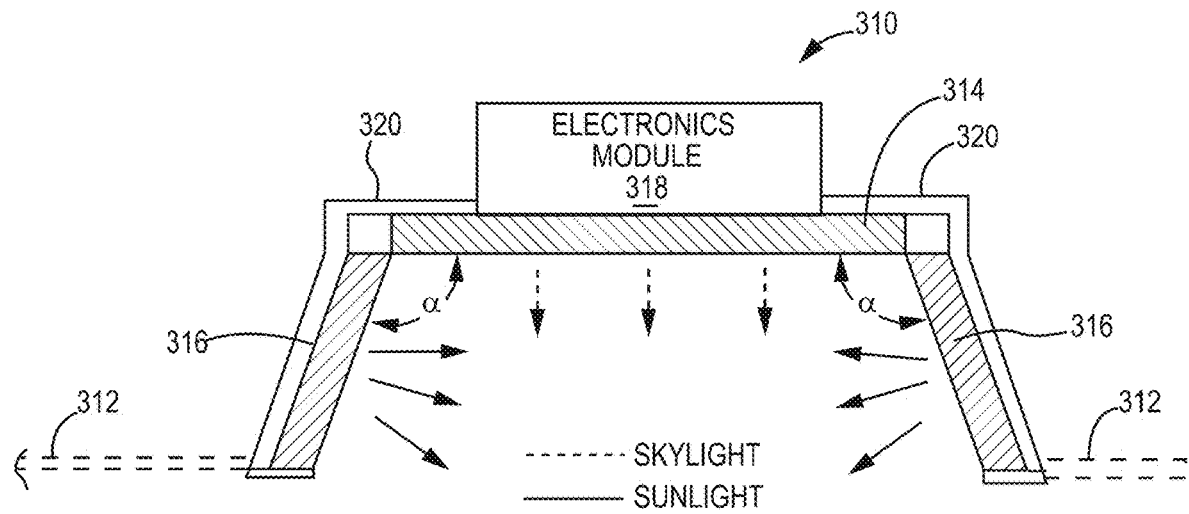

FIG. 32B as a cross-section of a skylight fixture according to a second embodiment.

Figure 33:
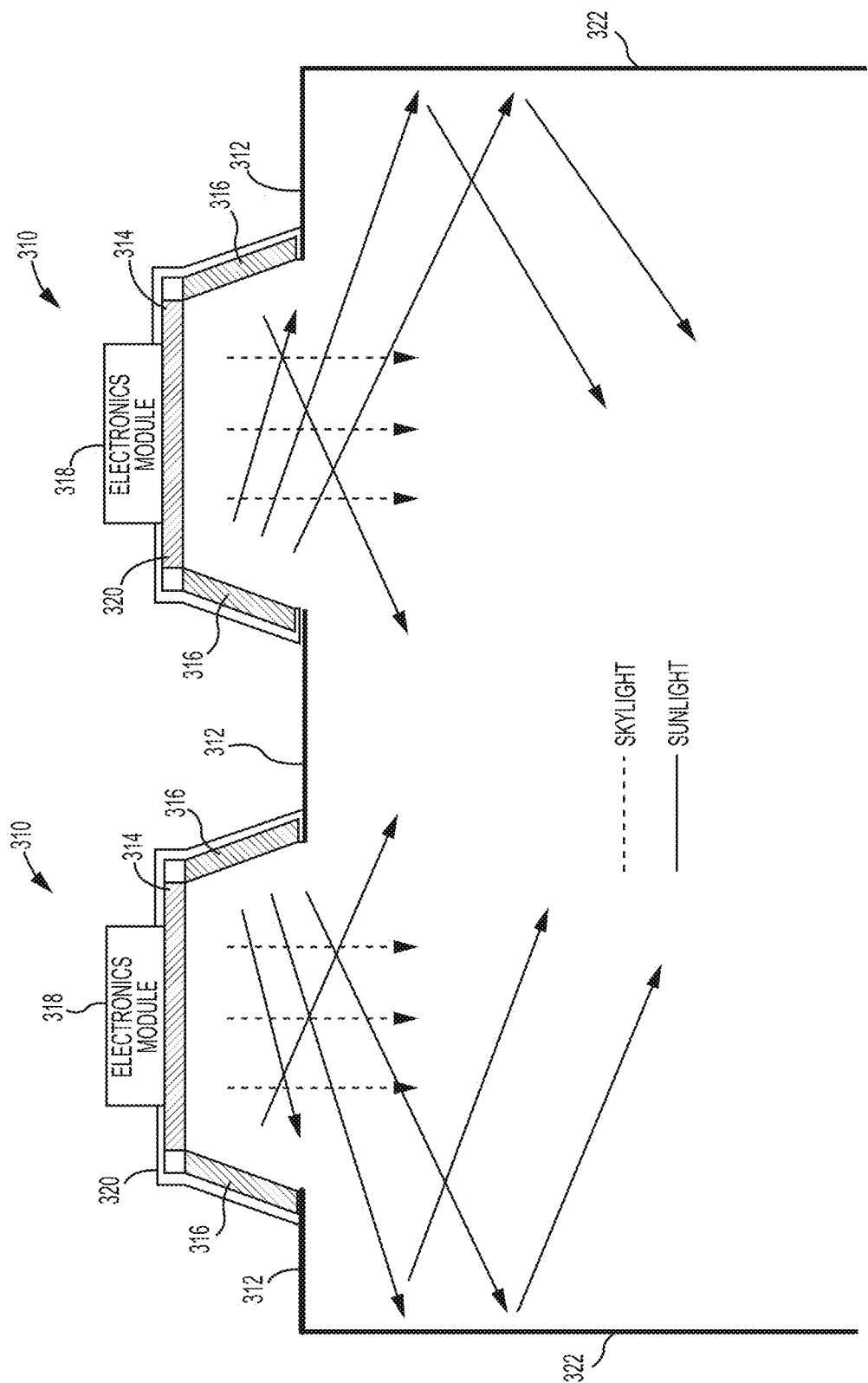

FIG. 33 illustrates multiple skylight fixtures mounted in a ceiling in a room.

Figure 34:
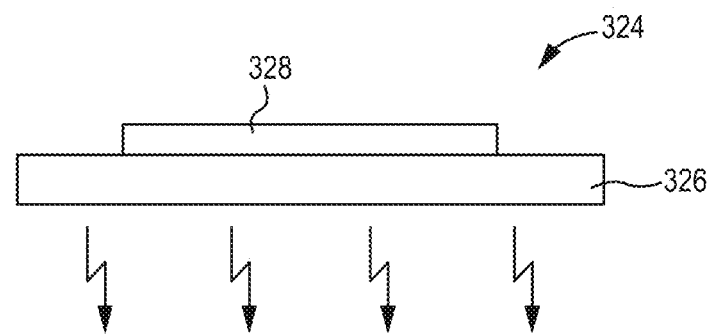

FIG. 34 illustrates a display, which can be used as either a sky-resembling assembly or a sun-resembling assembly of a skylight fixture.

Figure 35:
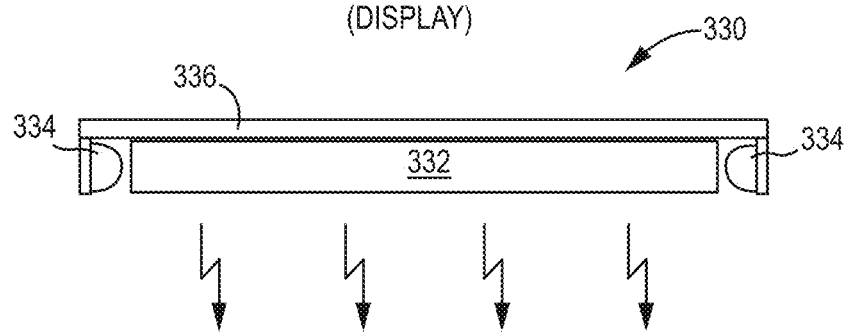

FIG. 35 illustrates a first light engine embodiment, which can be used as either a sky-resembling assembly or a sun-resembling assembly of a skylight fixture.

Figure 36:
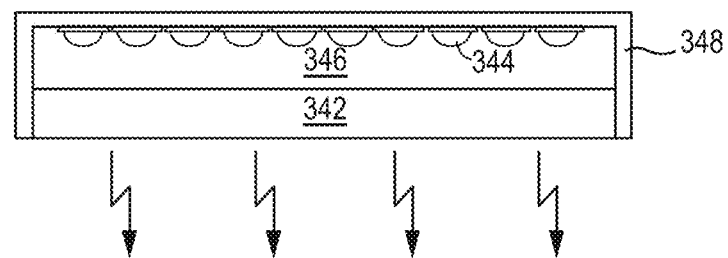

FIG. 36 illustrates a second light engine embodiment, which can be used as either a sky-resembling assembly or a sun-resembling assembly of a skylight fixture.

Figure 37:
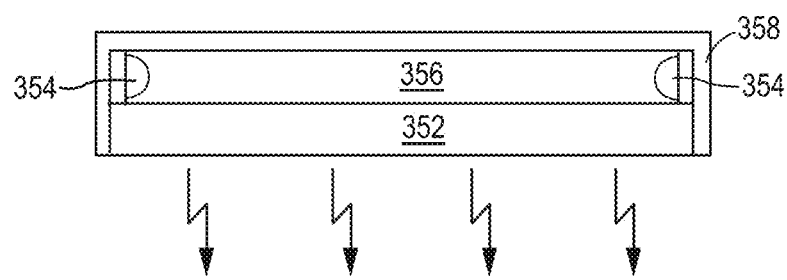

FIG. 37 illustrates a third light engine embodiment, which can be used as either a sky-resembling assembly or a sun-resembling assembly of a skylight fixture.

Figure 38:
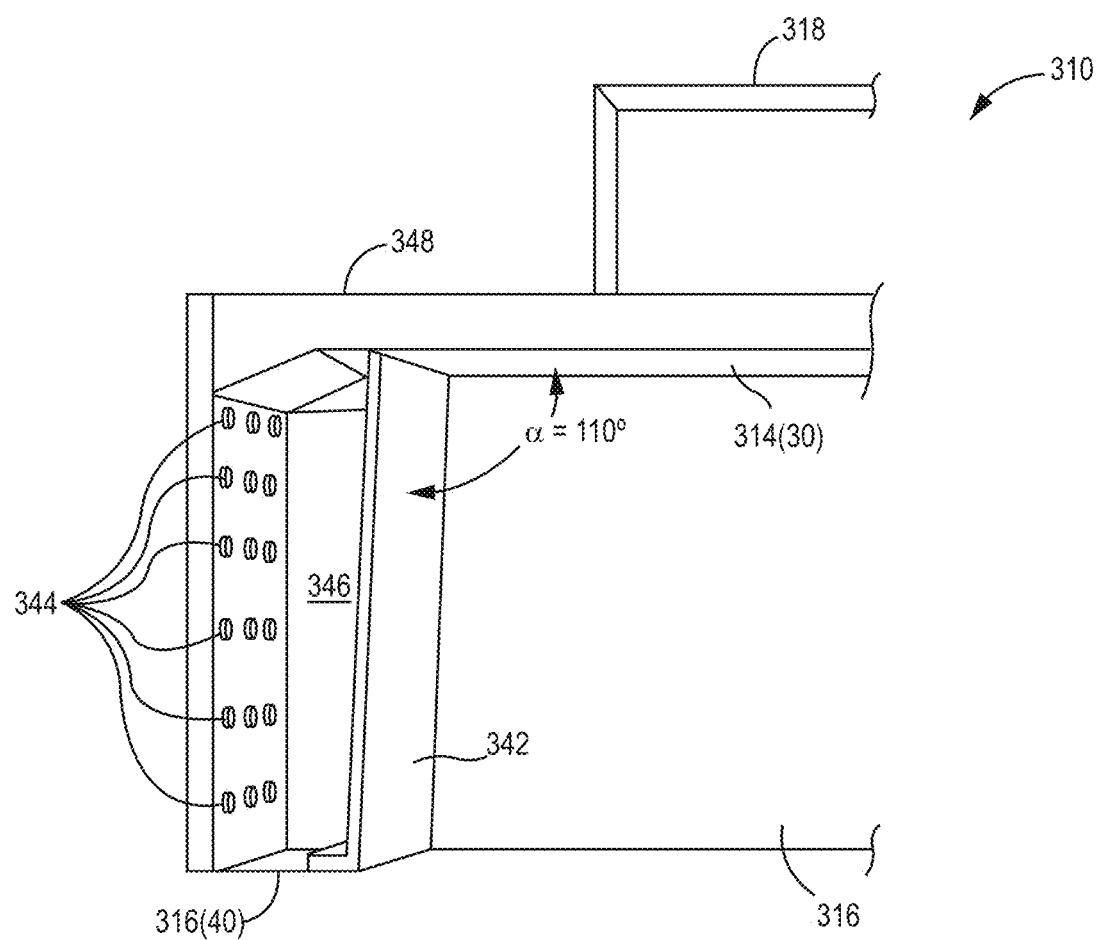

FIG. 38 is a partial cross-section of a skylight fixture according to a third embodiment.

Figure 39:
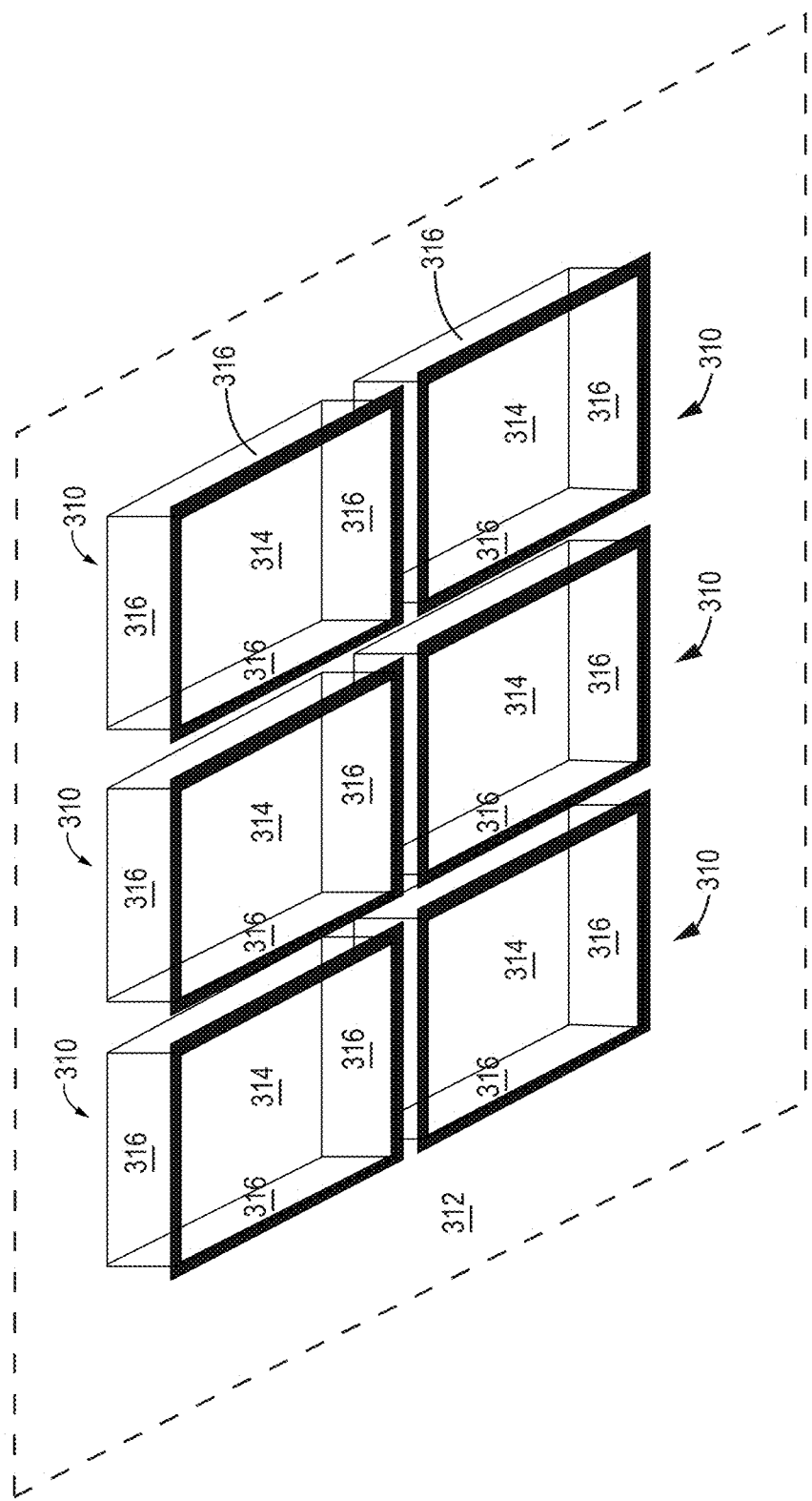

FIG. 39 illustrate multiple skylight fixtures arranged in an array in a ceiling.

Figures 40A, 40B:
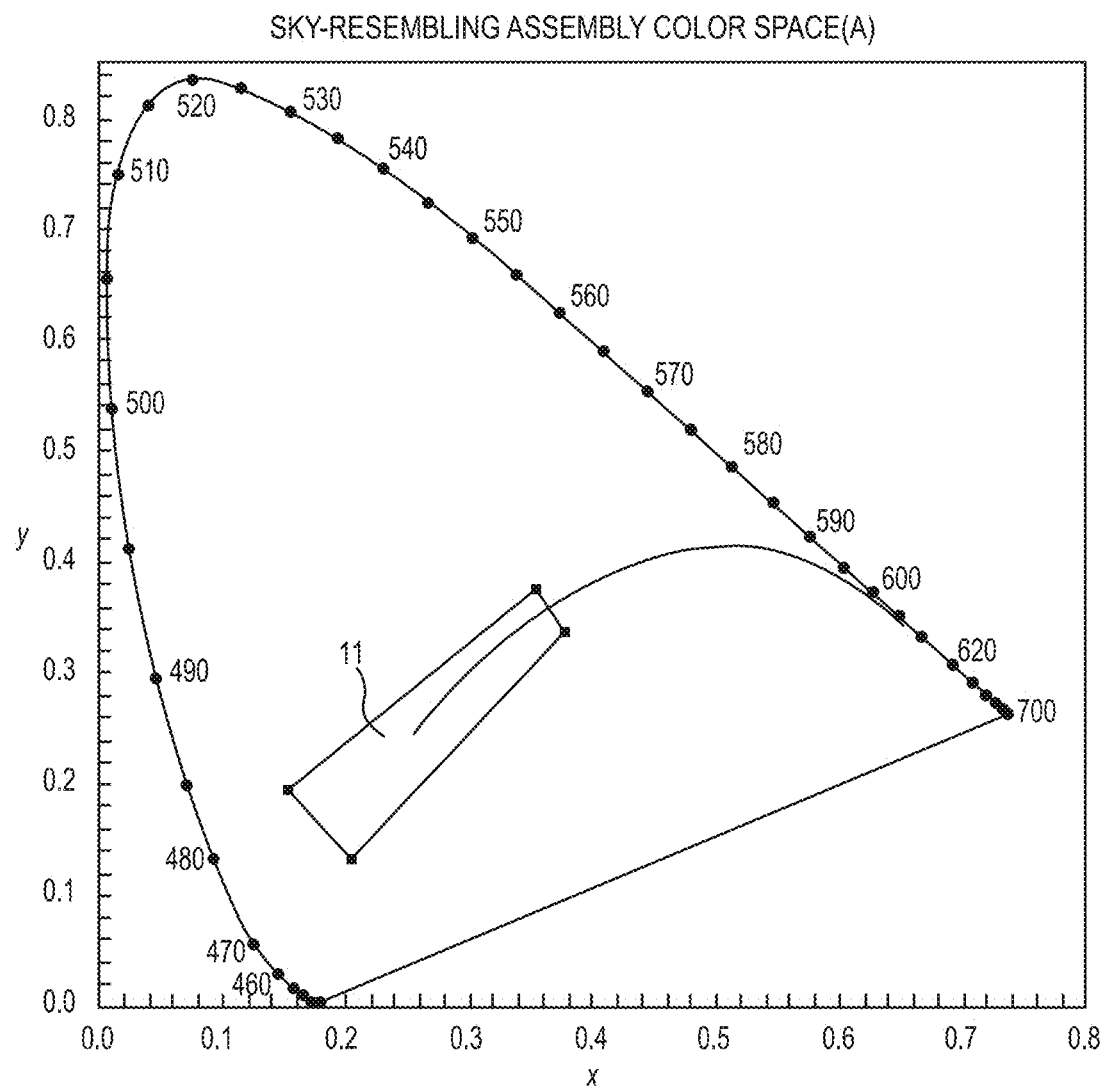

FIG. 40A is a 1931 CIE Chromaticity Diagram on which a color space for a first embodiment of a sky-resembling assembly is provided.

FIG. 40B is a table of coordinates that define the color space illustrated in FIG. 40A.

Figures 41A, 41B:
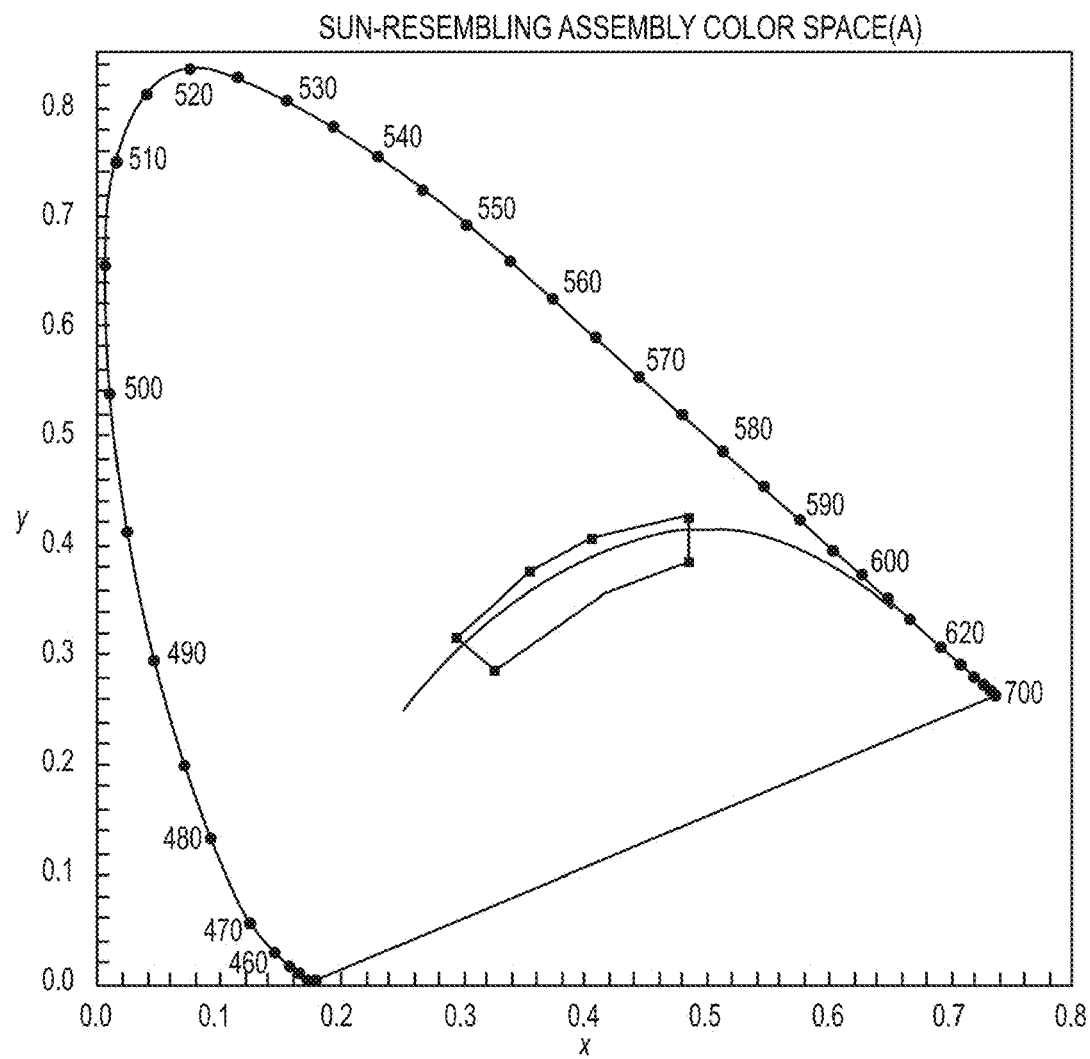

FIG. 41A is a 1931 CIE Chromaticity Diagram on which a color space for a first embodiment of a sun-resembling assembly is provided.

FIG. 41B is a table of coordinates that define the color space illustrated in FIG. 41A.

Figures 42A, 42B:
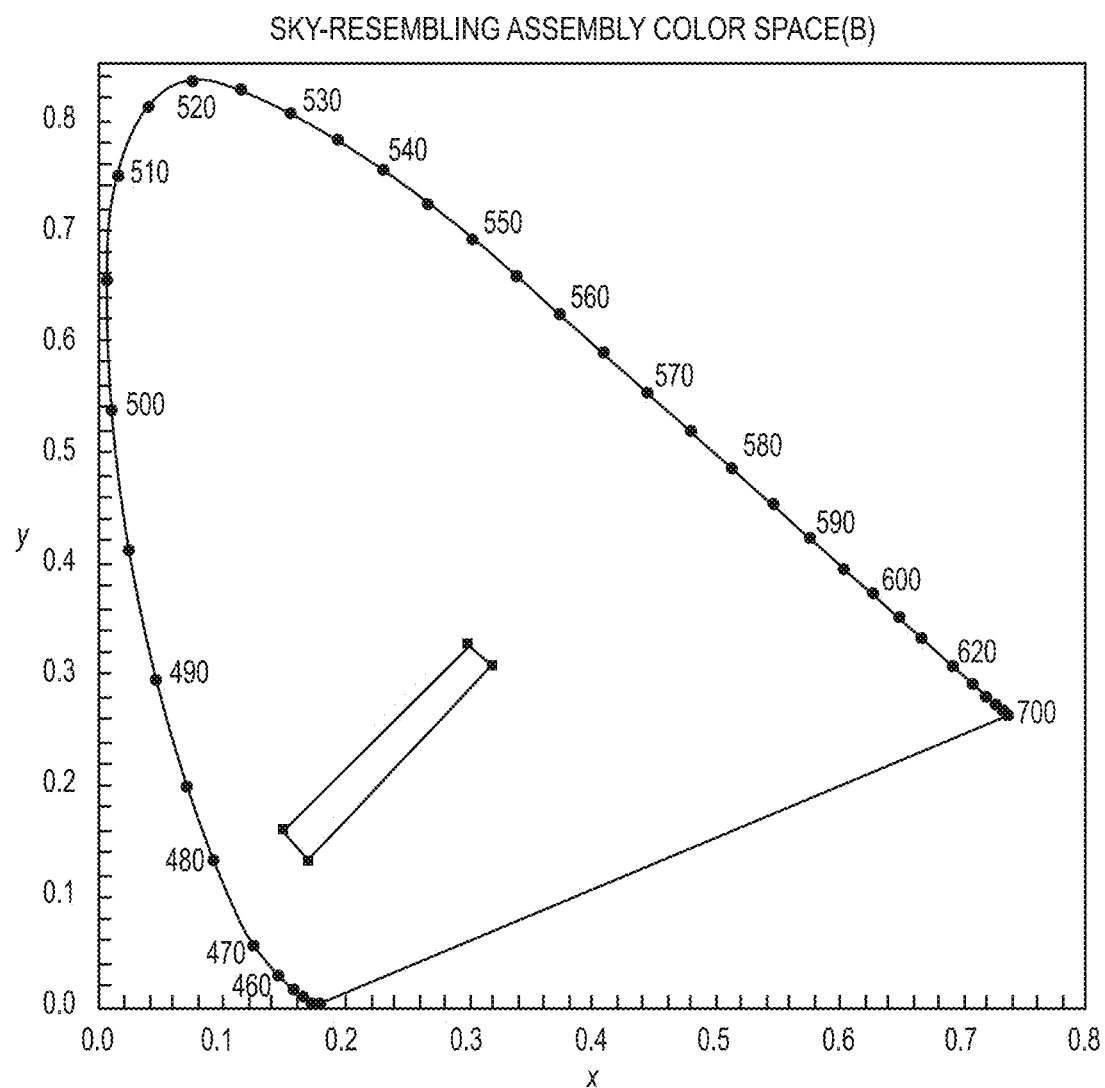

FIG. 42A is a 1931 CIE Chromaticity Diagram on which a color space for a second embodiment of a sky-resembling assembly is provided.

FIG. 42B is a table of coordinates that define the color space illustrated in FIG. 42A.

Figures 43A, 43B:
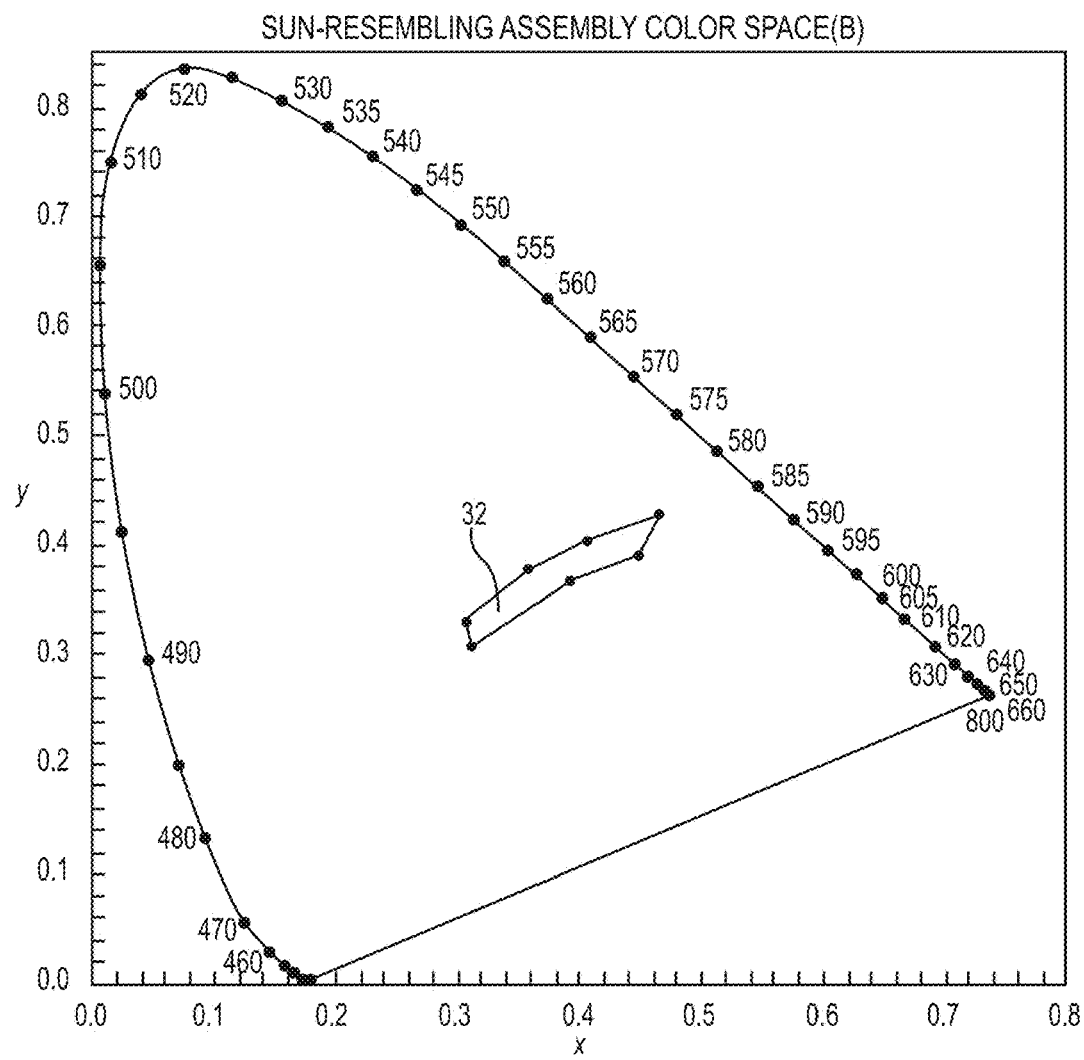

FIG. 43A is a 1931 CIE Chromaticity Diagram on which a color space for a second embodiment of a sun-resembling assembly is provided.

FIG. 43B is a table of coordinates that define the color space illustrated in FIG. 43A.

Figures 44A, 44B:
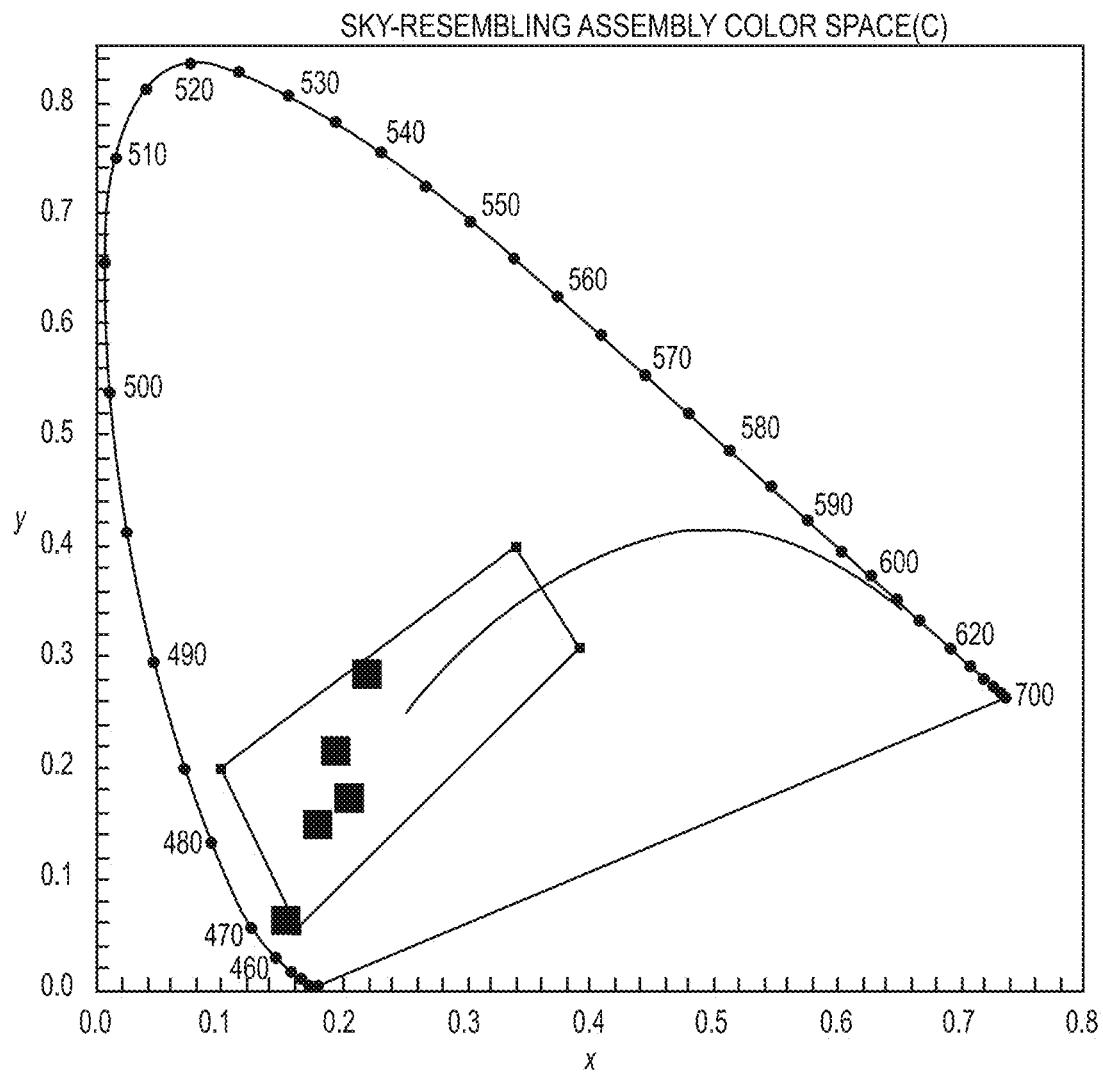

FIG. 44A is a 1931 CIE Chromaticity Diagram on which a color space for a third embodiment of a sky-resembling assembly is provided.

FIG. 44B is a table of coordinates that define the color space illustrated in FIG. 44A.

Figures 45A, 45B:
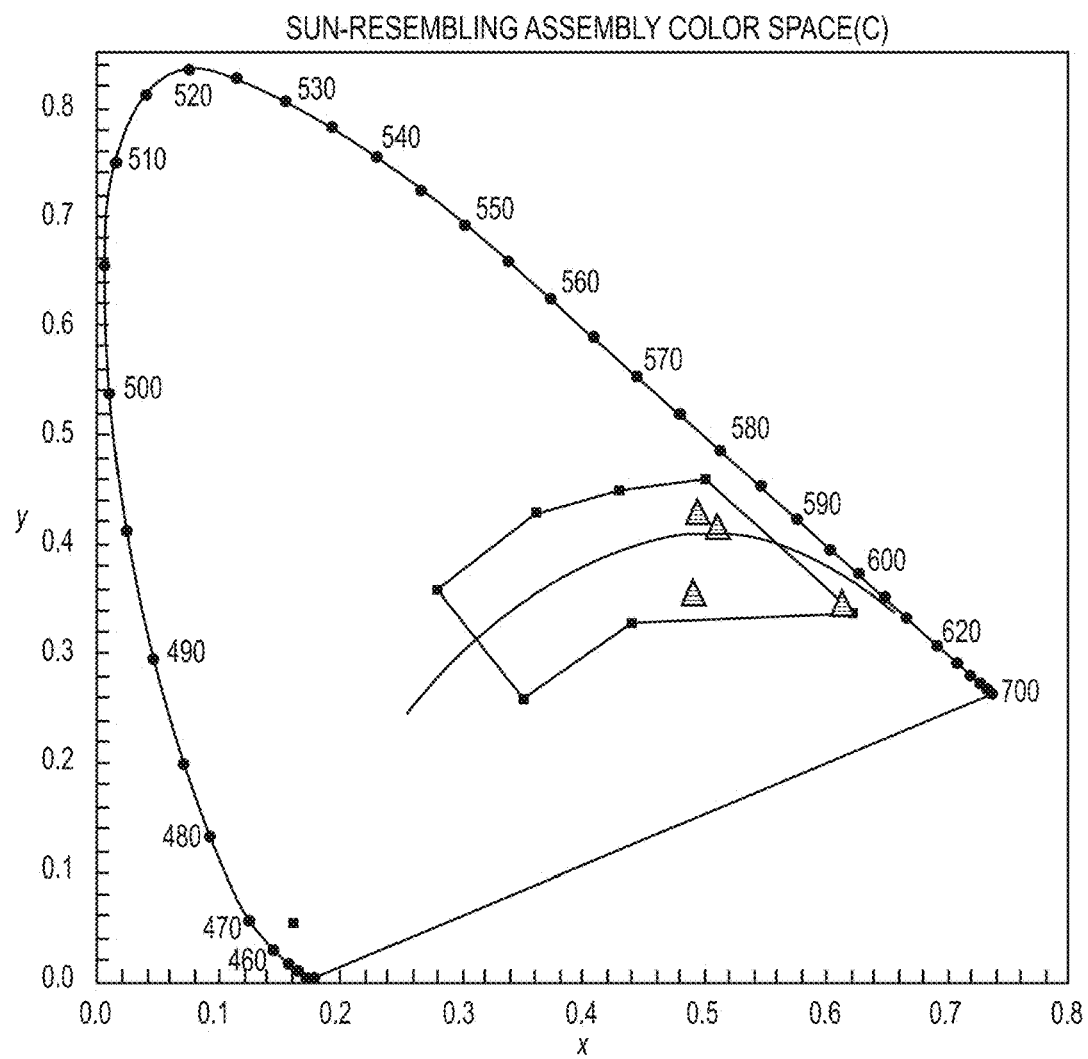

FIG. 45A is a 1931 CIE Chromaticity Diagram on which a color space for a third embodiment of a sun-resembling assembly is provided.

FIG. 45B is a table of coordinates that define the color space illustrated in FIG. 45A.

Figures 46A, 46B:
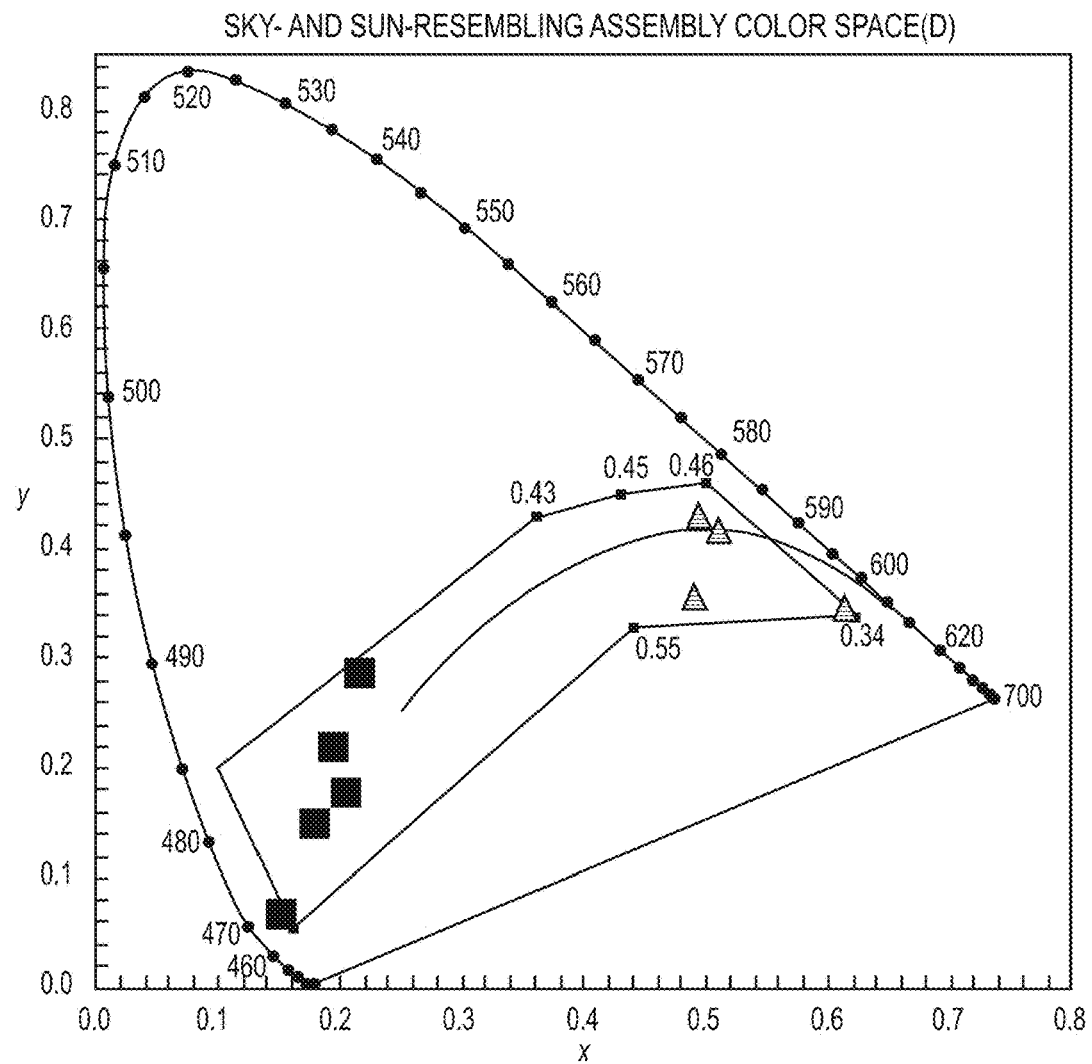

FIG. 46A is a 1931 CIE Chromaticity Diagram on which a color space for a fourth embodiment of both sky-resembling and sun-resembling assembly is provided.

FIG. 46B is a table of coordinates that define the color space illustrated in FIG. 46A.

Figure 47:
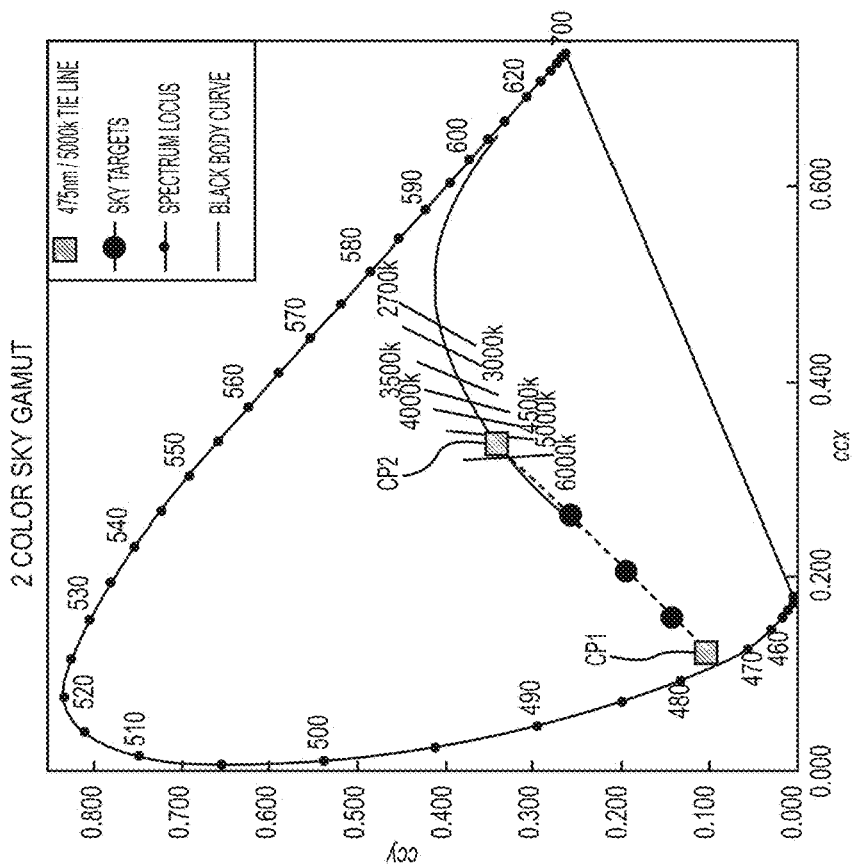

FIG. 47 is a 1931 CIE Chromaticity Diagram on which a color gamut for a sky-resembling assembly that employs two different colors of LEDs is provided according to a first embodiment.

FIG. 48 is a graph of the emission spectrum for a bluish LED for the embodiment of FIG. 47.

FIG. 49 is a graph of the emission spectrum for a white LED for the embodiment of FIG. 47.

Figure 50:
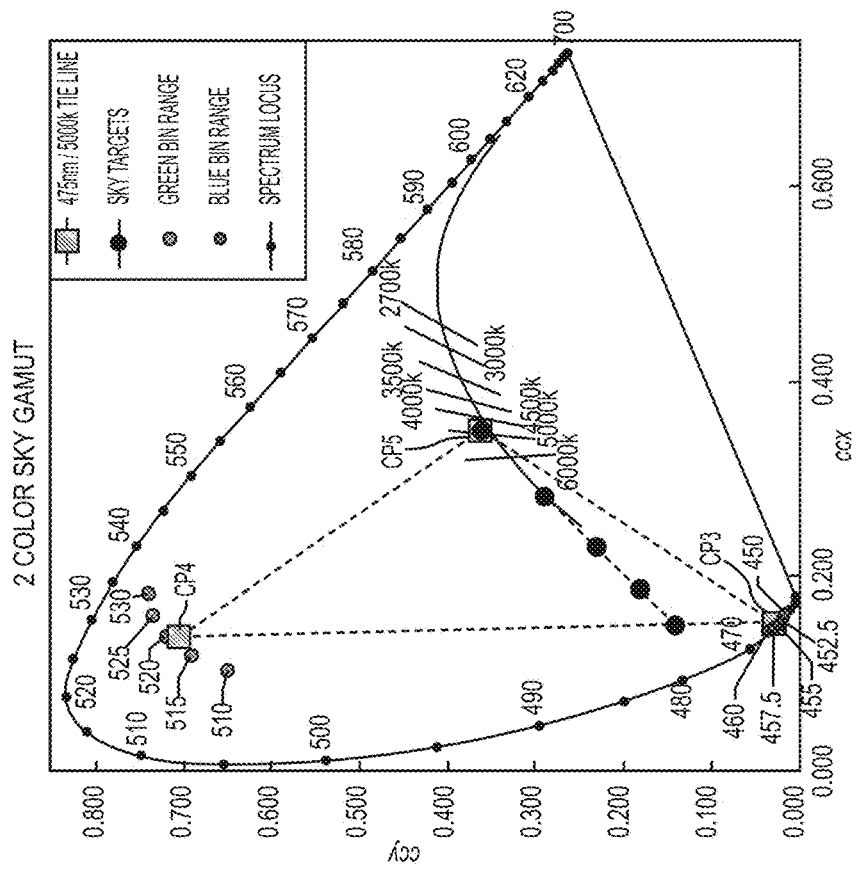

FIG. 50 is a 1931 CIE Chromaticity Diagram on which a color gamut for a sky-resembling assembly that employs three different colors of LEDs is provided according to a second embodiment.

Figure 51:
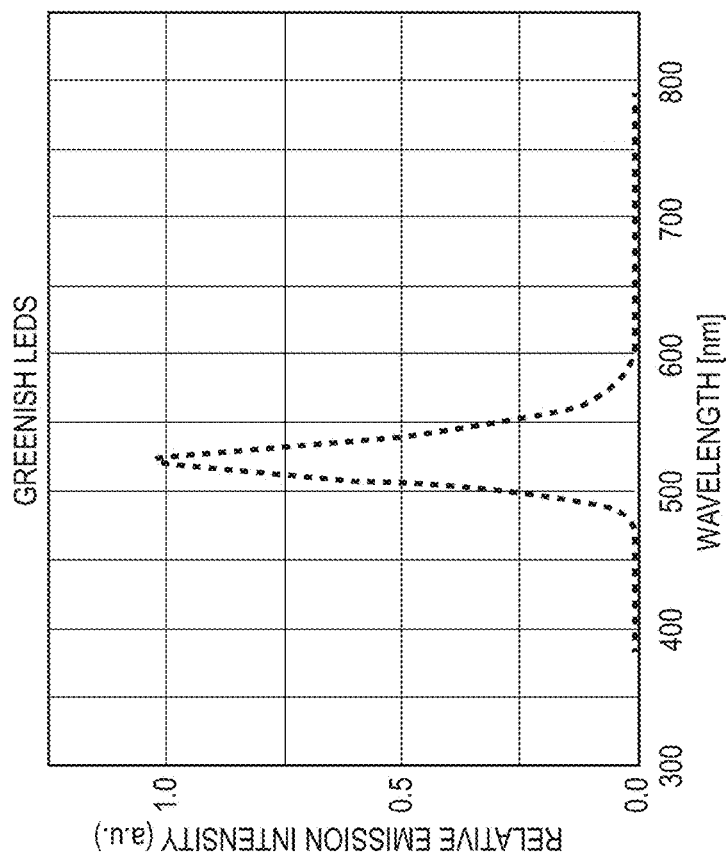

FIG. 51 is a graph of the emission spectrum for a bluish LED for the embodiment of FIG. 50.

Figure 52:
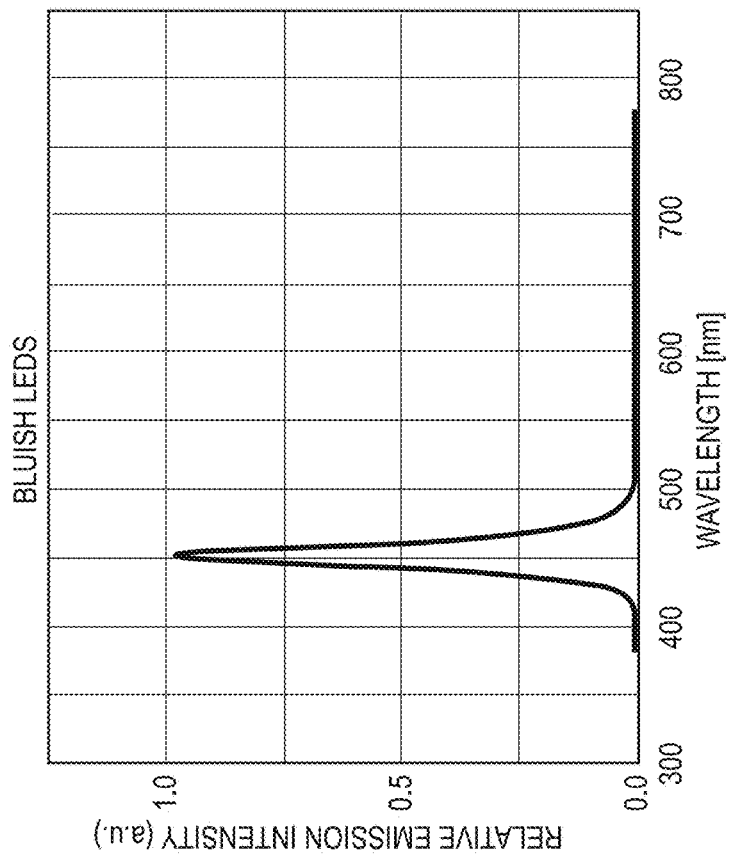

FIG. 52 is a graph of the emission spectrum for a greenish LED for the embodiment of FIG. 50.

Figure 53:
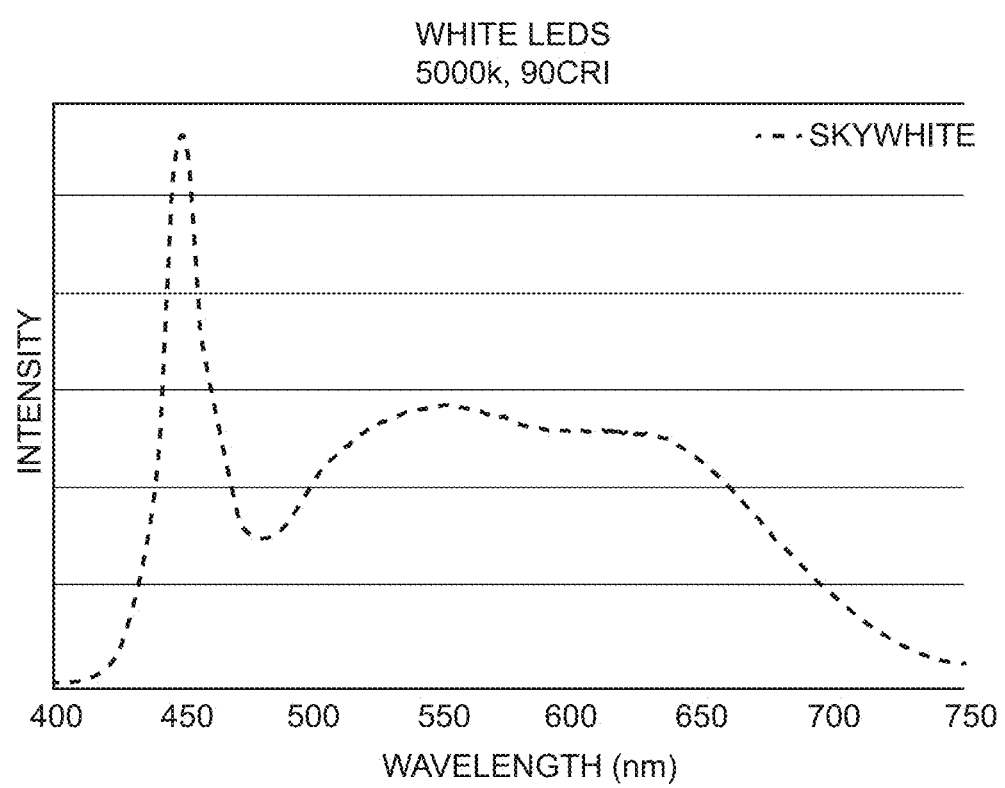

FIG. 53 is a graph of the emission spectrum for a white LED for the embodiment of FIG. 50.

Figure 54:
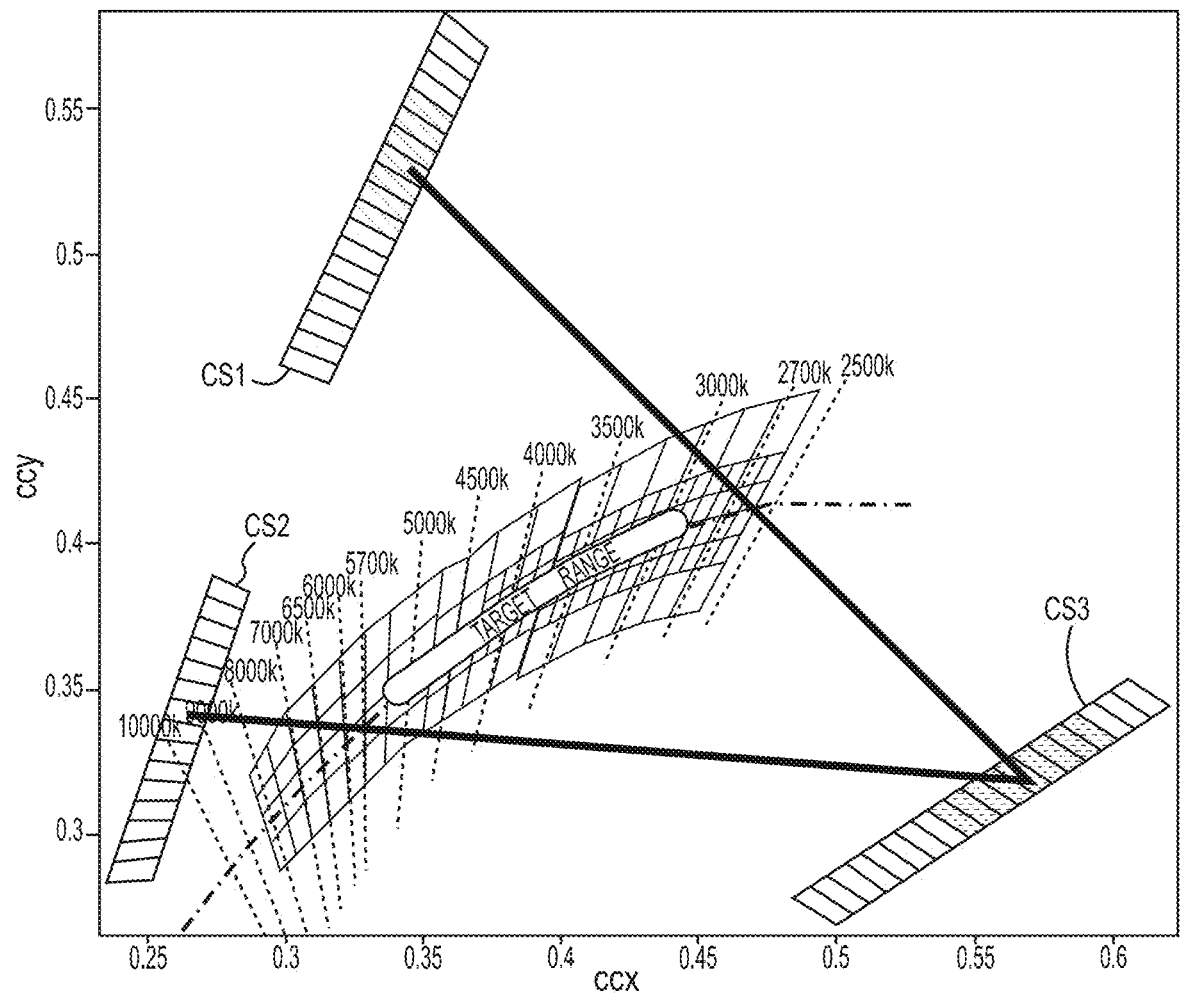

FIG. 54 is a 1931 CIE Chromaticity Diagram on which a color gamut for a sun-resembling assembly that employs three different colors of LEDs is provided according to a one embodiment.

Figure 55:
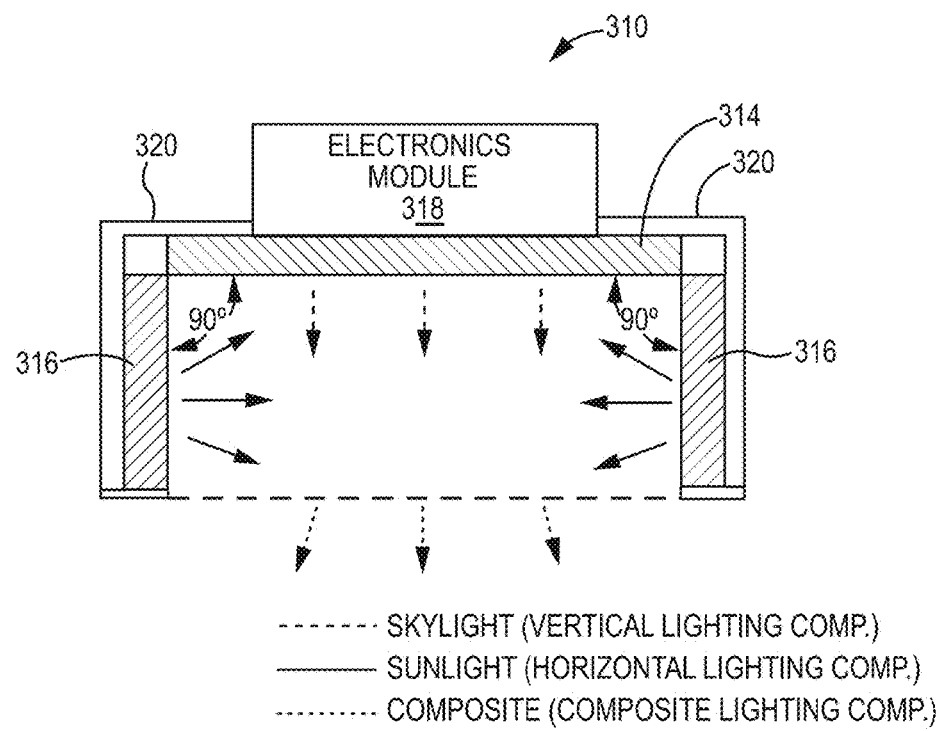

FIG. 55 is a cross-section of a skylight fixture according to a first embodiment and illustrates the various lighting components of the skylight fixture.

Figure 56:
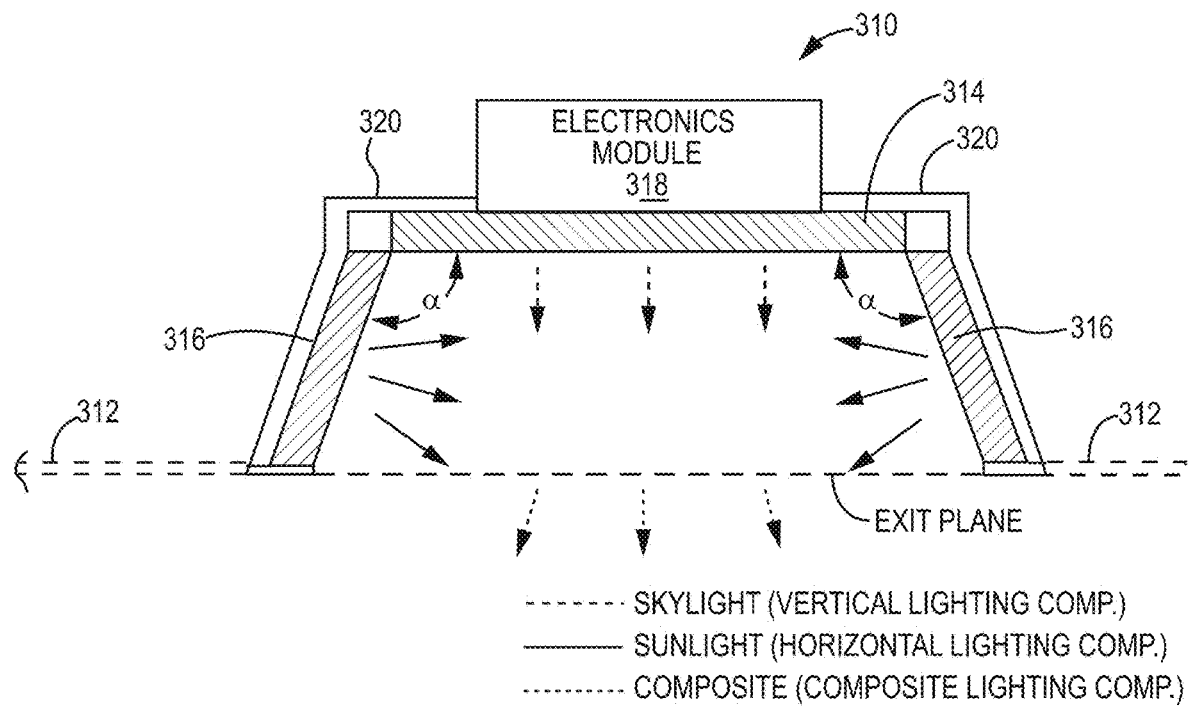

FIG. 56 as a cross-section of a skylight fixture according to a second embodiment and illustrates the various lighting components of the skylight fixture.

Figure 57:
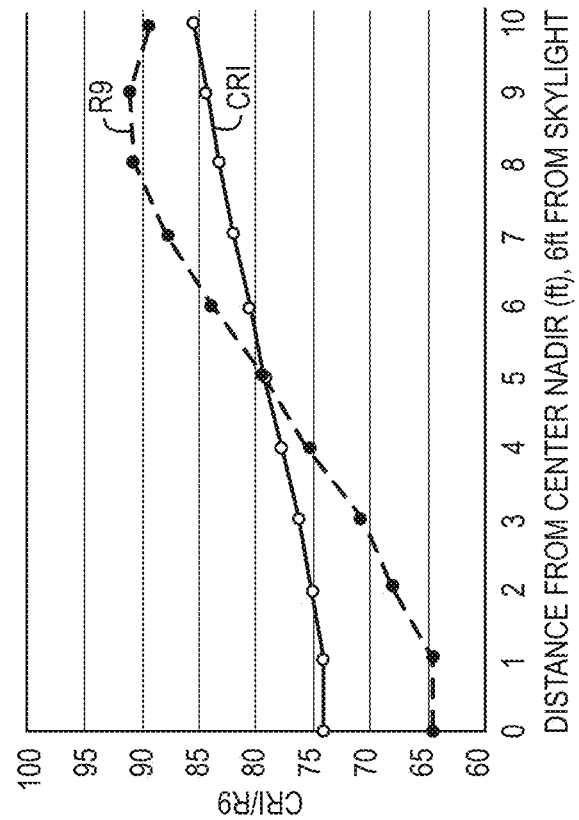

FIG. 57 is a graph of CRI and R9 versus distance from center nadir for an exemplary skylight fixture with sky- and sun-resembling assemblies that employ two different colors of LEDs.

Figure 58:
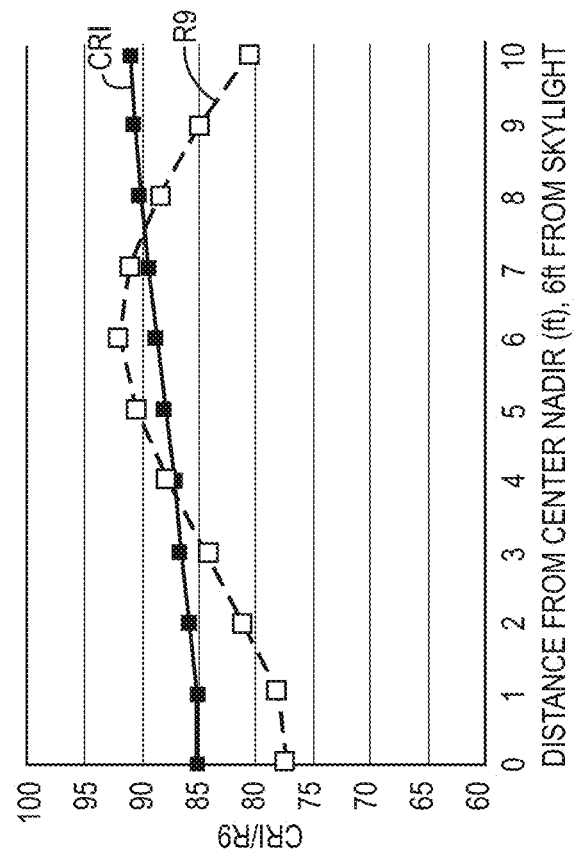

FIG. 58 is a graph of CRI and R9 versus distance from center nadir for an exemplary skylight fixture with sky- and sun-resembling assemblies that employ three different colors of LEDs.

Figure 59:
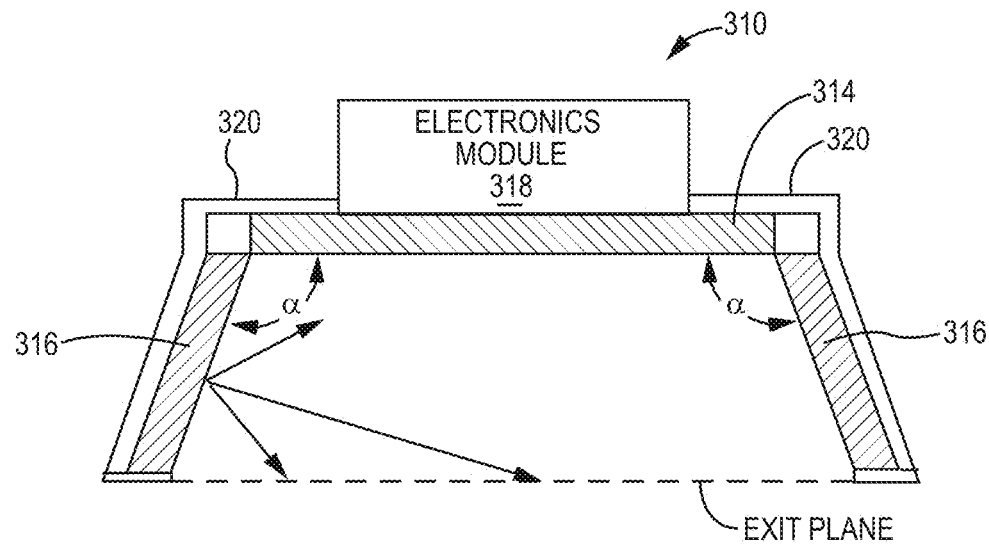

FIG. 59 is a cross-section of a skylight fixture according to a first embodiment and illustrates redirection of light emitted from the sun-resembling assemblies toward an exit pane of the skylight fixture.

Figure 60:
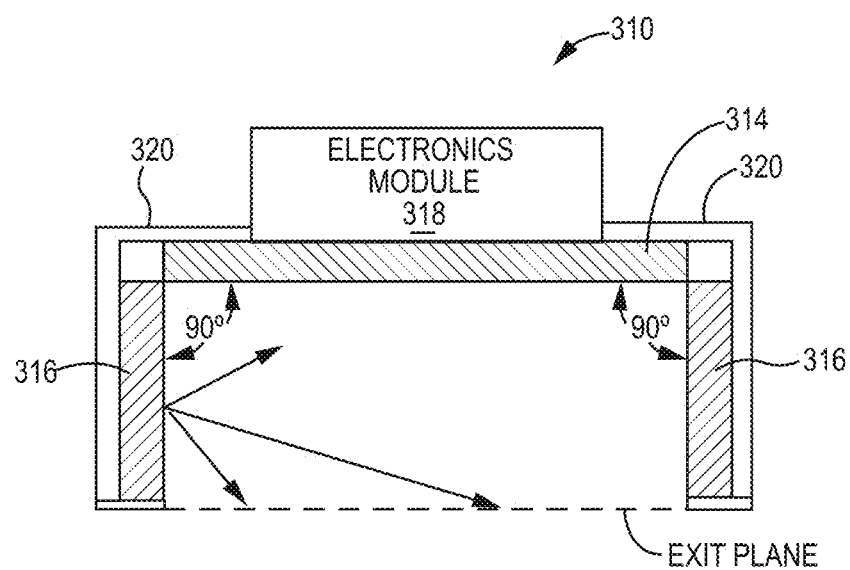

FIG. 60 as a cross-section of a skylight fixture according to a second embodiment and illustrates redirection of light emitted from the sun-resembling assemblies toward an exit pane of the skylight fixture.

Figure 61:
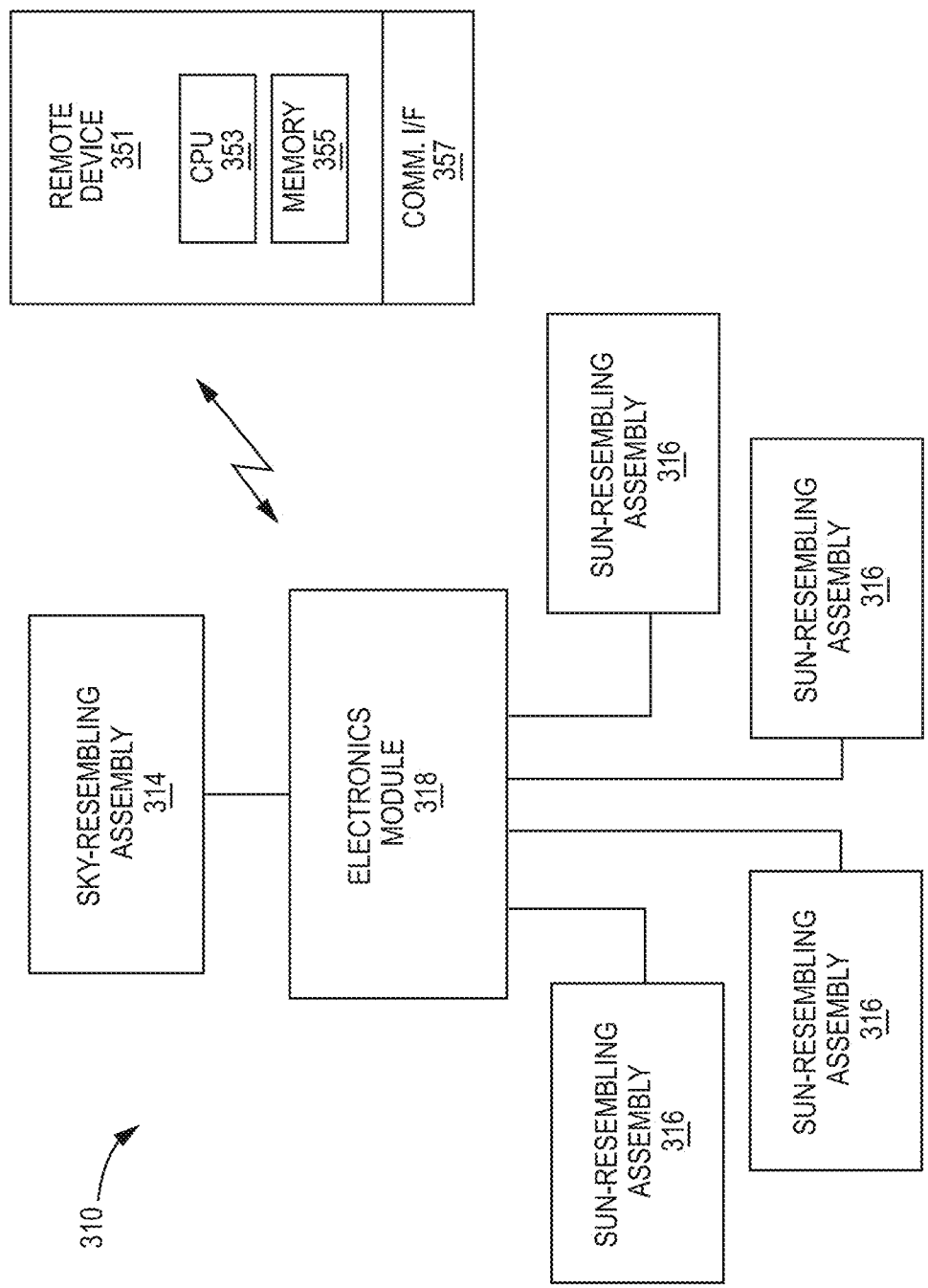

FIG. 61 is a block diagram of a skylight fixture in communication with a remote device according to one embodiment of the disclosure.

Figure 62:
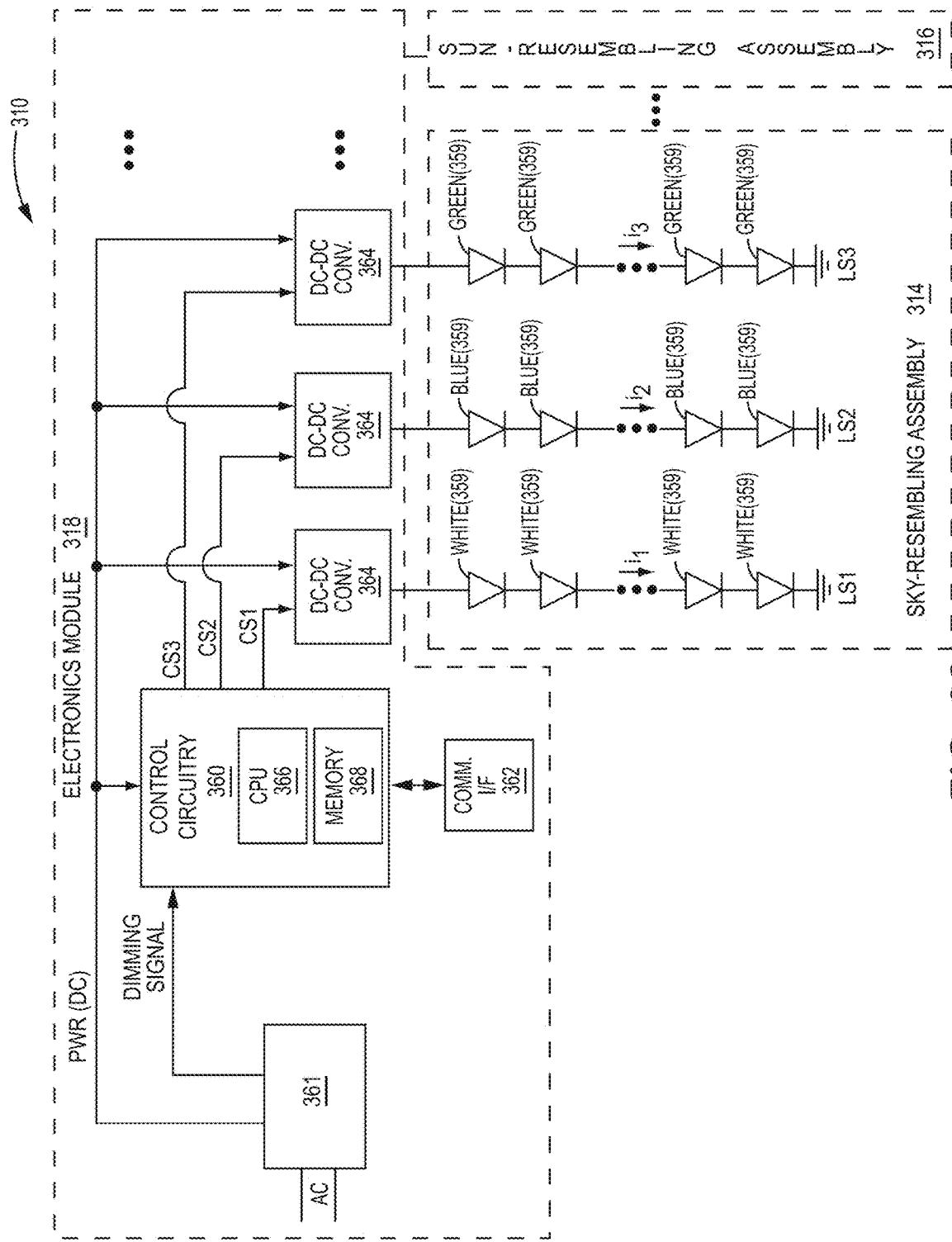

FIG. 62 is a schematic diagram of an exemplary electronics module and associated sky- and sun-resembling assemblies according to one embodiment, with the sky-resembling assembly including first to third strings of connected LEDs (e.g., including series-connected LEDs).

Figure 63:
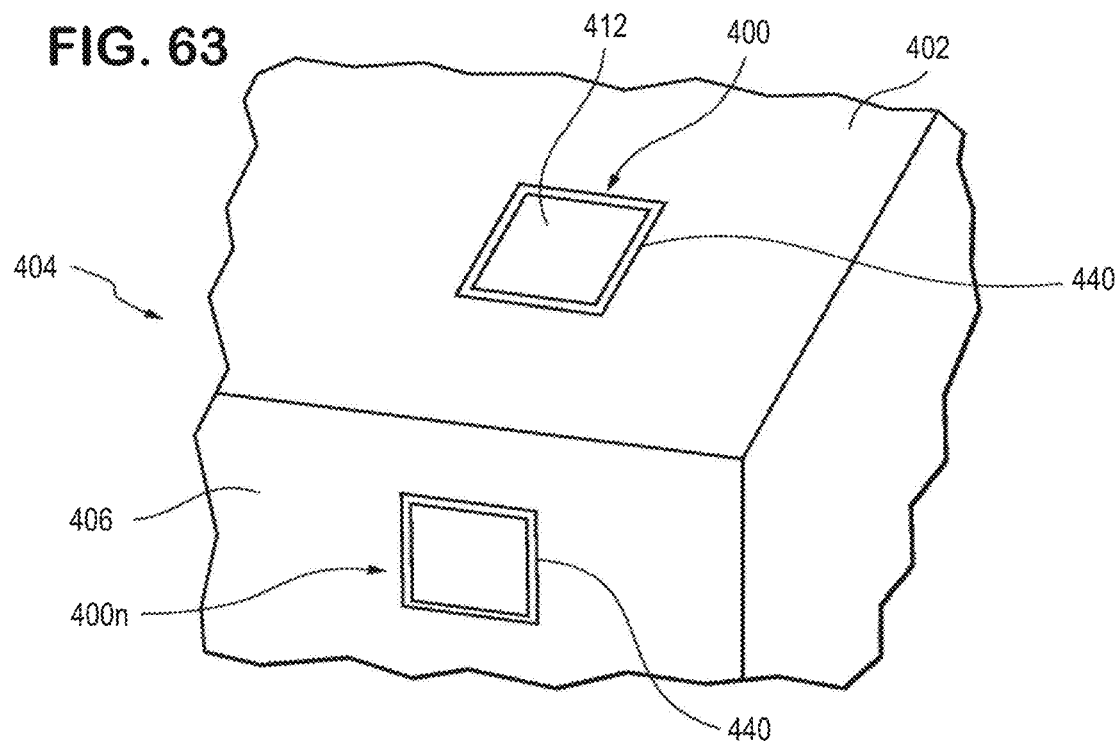

FIG. 63 illustrates a luminaire according to the present disclosure disposed in a ceiling and/or a wall.

Figure 64:
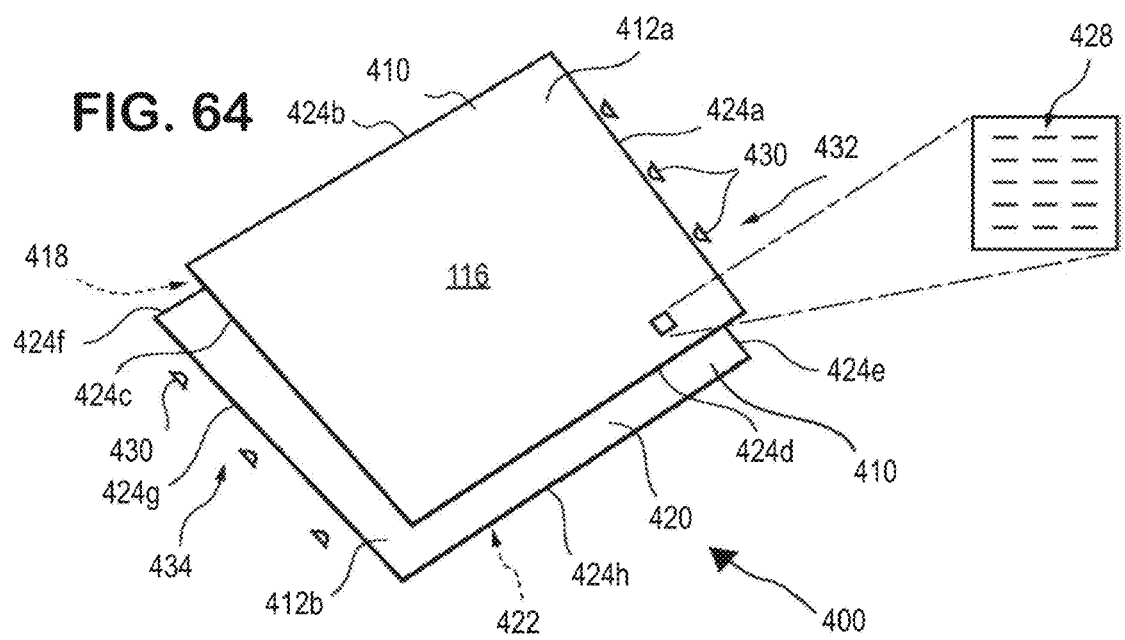

FIG. 64 is an isometric exploded view from above illustrating the luminaire of the present disclosure.

Figure 65:
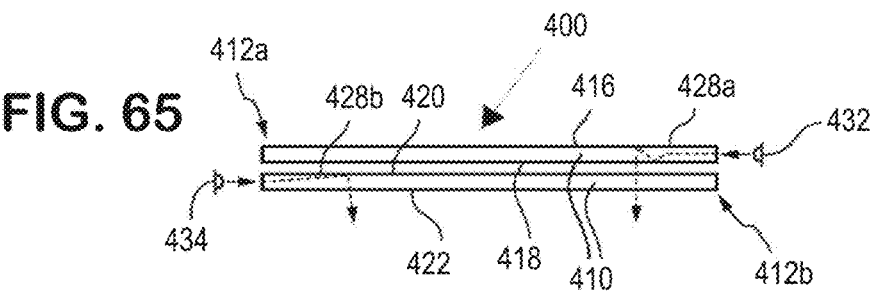

FIG. 65 is a side elevational view illustrating the luminaire of the present disclosure with a housing therefor omitted.

Figure 66:
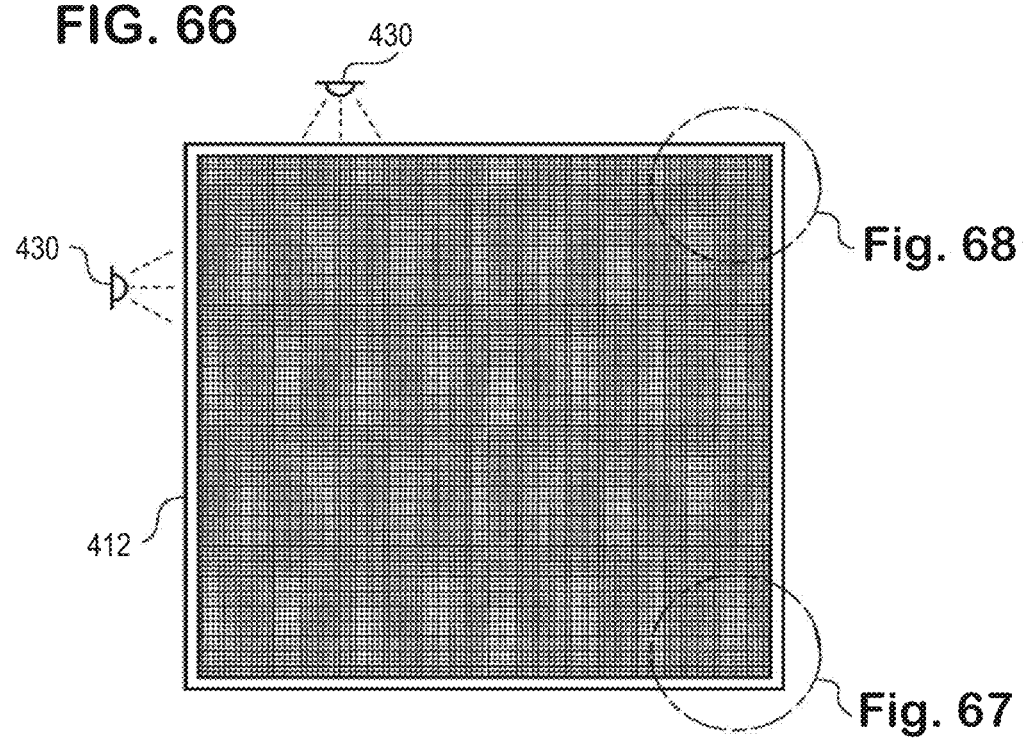

FIG. 66 is a plan view illustrating a planar surface of a waveguide of the luminaire of the present disclosure.

Figure 67:
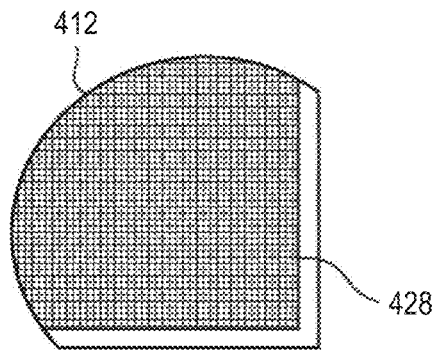
Figure 68:
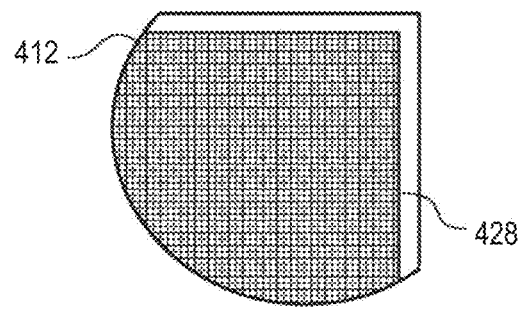

FIGS. 67 and 68 are enlarged views of the planar surface of the waveguide of FIG. 66 illustrating extraction features disposed thereon.

Figure 69:
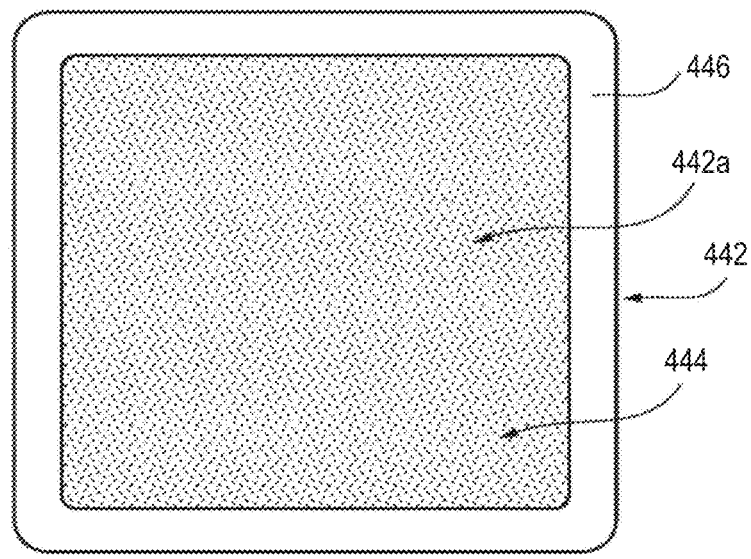

FIG. 69 is a plan view illustrating an extraction feature pattern disposed on a waveguide.

Figure 70:
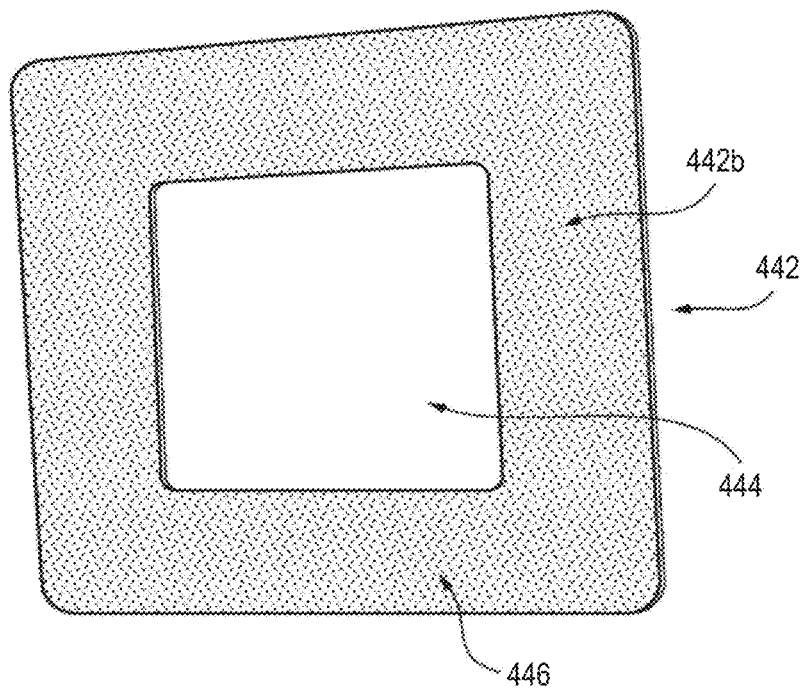

FIG. 70 is an isometric view illustrating another extraction feature pattern disposed on a waveguide.

Figure 71A:
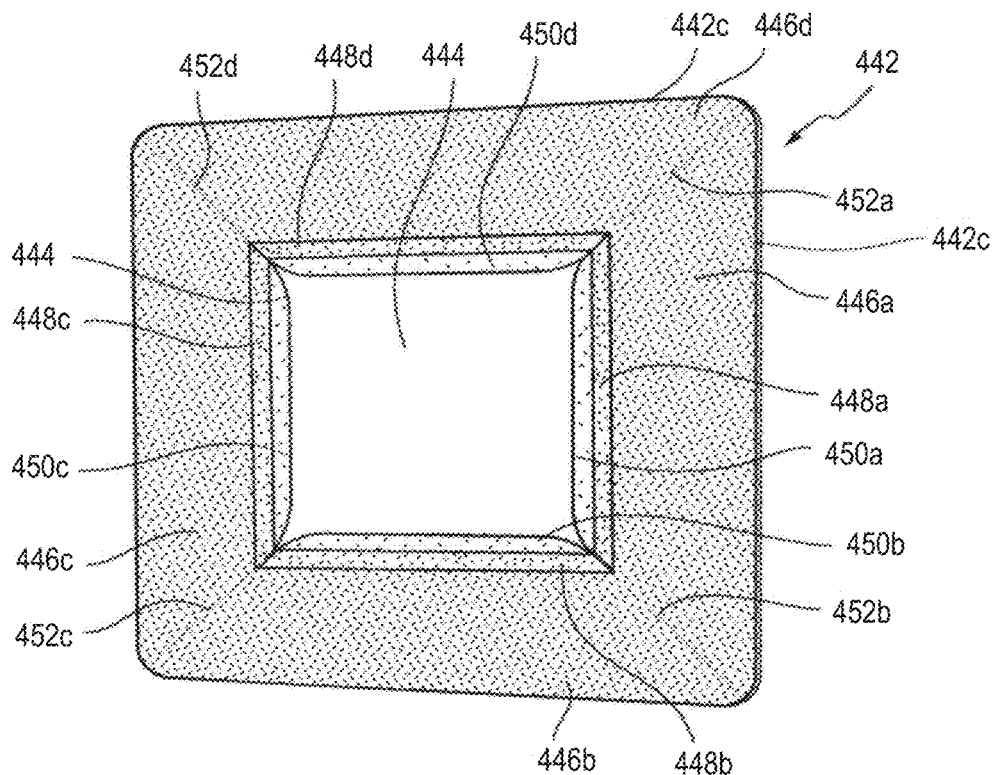

FIG. 71A is an isometric view illustrating another extraction feature pattern disposed on a waveguide.

Figure 71B:
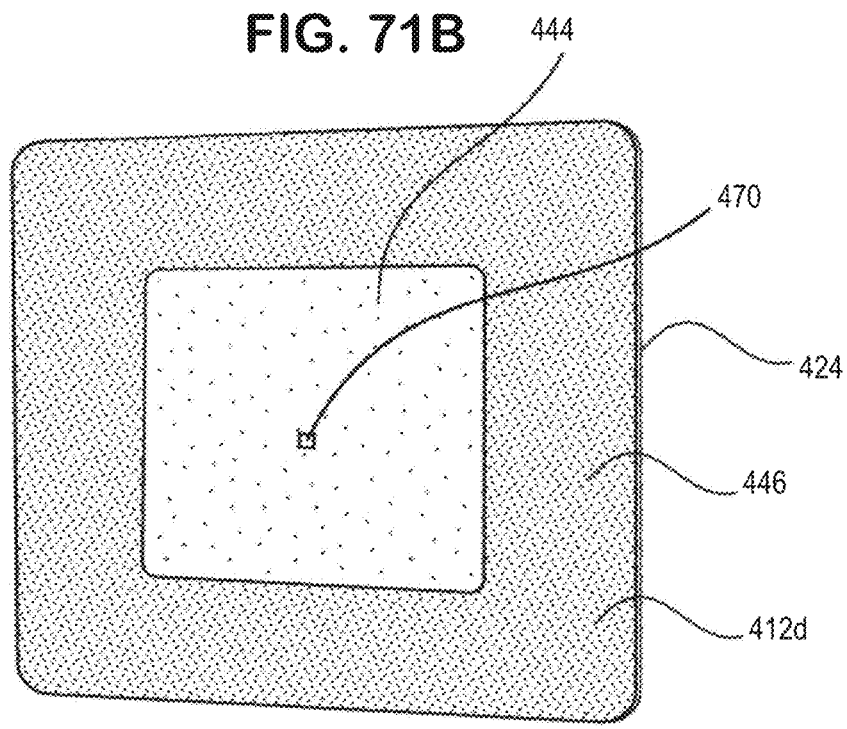

FIG. 71B is an isometric view illustrating another extraction feature pattern disposed on a waveguide.

Figure 72:
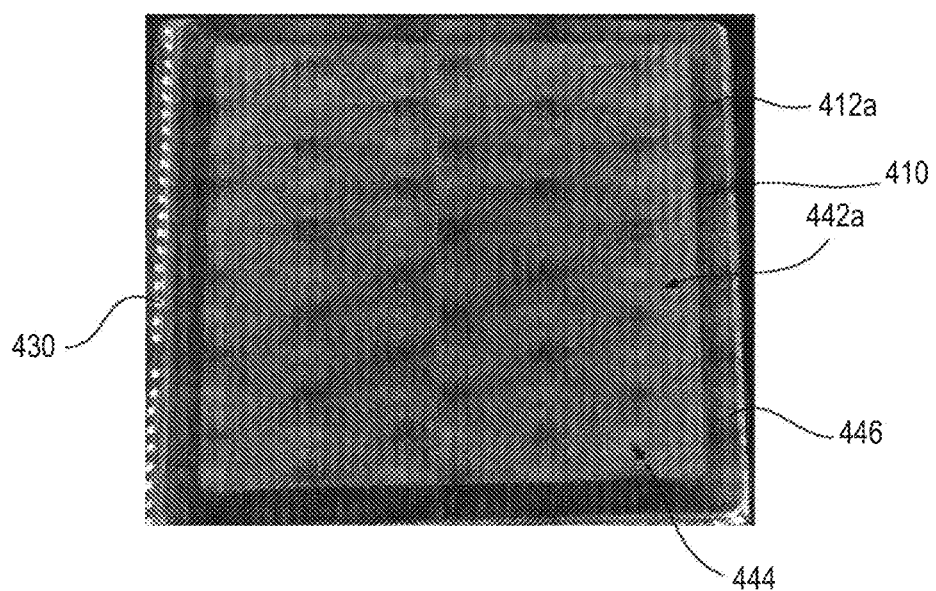

FIG. 72 is a color photograph from above of the waveguide of FIG. 69 lit by one or more blue and/or violet LEDs.

Figure 73:
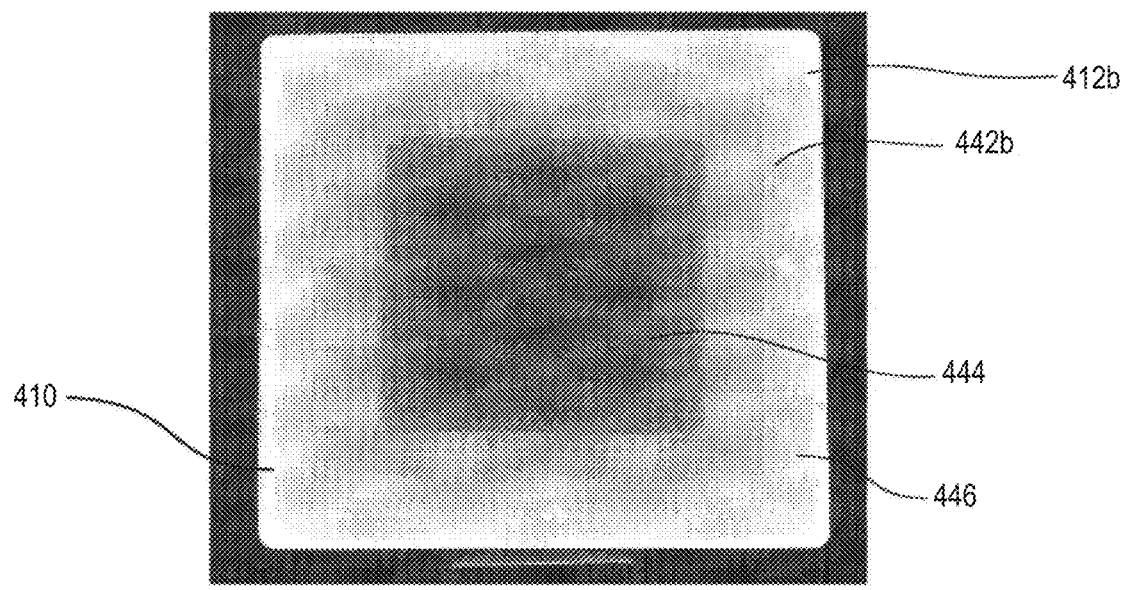

FIG. 73 is a color photograph from above of the waveguide of FIG. 70 lit by one or more yellow and/or warm white LEDs.

Figure 74:
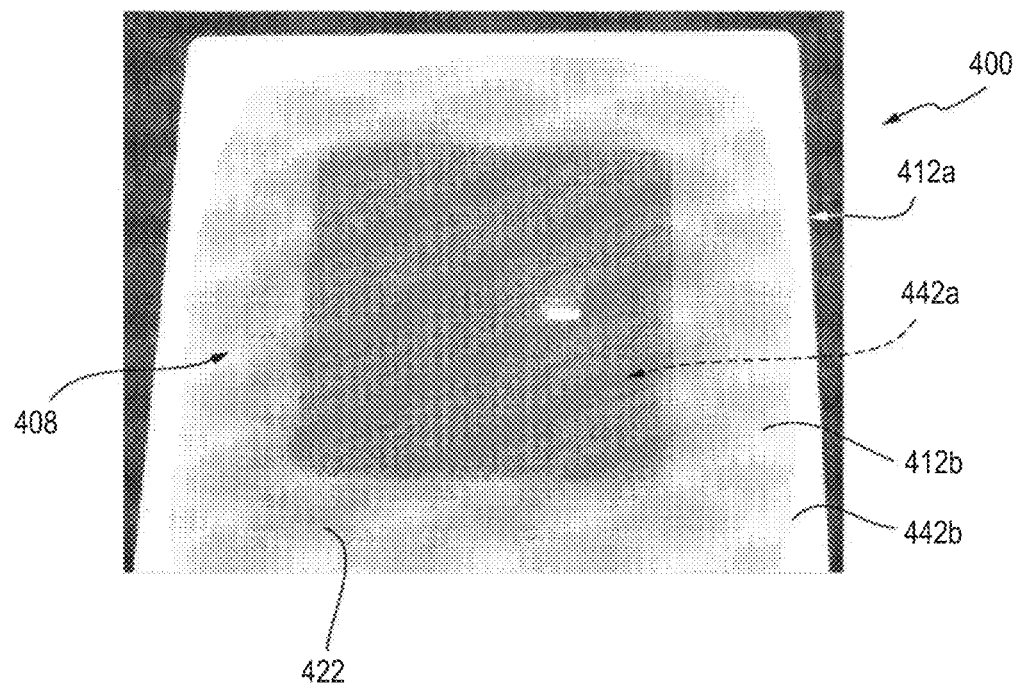

FIG. 74 is a color photograph of the luminaire of the present disclosure comprising the waveguide depicted in FIG. 72 disposed behind the waveguide of FIG. 73.

Figure 75:
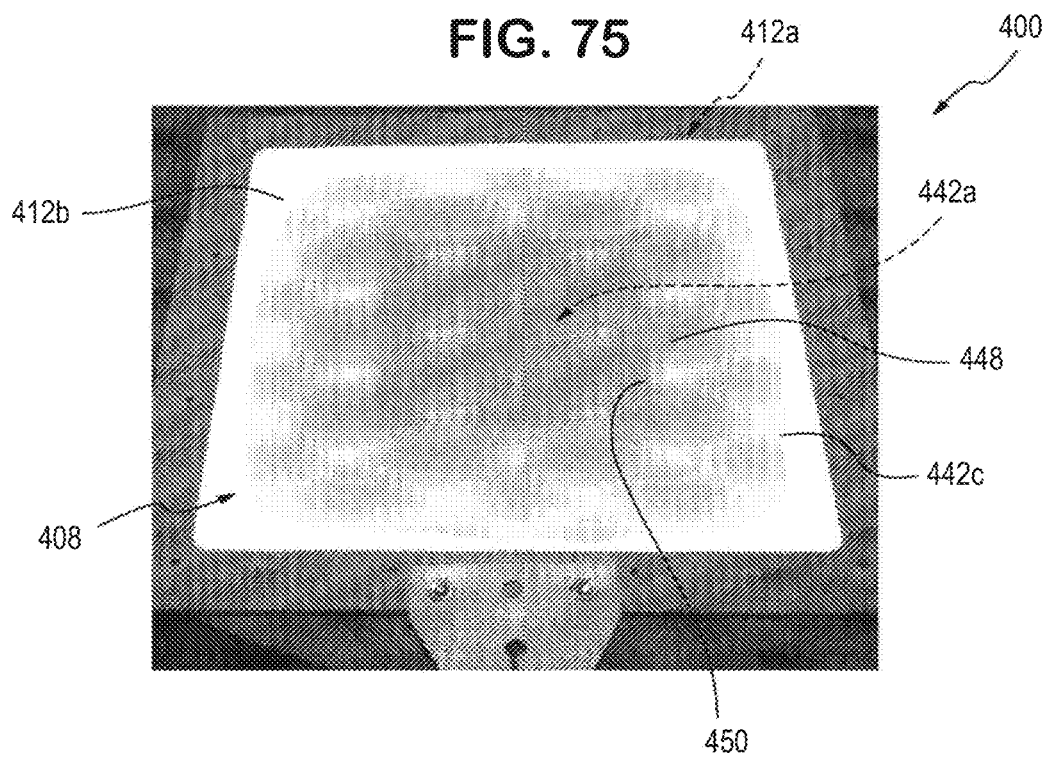

FIG. 75 is another color photograph of the luminaire depicted in FIG. 74.

Figure 76:
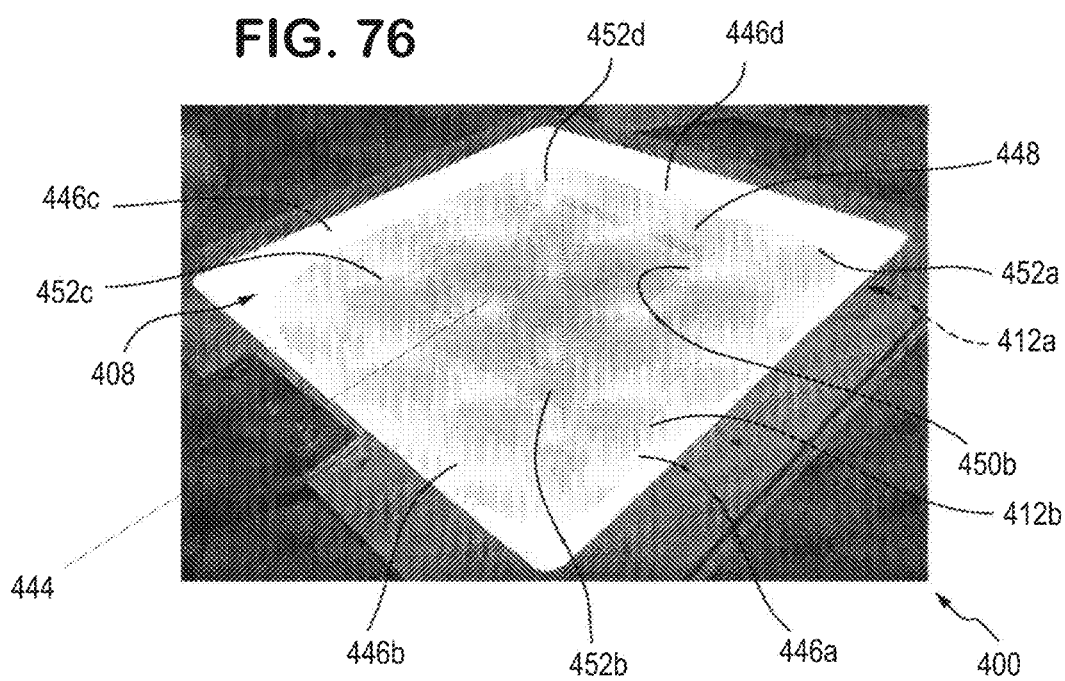

FIG. 76 is another color photograph of the luminaire depicted in FIG. 74.

Figure 77:
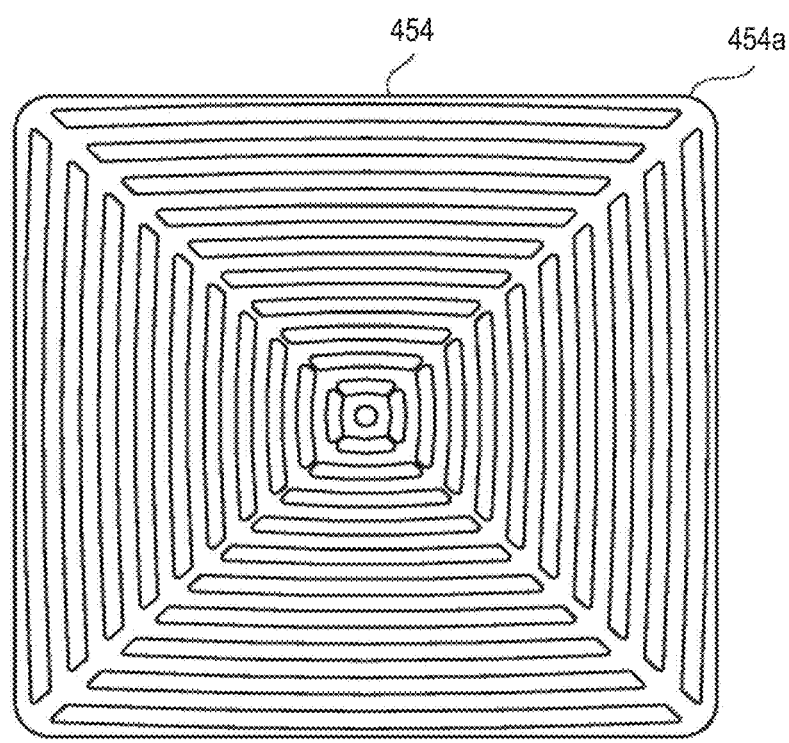

FIG. 77 is a plan view of a mask for fabricating extraction features according to a pattern.

Figure 78:
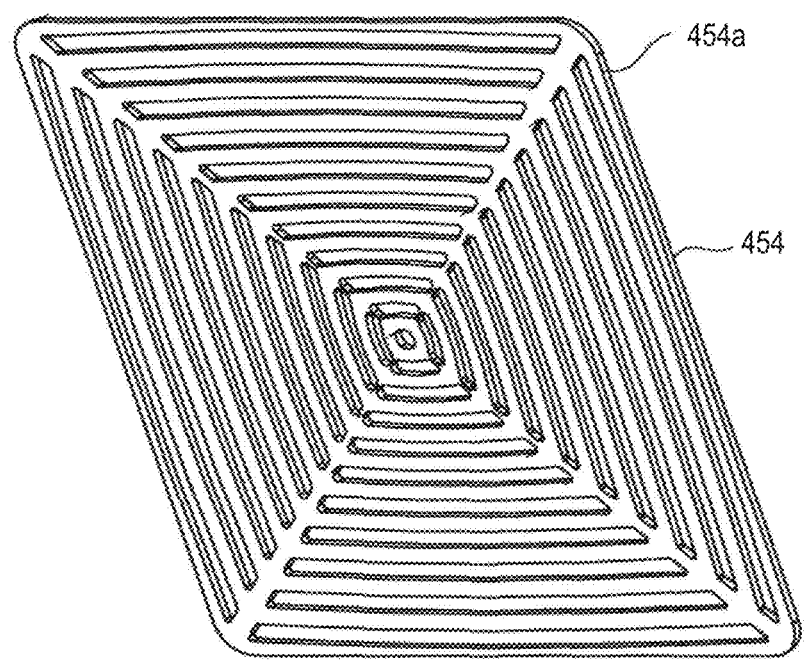

FIG. 78 is an isometric view of the mask of FIG. 77.

Figure 79:
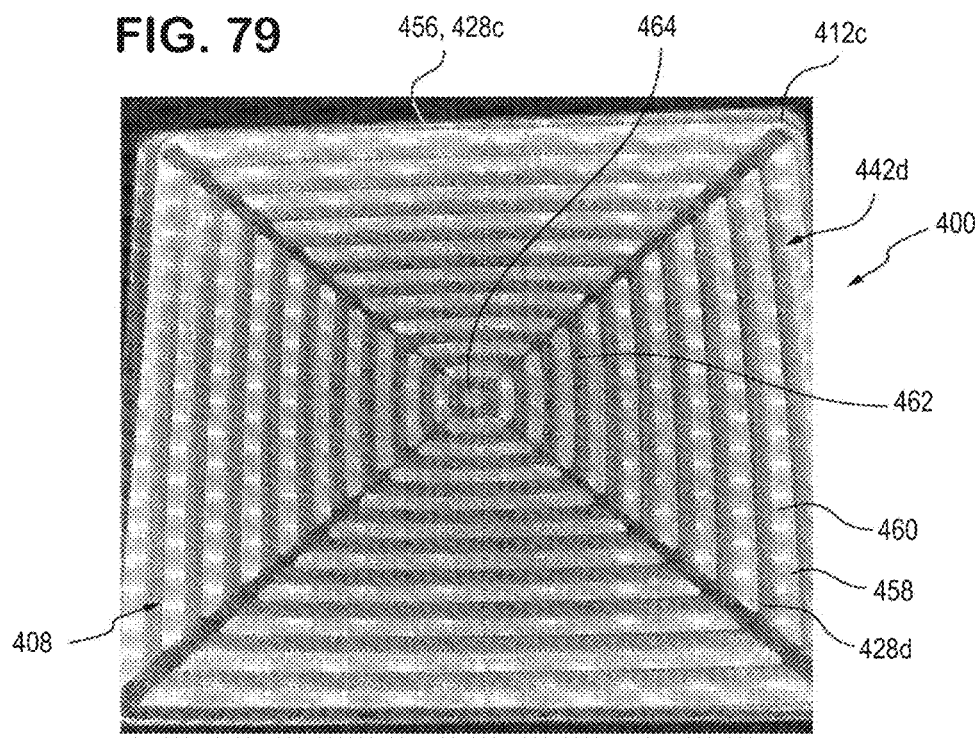

FIG. 79 is a color photograph from above of a waveguide comprising extraction features fabricated with the mask of FIG. 77 and lit by one or more yellow and/or warm white LEDs.

Figure 80:
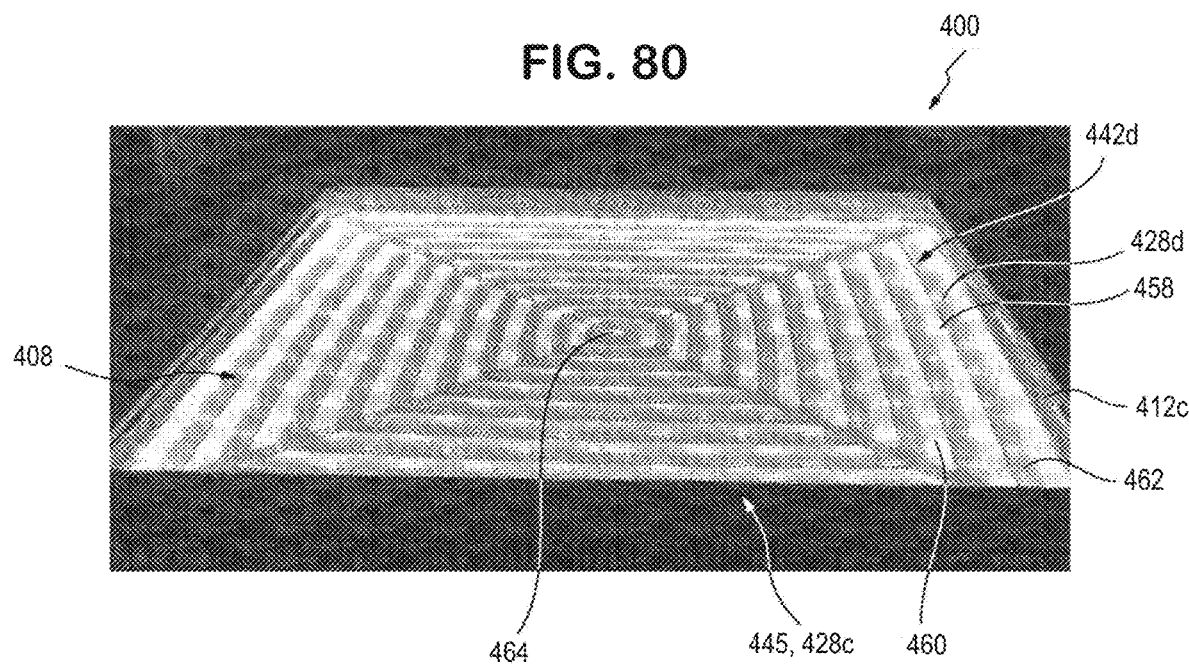

FIG. 80 is another color photograph from above and to the side of the waveguide lit by one or more yellow and/or warm white LEDs of FIG. 79.

Figure 81:
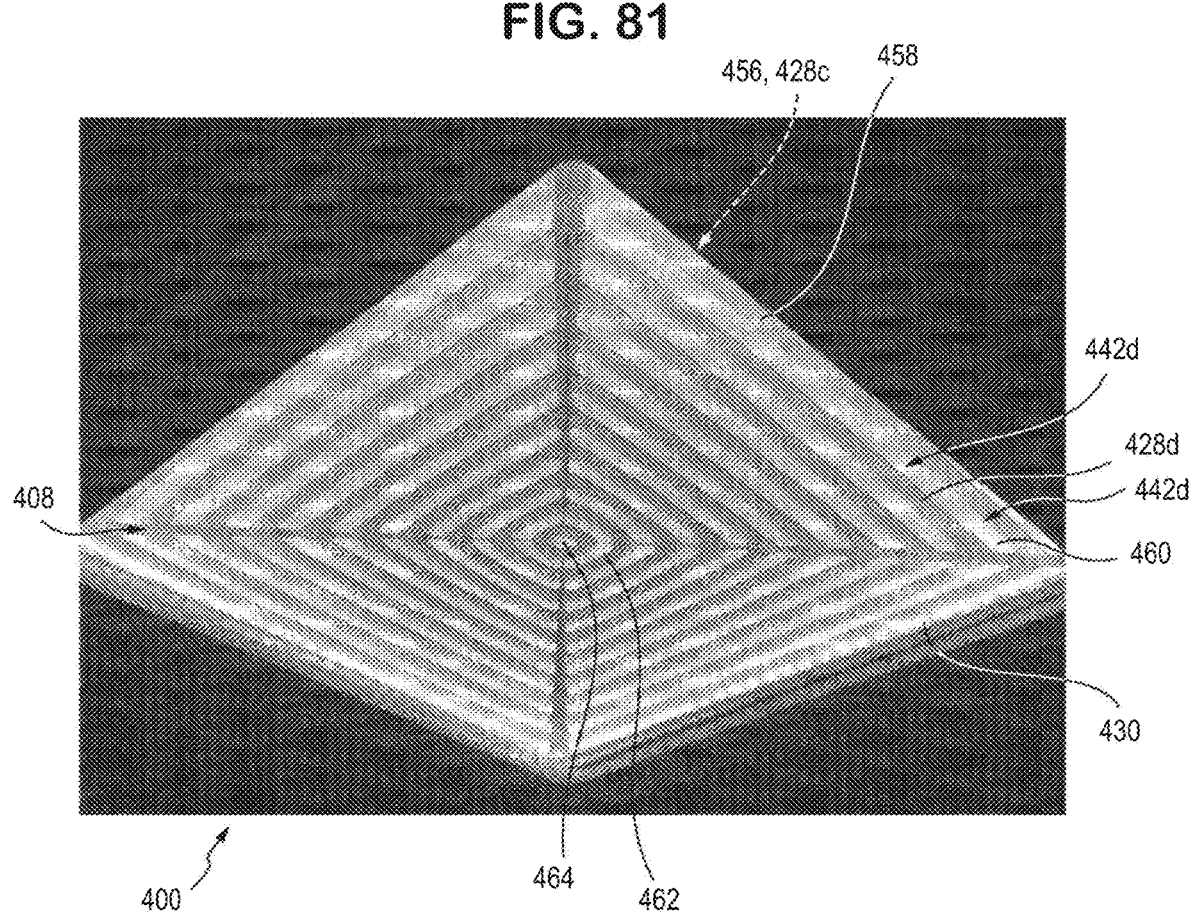

FIG. 81 is another color photograph from above and to the side of the waveguide lit by one or more yellow and/or warm white LEDs of FIG. 79.

Figure 82:
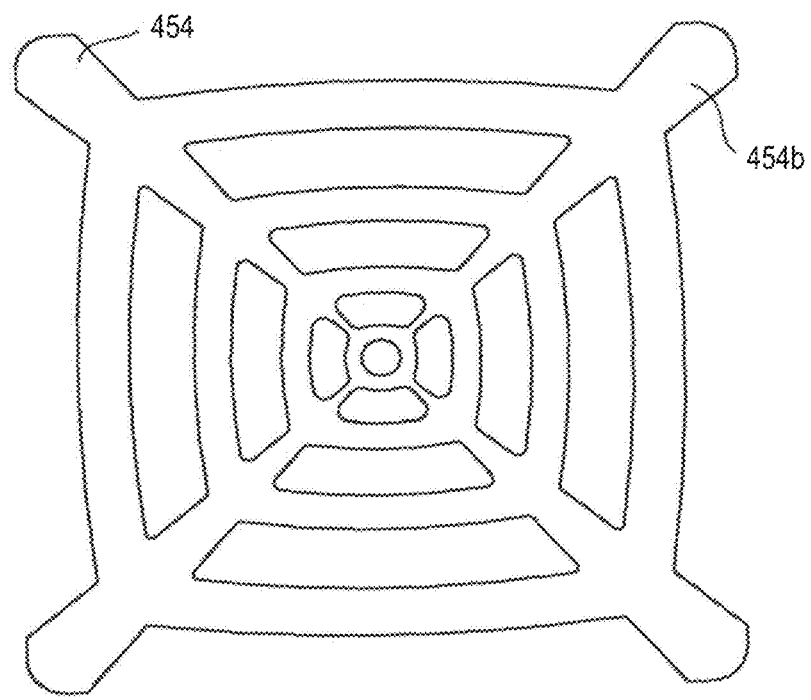

FIG. 82 is a plan view of a mask for fabricating extraction features according to a pattern.

Figure 83:
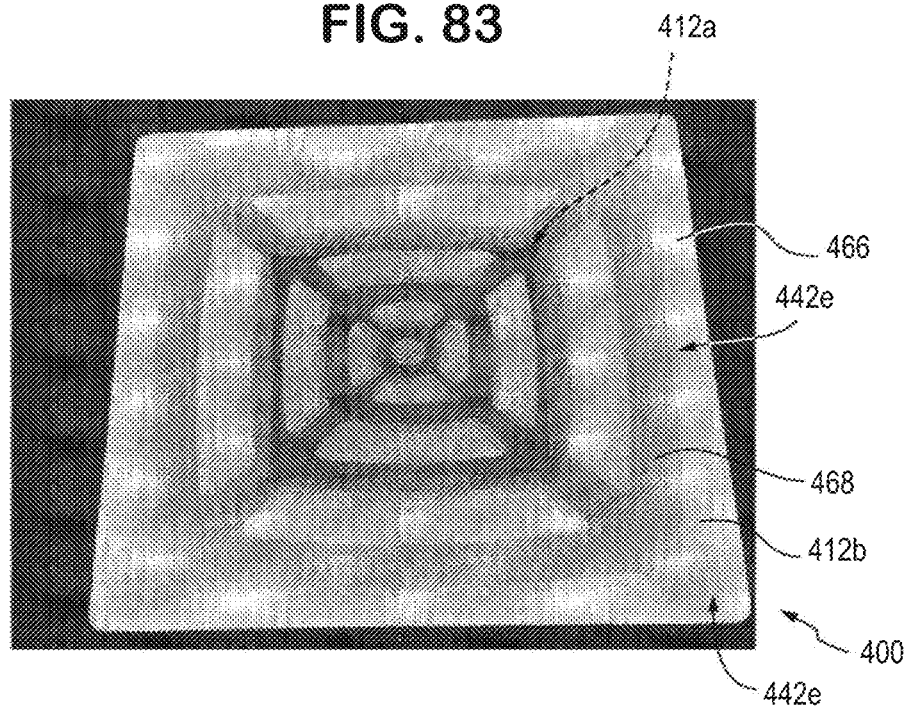

FIG. 83 is a color photograph from above of a waveguide comprising extraction features fabricated with the mask of FIG. 82 and lit by one or more yellow and/or warm white LEDs.

Figure 84:
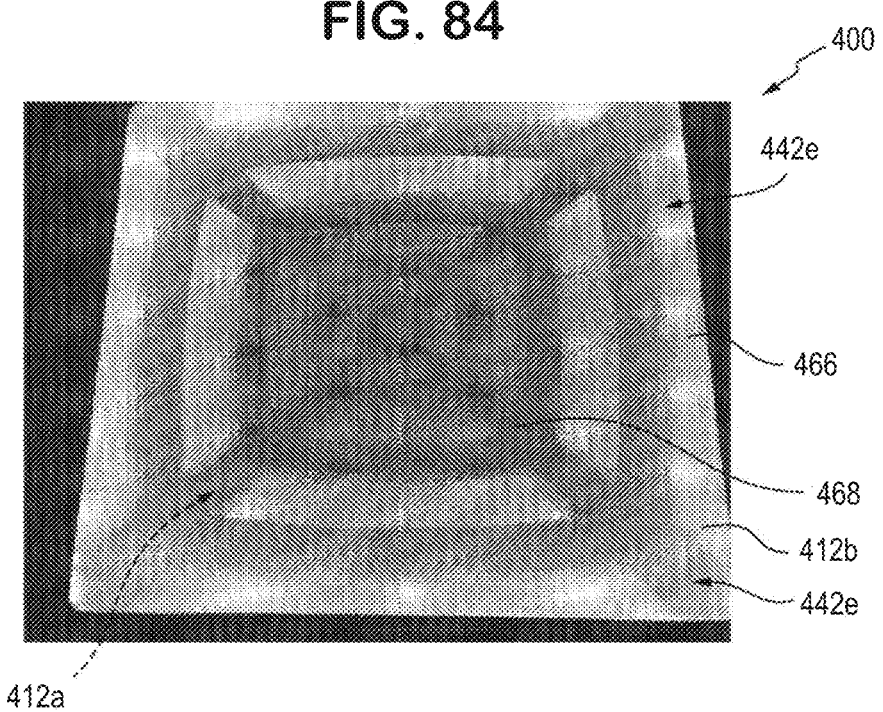

FIG. 84 is a color photograph from above of a luminaire comprising the waveguide depicted in FIG. 72 disposed behind the waveguide depicted in FIG. 83.

Figure 85:
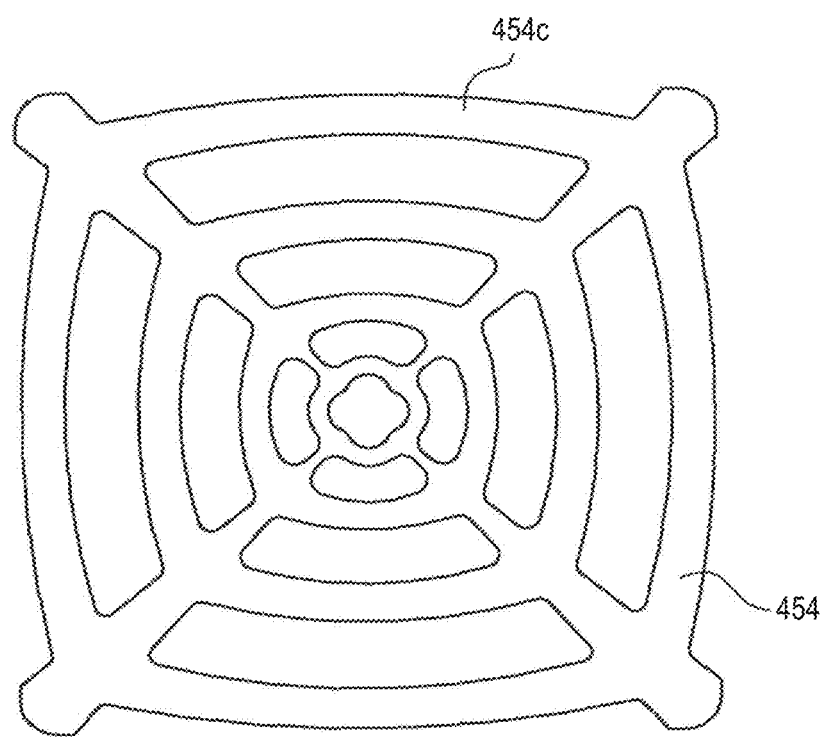

FIG. 85 is a plan view of a mask for fabricating extraction features according to a pattern.

Figure 86:
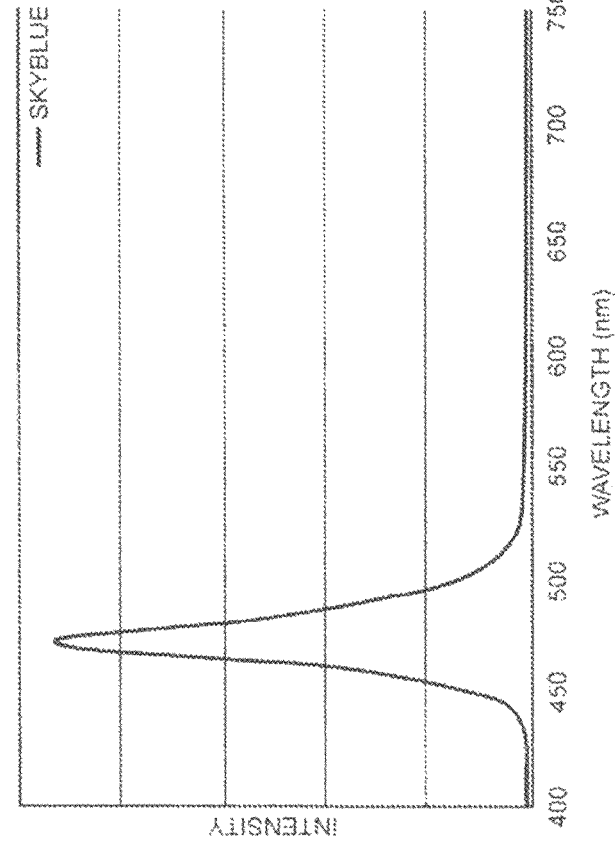

FIG. 86 is a graph of an emission spectrum for a bluish LED for use with embodiments.

Figure 87:
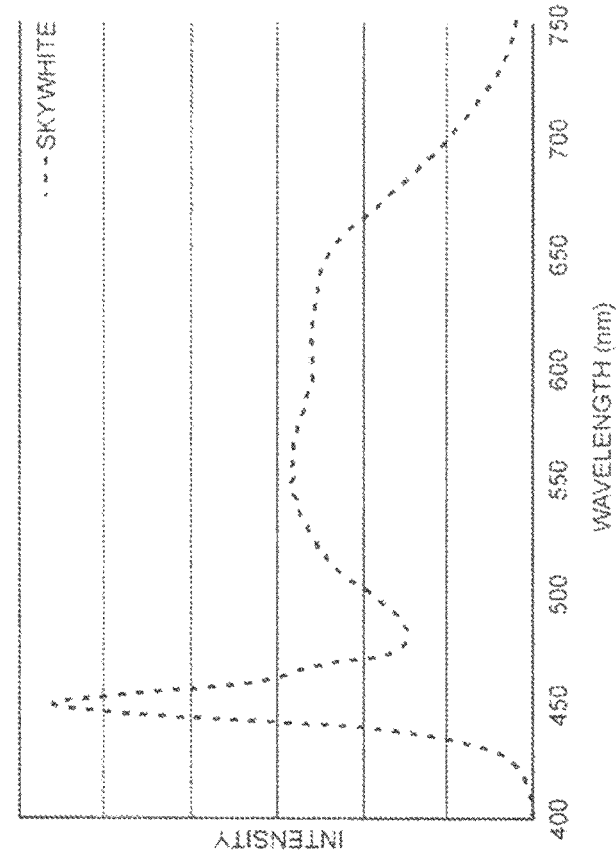

FIG. 87 is a graph of the emission spectrum for a white LED for use with embodiments.

Figure 88:
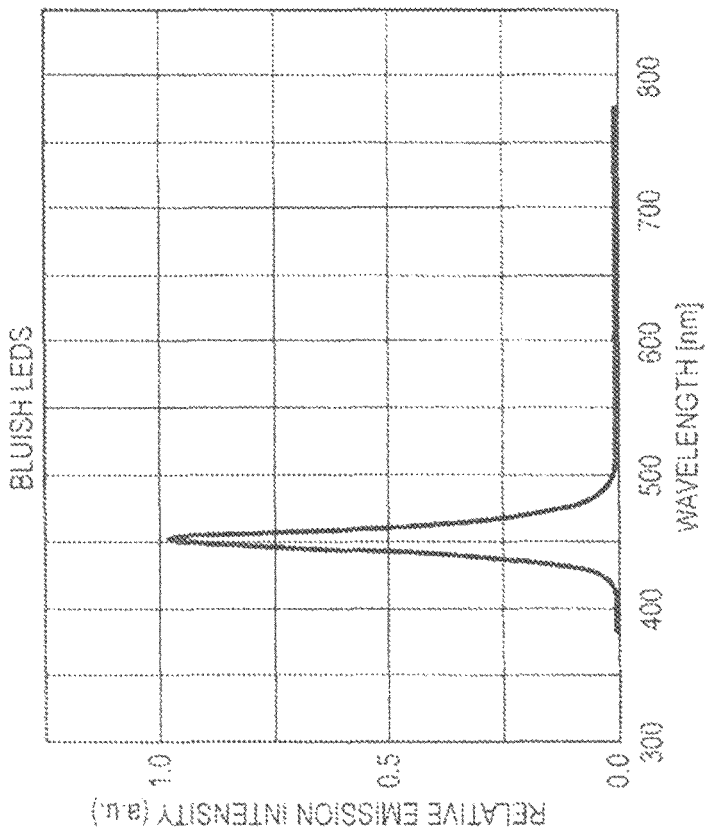

FIG. 88 is a graph of the emission spectrum for a bluish LED for use with embodiments.

Figure 89:
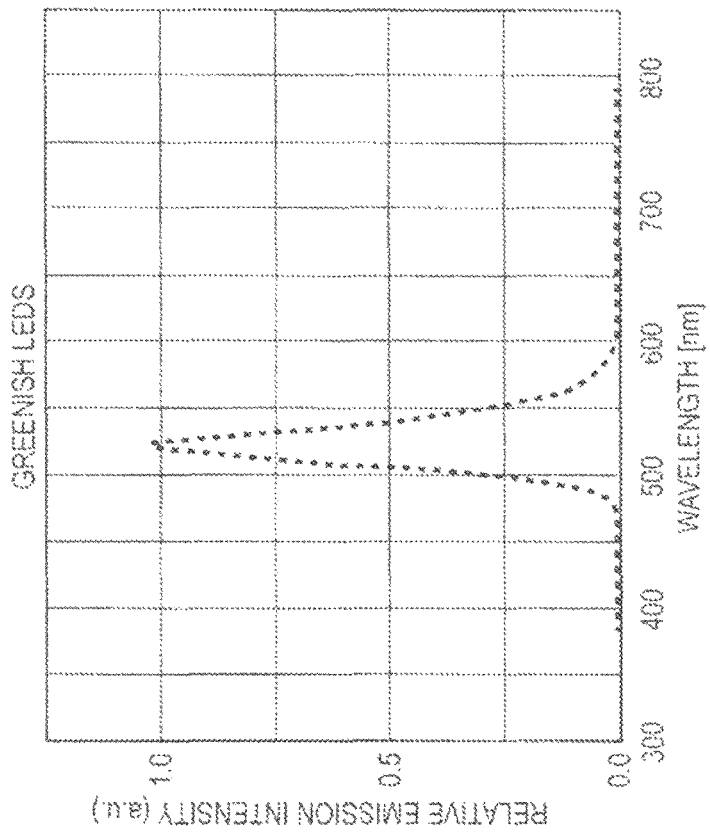

FIG. 89 is a graph of the emission spectrum for a greenish LED for use with embodiments.

Figure 90:
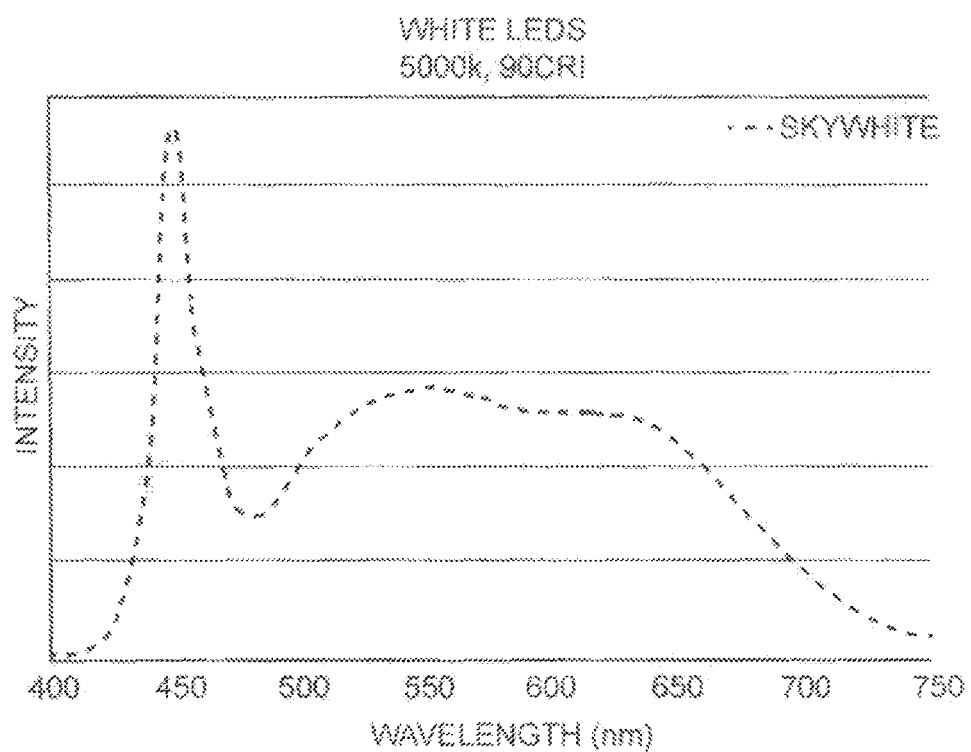

FIG. 90 is a graph of the emission spectrum for a white LED for use with embodiments.

Figures 91A, 91B, 91C, 91D:
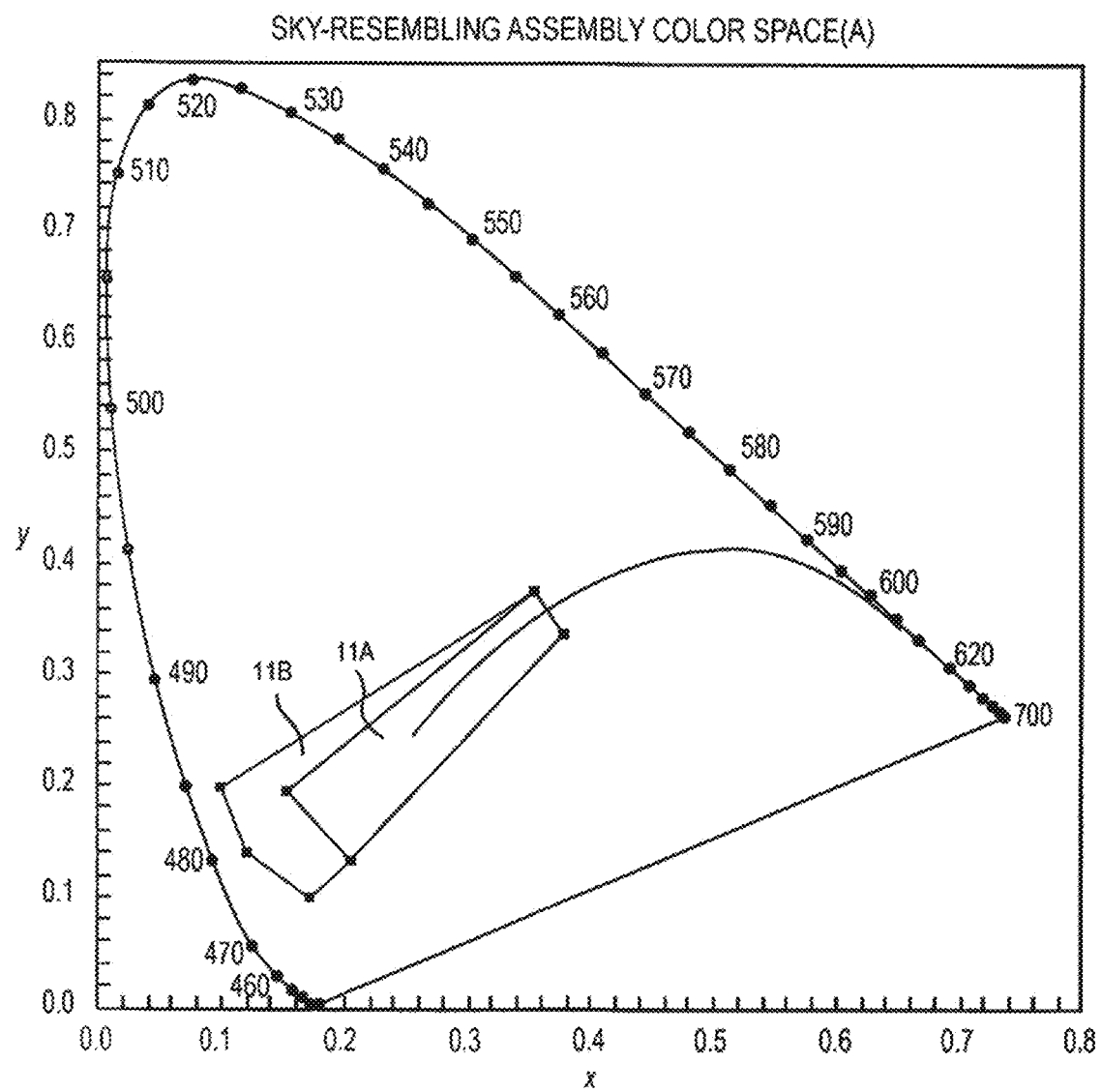

FIG. 91A is a 1931 CIE Chromaticity Diagram on which color spaces for a fourth embodiment of a sky-resembling assembly are provided.

FIG. 91B is a table of (x, y) coordinates that define a first color space 11A in FIG. 91A.

FIG. 91C is a table of (x, y) coordinates that define a second color space 11B in FIG. 91A.

FIG. 91D is a table of (x, y) coordinates that define a combined color space (including the first and second color spaces 11A and 11B) in FIG. 91A.

Figures 92A, 92B:
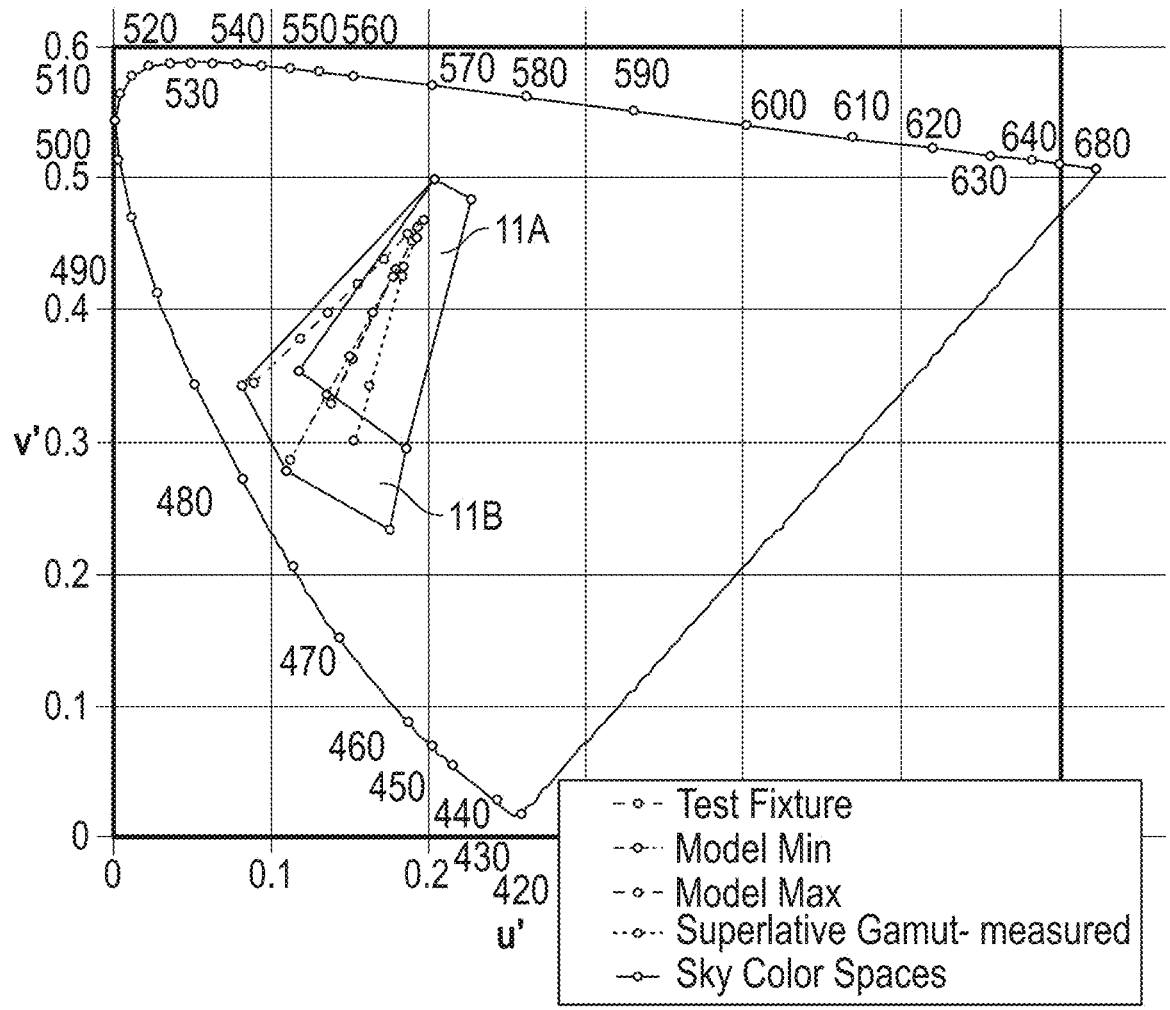

FIG. 92A is a 1976 CIE Chromaticity Diagram on which color spaces and exemplary color points for a fifth embodiment of a sky-resembling assembly are provided, including color spaces 11A and 11B corresponding to those represented in FIG. 91A.

FIG. 92B is a table of (u', v') coordinates of a 1976 CIE Chromaticity Diagram (with corresponding (x, y) coordinates of a 1931 CIE Chromaticity Diagram) that define one color space 11B in FIG. 92A.

Figure 93A:
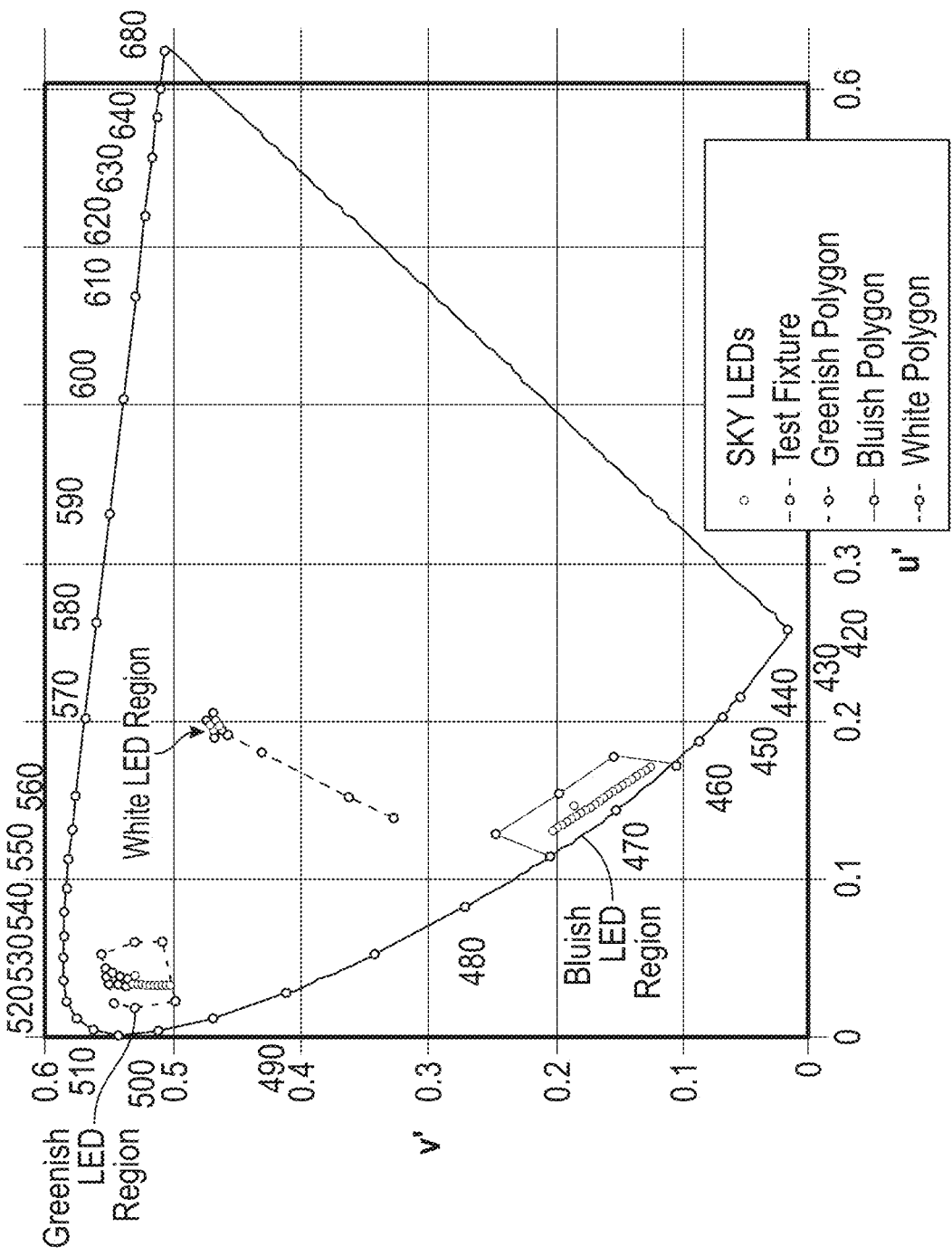

FIG. 93A is a 1976 CIE Chromaticity Diagram on which color spaces for bluish LEDs, greenish LEDs, and white LEDs, as well as exemplary color points for aggregated emissions of the foregoing LEDs, for a sixth embodiment of a sky-resembling assembly are provided.

FIG. 93B is a table of (u', v') coordinates of a 1976 CIE Chromaticity Diagram (with corresponding (x, y) coordinates of a 1931 CIE Chromaticity Diagram) that define the color space producible by the greenish LEDs in FIG. 93A.

FIG. 93C is a table of (u', v') coordinates of a 1976 CIE Chromaticity Diagram (with corresponding (x, y) coordinates of a 1931 CIE Chromaticity Diagram) that define the color space producible by the bluish LEDs in FIG. 93A.

FIG. 93D is a table of (u', v') coordinates of a 1976 CIE Chromaticity Diagram (with corresponding (x, y) coordinates of a 1931 CIE Chromaticity Diagram) that define the color space producible by the white LEDs in FIG. 93A.

Figure 94:
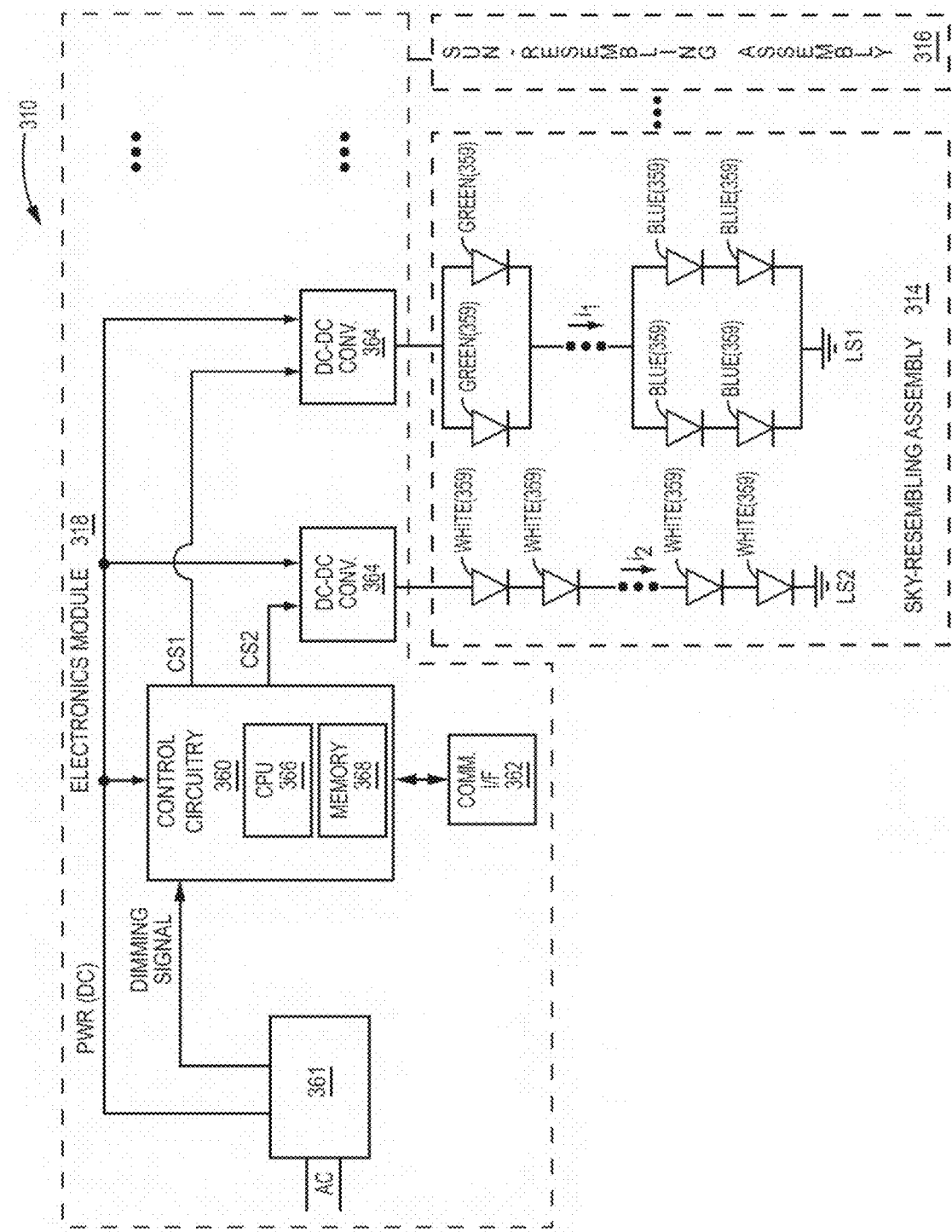

FIG. 94 is a schematic diagram of an exemplary electronics module and associated sky- and sun-resembling assemblies according to one embodiment, with the sky-resembling assembly including first and second strings of connected LEDs, including a white LED string of series-parallel connected white LEDs, and including a mixed color LED string including a parallel connected group of greenish LEDs arranged in series with a series-parallel connected group of bluish LEDs.

Figure 95:
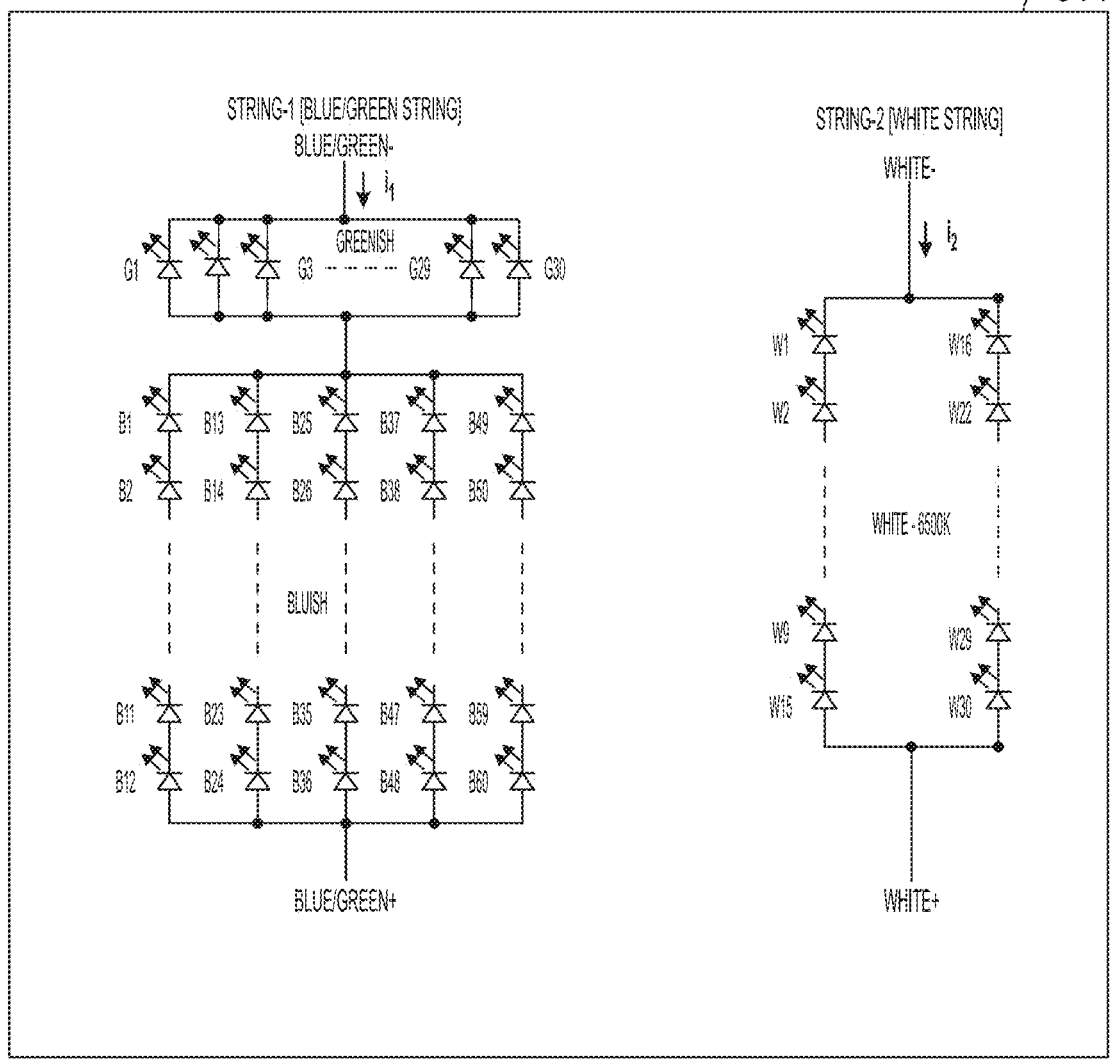

FIG. 95 is a schematic diagram of first and second strings of series-connected LEDs useable in the electronics module of FIG. 94 according to an exemplary embodiment.

Figure 96:
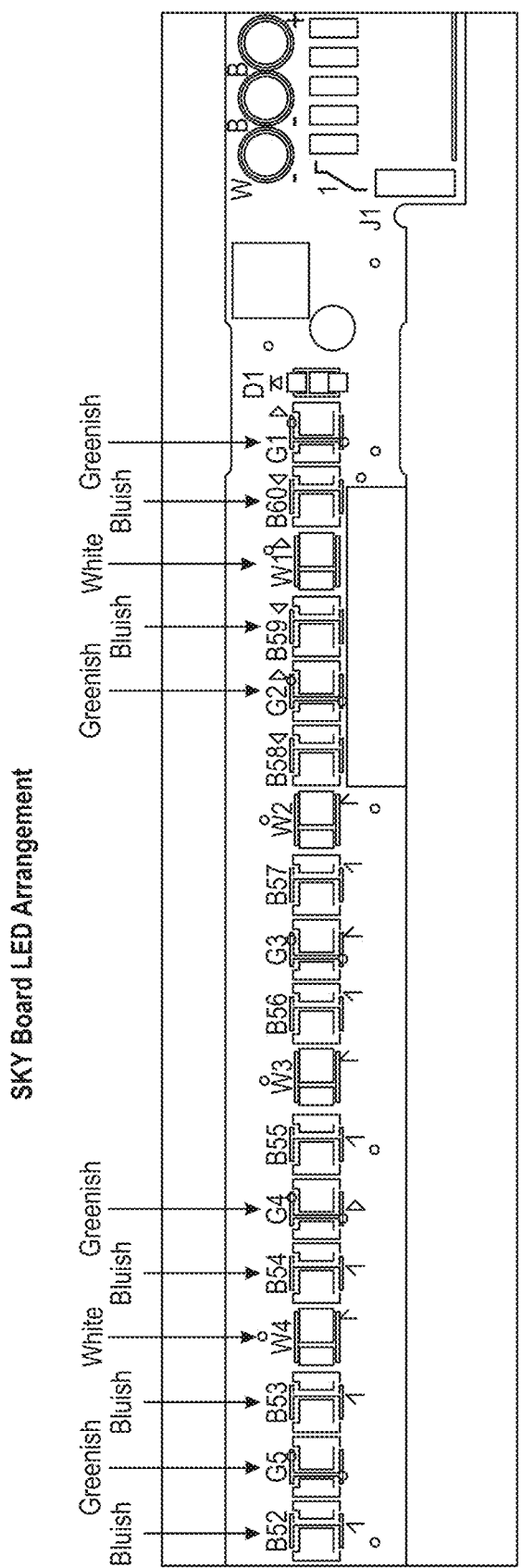

FIG. 96 illustrates a portion of a light engine as part of a sky-resembling assembly according to one embodiment, showing greenish and bluish LEDs of a first multi-LED string physically interspersed among white LEDs of a second multi-LED string.

Figure 97:
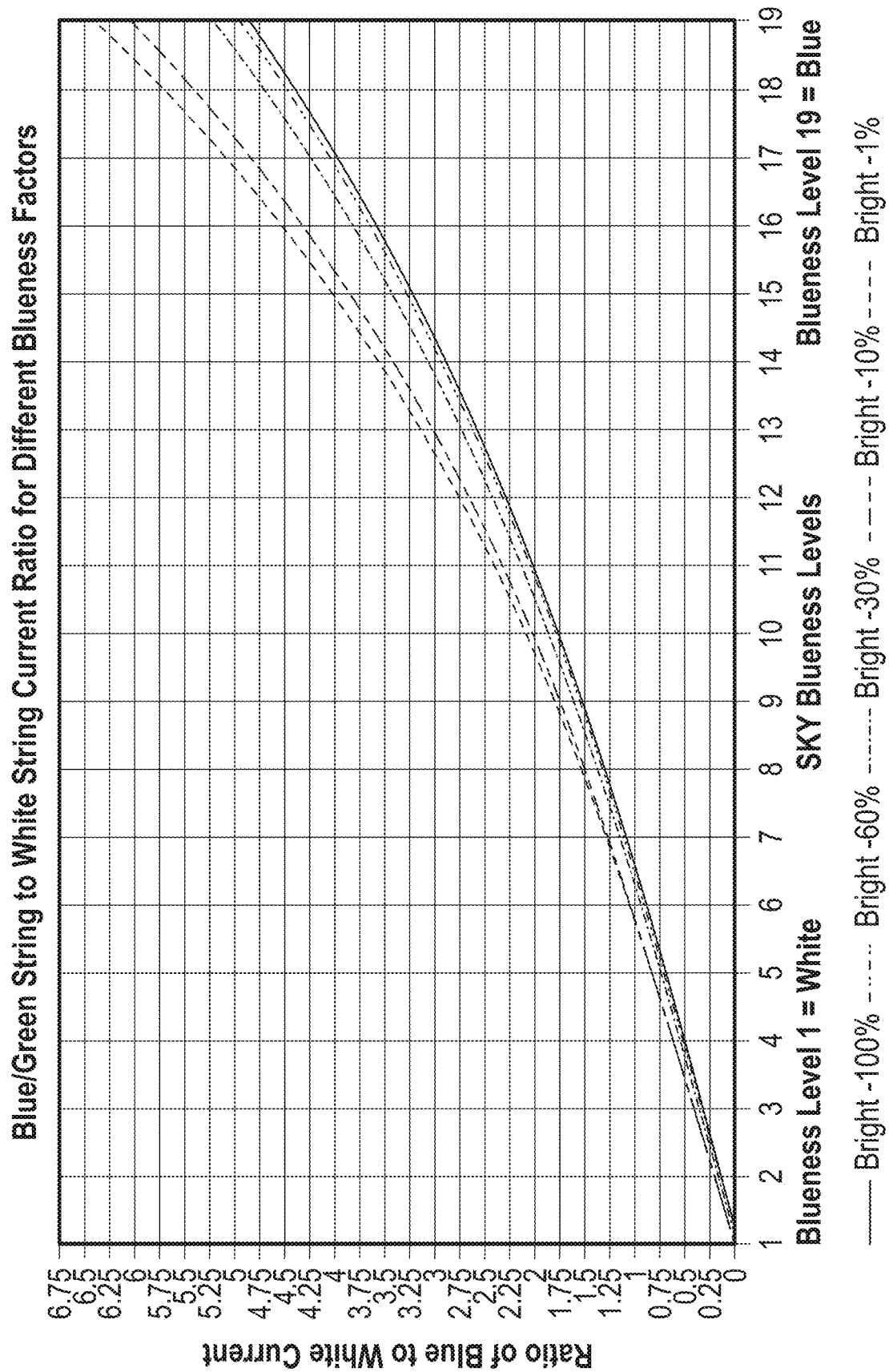

FIG. 97 is a plot of blue/green string to white string current ratio for different blueness factors (with factors ranging from 1 to 19) for a white LED string and a mixed color LED string according to one embodiment.

Figure 98:
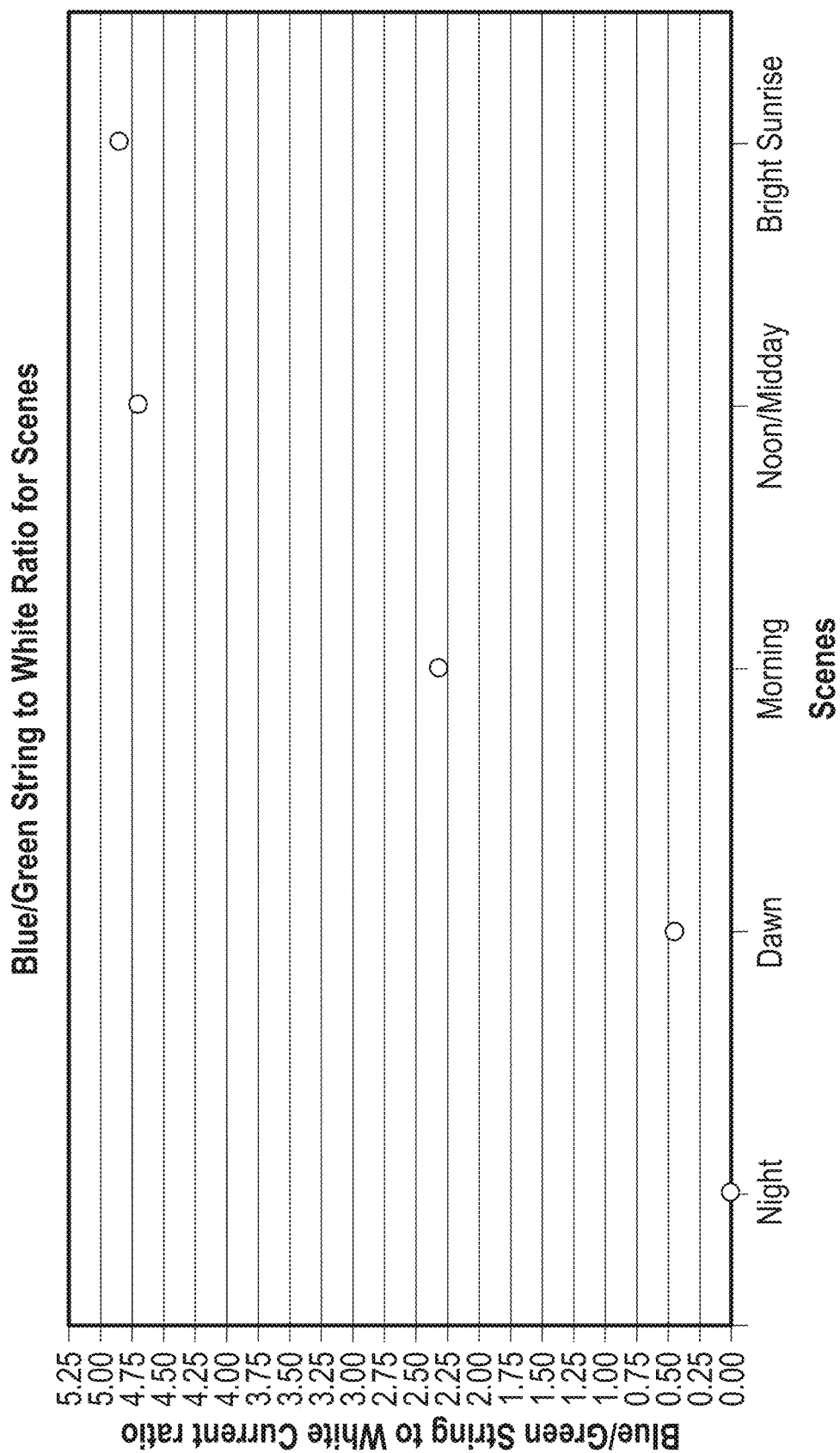

FIG. 98 is a plot of blue/green LED string to white LED string current ratio for an exemplary group of different scenes achievable by a sky-resembling assembly of skylight fixture according to one embodiment, with the scenes including night, dawn, morning, noon/midday, and bright sunrise.

Figure 99:
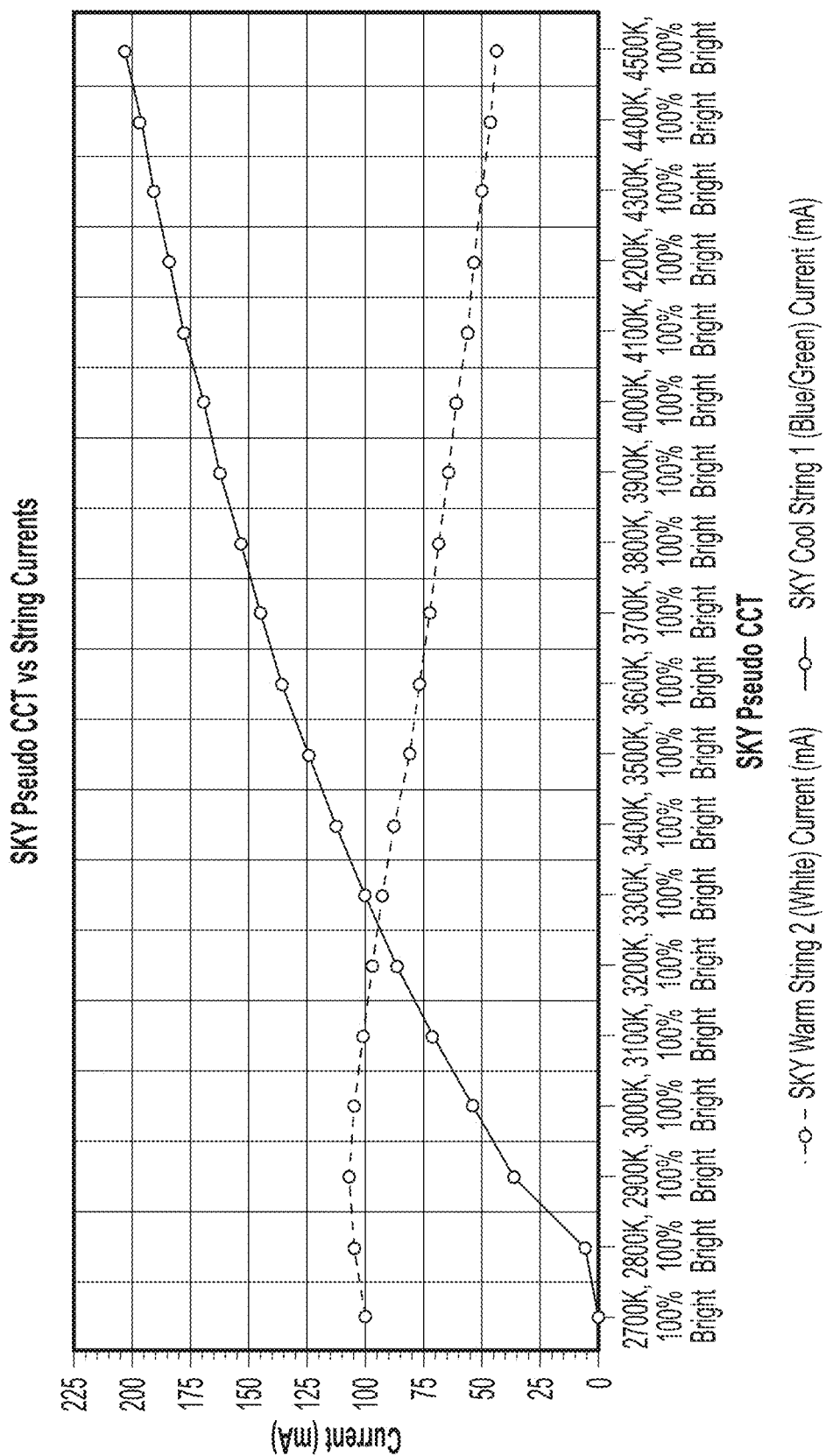

FIG. 99 is a plot of current versus sky pseudo correlated color temperature for nineteen pseudo CCT values ranging from 2700 K to 4500 K for a sky-resembling assembly of a skylight fixture including first and second LED strings according to one embodiment, the first LED string including greenish and bluish LEDs and the second LED string including white LEDs.

Figure 100:
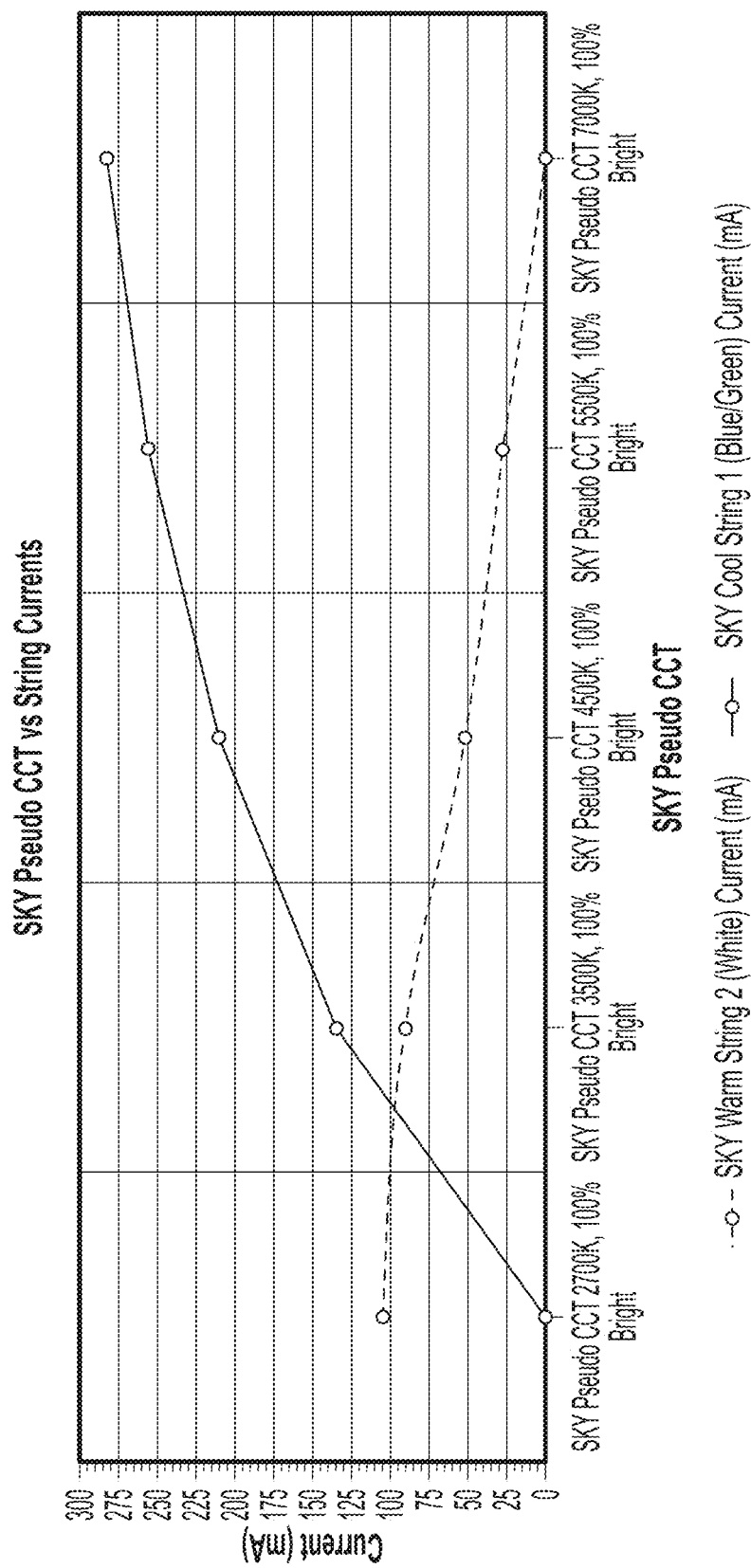

FIG. 100 is a plot of current versus sky pseudo correlated color temperature for five pseudo CCT values ranging from 2700 K to 7000 K for a sky-resembling assembly including first and second LED strings of a skylight fixture according to one embodiment, the first LED string including greenish and bluish LEDs and the second LED string including white LEDs.

Figure 101:
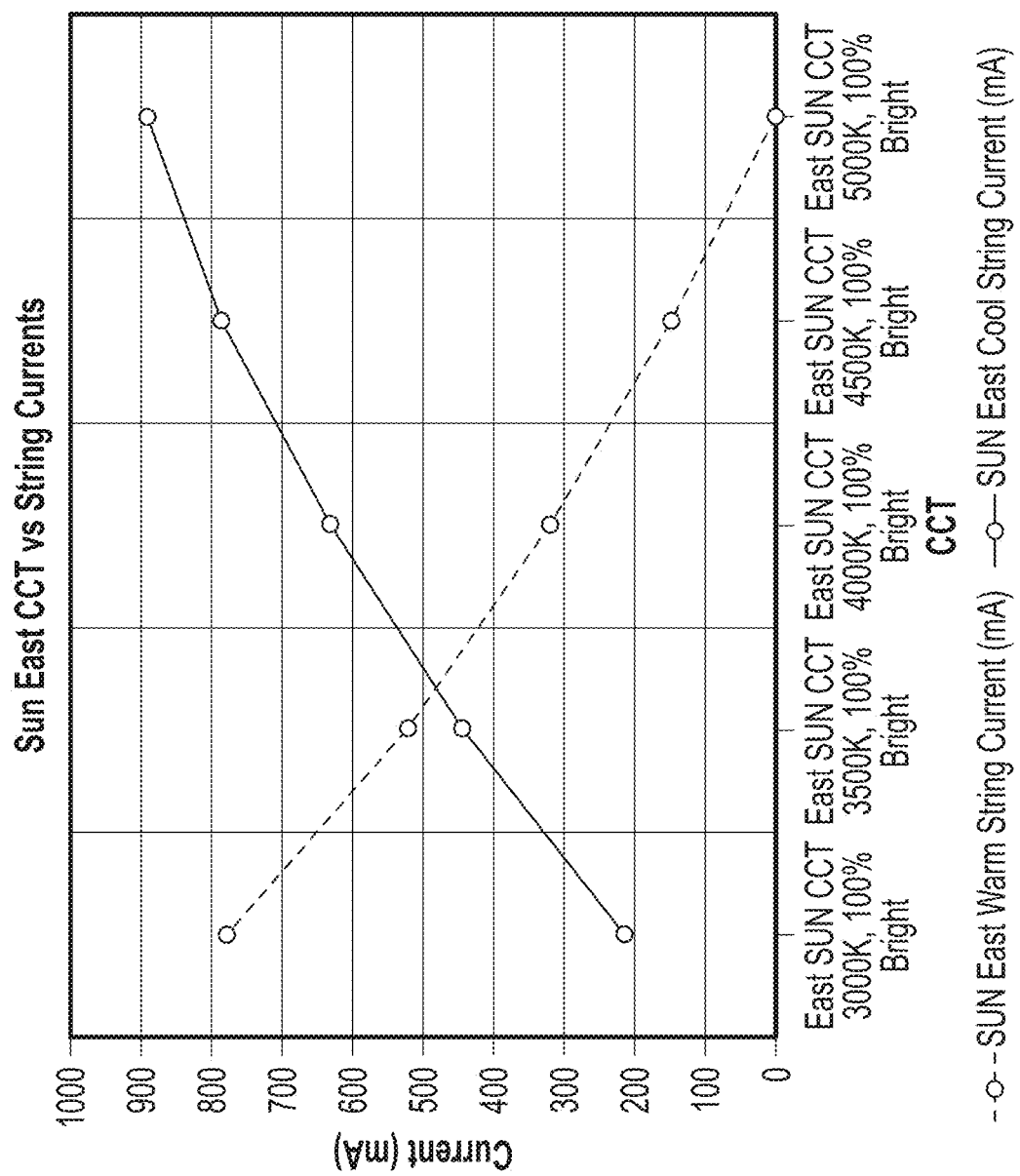

FIG. 101 is a plot of warm white versus cool white string currents for five CCT values ranging from 3000 K to 5000 K for a single sun-resembling assembly including first and second LED strings of one sun-resembling assembly of a skylight fixture according to one embodiment.

FIG. 102A is a table identifying preset names as well as time-dependent varying CCT and light level percentage values over a 24 hour period for east and west sun-resembling assemblies and a sky-resembling assembly of a skylight fixture according to one embodiment.

FIG. 102B is a table identifying three additional static presets with corresponding CCT and light level percentage values for east and west sun-resembling assemblies and a sky-resembling assembly of a skylight fixture according to one embodiment.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure. Throughout the drawings, identical reference numbers may designate similar, but not necessarily identical, elements. Use herein of a reference numeral without an index number, where such reference numeral is referred to elsewhere with an index number, may be a general reference to the corresponding plural elements, collectively or individually.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

As used herein the term "and/or" includes any and all combinations of one or more of the associated listed items.

The term "plurality," as used herein, means two or more, i.e., it encompasses two, three, four, five, etc. For example, the expression "plurality of positions" encompasses two positions, three positions, four positions, etc.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The expression "in contact with," as used herein, means that a first structure that is in contact with a second structure is in direct contact with the second structure or is in indirect contact with the second structure. The expression "in indirect contact with" means that the first structure is not in direct contact with the second structure, but that there are a plurality of structures (including the first and second structures), and each of the plurality of structures is in direct contact with at least one other of the plurality of structures (e.g., the first and second structures are in a stack and are separated by one or more intervening layers). The expression "direct contact", as used in the present specification, means that the first structure which is "in direct contact" with a second structure is touching the second structure and there are no intervening structures between the first and second structures at least at some location. A statement herein that two components in a device are "electrically connected," means that there are no components electrically between the components that affect the function or functions provided by the device. For example, two components can be referred to as being electrically connected, even though they may have a small resistor between them which does not materially affect the function or functions provided by the device (indeed, a wire connecting two components can be thought of as a small resistor); likewise, two components can be referred to as being electrically connected, even though they may have an additional electrical component between them which allows the device to perform an additional function, while not materially affecting the function or functions provided by a device which is identical except for not including the additional component; similarly, two components which are directly connected to each other, or which are directly connected to opposite ends of a wire or a trace on a circuit board, are electrically connected. A statement herein that two components in a device are "electrically connected" is distinguishable from a statement that the two components are "directly electrically connected", which means that there are no components electrically between the two components.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures. Likewise, relative terms, such as "front", "back", "behind", etc., are used herein to describe spatial relationships among elements or structures. Such relative terms are intended to encompass different orientations of the device in addition to the orientation described. For example, if a device is turned 180 degrees, an element in front of the light fixture (or in front of another component) would in the back of the light fixture (or behind the other component) from the same perspective prior to turning the device 180 degrees.

The expression "defines (or at least partly defines)", e.g., as used in the expression "The sidewall defines (or at least partly defines) a space" means that the element or feature that is defined, or at least partly defined by the structure (e.g., the sidewall in this example) is defined by that structure or is defined by that structure in combination with one or more additional structures.

The expression "defines at least part", e.g., as used in the expression "the sidewall comprises a second edge that defines at least part of a second edge-defined region" means that the element or feature that is defined, or at least part of which is defined by the structure, (e.g., the sidewall in this example) is defined by that structure or is defined by that structure in combination with one or more additional structures.

The expression "axis of light distribution", as used herein in connection with light output from one or more light sources (and/or light one or more light engines), means an axis of the light from a light source (and/or from a light engine), a direction of maximum brightness of a distribution of light, or a mean direction of a distribution of light. In other words, in the case of "a mean direction of a distribution of light," (1) if there is provided a light source (or a light engine) in which the distribution of the brightness of emitted light (or light exiting the light engine) is non-Lam bertian, the axis of light distribution might coincide with the an axis of the light source or light engine (e.g., because the mean direction of the maxima lies on the axis of the light source or light engine), even though the maximum directions of brightness do not themselves lie on the axis of the light source or light engine, or (2) if the maximum brightness is in a first direction, a brightness in a second direction ten degrees to one side of the first direction is larger than a brightness in a third direction ten degrees to an opposite side of the first direction, the mean direction of light emission would be moved somewhat toward the second direction as a result of the brightnesses in the second direction and the third direction.

The expression "correlated color temperature" ("CCT") is used according to its well-known meaning to refer to the temperature of a blackbody that is nearest in color, in a well-defined sense (i.e., can be readily and precisely determined by those skilled in the art). Persons of skill in the art are familiar with correlated color temperatures, and with Chromaticity diagrams that show color points to correspond to specific correlated color temperatures and areas on the diagrams that correspond to specific ranges of correlated color temperatures. Light can be referred to as having a correlated color temperature even if the color point of the light is on the blackbody locus (i.e., its correlated color temperature would be equal to its color temperature); that is, reference herein to light as having a correlated color temperature does not exclude light having a color point on the blackbody locus.

The term "edge" of a structure (e.g., "bottom edge of the first sidewall"), means any portion (or portions) of the structure where there is a non-flat topography (e.g., a location where a surface ends, a location where a first planar surface meets a second planar surface, or a location where a curved or other non-planar surface meets a planar surface, or a location where a first non-planar surface meets a second non-planar surface, etc.).

A "light engine" can be any structure (or combination of structures) from which light exits. In many cases, a light engine consists of one or more light sources plus one or more mechanical elements, one or more optical elements and/or one or more electrical elements. In many cases, a light engine is a component of a light fixture, i.e., it is not a complete light fixture, but it can be a discrete group or set of LEDs that is spatially segregated and controlled as a unit. In some embodiments, for instance, a light engine in a light fixture can be a discrete set of LEDs (e.g., an array of LEDs) mounted to a board (e.g., a printed circuit board) that is separate from one or more other light engines in the light fixture. In some embodiments, a larger board can comprise different sets or groups of LEDs occupying different portions of the board, and thereby comprise multiple light engines. A light engine can, for example, comprise chip-on-board, packaged LEDs, secondary optics and/or control/drive circuitry. In some embodiments, a light fixture can comprise a first light engine comprising multiple LEDs on a first board, and a second light engine comprising multiple LEDs on a second board. In some embodiments, a light engine can comprise multiple LEDs spaced from each other (in the aggregate) in one dimension, in two dimensions or in three dimensions. For example, a first light engine can be mounted adjacent or spaced laterally from but on the same plane with a second light engine and thereby spaced in one dimension.

A first light engine can be positioned adjacent or spaced from a second light engine but positioned at an angle or on a second plane from the second light engine and thereby in two dimensions. A first light engine can be offset from a second light engine in two or three dimensions. A first light engine can be offset or positioned relative to two, three or more dimensions of one or more other light engines. In some embodiments, a light engine can comprise a single light source (e.g., a single LED), or an array of light sources (e.g., a plurality of LEDs, a plurality of other light sources, or a combination of one or more LEDs and/or one or more other light sources). In some embodiments, a plurality of light source (e.g., a plurality of LEDs) can be on a board and controlled together, for example, a control device (that controls color point of a mixture of light from the plurality of light sources, and/or that controls brightness of light emitted from one or more of the plurality of light sources, etc.) can control a plurality of light sources on a board (and/or can control all of the light sources on a board.

The expression "light exit region" (e.g., "at least a first light exit region is at a boundary of the space"), means any region through which light passes (e.g., as it travels from a space which is to one side of the light exit region to the other side of the light exit region, i.e., as it exits the space through the light exit region). For example, if a light fixture has a cylindrical surface that defines an internal space (closed at the top and open at the bottom), light can exit the space by traveling through the circular light exit region at the bottom of the cylindrical surface (i.e., such circular light exit region is defined by the lower edge of the cylindrical surface). Such a light exit region can be open, or it can be partially or completely occupied by a structure that is at least partially light-transmitting (e.g., transparent or translucent). For example, a light exit region can be an opening in an opaque structure (through which light can exit), a light exit region can be a transparent region in an otherwise opaque structure, a light exit region can be an opening in an opaque structure that is covered by a lens or a diffuser, etc.

The expression "defining a space" (e.g., in the expression "the first sidewall defines a space") means that portions of the structure which is being described as defining the space objectively define an identifiable space. As purely representative examples for illustration, a cylindrical surface defines a cylindrical space inside the cylindrical surface; likewise, a surface that is cylindrical except for not having closed ends (i.e., not having circular regions at the top and bottom) and having holes and/or gaps can define a cylindrical space; likewise, a series of planar surfaces extending around a region can define a space (e.g., four planar regions having respective edges that abut two neighbors on either side to define right angles can together define a rectangular prismatic or a square prismatic space); likewise, one or more irregular, non-flat surfaces can together define a space where each point in the space is along a line segment connecting respective points on one or more of the surfaces, etc.

The expression "boundary of the space" means any portion of an exterior of a space. For example, in the case of a cylindrical space, a "boundary of the space" can be either of the circular regions at the exterior of the space, or it can be the curved side of the exterior of the space (i.e., the entire exterior except for the two circular regions), or any portion of either of the circular regions or any portion of the curved side. Similarly, in the case of a space in the shape of a square prism or a rectangular prism, a "boundary of the space" can be any of the sides of the prism or any portion of any of the sides of the prism.

The expression "substantially flat," as used herein (e.g., in the expression "the first light exit surface can be substantially flat and rectangular") means that at least 90% of the points in a surface of the structure that is being characterized as substantially flat are located between a pair of planes which are parallel and which are spaced from each other by a distance of not more than 25% of the largest dimension of the surface (and in some cases, not more than 15%, not more than 10% or not more than 5% of the largest dimension of the surface).

The expression "visibly distinct color" means that a human with normal vision would be able to detect a difference in color between lights (e.g., between light that exits from a first light engine and light that exits from a second light engine).

The expression "light that exits a light engine is of a first color point" (and similar or analogous expressions) means the color point of light (or a mixture of light) exiting the light engine, i.e., if light that exits the light engine is all of a single color point (e.g., if the light engine includes only a single light source), the light that exits the light engine is of that color point, and if light that exits the light engine is a mixture of light of different color points (e.g., if the light engine includes two or more light sources that emit light of different color points), the light that exits the light engine is of the color point that the mixture of light is.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof. A statement that something comprises an element (e.g., an element of a type or group) does not preclude the presence of additional elements of the same type (for instance, recitation that a light fixture "comprises a first light engine" does not preclude the light fixture from having a second light engine or other light engines). The term "include" (or the like, e.g., "including") also specifies the presence of the listed item or items, but does not preclude the presence or addition of other items (e.g., "including" means including but not limited to).

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The color of visible light emitted by a light source, and/or the color of a mixture visible light emitted by a plurality of light sources can be represented on either the 1931 CIE (Commission International de l'Eclairage) Chromaticity Diagram or the 1976 CIE Chromaticity Diagram. Persons of skill in the art are familiar with these diagrams, and these diagrams are readily available (e.g., by searching "CIE Chromaticity Diagram" on the internet).

The CIE Chromaticity Diagrams map out the human color perception in terms of two CIE parameters, namely, x and y (in the case of the 1931 diagram) or u' and v' (in the case of the 1976 diagram). Each point (i.e., each "color point") on the respective Diagrams corresponds to a particular hue. For a technical description of CIE chromaticity diagrams, see, for example, "Encyclopedia of Physical Science and Technology", vol. 7, 230-231 (Robert A Meyers ed., 1987). The spectral colors are distributed around the boundary of the outlined space, which includes all of the hues perceived by the human eye. The boundary represents maximum saturation for the spectral colors.

The 1931 CIE Chromaticity Diagram can be used to define colors as weighted sums of different hues. The 1976 CIE Chromaticity Diagram is similar to the 1931 Diagram, except that similar distances on the 1976 Diagram represent similar perceived differences in color.

The expression "hue", as used herein, means light that has a color shade and saturation that correspond to a specific point on a CIE Chromaticity Diagram, i.e., a point that can be characterized with x, y coordinates on the 1931 CIE Chromaticity Diagram or with u', v' coordinates on the 1976 CIE Chromaticity Diagram.

In the 1931 Diagram, deviation from a point on the Diagram (i.e., "color point") can be expressed either in terms of the x, y coordinates or, alternatively, in order to give an indication as to the extent of the perceived difference in color, in terms of MacAdam ellipses (or plural-step MacAdam ellipses). For example, a locus of points defined as being ten MacAdam ellipses (also known as "a ten-step MacAdam ellipse) from a specified hue defined by a particular set of coordinates on the 1931 Diagram consists of hues that would each be perceived as differing from the specified hue to a common extent (and likewise for loci of points defined as being spaced from a particular hue by other quantities of MacAdam ellipses).

A typical human eye is able to differentiate between hues that are spaced from each other by more than seven MacAdam ellipses (and is not able to differentiate between hues that are spaced from each other by seven or fewer MacAdam ellipses).

Since similar distances on the 1976 Diagram represent similar perceived differences in color, deviation from a point on the 1976 Diagram can be expressed in terms of the coordinates, u' and v', e.g., distance from the point=$(\Delta u'^2 + \Delta v'^2)'$. This formula gives a value, in the scale of the u' v' coordinates, corresponding to the distance between points. The hues defined by a locus of points that are each a common distance from a specified color point consist of hues that would each be perceived as differing from the specified hue to a common extent.

A series of points that is commonly represented on the CIE Diagrams is referred to as the blackbody locus. The chromaticity coordinates (i.e., color points) that lie along the blackbody locus correspond to spectral power distributions that obey Planck's equation: $E(\lambda)=Ak^{-5}/(e^{(B/T)}-1)$, where E is the emission intensity, lamda is the emission wavelength, T is the temperature of the blackbody and A and B are constants. The 1976 CIE Diagram includes temperature listings along the blackbody locus. These temperature listings show the color path of a blackbody radiator that is caused to increase to such temperatures. As a heated object becomes incandescent, it first glows reddish, then yellowish, then white, and finally bluish. This occurs because the wavelength associated with the peak radiation of the blackbody radiator becomes progressively shorter with increased temperature, consistent with the Wien Displacement Law. Illuminants that produce light that is on or near the blackbody locus can thus be described in terms of their color temperature.

The expression "dominant wavelength" is used herein according to its well-known and accepted meaning to refer to the perceived color of a spectrum, i.e., the single wavelength of light which produces a color sensation most similar to the color sensation perceived from viewing light emitted by the light source, as opposed to "peak wavelength", which is well known to refer to the spectral line with the greatest power in the spectral power distribution of the light source. Because the human eye does not perceive all wavelengths equally (it perceives yellow and green better than red and blue), and because the light emitted by many solid state light emitters (e.g., light emitting diodes) is actually a range of wavelengths, the color perceived (i.e., the dominant wavelength) is not necessarily equal to (and often differs from) the wavelength with the highest power (peak wavelength). A truly monochromatic light such as a laser has a dominant wavelength that is the same as its peak wavelengths.

The expression "peak intensity angle" is used herein according to its well-known and accepted meaning to refer to an angle, relative to a plane, that a largest illuminance of light emitted from a light source (or light sources) is travelling, i.e., for each angle (e.g., whole numbers, i.e., 0 degrees, 1 degree, 2 degrees . . . 89 degrees and 90 degrees) relative to a defined plane, the illuminance of light travelling at such angle relative to the plane is determined, and the angle for which the largest illuminance is determined is the "peak intensity angle."

A statement that "light output from a first light engine provides a first CS value" (or the like) means that the light output from the first light engine would, in the absence of any other light, provide the first CS value. That is, such a statement does not indicate that the light output from the first light engine does not mix with other light from one or more other light engines, or that the total light output from a light fixture that comprises the first light engine provides such first CS value (e.g., the light output from the light fixture can comprise light output from at least a second light engine, and a mixture of light output from the first light engine and the second light engine can have an aggregate CS value that differs from the first CS value.

It is well known that light sources that emit light of respective differing hues (two or more) can be combined to generate mixtures of light that have desired hues (e.g., non-white light corresponding to desired color points or white light of desired color temperature, etc.). It is also well known that the color point produced by mixtures of colors can readily be predicted and/or designed using simple geometry on a CIE Chromaticity Diagram. It is further well known that starting with the notion of a desired mixed light color point, persons of skill in the art can readily select light sources of different hues that will, when mixed, provide the desired mixed light color point. For example, persons of skill in the art can select a first light engine (e.g., comprising a light emitting diode and phosphor), plot the color point of the light exiting from the first light engine (i.e., a first color point) on a CIE Chromaticity Diagram, plot a desired range of color points (or a single desired color point) for mixed light, and draw one or more line segments through the desired range of color points (or the single color point) for the mixed light such that the line segment(s) extend beyond the desired color point(s). Each line segment drawn in this way will have one end at the first color point, will pass through the range for the desired mixed light color point (or the desired single color point), and will have its other end at a second color point. A second light engine can be provided from which light of the second color point exits, and when the first light engine and a second light engine are energized so that light exits from them, the color point of the mixed light will necessarily lie along a line segment connecting the first color point and the second color point, and the location of the color point of the mixed light along the line segment will be dictated by (namely, proportional to) the relative brightnesses of the respective light that exits from the first and second light engines. That is, the greater the proportion of the mixed light that is from the second light engine, the closer the color point of the mixed light is to the second color point; this relationship is geometrically proportional, i.e., the fraction of the length of the line segment that the color point of the mixed light is spaced from the first color point is equal to the fraction of the mixed light that is from the second light engine (and vice-versa), or, in geometric terms, the ratio of (1) the distance from the first color point to the color point of the mixed light, divided by (2) the distance from the first color point to the second color point will be equal to the ratio of the brightness (in lumens) of the first light engine divided by the brightness (in lumens) of the combination of light in the mixed light. Accordingly, once one identifies light sources (or light engines) that provide the endpoints of a line segment that extends through the desired mixed light color point, the desired mixed light color point can be obtained by calculating the relative brightnesses of the first and second light sources (or light engines) necessary to arrive at the desired mixed light color point.

Where more than two light sources (and/or light engines) are used (e.g., where there are mixed light of a first color point from a first light source, light of a second color point from a second light source, and light of a third color point from a third light source), the geometrical relationships can be used to ensure that the desired mixed light color point is obtained (e.g., conceptually, the color point of a sub-mixture of light from the first light source (or the first light engine) and the 35aralld light source (or the second light engine) can be determined, and then the color point of a mixture of sub-mixture (having a brightness of the combined brightnesses of the first light source (or the first light engine) and the second light source (or the second light engine)) and the third light source (or the third light engine) can be determined, and the range of mixed light color points that can be reached is defined by the perimeter obtained from drawing lines connecting the respective color points of the light sources (and/or light engines).

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

Figure 1:
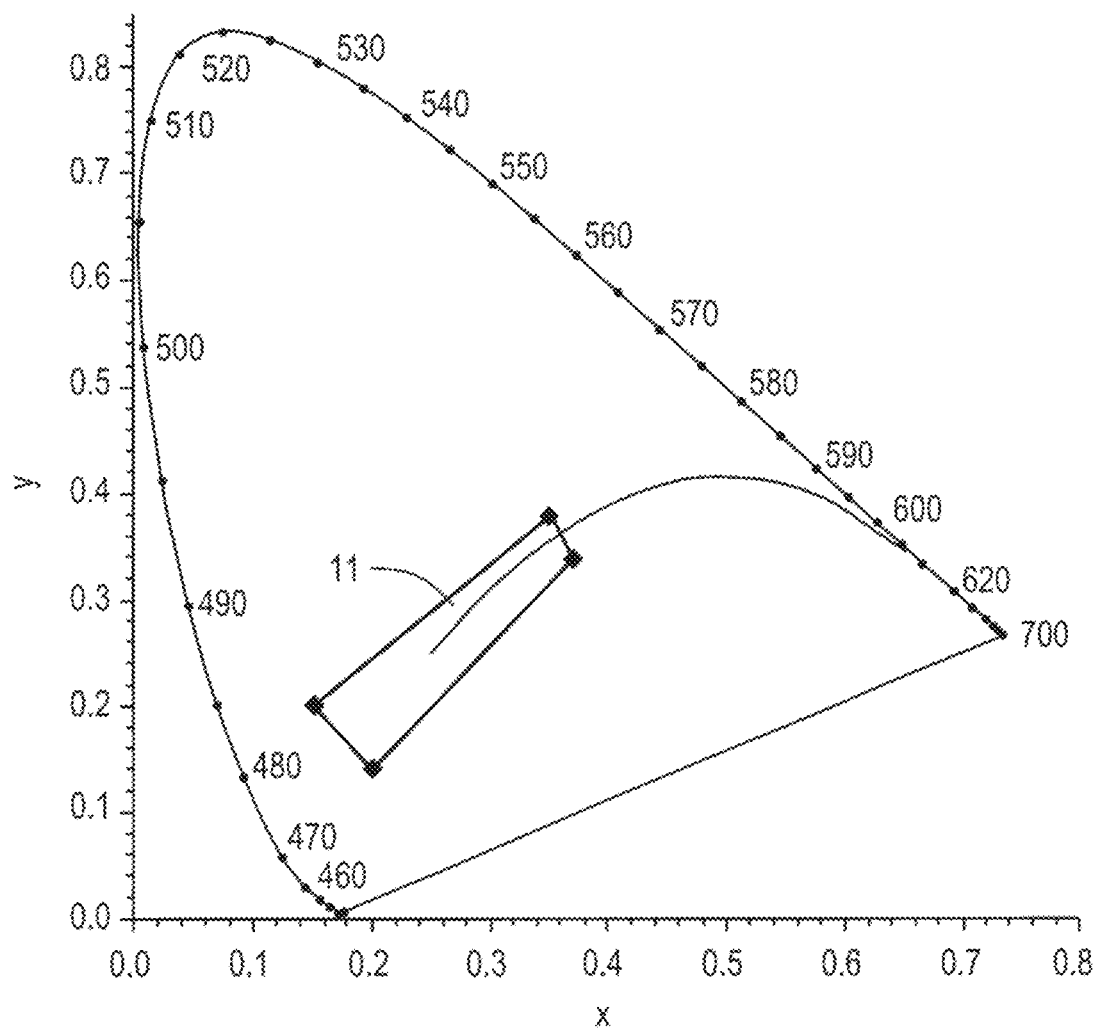
FIG. 1 depicts (on a 1931 CIE Chromaticity Diagram) a region within which is located a first representative range of color points for a first light engine for use in light fixtures in accordance with the present inventive subject matter.
Figure 2:
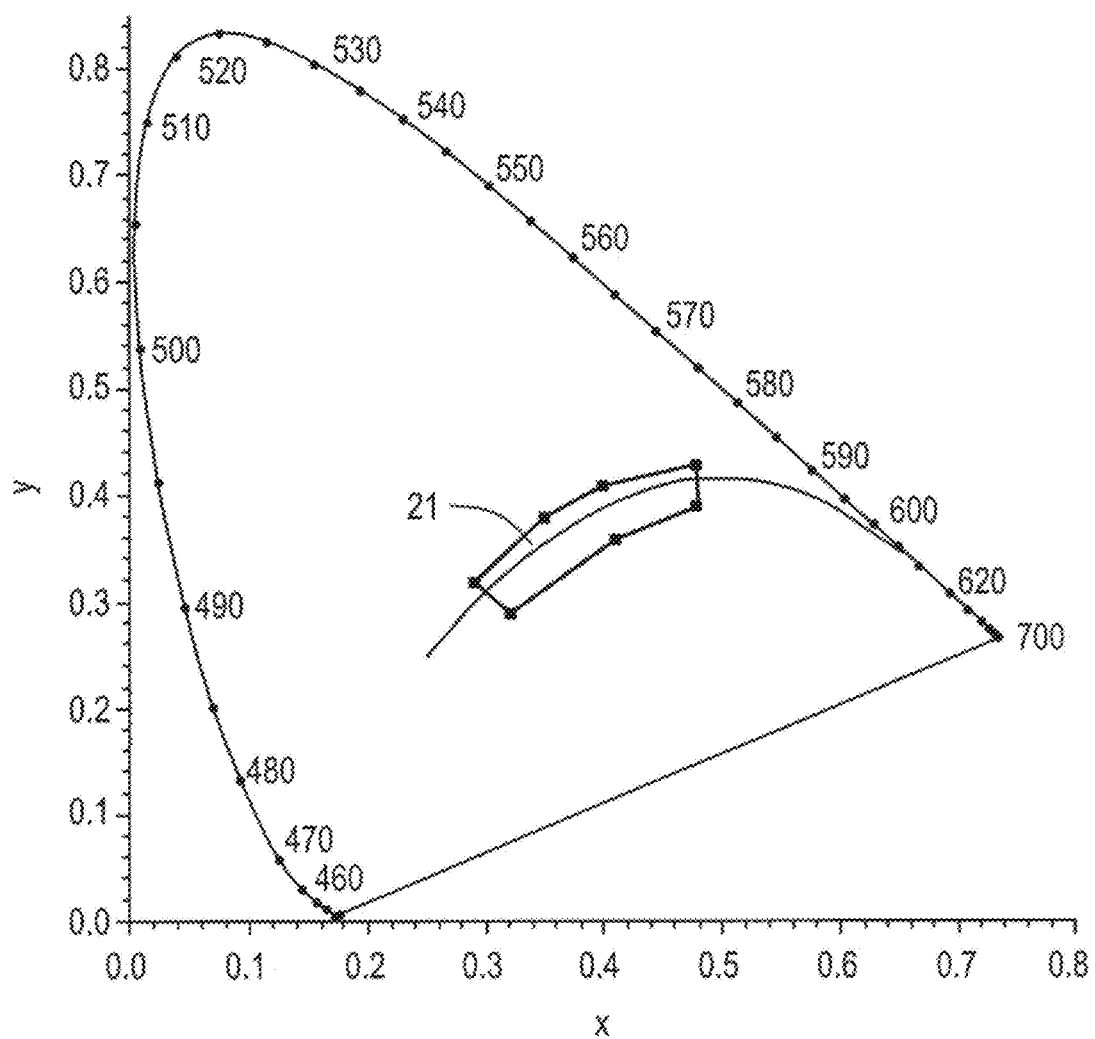
FIG. 2 depicts (on a 1931 CIE Chromaticity Diagram) a region within which is located a first representative range of color points for a second light engine for use in light fixtures in accordance with the present inventive subject matter.
Figure 3A:
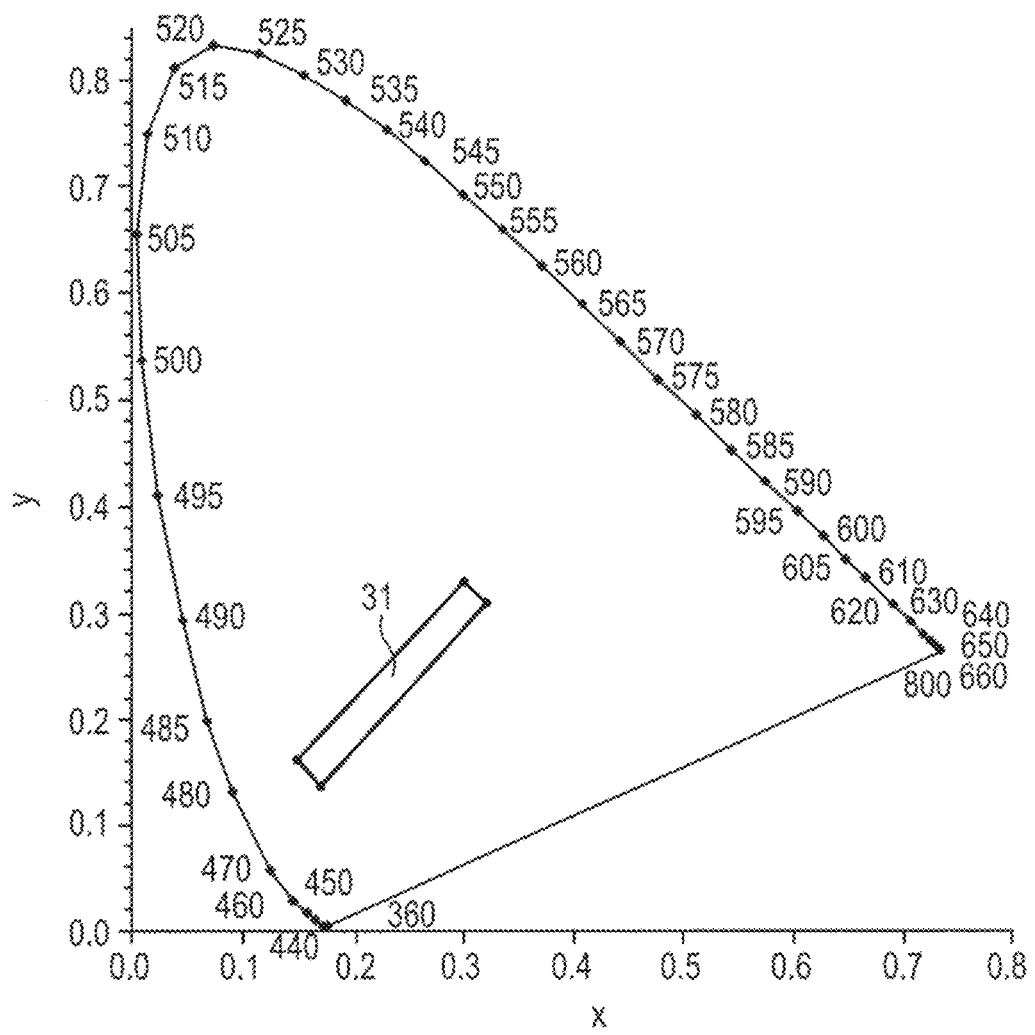
FIG. 3A depicts (on a 1931 CIE Chromaticity Diagram) a region within which is located a second representative range of color points for a first light engine for use in light fixtures in accordance with the present inventive subject matter.
Figure 3B:
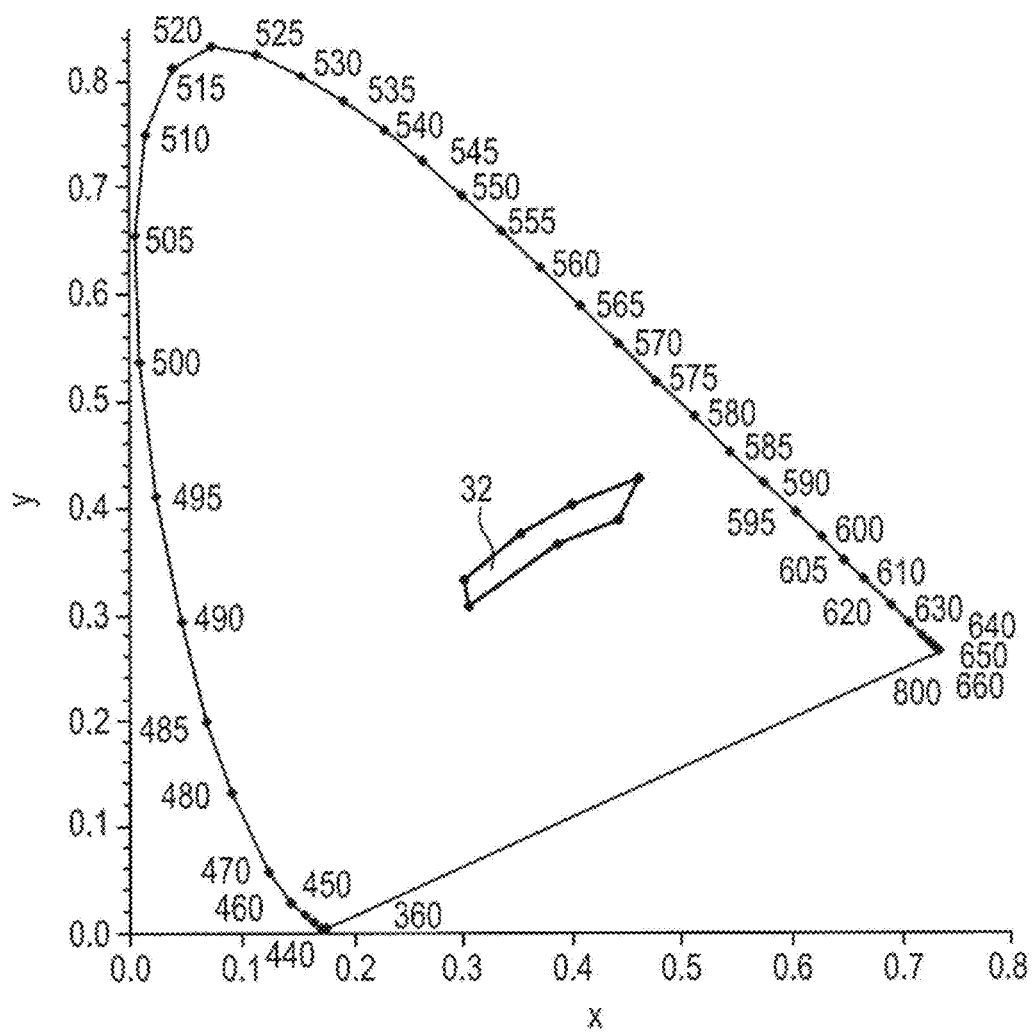
FIG. 3B depicts (on a 1931 CIE Chromaticity Diagram) a region within which is located a second representative range of color points for a second light engine for use in light fixtures in accordance with the present inventive subject matter.

In some embodiments of light fixtures in accordance with the first aspect of the present inventive subject matter, including some embodiments that include or do not include any of the features described herein:

the light fixture comprises at least a first light engine and a second light engine;

light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (FIG. 1 is a plot, on a 1931 CIE Chromaticity Diagram, of a region 11 defined as such, i.e., the quadrilateral area with vertices having such x, y coordinates) (and in some embodiments, within a quadrilateral area with vertices having x, y coordinates of (0.32, 0.31), (0.30, 0.33), (0.15, 0.17), and (0.17, 0.14), FIG. 3a being a plot, on a 1931 CIE Chromaticity Diagram, of a region 31 defined as such);

light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (FIG. 2 is a plot, on a 1931 CIE Chromaticity Diagram, of a region 21 defined as such, i.e., the area with vertices having such x, y coordinates) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38), FIG. 3b being a plot, on a 1931 CIE Chromaticity Diagram, of a region 32 defined as such); and the color point (i.e., the combination of x, y color coordinates) of the light exiting the first light engine may be but typically is not the same as the color point of the light exiting the second light engine.

A first group of embodiments within the first aspect of the present inventive subject matter includes light fixtures that comprise at least first and second light engines and a first sidewall, in which:

the first light engine comprises at least a first light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the second light engine is positioned and oriented such that at least some light that exits the second light engine exits the space through the light exit region.

A second group of embodiments within the first aspect of the present inventive subject matter includes light fixtures that comprise a first light engine and at least a first sidewall, in which:

the first light engine comprises at least a first light exit surface;

the first sidewall comprises at least a second light exit surface;

the first sidewall defines a space;

at least a first light exit region is at a boundary of the space;

the first light engine is positioned and oriented such that at least some light that exits the first light exit surface passes through at least part of the space and exits the space through the first light exit region; and the first sidewall is positioned and oriented such that at least some light that exits the second light exit surface exits the space through the light exit region.

A third group of embodiments within the first aspect of the present inventive subject matter includes light fixtures that comprise at least first and second light engines, in which:

the first light engine comprises at least a first light exit surface; and the first and second light engines are positioned and oriented such that at least some light that exits the first light exit surface travels to a region (e.g., in an office or a room) to which at least some light that exits the second light engine travels.

As noted above, each of the first, second and third groups of embodiments in accordance with the first aspect of the present inventive subject matter comprises a first light engine that comprises at least a first light exit surface, and at least a portion of the first light engine (namely, the first light exit surface) resembles a view of the sky, e.g., a blue sky.

In addition, as noted above, in some embodiments in accordance with the first aspect of the present inventive subject matter, light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (such area is plotted in FIG. 1) (and in some embodiments, within a quadrilateral area with vertices having x, y coordinates of (0.32, 0.31), (0.30, 0.33), (0.15, 0.17), and (0.17, 0.14))

Light fixtures in accordance with the first aspect of the present inventive subject matter can, in some embodiments, have only a single light engine that has at least one light exit surface that resembles a view of the sky (i.e., part of the sky), or they can have any number of such light engines. Accordingly, each light engine that comprises a light exit surface that resembles a view of the sky (in light fixtures that comprise more than one such light engine) can have any of the features of a "first light engine" as described herein. In some embodiments, the first light engine is not extremely bright, is blue-ish, is substantially uniform, and the illumination pattern it creates in space beyond the light exit region is substantially non-directional.

Any "first light engine" (i.e., a light engine that comprises at least a first light exit surface that resembles a view of the sky) can have a single light exit surface that resembles a view of the sky or any number of light exit surfaces that each resemble a view of the sky. Accordingly, each light exit surface that resembles a view of the sky (in light engines that comprise more than one such light exit surface) can have any of the features of a "first light exit surface" as described herein.

The first light engine, and the first light exit surface (or surfaces) of the first light engine, can each be of any suitable shape and size, and persons of skill in the art can readily select a suitable shape for the first light engine and a suitable shape for the first light exit surface. For example, the first light engine and/or the first light exit surface can be any combination of flat (or substantially flat), curved (e.g., concave, convex, or a combination of concave regions and convex regions; dome-shaped, elliptical, parabolic), square, rectangular, circular, oval, stepped, of a shape that has a repeating pattern, irregular or random, mosaic, moth's eye, or any other shape. For example, the first light exit surface can be substantially flat and rectangular, substantially flat and square, substantially flat and circular, dome-shaped and rectangular, dome-shaped and square, dome-shaped and circular, etc.

The first light engine can comprise any suitable light engine structure, and persons of skill in the art can readily select such suitable light engine structures. The visible surface of the first light engine can be diffuse, specular or any combination thereof. The expression "specular" is used in accordance with its well-known meaning to refer to mirror-like reflectivity, whereas "diffuse" (in the context of reflectivity) is used to refer to non-mirror-like reflectivity. In some preferred embodiments in accordance with the present inventive subject matter, including some embodiments that include or do not include any of the features described herein, the visible surface of the first light engine has a specular glass-like finish, similar to a clear windowpane.

One representative example of a suitable light engine that can be employed as a first light engine in accordance with the first aspect of the present inventive subject matter is a troffer. Persons of skill in the art are familiar with a wide variety of troffers, and any suitable troffer can be employed. Troffers typically comprise a housing that has one or more reflective surfaces (and/or on which a reflective material is coated, or to which one or more reflective layers is laminated, etc.) and to which one or more light sources is attached. Such troffers often comprise one or more reflective surfaces that are slanted or curved to redirect light (i.e., by reflecting incident light) in a favorable distribution.

Another representative example of a suitable light engine that can be employed as a first light engine in accordance with the first aspect of the present inventive subject matter is an edge-lit panel. Persons of skill in the art are familiar with a wide variety of edge-lit panels, and any suitable edge-lit panel can be employed. As is well known, edge-lit panels typically comprise [1] a reflective housing and/or a reflective surface, [2] a substantially flat waveguide having first and second major surfaces on opposite sides, the waveguide configured to allow light to exit from one major surface more readily than from the other major surface, and [3] a plurality of light sources arranged along one or more of the edges of the waveguide, such that the light sources emit light into the waveguide and the light exits the waveguide through the major surface that faces away from the reflective housing and/or reflective surface (in some cases, including some light that exits the waveguide through a surface other than the major surface that faces away from the reflective housing and/or reflective surface, and [a] is reflected or back into the waveguide, and eventually exits the waveguide through the major surface that faces away from the reflective housing and/or reflective surface, or [b] is reflected away from the waveguide). A representative example of an edge-lit panel is similar to a backlight for a computer monitor or a cell phone backlight, and comprises one or more light sources (e.g., light emitting diodes) that emit light of any color or colors, a back reflector, a light guide panel, optionally one or more diffusion films and optionally one or more optical films (see also the discussion below in connection with FIG. 4); in some embodiments in accordance with the present inventive subject matter, such an edge-lit panel can be modified by removing the back reflector, whereby light can travel through the edge-lit panel, i.e., entering through a back surface of the edge-lit panel and exiting through a front surface of the edge-lit panel, in addition to light emitted by light sources (e.g., light emitting diodes) along an edge or edges of the panel (e.g., where a first light engine is positioned between a second light engine and a first light exit region as defined herein). In any light fixture in accordance with the present inventive subject matter in which an edge-lit panel is employed, a diffusion film (or plural diffusion films) is/are optional and an optical film (or plural optical films) is/are optional (unlike in the case of displays where diffusion films and optical films are essential).

In addition, in light fixtures in accordance with the present inventive subject matter in which an edge-lit panel is employed, light extraction elements that serve in the role of diffusion films (i.e., that provide or enhance diffusion) can optionally be fabricated directly into a light guide panel, and/or onto one or more surfaces of a light guide panel. A representative example of an edge-lit panel that is suitable for use in light fixtures in accordance with the present inventive subject matter is an Essentia flat panel available from Cree, Inc., Durham, N.C. (modified to include LEDs selected in accordance with the present description).

FIG. 4 schematically depicts a representative example of an edge-lit panel 40. Referring to FIG. 4, the edge-lit panel 40 comprises a plurality of LEDs 41, a back reflector 42, a light guide panel 43, a plurality of diffusion films 44 (optional) and a plurality of optical films 45 (optional).

In general, in light fixtures in accordance with the present inventive subject matter in which an edge-lit panel is employed and in which extraction elements are provided, extraction elements in/on the light guide panel and the films may be engineered in ways known to skilled practitioners so as to deliver any desired light distribution. In the case of the first light engine (i.e., the sky) especially desirable light distributions include Lambertian distributions or distributions oriented more perpendicular to the panel.

Another representative example of a suitable light engine that can be employed as a first light engine in accordance with the first aspect of the present inventive subject matter is a direct-lit panel, also known as a back-lit panel. Persons of skill in the art are familiar with a wide variety of direct-lit panels, and any suitable direct-lit panel can be employed. A representative example of a direct-lit panel comprises one or more light sources (e.g., LEDs) that emit light of any color or colors, a back reflector, an optical gap, a diffuser plate, optionally one or more diffusion films and optionally one or more optical films (see also the discussion below in connection with FIG. 5).

Representative examples of back-lit panels that are suitable for use in light fixtures in accordance with the present inventive subject matter are back-lit panels in the LR series available from Cree, Inc., Durham, N.C. (modified to include LEDs selected in accordance with the present description).

FIG. 5 schematically depicts a representative example of a back-lit panel 50. Referring to FIG. 5, the back-lit panel 50 comprises a plurality of LEDs 51, a back reflector 52, an optical gap 53, a diffuser plate 54, a plurality of diffusion films 55 (optional) and a plurality of optical films 56 (optional).

In any light fixture in accordance with the present inventive subject matter in which a back-lit panel is employed, a diffusion film (or plural diffusion films) is/are optional, and an optical film (or plural optical films) is/are optional.

Another representative example of a suitable light engine that can be employed as a first light engine in accordance with the first aspect of the present inventive subject matter is a side-lit panel. People of skill in the art are familiar with a wide variety of side-lit panels, and any suitable side-lit panel can be employed. A representative example of a side-lit panel comprises one or more light sources (e.g., LEDs) that emit light of any color or colors, a back reflector, an optical gap, a diffuser plate, optionally one or more diffusion films and optionally one or more optical films.

FIG. 6 schematically depicts a representative example of a side-lit panel 60. Referring to FIG. 6, the side-lit panel 60 comprises a plurality of LEDs 61, a back reflector 62, an optical gap 63, a diffuser plate 64, a plurality of diffuser films 65 (optional) and/or a plurality of optical films 65 (optional).

In any light fixture in accordance with the present inventive subject matter in which a side-lit panel is employed, a diffusion film (or plural diffusion films) is/are optional, and an optical film (or plural optical films) is/are optional.

As noted above, in some embodiments in accordance with the first aspect of the present inventive subject matter, the first light engine comprises at least a first light exit surface that resembles a sky, e.g., a blue sky. In some embodiments in accordance with the present inventive subject matter, including some embodiments that include or do not include any of the features described herein, the first light engine comprises at least a first light exit surface that resembles a sky that is other than a typical blue sky, e.g., the first light exit surface can resemble a light blue sky, a deep blue sky, an overcast sky, a partly cloudy sky, a stormy sky, etc.

In some embodiments in accordance with the first aspect of the present inventive subject matter, including some embodiments that include or do not include any of the features described herein, the color point of light that exits from the first light engine (or from a region or from respective regions thereof) can be changeable, e.g., based on the time of day, user input or actual conditions (e.g., a user can input a color point) of light to be delivered by the first light engine, or by one or more respective regions of the first light engine), and/or the color point (of the first light engine or respective regions of the first light engine) can automatically change over the course of a day. For example, the first light engine, or respective regions of the first light engine, can deliver light, the color point(s) of which automatically change, over the course of a day, along a curve on a CIE Chromaticity Diagram, e.g., along the blackbody locus (or near it), for example decreasing the correlated color temperature over the course of the day or altering other color characteristics of light delivery.

In some embodiments in accordance with the present inventive subject matter, including some embodiments that include or do not include any of the features described herein, the image of a sky that is viewable can be changeable, e.g., based on the time of day, user input, input from one or more sensors, or any other input. For example, the appearance of the first light exit surface of a first light engine can be adjusted (e.g., selected from among a number of designed images) based on sensing of actual conditions, based on user input (e.g., a user can input a type of sky image to be displayed), based on the time of day (e.g., the sky image can automatically change over the course of a day, such as from morning sky, to mid-day sky, to afternoon sky, to late-afternoon sky, to dusk, etc.), based on a report of actual conditions (e.g., actual conditions can be reported wirelessly or via a wired connection to the light fixture to cause the first light engine to present a sky image that correlates to actual conditions), based on images captured by a camera (e.g., a remote camera can capture images which are transmitted by wire or wirelessly to the light fixture and those actual images can be reproduced by the first light engine), etc. There exist a wide variety of components, apparatus or systems that are configured so as to have one or more light exit surfaces that display an image (which can be unchanging or which can change with any desired frequency). Representative examples of such components, apparatus or systems include (and are not limited to) LED panels with LED backlighting, plasma displays, LED displays, OLED displays, CRT displays, rear-projection screens, etc.

As noted above, each of the first, second and third groups of embodiments in accordance with the first aspect of the present inventive subject matter comprises a second light engine, and light exiting from the second light engine has one or more characteristics that resemble that (or those) of at least a portion of light emitted by (and received from) the sun.

Light fixtures in accordance with the first aspect of the present inventive subject matter can, in some embodiments, have only a single light engine that has one or more characteristics that resemble that (or those) of at least a portion of light emitted by (and received from) the sun, or they can have any number of such light engines. Accordingly, each light engine that has one or more characteristics that resemble that (or those) of at least a portion of light emitted by (and received from) the sun can have any of the features of a "second light engine" as described herein. Thus, light fixtures in accordance with the first aspect of the present inventive subject matter can have two or more light engines that have features of a "second light engine" as described herein.

As noted above, in some embodiments in accordance with the first aspect of the present inventive subject matter, light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (such area is plotted in FIG. 2 (and in some embodiments, within an area having vertices having x, y coordinates of (0.30, 0.34), (0.30, 0.30), (0.39, 0.36), (0.45, 0.39), (0.47, 0.43), (0.40, 0.41), and (0.35, 0.38)). That is to say, the light exiting the second light engine is yellow-ish to orange-ish white, and thus resembling the sun.

The second light engine can be of any suitable shape, and persons of skill in the art can readily select a suitable shape for the second light engine.

The second light engine can be any suitable size, and persons of skill in the art can readily select a suitable size.

The second light engine can comprise any suitable structure from which light exits, and persons of skill in the art can readily select such suitable structures.

In some embodiments in accordance with the present inventive subject matter, the second light engine has directionality, i.e., the direction or directions in which at least a portion of light that exits the second light engine is selected by features of elements in the second light engine and/or by orientation of such features (and/or by features of one or more other components in the light fixture that achieve selected directionality for light that exits the second light engine). Persons of skill in the art are familiar with, and are readily capable of, providing light engines that achieve specific directionality characteristics for exiting light (as well as components for altering directionality characteristics for light that has exited such light engines), and all such light engines and components are encompassed in the present description.

A representative example of a suitable device that can be employed as a second light engine in accordance with some embodiments of the present inventive subject matter is a downlight (e.g., a flood light or a spotlight). Persons of skill in the art are familiar with a wide variety of downlights, and any suitable downlight can be employed.

Another representative example of a suitable device that can be employed as a second light engine in accordance with some embodiments of the present inventive subject matter is an edge-lit panel (see the above discussion of edge-lit panels, as well as the discussion below in reference to FIG. 4). Such edge-lit panels can provide selected directionality for light that exits the second light engine, e.g., as discussed above with regard to FIG. 4, edge-lit panels can include specific elements, such as waveguides and/or films, to provide specific directionality features, i.e., to deliver one or more portions of light in particular directions and/or to achieve specific directional characteristics. In some embodiments in accordance with the present inventive subject matter, such an edge-lit panel can be modified by removing the back reflector, whereby light can travel through the edge-lit panel, i.e., entering through a back surface of the edge-lit panel and exiting through a front surface of the edge-lit panel, in addition to light emitted by light sources (e.g., LEDs) along an edge or edges of the panel (e.g., where a second light engine is positioned between a first light engine and a first light exit region as defined herein).

Another representative example of a suitable device that can be employed as a second light engine in accordance with some embodiments of the present inventive subject matter is a direct-lit panel (see the above discussion of direct-lit panels, as well as the discussion below in reference to FIG. 5).

Another representative example of a suitable device that can be employed as a second light engine in accordance with some embodiments of the present inventive subject matter is a side-lit panel (see the above discussion of side-lit panels, as well as the discussion below in reference to FIG. 6).

In some embodiments in accordance with the present inventive subject matter, including some embodiments that include or do not include any of the features described herein, the color point of light and/or wavelength distribution (e.g., selected from among a number of designed wavelength distributions) exiting from the second light engine (or from a region or from respective regions thereof) is changeable, e.g., based on the time of day, user input, input from one or more sensors, or any other input. For example, the color point and/or wavelength distribution of light exiting the second light engine can be adjusted based on sensing of actual conditions, based on user input (e.g., a user can input a color point and/or a wavelength distribution to be delivered), based on the time of day (e.g., the color point and/or wavelength distribution can automatically change over the course of a day). For example, the second light engine, or respective regions of the second light engine, is/are such that the color point(s) and/or wavelength distribution of light that exits therefrom automatically change, over the course of a day, according to one or more designed programs.

As discussed above, some embodiments of light fixtures in accordance with the first aspect of the present inventive subject matter comprise at least a first sidewall.

Some embodiments of light fixtures in accordance with the first aspect of the present inventive subject matter have no sidewall, some have only a single sidewall, and some have more than one sidewall. The sidewall in any light fixtures that have a single sidewall, or any of the sidewalls in any light fixtures that have two or more sidewalls, can have any of the features of a "first sidewall" as described herein. Since some embodiments have no sidewall, reference herein to "the first sidewall" or the like relates only to embodiments that have at least a first sidewall, and does not indicate that every embodiment has a sidewall.

The first sidewall can comprise only a single sidewall element, or it can comprise any number of sidewall elements (in such cases, the first sidewall is the combination of such multiple sidewall elements).

The first sidewall can be of any suitable size and shape.

In some embodiments in accordance with the present inventive subject matter, including some embodiments that include or do not include any of the features described herein, the first sidewall is annular. The expression "annular", as used herein, means a structure that extends around an unfilled region, and which can otherwise be of any general shape, and any cross-sections can be of any shape. For example, "annular" encompasses ring-like shapes which can be defined by rotating any shape about an axis in the same plane as, but spaced from, the shape (one example being where the shape is a rectangle with rounded edges, and a center of the rectangle is a constant distance from a single point on the axis throughout the entire rotation, and where at each stage during the rotation, the rectangle lies in a plane in which the axis also lies; such a shape would be a "circular annular" shape with a uniform substantially rectangular cross-section). "Annular" likewise encompasses shapes which can be defined by rotating a square (or any other two-dimensional shape) about an axis in the same plane as, but spaced from, the square. "Annular" likewise encompasses shapes that can be defined by moving any shape from a first position and orientation, through space along any path without ever moving to a position where part of the shape occupies a space previously occupied by any part of the shape, and eventually returning to the first position and orientation. "Annular likewise encompasses shapes that can be defined by moving any shape from a first position and orientation, through space along any path without ever moving to a position where part of the shape occupies a space previously occupied by any part of the shape, and eventually returning to the first position and orientation, and where the shape and size of the shape being moved can be altered at any location, and any number of times, during its movement.

In some embodiments in accordance with the present inventive subject matter, including some embodiments that include or do not include any of the features described herein, the first sidewall can be substantially rectangular annular and of substantially uniform rounded rectangular cross-section (edges where surfaces meet are rounded, i.e., such that a cross-section has four rounded corners, i.e., a shape that resembles a rectangular cardboard box with the top and bottom removed).

In some embodiments in accordance with the present inventive subject matter, including some embodiments that include or do not include any of the features described herein, the first sidewall can be substantially rectangular annular and of substantially uniform rectangular cross-section (cross-section has four substantially non-rounded corners, e.g., about 90 degrees each).

In some embodiments in accordance with the present inventive subject matter, including some embodiments that include or do not include any of the features described herein, the first sidewall (or portions of the first sidewall, or sidewall elements that together make up the first sidewall) is substantially vertical, and/or cross-sections of at least a portion of the first sidewall taken perpendicular to a vertical axis (or to any line segment) are substantially uniform, and/or a space defined by the first sidewall would have first and second surfaces that are parallel to each other and perpendicular to regions of the sidewall (e.g., a cubical or orthorhombic space).

In other embodiments in accordance with the present inventive subject matter, including some embodiments that include or do not include any of the features described herein, the first sidewall (or portions of the first sidewall, or sidewall elements that together make up the first sidewall) is slanted (angled) or curved, e.g., the first sidewall defines a three-dimensional space that is a truncated cone, a truncated pyramid, etc., or cross-sections of at least a portion of the first sidewall taken perpendicular to a vertical axis (or to any line segment) increase linearly, geometrically or non-linearly in one direction along the axis or line segment.

In some embodiments in accordance with the present inventive subject matter, including some embodiments that include or do not include any of the features described herein, the first sidewall is configured to be mounted in any suitable space, e.g., a hole in a ceiling structure (or the first sidewall is connected to a housing or is part of a housing that can be mounted in any suitable space), e.g., the external shape of the first sidewall corresponds to the internal shape of a hole in a conventional ceiling structure. In some situations, a hole in a ceiling structure can be made to be of any suitable size.

In some embodiments in accordance with the present inventive subject matter, including some embodiments that include or do not include any of the features described herein, the first sidewall is configured to be mounted in a ceiling of a commercial building, e.g., in a two foot by one foot space or in a one foot by one foot space (or multiples, e.g., two one foot by one foot housings can be mounted in a one foot by two foot space, etc.)(or the first sidewall is connected to a housing or is part of a housing that is configured to be mounted in such a ceiling.

The first sidewall defines (or at least partly defines) a space. In other words, at least a portion of the boundary of the space is defined by at least a portion of the first sidewall. In some embodiments in accordance with the present inventive subject matter, including some embodiments that include or do not include any of the features described herein, at least some points within the space are along respective line segments that connect respective points on the first sidewall (e.g., on opposite sides of the space). In some embodiments in accordance with the present inventive subject matter, including some embodiments that include or do not include any of the features described herein, the first sidewall is annular, and the space comprises every point that is located between a respective pair of points on the first sidewall (e.g., if the first sidewall is circular annular, the space is cylindrical; if the first sidewall is rectangular annular, the space is a rectilinear prism, etc.). In some embodiments in accordance with the present inventive subject matter, including some embodiments that include or do not include any of the features described herein, the first sidewall and one or more other structure(s) define the space, i.e., each point in the space is between two respective points, each of which is on the first sidewall or on one of the one or more other structure(s).

The first sidewall can comprise [1] one or more regions from which light exits into the space, [2] one or more regions that reflect light and/or [3] one or more regions that do not substantially reflect light and from which light does not exit (e.g., a sidewall can be partially transmitting and partially reflecting). That is, the first sidewall can reflect light, transport light, transmit light and/or emit light.

In some embodiments in accordance with the present inventive subject matter, to an observer, a majority of the light exiting the light fixture appears to come from the sidewall (in other words, the sidewall appears to be illuminated). In some of such embodiments, the sidewall appears to have a significantly different color from light that exits from the first light engine (i.e., resembling the sky). This contrast can be very effective in providing the illusion of a skylight.

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun; and:

[1] a first group of embodiments within the first aspect of the present inventive subject matter includes light fixtures that comprise at least first and second light engines and a first sidewall, in which:
  the first light engine comprises at least a first light exit surface;
  the first sidewall defines a space;
  at least a first light exit region is at a boundary of the space;
  the first light engine is positioned and oriented such that at least some light that exits the first light exit surface passes through at least part of the space and exits the space through the first light exit region; and
  the second light engine is positioned and oriented such that at least some light that exits the second light engine exits the space through the light exit region;

[2] a second group of embodiments within the first aspect of the present inventive subject matter includes light fixtures that comprise a first light engine and at least a first sidewall, in which:
  the first light engine comprises at least a first light exit surface;
  the first sidewall comprises at least a second light exit surface;
  the first sidewall defines a space;
  at least a first light exit region is at a boundary of the space;
  the first light engine is positioned and oriented such that at least some light that exits the first light exit surface passes through at least part of the space and exits the space through the first light exit region; and
  the first sidewall is positioned and oriented such that at least some light that exits the second light exit surface exits the space through the light exit region, and

[3] a third group of embodiments within the first aspect of the present inventive subject matter includes light fixtures that comprise at least first and second light engines, in which:
  the first light engine comprises at least a first light exit surface;
  the first and second light engines are positioned and oriented such that at least some light that exits the first light exit surface travels to a region (e.g., in an office or a room) to which at least some light that exits the second light engine travels.

In some embodiments in accordance with the first group of embodiments within the first aspect of the present inventive subject matter, the first sidewall comprises an interior wall that extends around and defines a space, and the entirety of the surface (or surfaces) of the interior wall of the first sidewall is/are substantially reflective; in some embodiments in accordance with the first group or the third group within the first aspect of the present inventive subject matter, light exits from a portion of the first sidewall into the space, i.e., the space defined at least in part by the first sidewall; in some embodiments in accordance with the first or the third group within the first aspect of the present inventive subject matter, light exits (into a space) from the entirety of a surface of the first sidewall that extends around and defines the space; in some embodiments in accordance with the first group or the third group within the first aspect of the present inventive subject matter, one portion of an interior wall of the first sidewall (that defines an internal space) is reflective, and light exits from another portion of the first sidewall into the space, etc.

There are many ways that a sidewall can be configured such that it has one or more light exit surface (i.e., such that light exits from at least part of its surface or from at least part of one of its surfaces). For example, a sidewall can be configured such that it has one or more light exit surfaces by:
  the sidewall being light-transporting (e.g., translucent or transparent) and comprising one or more light sources within the sidewall (e.g., embedded in it) or behind the sidewall;
  the sidewall comprising one or more waveguides to which light can be delivered,
  the sidewall comprising one or more waveguides and one or more light sources that deliver light to such waveguide(s);
  the sidewall being light-transporting and comprising one or more waveguides (to which light can be delivered) within the sidewall or behind the sidewall;
  the sidewall being light-transporting, the sidewall comprising one or more waveguides within the sidewall or behind the sidewall, and the sidewall comprising one or more light sources that deliver light to the one or more waveguides, etc.

Representative examples of suitable sidewalls that have one or more light exit surface (or sidewall elements making up such sidewalls, or components in such sidewalls) include:
  waveguides (to which light is delivered), optionally with one or more translucent films, translucent coatings and/or paint compositions applied to any portion or portions thereof;
  any suitable transparent or translucent material or materials (i.e., a material or materials that permits/permit at least some incident light to pass through, e.g., transparent acrylic, a diffuser sheet, frosted glass or acrylic, painted/coated glass or acrylic, and laminates) through which light is delivered;
  a coating (in some cases a white coating) or a film (in some cases a white film), so that light exiting from the sidewall is distributed more evenly and so that, from outside the light fixture, the light that exits from the sidewall looks like "reflected" light from the sun (rather than light from an artificial light source);
  a light-emitting panel (e.g., an OLED panel);
  any suitable light sources or light sources; and
  any combinations thereof (e.g., a combination of a waveguide and a light source that delivers light to the waveguide; a combination of an acrylic sheet, a white coating on the acrylic sheet and a light source behind the acrylic sheet; etc.).

Light that exits from a light exit surface of a sidewall can have any suitable characteristics. In some embodiments in accordance with the present inventive subject matter, including some embodiments that include or do not include any of the features described herein, light that exits from a light exit surface of a sidewall has one or more characteristics that are described herein for the light that exits from the second light engine (including characteristics such as its color point as well as how it can be adjusted).

There are many ways that a sidewall can be configured such that it is reflective in at least part of its surface. Such reflectivity can be diffuse, specular or any combination thereof. The expression "specular" is used in accordance with its well-known meaning to refer to mirror-like reflectivity, whereas "diffuse" (in the context of reflectivity) is used to refer to non-mirror-like reflectivity. Persons of skill in the art are familiar with a wide variety of reflective materials, laminates, coatings, etc., e.g., MCPET (i.e., foamed sheets made of extra-fine, foamed polyethylene terephthalate (PET) available from Furukawa Electric in Japan), and so a detailed discussion of the various reflective materials that can be employed is not necessary. In some embodiments in accordance with the present inventive subject matter, including some embodiments that include or do not include any of the features described herein, the first sidewall, or at least a portion of the first sidewall, can comprise plasterboard or drywall (e.g., Sheetrock).

A sidewall can affect the far-field illumination pattern from the first and/or second light engines in a way that helps create the illusion of light originating from elsewhere (i.e., from the outside sky and sun).

The light sources employed in light fixtures in accordance with the present inventive subject matter (e.g., for a first light engine, a second light engine, or a sidewall in a light fixture in accordance with the first aspect of the present inventive subject matter (including the first group of embodiments, discussed above, and the second and third groups of embodiment, discussed below) or the second aspect of the present inventive subject matter (discussed below), or for generating light in accordance with the third aspect of the present inventive subject matter) can comprise any suitable light source (or light sources). Persons of skill in the art are familiar with, and have ready access to, a wide variety of light sources that emit light in different respective colors, and any suitable light sources can be employed. In any light fixtures, that comprise more than one light source, the light sources can be similar or different, or can include some light sources that are similar and some that are not). Representative examples of types of light sources include light emitting diodes (LEDs), (inorganic or organic, including polymer light emitting diodes (PLEDs)), incandescent lights, fluorescent lamps, laser diodes, thin film electroluminescent devices, light emitting polymers (LEPs), halogen lamps, high intensity discharge lamps, electron-stimulated luminescence lamps, etc.

Although the invention could be made using any of these light sources, or a combination of these light sources, LEDs are particularly convenient light sources because LEDs are (a) available in many colors of interest to the invention, (b) compact, (c) energy efficient.

Many of the embodiments are described as comprising LEDs, and much other disclosure below refers to LEDs, but the present inventive subject matter is not limited to any particular type of light source, i.e., as noted above, lighting fixtures in accordance with the present inventive subject matter can comprise any suitable light source (or light sources).

Embodiments in accordance with the present inventive subject matter are described herein in detail in order to provide exact features of representative embodiments that are within the overall scope of the present inventive subject matter. The present inventive subject matter should not be understood to be limited to such detail.

Embodiments in accordance with the present inventive subject matter are also described with reference to cross-sectional (and/or plan view) illustrations that are schematic illustrations of idealized embodiments of the present inventive subject matter. As such, variations from the shapes of the illustrations as a result, for example, of manufacturing techniques and/or tolerances, are to be expected. Thus, embodiments of the present inventive subject matter should not be construed as being limited to the particular shapes of regions illustrated herein but are to include deviations in shapes that result, for example, from manufacturing. For example, a molded region illustrated or described as a rectangle will, typically, have rounded or curved features. Thus, the regions illustrated in the figures are schematic in nature and their shapes are not intended to illustrate the precise shape of a region of a device and are not intended to limit the scope of the present inventive subject matter.

FIGS. 7, 8, 11-16 and 21-23 schematically depict various embodiments within the scope of the first aspect of the present inventive subject matter. In each of these embodiments, the light fixture is depicted (cross-sectionally) mounted in a ceiling, such that the mean distribution of light exiting the light fixture is generally downward, and the descriptions of spatial relationships is described herein in reference to such orientation (e.g., with terms such as "bottom," "upper," "below," "above," etc.). The light fixtures depicted in FIGS. 7, 8, 11-16 and 21-23 (like all the light fixtures in accordance with the present inventive subject matter) can be mounted in any orientation (and in any suitable structure), e.g., in a vertical wall, in a floor, in a slanted structure, etc., and spatial relationships in such situations would be altered accordingly (e.g., a first structure that is below a second structure if the light fixture is mounted in a ceiling with the mean distribution of light exiting the light fixture generally downward would instead be above the second structure if the light fixture were mounted in a floor with the mean distribution of light exiting the light fixture generally upward).

In addition, in each of the embodiments depicted in FIGS. 7, 8, 11-16 and 21-23, light rays are depicted. The depictions of light rays are not intended to be specific, and are instead intended merely to indicate that light is exiting from respective light engines, and that it travels into the room schematically depicted below each of the light fixtures. Characteristics of light distribution with respect to some specific embodiments are described textually in more detail herein.

The expression "group of embodiments," as used herein, refers to any and all embodiments that have the combination elements and/or features specified. For example, the "first group of embodiments within the first aspect of the present inventive subject matter" refers to embodiments that are light fixtures (artificial skylights), that comprise at least first and second light engines and a first sidewall, in which:

at least a portion of the first light engine resembles a sky (e.g., a surface of the first light engine looks like the sky to a viewer), light exiting from the second light engine has one or more characteristics that resemble that (or those) of at least a portion of light emitted by (and received from) the sun, the first light engine comprises at least a first light exit surface, the first sidewall defines a space, at least a first light exit region is at a boundary of the space, the first light engine is positioned and oriented such that at least some light that exits the first light exit surface passes through at least part of the space and exits the space through the first light exit region, and the second light engine is positioned and oriented such that at least some light that exits the second light engine exits the space through the light exit region.

Similarly, the second group of embodiments within the first aspect of the present inventive subject matter, the third group of embodiments within the first aspect of the present inventive subject matter, etc., encompass any and all embodiments that have the respective combination of features specified.

As discussed above, a first group of embodiments within the first aspect of the present inventive subject matter includes light fixtures that comprise at least first and second light engines and a first sidewall, in which the first sidewall defines a space. FIGS. 7, 8 and 11-15 schematically depict various embodiments within the scope of the first group within the first aspect of the present inventive subject matter.

Referring to FIG. 7, there is shown a light fixture 70 that comprises a first light engine 71, a second light engine 72 and a first sidewall 73 that defines a space (in the form of the recessed box, i.e., a horizontal plane through the first sidewall 73 would intersect the sidewall 73 in a hollow square pattern). The light fixture 70 is mounted in a ceiling 74 which adjoins a wall 75. A beam of light 76 exits from the second light engine 72.

The first light engine 71 comprises an edge-lit panel (or a direct-lit panel), and the second light engine 72 comprises a downlight. The first sidewall 73 comprises at least a first sidewall aperture 77. The second light engine 72 is positioned and oriented such that at least a portion of it extends through the first sidewall aperture 77 and/or light that exits the second light engine 72 passes through the first sidewall aperture 77.

In some embodiments that comprise one or more sidewall apertures, including some embodiments that include or do not include any of the features described herein, one or more screen structure(s) is/are provided to block from view at least part of the second light engine(s). Such screen structure(s), if provided, can be of any suitable material and can be of any suitable size and shape. In embodiments that comprise one or more screen structure(s), the screen structure(s) can cover as much of the second light engine(s) as desired, and/or the screen structure(s) can partially or completely cover the sidewall aperture(s).

FIG. 8 depicts a light fixture 80 that is similar to the light fixture 70 depicted in FIG. 7, except that the light fixture 80 also comprises a screen 88 that covers a sidewall aperture 87, and the light fixture 80 comprises a second light engine 82 that is behind the screen 88, i.e., no portion of the second light engine 82 extends through the sidewall aperture 87. Thus, the light fixture 80 comprises a first light engine 81, the second light engine 82 and a first sidewall 83 that defines a space in the form of the recessed box. The light fixture 80 is mounted in a ceiling 84 which adjoins a wall 85. A beam of light 86 exits from the second light engine 82. The first light engine 81 comprises an edge-lit panel (or a direct-lit panel or a side-lit panel), and the second light engine 82 comprises a downlight. The first sidewall 83 comprises the sidewall aperture 87. The second light engine 82 is positioned and oriented such that at least some light that exits the second light engine 82 passes through the first sidewall aperture 87 and through the screen 88.

In embodiments in which one or more screen structure(s) is/are provided, the screen structure can have any suitable properties. In some embodiments in which one or more screen structure(s) is/are provided, the screen structure allows passage of a large percentage of light within a first wavelength range and allows passage of a much lower percentage of light within a second wavelength range, e.g., the screen structure filters very little of the light that exits the second light engine and it filters a high percentage of light of other wavelengths. In some embodiments, a screen structure can be provided which reduces glare of light that exits from the second light engine.

The bottom surface of the first light engine 71 can be any desired distance above the ceiling 74 (e.g., about six to about ten inches above the ceiling 74—in respective exemplary embodiments corresponding to this embodiment, the bottom surface of the first light engine 71 can be about six inches above the ceiling 74, the bottom surface of the first light engine 71 can be about ten inches above the ceiling 74, or the bottom surface of the first light engine 71 can be any distance between about six inches and about ten inches above the ceiling 74).

The beam of light 76 that exits from the second light engine 72 provides a sharp shadow and illuminates a portion of the wall 75 (providing an effect in the nature of a wall wash).

The overall visual impression created by some embodiments in accordance with the present inventive subject matter, e.g., the embodiment depicted in FIG. 7 (and other embodiments herein) is similar to the visual impression created by light delivered from a conventional skylight on a sunny day. FIG. 9A schematically depicts the visual impression created by a conventional skylight, and FIGS. 9B and 9C depict the visual impression created by representative embodiments of light fixtures in accordance with the present inventive subject matter (e.g., the embodiment depicted in FIG. 7), from a location below and to the side of the light fixture (FIG. 9B) and from a location below the light fixture (FIG. 9C). Additional similarities between [1] the visual impression created by light delivered from some embodiments of light fixtures in accordance with the present inventive subject matter and [2] the visual impression created by light delivered from conventional skylights can include:

light from the second light engine delivers yellow-ish white light and/or shadows (on a nearby wall or walls) in a way that is similar to yellowish-white light and/or shadows (on a nearby wall or walls) delivered from the sun in a conventional skylight;

a bottom surface of the light fixture (e.g., the bottom of the first light engine 71 in the embodiment depicted in FIG. 7) when viewed directly appears uniform, blue-ish white, similar to a view if looking at the sky through a conventional skylight;

overall (i.e., average) color of light delivered to the room from the light fixture is less yellow and more white in comparison the light delivered to a nearby wall (or walls), similar to the light delivered from a mixture of light from the sun and the sky through a conventional skylight.

FIG. 10 depicts a room in which three light fixtures 100 (each similar to the light fixture 70 depicted in FIG. 7) are mounted in a ceiling 104, providing illumination in a work space and also on a wall 105. The illuminance on table tops in the work space is about 600 lux, and the illuminance on the brightly-lit parts of the wall is about 2700 lux.

FIG. 11 depicts a light fixture 110 that comprises a first light engine 111, a second light engine 112 and a first sidewall 113 that defines a space (in the form of the recessed box). The light fixture 110 is mounted in a ceiling 114 which adjoins a wall 115. The first light engine 111 comprises a troffer, and the second light engine 112 comprises a downlight. In this embodiment, the first light engine 111 is configured to deliver sky blue light.

The troffer 111 comprises at least a first troffer aperture 117. The second light engine 112 is positioned and oriented such that at least a portion of it extends through the first troffer aperture 117 and/or light that exits the second light engine 112 passes through the first troffer aperture 117.

In some embodiments that comprise one or more troffer apertures, including some embodiments that include or do not include any of the features described herein, one or more screen structure(s) is/are provided to block from view at least part of the second light engine(s). The description of screen structures above in connection with FIG. 7 is applicable to screen structures that can be employed with regard to troffer apertures, e.g., in the embodiment depicted in FIG. 11.

FIG. 12 depicts a light fixture 120 that comprises a first light engine 121, a second light engine 122 and a first sidewall 123 that defines a space (in the form of the recessed box). The light fixture 120 is mounted in a ceiling 124 which adjoins a wall 125. The first light engine 121 comprises an edge-lit panel or a direct-lit panel, and the second light engine 121 comprises a downlight, and is mounted within the space defined by the first sidewall 123. In this embodiment, the first light engine 121 is configured to deliver sky blue light.

FIG. 13 depicts a light fixture 130 that comprises a first light engine 131, a second light engine 132, a first sidewall 133 that defines a space (in the form of the recessed box), and a diffuser 138. The light fixture 130 is mounted in a ceiling 134 which adjoins a wall 135.

The first light engine 131 comprises an edge-lit panel (or a direct-lit panel), and the second light engine 132 comprises a downlight.

The first sidewall 133 comprises at least a first sidewall aperture 137. The second light engine 132 is positioned and oriented such that at least a portion of it extends through the first sidewall aperture 137 and/or light that exits the second light engine 132 passes through the first sidewall aperture 137. The light fixture 130 is similar to the light fixture 70 depicted in FIG. 7, except that the light fixture 130 comprises a diffuser 138. In some embodiments, the diffuser reduces glare and softens shadows by expanding the distribution of light from the second light engine 132.

In FIG. 13, the diffuser 138 is depicted as being oriented substantially flush with the bottom edge of the first sidewall 133, as having top and bottom substantially flat surfaces, and as being oriented substantially horizontally. The diffuser 138 can instead be mounted in any other suitable orientation, and can be of any other suitable shape (e.g., it can be recessed from the ceiling, i.e., raised somewhat relative to the sidewall). Persons of skill in the art are familiar with a wide variety of diffusers, and any such diffusers can be used in light fixtures in accordance with the present inventive subject matter.

One or more diffusers can be added to any of the embodiments depicted in FIGS. 8, 11 and 12, in a manner similar to the manner in which the diffuser 138 is added to the embodiment depicted in FIG. 7, or in any manner as described above in connection with FIG. 13.

FIG. 14 depicts a light fixture 140 that comprises a first light engine 141, a second light engine 142 and a first sidewall 143 that defines a space (in the form of the recessed box). The light fixture 140 is mounted in a ceiling 144. The first light engine 141 comprises a first edge-lit panel (or a direct-lit panel), and the second light engine 142 comprises a second edge-lit panel with its back reflector removed. In this embodiment, the first light engine 141 is configured to deliver sky blue light. The second light engine 142 is configured to deliver sun-like yellow-ish white light.

In some embodiments in accordance with the present inventive subject matter (including the embodiment depicted in FIG. 14), the far-field light distribution characteristics of the first and second light engines are different from each other. In a representative example of a preferred embodiment, light exiting at high angles (i.e., relative to vertical in FIG. 14) is more yellow-ish white compared to the light directly below the fixture, which is more blue-ish white. In some embodiments, providing a far-field light distribution for the first light engine that differs from a far-field light distribution for the second light engine can be achieved by having different light extraction elements in the first and second light engines, and skilled practitioners are familiar with ways to achieve such differing far-field light distribution (including with different light extraction elements), all of such ways to achieve differing far-field light distribution being included in the present disclosure.

FIG. 15 depicts a light fixture 150 that comprises a first light engine 151, a second light engine 152 and a first sidewall 153 that defines a space (in the form of the recessed box). The light fixture 150 is mounted in a ceiling 154. The first light engine 151 comprises a first edge-lit panel, and the second light engine 152 comprises a second edge-lit panel (or a direct-lit panel). In this embodiment, the first light engine 151 is configured to deliver sky blue light, and has its back reflector removed. Thus, the light fixture 150 is analogous to the light fixture 140, except that in the light fixture 150, the first light engine and the second light engine are switched (i.e., in the light fixture 150, the first light engine is below the second light engine, whereas in the light fixture 140, the second light engine is below the first light engine).

One or more diffusers can be added to either of the embodiments depicted in FIGS. 14 and 15, in a manner similar to the manner in which the diffuser 138 is added to the embodiment depicted in FIG. 7, or in any manner as described above in connection with FIG. 13.

Each of the embodiments depicted in FIGS. 7, 8 and 11-15 comprises a sidewall that does not comprise any light exit surfaces. Any of the sidewalls (and any portion or portions thereof) in any of the light fixtures depicted in FIGS. 7, 8 and 11-15, like the sidewalls in any light fixture disclosed herein that comprises one or more sidewalls, can comprise one or more light exit surfaces, i.e., the sidewall (or one or more of the sidewalls) can be part of a light engine (or parts of light engines), within which light is emitted and such light (or at least part of such light) exits through the light exit surface(s).

In some of the first group of embodiments of light fixtures in accordance with the first aspect of the present inventive subject matter: light exiting the first light engine has a first peak intensity angle relative to a first plane defined by at least three points on the first light exit region, light exiting the second light engine has a second peak intensity angle relative to the first plane; and the first peak intensity angle differs from the second peak intensity angle.

As discussed above, a second group of embodiments within the first aspect of the present inventive subject matter includes light fixtures that comprise at least a first light engine and a first sidewall, in which:

the first light engine comprises at least a first light exit surface;

the first sidewall comprises at least a second light exit surface (i.e., the first sidewall has one or more light exit surfaces);

the first sidewall defines a space;

at least a first light exit region is at a boundary of the space;

the first light engine is positioned and oriented such that at least some light that exits the first light exit surface passes through at least part of the space and exits the space through the first light exit region; and the first sidewall is positioned and oriented such that at least some light that exits the second light exit surface exits the space through the light exit region.

As noted above, the first sidewall comprises at least a second light exit surface. That is, the first sidewall has one or more surfaces through which light exits, e.g., the first sidewall can be part of a light engine within which light is emitted, and such emitted light (or at least part of such emitted light) exits through the light exit surface(s) into the space, and/or the first sidewall can comprise a light-transporting structure (or part of a light-transporting structure) from which light exits into the space, and/or the first sidewall can comprise a light-transmitting structure (or part of a light-transmitting structure) from which light exits into the space. In some preferred embodiments in accordance with the present inventive subject matter, including some embodiments that include or do not include any of the features described herein, the visible surface of the first sidewall has a matte appearance, similar to frosted glass or a matte white-painted surface.

FIG. 16 schematically depicts an embodiment within the scope of the second group within the first aspect of the present inventive subject matter.

FIG. 16 depicts a light fixture 160 that comprises a first light engine 161 and a second light engine in the form of a first sidewall 162 which comprises four light exit surfaces that define an internal space. The light fixture 160 is mounted in a ceiling 164.

The first sidewall 162 is in the form of the recessed box comprising four surfaces, each of which is, in its entirety, a light exit surface.

The first light engine 161 comprises an edge-lit panel (or a direct-lit panel). The first light engine 161 is configured to deliver sky blue light, and the second light engine is configured to deliver light that has one or more characteristics that resemble that (or those) of at least a portion of light emitted by (and received from) the sun.

In representative embodiments that correspond to FIG. 16, the first sidewall 162 can comprise (or be part of) a light engine that comprises one or more light emitters, and light emitted by such light emitter(s) exit through the first sidewall 162 into the space, and/or the first sidewall can comprise a light-transporting structure (or part of a light-transporting structure) from which light exits into the space, and/or the first sidewall can comprise a light-transmitting structure (or part of a light-transmitting structure) from which light exits into the space.

One or more diffusers can be added to any of the embodiments depicted in FIG. 16 (or in any other embodiment in accordance with the second group within the first aspect of the present inventive subject matter), in a manner similar to the manner in which the diffuser 138 in FIG. 13 is added to the embodiment depicted in FIG. 7, or in any manner as described above in connection with FIG. 13.

In the embodiment depicted in FIG. 16, the far-field light distribution characteristics of the first and second light engines are different from each other. In a preferred embodiment corresponding to FIG. 16, the light exiting at high angles (i.e., relative to vertical in the orientation depicted) from the fixture 160, which is mostly light from the second light engine(s) by virtue of geometry, is more yellow-ish white, whereas the light exiting nearer vertical (in the orientation depicted), which is mostly light from the first light engine(s) by virtue of geometry, is more blue-ish white. In addition to the main geometric effects, the light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

In some of the second group of embodiments of light fixtures in accordance with the first aspect of the present inventive subject matter: light exiting the first light engine has a first peak intensity angle relative to a first plane defined by at least three points on the first light exit region, light exiting the at least a first sidewall has a second peak intensity angle relative to the first plane; and the first peak intensity angle differs from the second peak intensity angle.

In the embodiment depicted in FIG. 16, the first sidewall 162, which comprises four light exit surfaces, can provide to the light fixture the following advantageous properties:

the first sidewall 162 has substantially uniform luminance (i.e., there is no obviously artificial light source, e.g., there are no hot spots or patterns of light);

the first sidewall 162 appears as if it is illuminated from afar, rather than comprising an artificial light source (i.e., the first sidewall 162 appears as if sunlight were incident on it from outside a skylight); and light exiting from the first sidewall 162 has a color that is distinctly different from the color of light exiting from the first light engine (which resembles the sky).

In some preferred embodiments, for each surface of the first sidewall, the ratio of the maximum luminance to the minimum luminance is 2.5:1 or less (for example, for each surface of the sidewall, if such surface is conceptually divided into 1000 regions of equal size, the largest luminance in any of such regions is not more than two and a half times the luminance in any other of such regions), and/or the ratio of the maximum luminance of each surface of the first sidewall to the average luminance (averaged across the surface) is 2:1 or less.

In some preferred embodiments, one or more of the four surfaces of the first sidewall may emit little or even no light directly (i.e. only light reflected from elsewhere) to enhance the visual illusion that the first sidewall is being illuminated obliquely by the sun (i.e. one or more of the surfaces appears to be in the shade while the remainder are illuminated.)

FIG. 17 schematically depicts a cross-sectional view of a portion of a sidewall 170 that comprises a first translucent element 171, a light source 172 within the first translucent element 171, and an opaque reflective back panel 173. Emitted light 174 exits from the sidewall 170 (in the embodiment depicted in FIG. 17, the emitted light 174 exits from a side of the sidewall 170 opposite to the side on which the reflective back panel 173 is provided.

FIG. 18 schematically depicts a cross-sectional view of a portion of a sidewall 180 that comprises a first translucent element 181, a light source 182 behind the first translucent element 181, an opaque reflective back wall 183a and opaque reflective side walls 183b, such that light 184 that exits from the light source 182 passes through the first translucent element 181 (and in the embodiment depicted in FIG. 18, light 184 exits from a side of the sidewall 180 that is opposite the opaque reflective back wall 183a).

FIG. 19 schematically depicts a cross-sectional view of a portion of a sidewall 190 that comprises a first waveguide 191, a light source 192 that delivers light to the first waveguide 191, and an opaque reflective back panel 193, such that light 194 exits from the sidewall 190 (and in the embodiment depicted in FIG. 19, light 194 exits from a side of the sidewall 190 that is opposite the opaque reflective back panel 193).

FIG. 20 schematically depicts a cross-sectional view of a portion of a (side-lit direct lit) sidewall 200 that comprises a first translucent element 201, a light source 202 adjacent to the translucent element 201, an opaque reflective back wall 203a, and opaque reflective side walls 203b, such that light 204 exits from the sidewall 200 (and in the embodiment depicted in FIG. 20, light 204 exits from a side of the sidewall 200 that is opposite the opaque reflective back wall 203a).

In FIGS. 17-20, while a single light source is depicted, multiple light sources may be employed.

As discussed above, a third group of embodiments within the first aspect of the present inventive subject matter includes light fixtures that comprise at least a first and second light engines, in which:

the first light engine comprises at least a first light exit surface;

the first and second light engines are positioned and oriented such that at least some light that exits the first light exit surface travels to a region (e.g., in an office or a room) to which at least some light that exits the second light engine travels.

FIGS. 21-23 schematically depict embodiments within the scope of the third group within the first aspect of the present inventive subject matter.

FIG. 21 depicts a light fixture 210 that comprises a first light engine 211 and a second light engine 212. The light fixture 210 is similar to the light fixture 140 depicted in FIG. 14, except that in the light fixture 140, the lower surface of the second light engine 142 is recessed relative to the ceiling 144, whereas in the light fixture 210 depicted in FIG. 21, the lower surface of the second light engine 212 is substantially flush with the ceiling 214.

In some embodiments in which a surface of a second light engine is substantially flush with a ceiling (or other structure), the far-field light distribution characteristics of the first and second light engines are different from each other. The differing far-field light distribution characteristics of such embodiments are particularly important in such embodiments, because otherwise the combination of blue-ish and yellow-ish light would simply be white and no different from a conventional panel light. In a preferred embodiment in accordance with the present inventive subject matter, light exiting at high angles (i.e., relative to an axis of the light fixture, e.g., relative to vertical from the fixture 210 as depicted in FIG. 21) is mostly light from the second light engine(s) and is more yellow-ish white, whereas the light exiting nearer vertical (as depicted in FIG. 21) is mostly light from the first light engine and is more blue-ish white. In some embodiments, light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

Another embodiment is similar to the embodiment depicted in FIG. 21, except that the first light engine 211 and the second light engine 212 are switched (and the back reflector is removed from the first light engine 211 instead of the second light engine 212.

FIG. 22 depicts a light fixture 220 that comprises a first light engine 221 and a second light engine 222. The light fixture 220 is similar to the light fixture 210 depicted in FIG. 21, except that in the light fixture 210 depicted in FIG. 21, the lower surface of the second light engine 212 is substantially flush with the ceiling 214, whereas in the light fixture 220 depicted in FIG. 22, the first light engine 221 and the second light engine 222 are mounted on the surface of the ceiling 224.

In some embodiments in which a first light engine and a second light engine are mounted on a surface of a ceiling (or other structure), the far-field light distribution characteristics of the first and second light engines are different from each other. The differing far-field light distribution characteristics of such embodiments is particularly important in such embodiments, because otherwise the combination of blue-ish and yellow-ish light would simply be white and no different from a conventional panel light. In a preferred embodiment in accordance with the present inventive subject matter, light exiting at high angles (i.e., relative to an axis of the light fixture, e.g., relative to vertical from the fixture 220 as depicted in FIG. 22) is mostly light from the second light engine(s) and is more yellow-ish white, whereas the light exiting nearer vertical (as depicted in FIG. 22) is mostly light from the first light engine and is more blue-ish white. In some embodiments, light distribution from one or both light engines can be engineered by having different light extraction elements in the first and/or second light engines, and skilled practitioners are familiar with ways to achieve such differing far-field light distribution (including with different light extraction elements), all of such ways to achieve differing far-field light distribution being included in the present disclosure.

Another embodiment is similar to the embodiment depicted in FIG. 22, except that the first light engine 221 and the second light engine 222 are switched (and the back reflector is removed from the first light engine 221 instead of the second light engine 222.

FIG. 23 depicts a light fixture 230 that comprises a first light engine 231, a second light engine 232 and a bracket 237 that holds the second light engine 232 in place relative to the first light engine 231. The bracket 237 (or a bracket in any other embodiment within the scope of the present inventive subject matter) can be of any suitable size, shape and material, and persons of ordinary skill in the art can readily select suitable materials, sizes and shapes for such brackets.

An embodiment as depicted in FIG. 23 can, e.g., be used in an existing sidewall (or in combination with a sidewall that can be installed, or a sidewall that has been installed), to provide any one or more of the features as described herein.

One or more diffusers can be added to any of the embodiments depicted in FIGS. 21-23 (or in any other embodiment in accordance with the third group within the first aspect of the present inventive subject matter), in a manner similar to the manner in which the diffuser 138 in FIG. 13 is added to the embodiment depicted in FIG. 7, or in any manner as described above in connection with FIG. 13.

In some embodiments in accordance with the present inventive subject matter, including some embodiments that include or do not include any of the features described herein, the far-field distribution of light that exits the first light engine differs from the far-field distribution of light that exits from a second light engine and/or light that exits from a sidewall (including any first light engines, second light engines and/or sidewalls described herein).

In one aspect of the respective far-field distributions of light, the distribution of light that exits from the first light engine is closer to perpendicular to a plane defined by a light exit region from the space defined by the sidewall than the distribution of light that exits from the second light engine (e.g., in each of the embodiments depicted in FIGS. 7 and 11-15, the distribution of light that exits from the first light engine is closer to vertical than the distribution of light that exits from the second light engine).

Representative examples where light that exits from a first light engine is closer to a particular direction than light that exits from a second light engine include:

[1] where 60% of light that exits from a first light engine defines an angle between 0 degrees and 45 degrees relative to such direction and 40% of light that exits from the first light engine defines an angle between 45 degrees and 90 degrees relative to such direction, and 30% of light that exits from a second light engine defines an angle between 0 degrees and degrees relative to such direction and 70% of light that exits from the second light engine defines an angle between 45 degrees and 90 degrees relative to such direction, or

[2] where 30% of light that exits from a first light engine defines an angle between 0 degrees and 25 degrees relative to such direction and 65% of light that exits from the first light engine defines an angle between 25 degrees and 90 degrees relative to such direction, and 20% of light that exits from a second light engine defines an angle between 0 degrees and degrees relative to such direction and 80% of light that exits from the second light engine defines an angle between 25 degrees and 90 degrees relative to such direction, etc.

In some embodiments, a distribution of light that exits from a second light engine having a larger angle relative to perpendicular to a light exit region than light that exits from a first light engine contributes to an illusion of comparatively bright sunlight being reflected and the sky being visible and not as bright.

In another aspect of the respective far-field distributions of light, the distribution of light that exits from the first light engine is closer to perpendicular to a plane defined by a light exit region from the space defined by the sidewall than the distribution of light that exits from the sidewall (e.g., in the embodiment depicted in FIG. 16, the distribution of light that exits from the first light engine is closer to vertical than the distribution of light that exits from the sidewall).

In the above discussion, the distribution of light is described in relation to perpendicular to a plane defined by a light exit region from the space defined by the sidewall. In some embodiments, the distribution of light would be described in relation to perpendicular to a plane defined by a largest periphery of the light fixture, or in relation to an axis of rotational symmetry, or in relation to the intersection of two planes of symmetry, or in relation to perpendicular to a plane defined by a light exit surface of the first light engine, or in relation to perpendicular to a plane that is tangential to a curved or dome-shaped light exit surface of the first light engine, or in relation to a plane defined by a surface in which the light fixture is mounted, e.g., a ceiling, a wall, a floor, a slanted structure, etc.

In another aspect of the respective far-field distributions of light, the distribution of light that exits from the first light engine is closer to perpendicular to a plane defined by a light exit surface of the first light engine (or a plane that is tangential to a curved or dome-shaped light exit surface of the first light engine) than the distribution of light that exits from the second light engine (e.g., in each of the embodiments depicted in FIGS. 21-23, the distribution of light that exits from the first light engine is closer to vertical than the distribution of light that exits from the second light engine).

In some of the third group of embodiments of light fixtures in accordance with the first aspect of the present inventive subject matter:

light exiting the first light engine has a first peak intensity angle relative to a first plane defined by at least three points on the first light exit surface, light exiting the second light engine has a second peak intensity angle relative to the first plane; and the first peak intensity angle differs from the second peak intensity angle.

In some embodiments of light fixtures and/or methods in accordance with the present inventive subject matter, including some embodiments that include or do not include any of the features described herein, there is at least some variation in light color among light exiting a light fixture, e.g., the color point of light traveling at a first angle relative to the axis of light distribution differs from the color point of light traveling at a second angle relative to the axis of light distribution. Such differences in color point can be relatively small or relatively large, e.g., a 10-step MacAdam ellipse, a 20-step MacAdam ellipse, at least 0.05 units on a 1931 CIE Chromaticity Diagram, at least 0.10 (or 0.15, 0.20. 0.25. 0.30. 0.35, 0.40, 0.45 or 0.50) units on a 1931 CIE Chromaticity Diagram.

In some of such embodiments (i.e., embodiments in which there is at least some variation in light color among light exiting a light fixture), at least a portion of such color point variance results from different far-field distribution contributions from a first light engine (resembling the sky) and from a second light engine (resembling the sun). The present specification includes a number of descriptions relating to light fixtures and methods in which the far-field light distribution characteristics of first and second light engines are different from each other.

For conventional lights, color variation over angle (i.e., lighting in which there is a significant difference in the color point of light traveling at different angles relative to an axis of light distribution differs from the color point of light traveling at a second angle relative to the axis of light distribution) is generally not a desirable feature. However, color variation is an important element of natural skylights and therefore is desirable for creating or enhancing the illusion of an artificial skylight. Due to (1) the basic geometry of typical skylights (i.e. a recessed box in ceiling with central window), (2) the sun being visible only at specific angles depending on time of day, and (3) the sky being visible over a relatively large range of angles, the light delivered into a space from a skylight will typically have regions of high CCT (i.e. bluish white) and regions of low CCT (i.e. yellowish light). Some embodiments of the present invention provide this feature.

FIG. 24A shows a plot of CCT over viewing angle measured using a light fixture similar to FIG. 16 and a gonio-spectrophotometer arrangement where the detector is located about 6.5 feet away from the fixture. At an angle of zero degrees, which corresponds to directly below the fixture if it were in a ceiling, the CCT is approximately 6500 K. The CCT decreases to about 4700 K at a viewing angle of 75 degrees. Broadly speaking such characteristics are similar to light from a natural skylight when the sun is low in the sky. These CCT values and ranges are representative—the present inventive subject matter is not limited to these CCT values and ranges, and persons of skill in the art will recognize that the present inventive subject matter encompasses other CCT ranges, and a variety of CCT ranges can be employed and are desirable.

Another feature of natural daylight is that it generally provides very high quality light having a color rendering index (CRI) of approximately 100. This is because daylight is typically full spectrum light (and also reflects the definition of CRI). Moreover, very high CRI is maintained regardless of the CCT. Thus, a desirable feature of an artificial skylight is that it delivers light having high CRI.

FIG. 24B shows a plot of the measured CRI over viewing angle measured using the same set-up as described above. The delivered light has high CRI (about 85) at all viewing angles, irrespective of the CCT. As a result, the quality of light as perceived in the space being lit is high, which adds to the illusion of a skylight. In some embodiments in accordance with the present inventive subject matter, the CRI of the light delivered by the light fixtures is at least 80 at all angles (and in some of those embodiments, the CRI of the light delivered by the light fixtures is at least 85). Alternative color quality metrics to CRI can also be used (e.g. those described in TM30-15.)

Persons of skill in the art are familiar with ways to achieve high CRI values, and selecting suitable components (e.g., LED components) to achieve high CRI values is straightforward, and therefore discussion of the many ways to achieve such high CRI values is not necessary.

As noted above, in a second aspect, the present inventive subject matter relates to light fixtures that comprise first and second light engines, in which the second light engine comprises at least a first sidewall from which light exits.

In some embodiments in accordance with the second aspect, the at least a first sidewall defines a space, the first light engine delivers light to the space, and at least a first light exit region is at a boundary of the space.

In some embodiments of light fixtures in accordance with the second aspect of the present inventive subject matter, including some embodiments that include or do not include any of the features described herein, the first light engine comprises a light exit surface that defines a first plane, the light exit region defines a second plane, the first plane and the second plane are substantially parallel, and: the first plane is spaced from the second plane by at least three inches, and in some embodiments at least four inches, and in some embodiments at least six inches, and/or at least one surface of the first sidewall defines a plane that defines an angle of at least 75 degrees (and in some embodiments at least 80 degrees, and in some embodiments at least 85 degrees, and in some embodiments about 90 degrees) relative to the first plane and relative to the second plane.

In some embodiments of light fixtures in accordance with the second aspect of the present inventive subject matter, including some embodiments that include or do not include any of the features described herein, the first light engine comprises a light exit surface, a first plane is tangential to the light exit surface, the light exit region defines a second plane, the first plane and the second plane are substantially parallel, and:

the first plane is spaced from the second plane by at least three inches, and in some embodiments at least four inches, and in some embodiments at least six inches, and/or at least one surface of the first sidewall defines a plane that defines an angle of at least 75 degrees (and in some embodiments at least 80 degrees, and in some embodiments at least 85 degrees, and in some embodiments about 90 degrees) relative to the first plane and relative to the second plane.

In relation to the second aspect of the present inventive subject matter, the respective characteristics of light that exits from the first light engine and light that exits from the second light engine are not limited to the descriptions above of the respective characteristics of light that exits from the first light engine and light that exits from the second light engine. The descriptions above of components and materials that are suitable for making a sidewall that has one or more light exit surfaces in accordance with the first aspect of the present inventive subject matter are applicable to the sidewall that has one or more light exit surfaces in accordance with the second aspect of the present inventive subject matter.

FIG. 25 schematically depicts a representative embodiment in accordance with the second aspect of the present inventive subject matter. FIG. depicts a light fixture 250 that comprises a first light engine 251 and a first sidewall 252 which comprises four light exit surfaces. The light fixture 250 is mounted in a ceiling 254.

The first sidewall 252 is in the form of the recessed box comprising four surfaces, each of which is, in its entirety, a light exit surface.

The first light engine 251 comprises an edge-lit panel (or a direct-lit panel).

One or more diffusers can be added to the embodiment depicted in FIG. 25 (or in any other embodiment in accordance with the second group within the first aspect of the present inventive subject matter), in a manner similar to the manner in which the diffuser 138 in FIG. 13 is added to the embodiment depicted in FIG. 7, or in any manner as described above in connection with FIG. 13.

In some embodiments in accordance with the first aspect or the second aspect of the present inventive subject matter, including some embodiments that include or do not include any of the features described herein, a periphery of the first light engine is substantially similar to a periphery of the sidewall (or at least a portion of a periphery of the first light engine is substantially similar to a periphery of the sidewall, or a portion of a periphery of the sidewall). For example, in some embodiments in accordance with the present inventive subject matter, including some embodiments that include or do not include any of the features described herein, the sidewall is substantially rectangular annular and a periphery of the first light engine is substantially rectangular (e.g., such that the first light engine covers substantially all of the space defined by the annular sidewall, except for a relatively thin peripheral border of the space defined by the annular sidewall); in some embodiments in accordance with the present inventive subject matter, including some embodiments that include or do not include any of the features described herein, the sidewall is substantially circular annular and a periphery of the first light engine is substantially circular.

In some embodiments in accordance with the first aspect or the second aspect of the present inventive subject matter, including some embodiments that include or do not include any of the features described herein, the sidewall defines (and in some cases extends around) the sides of a space, the sidewall has a first edge that defines (and in some cases extends around) a top boundary of the space and the sidewall has a second edge that defines (and in some cases extends around) a bottom boundary of the space (recognizing that top and bottom are relative, and the sidewall could be in any orientation, such that orientations of the "top" and "bottom" would be affected accordingly). In such embodiments, the bottom boundary can be the light exit region (through which light that exits from the first light engine and light that exits from the second light engine passes), and the top boundary can be space in which the first light engine can be accommodated (e.g., the first light engine is partially within the space), and/or through which light that exits the first light engine can enter the space (e.g., the first light engine is partially or completely outside the space), and/or within which the first light engine is positioned (e.g., the first light engine is completely in the space).

As is evident from the discussion above, in some embodiments in accordance with the first aspect or the second aspect of the present inventive subject matter, including some embodiments that include or do not include any of the features described herein, at least some of the dimensions of the first light engine bear a relation to some of the dimensions of the sidewall, and/or the dimensions of the space defined (at least in part) by the sidewall.

In some embodiments of light fixtures in accordance with the first aspect or the second aspect of the present inventive subject matter, including some embodiments that include or do not include any of the features described herein, the first light engine can be positioned relative to the sidewall in any suitable position In some embodiments of light fixtures in accordance with the first aspect or the second aspect of the present inventive subject matter, including some embodiments that include or do not include any of the features described herein, the light fixture can further comprise a back wall, i.e., a structure that partially or completely covers the "top" boundary of the space (and in such embodiments, the first light engine can be partially or completely inside the space).

In some embodiments of light fixtures in accordance with the first aspect or the second aspect of the present inventive subject matter, including some embodiments that include or do not include any of the features described herein, the light fixture can further comprise one or more heat dissipation structures and/or one or more heat transfer structures, e.g., heat fins or heat pins can be provided on the side of a back wall (if included) opposite to the space.

The light exit surface of the first light engine can be recessed by any suitable or desired distance relative to the light exit region and/or the sidewall. For example, a ratio of the distance the first light engine is recessed relative to the overall size of the first light engine or the light fixture is not limited. In addition, as noted below, the light fixtures of the present inventive subject matter are scalable (i.e., the size of the light fixtures, or any portion or portions thereof, can be modified by being magnified or shrunk to any degree—see the definition and discussion of "scalable" below). As representative distances of recess, in some embodiments in accordance with the present inventive subject matter, including some embodiments that include or do not include any of the features described herein, the light exit surface of the first light engine is recessed about one inch to about 40 inches or more (particularly in view of the scalability, the distance of recess can be much larger), in some cases about three inches to about nine inches (e.g., about five inches), for example, the distance between the light exit surface of the first light engine and the light exit region in some embodiments is about three inches to about nine inches, and in some embodiments about five inches, about six inches, about seven inches, about three inches to about five inches, about three inches to about seven inches, or about five inches to about seven inches.

In some embodiments of light fixtures in accordance with the first aspect or the second aspect of the present inventive subject matter, including some embodiments that include or do not include any of the features described herein, the "top" boundary of the space is of a shape and/or size that is substantially similar to a shape of the "bottom" boundary of the space, and/or the "top" boundary of the space is substantially aligned with the "bottom" boundary of the space (e.g., vertical planes that bisect the "top" of the boundary also bisect the "bottom" of the boundary).

In some embodiments in accordance with the first aspect or the second aspect of the present inventive subject matter, including some embodiments that include or do not include any of the features described herein, the light fixture can further comprise at least one baffle element. In such embodiments, the baffle element is positioned and oriented such that it increases collimation of light that exits from the second light engine. In embodiments in which one or more baffle element(s) is/are provided, the baffle element(s) can be of any suitable shape (e.g., in a rectilinear grid pattern, in a substantially cylindrical shape, and/or in a honeycomb shape), and can, if desired, be reflective or light-absorbing (for example, in some instances, a baffle element can be colored (or painted) black, so that off-angle light will be absorbed and only light that is substantially parallel (e.g., aligned with an axis of light distribution) will pass through the baffle element. Additionally, reflectors can be used to limit or cut off spill light. Representative examples of baffle elements are depicted in FIGS. 26 and 27.

FIG. 26 schematically depicts a representative example of a baffle element 260 suitable for use in accordance with the present inventive subject matter.

FIG. 27 schematically depicts a representative example of a baffle element 270 suitable for use in accordance with the present inventive subject matter.

As mentioned above, in a third aspect, the present inventive subject matter relates to light fixtures that output light having specific characteristics. As discussed in more detail below, the third aspect of the present inventive subject matter (i.e., the "third aspect") relates in general to any light fixtures that comprise the features described herein in relation to the third aspect and/or that provide the effects described herein in relation to the third aspect. Some of the light fixtures described herein in relation to the first and second aspects of the present inventive subject matter (as well as the fourth through seventh aspects of the present inventive subject matter, discussed below) comprise such features and/or provide such effects, but the third aspect is not limited to only light fixtures in accordance with the first and second aspects (or the fourth through seventh aspects). That is, the scope of the light fixtures in accordance with the third aspect is not limited to any of the features of the first and second aspects of the present inventive subject matter (or the fourth through seventh aspects of the present inventive subject matter).

Light fixtures in accordance with the third aspect of the present inventive subject matter are capable of providing light output that can achieve specific biological effects, such as adjusting a person's biological melatonin levels in a desired way (e.g., during twenty-four-hour periods), for instance to adjust a person's circadian rhythm, to ameliorate a person's circadian rhythm disorders, and/or to adjust a person's alertness (e.g., to increase the person's alertness during some daily time periods and/or to increase the person's drowsiness during other daily time periods).

In animals, circulating levels of the hormone melatonin (N-acetyl-5-methoxytryptamine) typically vary in a daily cycle. The melatonin signal forms part of the system that regulates the sleep-wake cycle by chemically causing drowsiness and lowering body temperature.

Lux is a measure of the intensity of illumination as distinguished by the human eye. This value does not correlate to an objective value of energy radiated or reflected, because different wavelengths within the visible spectrum are perceived with varying sensitivity by the eye. Lux is quantified by evaluating light intensity in consideration of this variable.

The apparent sensitivity of the human circadian system differs from the luminosity function used in determining lux.

While not wishing to be bound by any theories, some have correlated relative suppression of melatonin production in humans vs. wavelength of light to which subjects are exposed. One representative example of such a correlation might be that:

light of wavelength of about 410 nm provides a relative melatonin suppression in humans of about 0.35; light of wavelength of about 425 nm provides a relative melatonin suppression in humans of about 0.7;

light of wavelength in the range of from about 437 to about 462 nm provides a relative melatonin suppression in humans of about 0.95;

light of wavelength of about 475 nm provides a relative melatonin suppression in humans of about 0.8;

light of wavelength of about 500 nm provides a relative melatonin suppression in humans of about 0.4; and light of wavelength of about 600 nm provides a relative melatonin suppression in humans of about 0.

An example of a plot of relative suppression of melatonin production in humans vs. wavelength of light to which subject are exposed can be found in Rea et al., Journal of Circadian Rhythms, 2010, 8:2 (http://www.jcircadianrhythms.com/content/8/1/2) (see FIG. 3).

CS value ("circadian stimulus value") for a light source is a measure of the percentage of melatonin suppression when exposed (i.e., illuminance received at the eye) to the light source (i.e., a CS value of 0.2 correlates to 20% melatonin suppression, a CS value of 0.4 correlates to 40% melatonin suppression, a CS value of 0.6 correlates to 60% melatonin suppression, a CS value of 0.8 correlates to 80% melatonin suppression, etc. CS values are described in M. S. Rea et al, "Modeling the spectral sensitivity of the human circadian system," 2012; see also online link to calculator http://www.irc.rpi.eduiproqramsilightHealth/index.asp.

Circadian rhythm disorders have been associated by some with change in nocturnal activity (e.g., nighttime shift workers), change in longitude (e.g., jet lag), and/or seasonal change in light duration (e.g., seasonal affective disorder, with symptoms including depression). In 2007, the World Health Organization named late-night shift work as a probable cancer-causing agent.

Aspects that relate to melatonin levels and the human circadian cycle are described in U.S. Pat. Nos. 9,030,103, 9,039,746, 9,681,510, and 9,532,382, the entireties of which are incorporated herein by reference as if set forth fully herein.

In accordance with the third aspect of the present inventive subject matter, there is provided a light fixture that comprises at least a first light engine and a second light engine, in which:

the first light engine has the ability to output light that provides a first CS value at a given illuminance, the second light engine has the ability to output light that provides a second CS value at the same illuminance, and the first CS value is different from the second CS value.

In some embodiments in accordance with the third aspect of the present inventive subject matter, there is provided a light fixture that comprises one or more light engines that output light that provides strong suppression of melatonin (and/or a high CS value) at a given photopic illuminance, as well as one or more light engines that output light that does not (and/or a light fixture that comprises one or more light engines that can be controlled or adjusted to selectively output (1) light that provides strong suppression of melatonin (and/or a high CS value), e.g., at a given photopic illuminance and (2) light that does not provide strong suppression of melatonin), e.g., at said given photopic illuminance. The present inventive subject matter also comprises methods that comprise exposing a subject, e.g., a human, to light output from such light fixtures. In some embodiments in accordance with the third aspect of the present inventive subject matter, controls are provided to adjust the light output by the light fixture to adjust the degree of melatonin suppression provided to a person subjected to the light output by the light fixture (and/or to adjust the CS value provided by such light). For example, light fixtures can have multiple melatonin suppression settings (and/or CS value settings), incremental melatonin suppression settings (and/or CS value settings), or a substantially continuous range of melatonin suppression capabilities (and/or CS value settings). Melatonin suppression (and/or CS value of output light) of such light fixtures can be controlled automatically (e.g., in accordance with a daily cycles or selection of one of a number of selectable daily cycles, in accordance with user input, in response to feedback of a person's biological melatonin levels, in response to one or more sensed conditions, etc.). Control signals can be received by the light fixtures in any suitable way, e.g., wirelessly or through a wired connection. The present inventive subject matter also comprises methods that comprise exposing a subject, e.g., a human, to light output from such light fixtures.

Light fixtures in accordance with the third aspect of the present inventive subject matter can comprise solid state light emitters (e.g., LEDs) or any other light sources, any of which optionally include wavelength conversion material (e.g., phosphors), to provide the capability of outputting light of different color points at different times. Such light fixtures can comprise controls for controlling the light source(s) to output light of different color points at different times (e.g., light fixtures in accordance with the third aspect of the present inventive subject matter can comprise any LED lights where individual and/or groups of LEDs with different colors (e.g., of wavelength converted colored or white LEDs and/or non-wavelength converted LEDs) are controlled to produce different mixtures of the light to provide some or all of the effects described in relation to the third aspect of the present inventive subject matter, e.g., to adjust one or more persons' circadian rhythm, to ameliorate one or more persons' circadian rhythm disorders, to adjust one or more persons' alertness, to provide a particular CS value in a subject or to bring a subject's CS value to above or below a particular CS value, and/or to provide a desired melatonin suppression or to bring melatonin suppression to above or below a particular degree of suppression).

In some embodiments of light fixtures in accordance with the third aspect of the present inventive subject matter, including some embodiments that include or do not include any of the features described herein:

the first light engine is configured to output light of a first color point, the second light engine is configured to output light of a second color point, and the first color point is spaced from the second color point.

In some embodiments of light fixtures in accordance with the third aspect of the present inventive subject matter, including some embodiments that include or do not include any of the features described herein, upon supplying electricity to the light fixture:

light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) exits from the first light engine, and light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) exits from the second light engine.

In some embodiments of light fixtures in accordance with the third aspect of the present inventive subject matter, including some embodiments that include or do not include any of the features described herein, the first light engine has the ability to output light that provides a CS value of at least 0.3 at an illuminance of 300 lux (or more), and the second light engine has the ability to output light that provides a CS value of less than 0.15 at an illuminance of 200 lux (or less) (and/or the ability to output light that provides a CS value of less than 0.2 at an illuminance of 300 lux).

In some embodiments of light fixtures in accordance with the third aspect of the present inventive subject matter, including some embodiments that include or do not include any of the features described herein, there is provided a light fixture in which:

the light fixture further comprises a first sidewall, the first sidewall defines a space, at least a first light exit region is at a boundary of the space, the first light engine is positioned and oriented such that at least some light that exits the first light engine passes through at least part of the space and exits the space through the first light exit region, and the second light engine is positioned and oriented such that at least some light that exits the second light engine exits the space through the first light exit region. In some of such embodiments, at least some light that exits from the second light engine exits from the first sidewall.

In some embodiments of light fixtures in accordance with the third aspect of the present inventive subject matter, including some embodiments that include or do not include any of the features described herein:

the second light engine comprises a first sidewall, the first sidewall defines a space, at least a first light exit region is at a boundary of the space, the first light engine is positioned and oriented such that at least some light that exits the first light engine passes through at least part of the space and exits the space through the first light exit region, and the second light engine is positioned and oriented such that at least some light that exits the second light engine exits the space through the first light exit region.

In some embodiments of light fixtures in accordance with the third aspect of the present inventive subject matter, including some embodiments that include or do not include any of the features described herein:

the light fixture further comprises at least a first control element, and the at least a first control element controls independently at least a brightness of light exiting from the first light engine and a brightness of light exiting from the second light engine.

In some embodiments of light fixtures in accordance with the third aspect of the present inventive subject matter, including some embodiments that include or do not include any of the features described herein:

the light fixture further comprises at least a first control element, and the at least a first control element is configured to vary the CS value of light output from the light fixture.

In some embodiments of light fixtures in accordance with the third aspect of the present inventive subject matter, including some embodiments that include or do not include any of the features described herein:

the light fixture further comprises at least a first control element, and the at least a first control element is configured to vary the CS value based on the time of day.

In some embodiments of light fixtures in accordance with the third aspect of the present inventive subject matter, including some embodiments that include or do not include any of the features described herein:

the light fixture further comprises at least a first control element, the first control element is configured to cause the light fixture to output light having a CS value of at least 0.3 at an illuminance of 300 lux during a first part of the day, and the first control element is configured to cause the light fixture to output light having a CS value of less than 0.15 at an illuminance of 200 lux (and/or to cause the light fixture to output light having a CS value of less than 0.2 at an illuminance of 300 lux) during a second part of the day.

In some embodiments of light fixtures in accordance with the third aspect of the present inventive subject matter, including some embodiments that include or do not include any of the features described herein:

the light fixture further comprises at least a first control element, the first control element is configured to vary a ratio of brightness of light output from the first light engine to brightness of light output from the second light engine. In some of such embodiments:

the at least a first control element causes the ratio of brightness of light output from the first light engine to brightness of light output from the second light engine to be at least a first value during a first part of the day, the at least a first control element causes the ratio of brightness of light output from the first light engine to brightness of light output from the second light engine to be not greater than a second value during a second part of the day, and the first value is greater than the second value.

In some embodiments of light fixtures in accordance with the third aspect of the present inventive subject matter, including some embodiments that include or do not include any of the features described herein, the light fixture is capable of outputting light that provides a CS value of at least 0.3 at a photopic illuminance of 300 lux. In some of such embodiments, the light fixture is also capable of outputting light that provides a CS value of less than 0.15 at a photopic illuminance of 200 lux.

In some embodiments of light fixtures in accordance with the third aspect of the present inventive subject matter, including some embodiments that include or do not include any of the features described herein:

the first light engine has the ability to output light that provides a first suppression of melatonin at a first photopic illuminance, the second light engine has the ability to output light that provides a second suppression of melatonin at said first photopic illuminance, and the first suppression of melatonin differs from the second suppression of melatonin.

In some embodiments of light fixtures in accordance with the third aspect of the present inventive subject matter, including some embodiments that include or do not include any of the features described herein, the light fixtures are capable of outputting light that provides a CS value (in at least some humans) of at least 0.3 during at least a first part of the day, and outputting light that provides a CS value (in at least some humans) of less than 0.15 during at least a second part of the day, the photopic lux output during the second part of the day comprising at least 50% (and in some embodiments at least 60%, 70%, 80% or 90%) of the photopic lux output during the first part of the day.

Some embodiments of light fixtures in accordance with the first aspect or the second aspect of the present inventive subject matter are particularly well suited to being used to affect a person's biological melatonin levels in a desired way. In some of such embodiments, for example, the light fixture (artificial skylight) comprises one or more light engines (e.g., the first light engine, which resembles the sky) that output light that provides strong suppression of melatonin, as well as one or more light engines (e.g., the second light engine, which has one or more characteristics that resemble that (or those) of at least a portion of light emitted by (and received from) the sun) that output light that provides less suppression of melatonin. In other words, a light fixture in accordance with the third aspect of the present inventive subject matter can comprise features described herein in connection with the first and/or the second aspect of the present inventive subject matter. In some of these embodiments, controls are provided to adjust the light output by the light fixture to adjust a predicted degree of melatonin suppression provided to a person subjected to the light output by the light fixture (and/or to provide a specific CS value or a CS value greater than or less than a specific value). For example, light fixtures can have multiple predicted melatonin suppression settings (and/or CS value settings or range settings), incremental predicted melatonin suppression settings (and/or CS value settings or range settings), or a substantially continuous range of predicted melatonin suppression capabilities (and/or CS value settings). Predicted melatonin suppression of such light fixtures (and/or CS values) can be controlled automatically (e.g., in accordance with a daily cycles or selection of one of a number of selectable daily cycles, in accordance with user input, in response to feedback of a person's biological melatonin levels, in response to one or more sensed conditions, etc.). Control signals can be received by the light fixtures in any suitable way, e.g., wirelessly or through a wired connection.

In accordance with a fourth aspect of the present inventive subject matter, there is provided a light fixture comprising:
at least a first light engine, and at least a first surface,
the light fixture configured such that upon supplying electricity to the light fixture: light having a first color point is incident on at least a portion of the first surface, and light exiting the light fixture has a cumulative color of a second color point, the first color point spaced from the second color point.

Light fixtures in accordance with the fourth aspect of the present inventive subject matter are capable of providing a phenomenon in which a person (e.g., a person in a room in which such a light fixture is installed) can see light of a first color point incident on a surface (i.e., the first surface) of the light fixture (e.g., a sidewall as discussed herein) and feel the sensation of perceiving the light from the light fixture to have such color point, while the actual cumulative light output from the light fixture is of a different color point ("cumulative light output from the light fixture" meaning a mixture of all of the light output from the light fixture, or substantially all of such light, or at least 90% of such light). Such a light fixture can thus achieve such a phenomenon where desired, e.g., in some instances it can be advantageous to provide to a person a sensation that a light fixture is outputting light that is of an aesthetically more pleasing color point when the light fixture is actually outputting (in aggregate, or cumulatively) light that is of an aesthetically less pleasing color point. In a representative example, light output from a light fixture having a cumulative color temperature (or correlated color temperature) of 5300 K is frequently considered not aesthetically pleasing, and in accordance with a light fixture described in the present paragraph (and the paragraph preceding the present paragraph), a person's vision can be "tricked" into thinking that the light output from the light fixture is of a more pleasing color temperature (i.e., a lower color temperature, providing a sensation of "warmer" light) by having at least a first surface of the light fixture on which light of such more pleasing color temperature is incident (and typically a large portion of such light is reflected by the first surface). The phenomenon described in the present paragraph can be enhanced where the light that is incident on the at least a first surface is of comparatively high luminosity, i.e., is of wavelength (or wavelengths and/or wavelength ranges) for which human visual perception of brightness is comparatively high; as is well known by persons of skill in the art, the photopic luminosity function (also known as luminous efficiency function) describes the average spectral sensitivity of human visual perception of brightness, based on subjective judgments of which of a pair of different-colored lights is brighter, to describe relative sensitivity to light of different wavelengths. The color temperatures that are typically considered more pleasant are typically of higher luminosity, thereby further enhancing the phenomenon described in the present paragraph where light of an aesthetically pleasing color temperature that also has high luminosity is incident on the at least a first surface.

As noted above, in accordance with the fourth aspect of the present inventive subject matter, there is provided a light fixture comprising: at least a first light engine, and at least a first surface, the light fixture configured such that upon supplying electricity to the light fixture:
light having a first color point is incident on at least a portion of the first surface, and
light exiting the light fixture has a cumulative color of a second color point, the first color point spaced from the second color point.

In some embodiments of light fixtures in accordance with the fourth aspect of the present inventive subject matter, including some embodiments that include or do not include any of the features described herein:
said first color point is of a first correlated color temperature, said second color point is of a second correlated color temperature, and said first correlated color temperature is lower than said second correlated color temperature.

In some embodiments of light fixtures in accordance with the fourth aspect of the present inventive subject matter, including some embodiments that include or do not include any of the features described herein: the light fixture further comprises at least a first sidewall, and the first surface is on the first sidewall.

In some embodiments of light fixtures in accordance with the fourth aspect of the present inventive subject matter, including some embodiments that include or do not include any of the features described herein:

the light fixture further comprises a second light engine, said light incident on the first surface has a first ratio (which can be as high as infinity) of light output from the second light engine to light output from the first light engine, said light exiting the light fixture has a second ratio (which can be as low as zero) of light output from the second light engine to light output from the first light engine, and said first ratio is larger than said second ratio.

In some embodiments in accordance with the third aspect of the present inventive subject matter, there are provided light fixtures that comprise at least some of the features described above in connection with the first aspect of the present invention, e.g., light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun. In some of such embodiments, as discussed above in accordance with the first aspect of the present inventive subject matter:

the light fixture comprises at least a first light engine and a second light engine;

light exiting the first light engine (i.e., upon supplying electricity to a light source of the first light engine) has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (FIG. 1 is a plot, on a 1931 CIE Chromaticity Diagram, of a region 11 defined as such, i.e., the quadrilateral area with vertices having such x, y coordinates (and in some embodiments, light exiting the first light engine has x, y color coordinates which define a point which is within a quadrilateral area with vertices having x, y coordinates of (0.32, 0.31), (0.30, 0.33), (0.15, 0.17), and (0.17, 0.14));

light exiting the second light engine (i.e., upon supplying electricity to a light source of the second light engine) has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (FIG. 2 is a plot, on a 1931 CIE Chromaticity Diagram, of a region 21 defined as such, i.e., the area with vertices having such x, y coordinates) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)); and the color point (i.e., the combination of x, y color coordinates) of the light exiting the first light engine may be but typically is not the same as the color point of the light exiting the second light engine.

In accordance with a fifth aspect in accordance with the present inventive subject matter, there is provided a light fixture comprising:

at least first and second light engines, the first light engine configured to output light of a first color point, the second light engine configured to output light of a second color point, the first color point spaced from the second color point, light distribution characteristics of the first and second light engines different from each other.

In some embodiments of light fixtures in accordance with the fifth aspect of the present inventive subject matter, including some embodiments that include or do not include any of the features described herein: the first light engine comprises at least one light emitter, and/or the second light engine comprises at least one light emitter.

In some embodiments of light fixtures in accordance with the fifth aspect of the present inventive subject matter, including some embodiments that include or do not include any of the features described herein: the first light engine comprises at least one LED, and/or the second light engine comprises at least one LED.

In some embodiments of light fixtures in accordance with the fifth aspect of the present inventive subject matter, including some embodiments that include or do not include any of the features described herein: the first light engine comprises at least two light emitters, and/or the second light engine comprises at least two light emitters.

In some embodiments of light fixtures in accordance with the fifth aspect of the present inventive subject matter, including some embodiments that include or do not include any of the features described herein: the first light engine comprises at least two LEDs, and/or the second light engine comprises at least two LEDs.

In some embodiments of light fixtures in accordance with the fifth aspect of the present inventive subject matter, including some embodiments that include or do not include any of the features described herein, the first light engine is spaced from the second light engine laterally and/or vertically relative to the second light engine. The expression "first light engine spaced laterally relative to the second light engine" means that the first light engine is spaced from the second light engine in a plane perpendicular to an axis of light distribution of the second light engine. The expression "first light engine spaced vertically relative to the second light engine" means that the first light engine is spaced from the second light engine in a direction along the axis of light distribution of the second light engine. Accordingly, the expression "the first light engine is spaced from the second light engine laterally and/or vertically relative to the second light engine" means that the first light engine is [1] spaced from the second light engine in a plane perpendicular to an axis of light distribution of the second light engine, [2] spaced from the second light engine along the axis of light distribution of the second light engine, or [3] spaced from the second light engine along a line spaced from and parallel to the axis of light distribution of the second light engine. For instance, in some of such embodiments, there can be provided a plurality of light engines (in which at least two of such light engines are configured to output light of respective differing color points), in which a first of such light engines is in a first location and others of such light engines are spaced laterally around the first light engine (e.g., the first light engine has a generally square surface through which output light exits the first light engine, and other light engines are positioned as a ring around the first light engine)(i.e., as an example where a first light engine is spaced from a second light engine, and from other light engines, laterally.

In some embodiments of light fixtures in accordance with the fifth aspect of the present inventive subject matter, including some embodiments that include or do not include any of the features described herein, the light fixture further comprises at least a third light engine.

In some embodiments of light fixtures in accordance with the fifth aspect of the present inventive subject matter, including some embodiments that include or do not include any of the features described herein: the first light engine is configured to output light that has a first axis of light distribution, the second light engine is configured to output light that has a second axis of light distribution, and the first axis of light distribution differs from the second axis of light distribution.

In some of such embodiments, an angle of the first axis of light distribution relative to a first plane differs from an angle of the second axis of light distribution relative to the first plane, and in some of those embodiments, the first and second light engines are configured and oriented such that the first plane is defined by a region through which at least some light output from the first light engine and at least some light output from the second light engine exits the light fixture.

In some embodiments of light fixtures in accordance with the fifth aspect of the present inventive subject matter, including some embodiments that include or do not include any of the features described herein: the first light engine is configured to output light that has a first peak intensity angle relative to a first plane, the second light engine is configured to output light that has a second peak intensity angle relative to the first plane, and the first peak intensity angle differs from the second peak intensity angle. In some of such embodiments, the first and second light engines are configured and oriented such that the first plane is defined by a region through which at least some light output from the first light engine and at least some light output from the second light engine exits the light fixture.

In some embodiments of light fixtures in accordance with the fifth aspect of the present inventive subject matter, including some embodiments that include or do not include any of the features described herein: the light fixture further comprises at least a first control element, the at least a first control element controls independently at least a brightness of light exiting from the first light engine and a brightness of light exiting from the second light engine.

In some embodiments of light fixtures in accordance with the fifth aspect of the present inventive subject matter, including some embodiments that include or do not include any of the features described herein: the light fixture further comprises at least a first control element, the at least a first control element controls at least a brightness of light exiting from the first light engine and a brightness of light exiting from the second light engine. In some of such embodiments: the first control element controls the brightness of light exiting from the second light engine based on the brightness of light exiting from the first light engine; or the first control element controls the brightness of light exiting from at least one of the first light engine and the second light engine based on a parameter selected from among (1) a color point of a mixture of light exiting from the light fixture, (2) a brightness of light exiting from the light fixture, (3) a time of day and (4) a melatonin suppression setting.

In some embodiments of light fixtures in accordance with the fifth aspect of the present inventive subject matter, including some embodiments that include or do not include any of the features described herein, the light fixture further comprises at least a first light extraction element that affects light distribution characteristics of light exiting from at least one of the first and second light engines.

In some embodiments of light fixtures in accordance with the fifth aspect of the present inventive subject matter, including some embodiments that include or do not include any of the features described herein, the light fixture further comprises at least a first diffuser that affects light distribution characteristics of light exiting from at least one of the first and second light engines.

In accordance with a sixth aspect in accordance with the present inventive subject matter, there is provided a light fixture comprising:
  at least a first light engine and a second light engine; and
  a first sidewall,
  the first light engine comprising at least a first light exit surface,
  the first sidewall defining a space,
  at least a first light exit region at a boundary of the space,
  the first light engine positioned and oriented such that at least some light that exits the first light exit surface passes through at least part of the space and exits the space through the first light exit region, and
  the second light engine positioned and oriented such that at least some light that exits the second light engine exits the space through the first light exit region.

In some embodiments of light fixtures in accordance with the sixth aspect of the present inventive subject matter, including some embodiments that include or do not include any of the features described herein: the first light engine is configured to output light of a first color point, the second light engine is configured to output light of a second color point, and the first color point is spaced from the second color point.

In some embodiments of light fixtures in accordance with the sixth aspect of the present inventive subject matter, including some embodiments that include or do not include any of the features described herein: light incident on the first sidewall has a first ratio (which can be as high as infinity) of light output from the second light engine to light output from the first light engine, light output from the light fixture has a second ratio (which can be as low as zero) of light output from the second light engine to light output from the first light engine, and the first ratio is larger than the second ratio.

In some embodiments of light fixtures in accordance with the sixth aspect of the present inventive subject matter, including some embodiments that include or do not include any of the features described herein, the second light engine is movable relative to the first light engine and the first sidewall. In some of such embodiments:
  movement of the second light engine relative to the first light engine corresponds to passage of time,
  a first position of the second light engine relative to the first light engine is substantially the same at a first time of day on at least two consecutive days,
  a second position of the second light engine relative to the first light engine is substantially the same at a second time of day on said at least two consecutive days, said first position differs from said second position, and
  said first time of day differs from said second time of day.

In some embodiments of light fixtures in accordance with the sixth aspect of the present inventive subject matter, including some embodiments that include or do not include any of the features described herein:

[the first sidewall has at least a first sidewall aperture, and at least some light that exits the second light engine enters the space through the first sidewall aperture. In some of such embodiments:

the light fixture further comprises at least a first screen; and at least some light that exits the second light engine passes through the first screen.

In some embodiments of light fixtures in accordance with the sixth aspect of the present inventive subject matter, including some embodiments that include or do not include any of the features described herein, the second light engine is in the space.

In some embodiments of light fixtures in accordance with the sixth aspect of the present inventive subject matter, including some embodiments that include or do not include any of the features described herein: the first sidewall comprises at least a second light exit surface, and upon supplying electricity to the light fixture, light exits the second light exit surface. In some of such embodiments, at least one of [A], [B], [C] or [D] (below) is satisfied:

[A] the first sidewall comprises at least a first light emitter, the first sidewall comprises at least one light-transporting structure, and/or the first sidewall comprises at least one light-transmitting structure, or

[B] the light fixture further comprises at least a first control element, the at least a first control element controls independently at least a brightness of light exiting from the first light exit surface and a brightness of light exiting from the second light exit surface, or

[C] the light fixture further comprises at least a first control element, the at least a first control element controls independently at least a color point of light exiting from the first light exit surface and a color point of light exiting from the second light exit surface, or

[D] the light fixture further comprises at least a first control element, the at least a first control element controls at least one of: a brightness of light exiting from at least a first portion of the sidewall, a color point of light exiting from the first light engine, and a color point of light exiting from the second light engine.

In accordance with a seventh aspect in accordance with the present inventive subject matter, there is provided a light fixture comprising:

a first sidewall; and
at least a first control element,
the first sidewall defining a space,
at least a first light exit region at a boundary of the space,
a first light engine positioned and oriented such that at least some light that exits the first light engine passes through the first sidewall into the space,
the at least a first control element: (1) independently controls a brightness of light exiting from a first portion of the sidewall and a brightness of light exiting from a second portion of the sidewall, and/or (2) independently controls a color point of light exiting from a first portion of the sidewall and a color point of light exiting from a second portion of the sidewall.

In some embodiments of light fixtures in accordance with the seventh aspect of the present inventive subject matter, including some embodiments that include or do not include any of the features described herein, the first control element is configured to adjust the brightness of light exiting from a first portion of the sidewall and a brightness of light exiting from a second portion of the sidewall based on the time of day (e.g., according to a repeating 24-hour cycle).

In some embodiments of light fixtures in accordance with the seventh aspect of the present inventive subject matter, including some embodiments that include or do not include any of the features described herein, the first control element is configured to adjust the color point of light exiting from a first portion of the sidewall and the color point of light exiting from a second portion of the sidewall based on the time of day (e.g., according to a repeating 24-hour cycle), and (1) the color point of light exiting from the first portion of the sidewall at a first time of day differs from the color point of light exiting from the first portion of the sidewall at a second time of day, (2) the color point of light exiting from the second portion of the sidewall at the first time of day differs from the color point of light exiting from the second portion of the sidewall at the second time of day, and (3) the color point of light exiting from the first portion of the sidewall at the first time of day differs from the color point of light exiting from the second portion of the sidewall at the first time of day.

In some embodiments of light fixtures in accordance with the seventh aspect of the present inventive subject matter, including some embodiments that include or do not include any of the features described herein, the first control element is configured to adjust the brightness and the color point of light exiting from a first portion of the sidewall, and the brightness and the color point of light exiting from a second portion of the sidewall based on the time of day (e.g., according to a repeating 24-hour cycle).

In some embodiments of light fixtures in accordance with the seventh aspect of the present inventive subject matter, including some embodiments that include or do not include any of the features described herein: the first sidewall has at least a first sidewall aperture, and at least some light that exits the first light engine enters the space through the first sidewall aperture. In some of such embodiments: the light fixture further comprises at least a first screen; and at least some light that exits the first light engine passes through the first screen.

In some embodiments of light fixtures in accordance with the seventh aspect of the present inventive subject matter, including some embodiments that include or do not include any of the features described herein: the first sidewall comprises at least said first light engine, the first sidewall comprises at least one light-transporting structure, and/or the first sidewall comprises at least one light-transmitting structure.

An eighth aspect of the present inventive subject matter is directed to a method of supplying light, comprising: supplying electricity to a light fixture, the light fixture comprising:

at least a first light engine and a second light engine; and
a first sidewall,
the first light engine comprising at least a first light exit surface,
whereby: light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) exits the first light engine through the first light exit surface, and light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) exits the second light engine, the first sidewall defining a space, at least a first light exit region at a boundary of the space, the first light engine positioned and oriented such that at least some light that exits the first light exit surface passes through at least part of the space and exits the space through the first light exit region, and the second light engine positioned and oriented such that at least some light that exits the second light engine exits the space through the first light exit region.

In some embodiments of methods in accordance with the eighth aspect of the present inventive subject matter, including some embodiments that include or do not include any of the features described herein, the method can optionally further comprise adjusting the brightness of light output from the first light engine and/or adjusting the brightness of light output from the second light engine so that a subject receives light that provides a CS value of at least 0.3 at an illuminance of 300 lux during a first part of the day, and a CS value of less than 0.15 at an illuminance of 200 lux (and/or a CS value of less than 0.2 at an illuminance of 300 lux) during a second part of the day.

A ninth aspect of the present inventive subject matter is directed to a method of supplying light, comprising:

moving a second light engine relative to a first light engine, the first light engine comprising at least a first light exit surface, outputting light that has x, y color coordinates which define a point on a 1931 CIE Chromaticity Diagram which is within a quadrilateral area with vertices having x, y coordinates of (0.37, 0.34), (0.35, 0.38), (0.15, 0.20), and (0.20, 0.14) (and in some embodiments, within a quadrilateral area with vertices having x, y coordinates of (0.32, 0.31), (0.30, 0.33), (0.15, 0.17), and (0.17, 0.14)) from the first light engine through the first light exit surface, and outputting light that has x, y color coordinates which define a point on a 1931 CIE Chromaticity Diagram which is within an area with vertices having x, y coordinates of (0.29, 0.32), (0.32, 0.29), (0.41, 0.36), (0.48, 0.39), (0.48, 0.43), (0.40, 0.41), and (0.35, 0.38) (and in some embodiments, within an area with vertices having x, y coordinates of (0.30, 0.34), (0.30, 0.30), (0.39, 0.36), (0.45, 0.39), (0.47, 0.43), (0.40, 0.41), and (0.35, 0.38)) from the second light engine, at least some light that exits the first light exit surface passing through at least part of a space and exiting the space through a first light exit region, and at least some light that exits the second light engine exiting the space through the first light exit region.

In some embodiments of methods in accordance with the ninth aspect of the present inventive subject matter, including some embodiments that include or do not include any of the features described herein: the first light engine and the second light engine are in a light fixture that further comprises a first sidewall that defines said space.

A tenth aspect of the present inventive subject matter is directed to a method of supplying light, comprising:

outputting light from at least a first light engine and a second light engine, at least the first light engine and the second light engine in a light fixture, light output from the first light engine providing a first CS value at a given illuminance, light output from the second light engine providing a second CS value at the same illuminance, the first CS value different from the second CS value.

In some embodiments of methods in accordance with the tenth aspect of the present inventive subject matter, including some embodiments that include or do not include any of the features described herein: the light output from the first light engine is of a first color point, the light output from the second light engine is of a second color point, and the first color point is spaced from the second color point.

An eleventh aspect of the present inventive subject matter is directed to methods of affecting a subject's (e.g., a human's) biological melatonin levels, comprising exposing such subject to light output from a light fixture (as described herein, including but not limited to light fixtures in accordance with the first, second, fourth, fifth, sixth and seventh aspects) in accordance with the present inventive subject matter.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during part of the day, and exposing said subject to light output from said light fixture to provide a CS value in said subject of less than 0.3 during a different part of the day (e.g., at an illuminance of 300 lux, and/or a CS value of less than 0.25 (in some cases less than 0.2) at an illuminance of 200 lux).

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during part of the day, and exposing said subject to light output from said light fixture to provide a CS value in said subject of less than 0.15 at an illuminance of 200 lux (and/or less than 0.2 at an illuminance of 300 lux) during a different part of the day.

In some embodiments of methods in accordance with the eleventh aspect of the present inventive subject matter, including some embodiments that include or do not include any of the features described herein, the method comprises exposing a subject to light output from a light fixture (e.g., a light fixture in accordance with the present inventive subject matter) to provide a CS value in said subject of at least 0.3 at an illuminance of 300 lux during at least a first part of the day, and exposing said subject to light output from said light fixture to provide a CS value in said subject of less than 0.15 during at least a second part of the day, the lumens output during the second part of the day comprising at least 50% (and in some embodiments at least 60%, 70%, 80% or 90%) of the lumens output during the first part of the day.

It is well known that the CCT or color of daylight changes over the course of a day, seasons, due to weather. Etc. In some of the embodiments described in the preceding two sentences, the CCT of light exiting from the first light engine (CCT1) differs from the CCT of light exiting from the second light engine (CCT2), whereby the CCT for the overall light exiting from the light fixture includes at least a contribution of CCT1 from the first light engine and a contribution of CCT2 from the second light engine. In such embodiments, change in CCT during the day can be achieved by changing the ratio of light contribution from the "sun" (second light engine) to light contribution from the "sky" (first light engine).

It is also well known that the color of the sun and the sky portions of daylight change over the course of a day, seasons, due to weather. Etc. In some of the embodiments described above, the CCT of the light exiting the first light engine (CCT1) may be made adjustable by including in its fabrication at least two different color light-emitting sources whose output is independently controlled. Likewise, the CCT of the light exiting the second light engine (CCT2) may made adjustable by including in its fabrication at least two different color light-emitting sources whose output is independently controlled.

In some embodiments of light fixtures in accordance with the present inventive subject matter, including some embodiments that include or do not include any of the features described herein, the color and/or the brightness of: light that exits from the first light engine (or any portion thereof), light that exits from the second light engine (or any portion thereof), and/or light that exits from a sidewall, can be varied over time (e.g., during the course of the day) automatically (e.g., programmed accordingly to a daily pattern, a monthly pattern, based on sensed condition, etc.) or manually by a user (e.g., by inputting commands in a control that provides signals wirelessly or through a wired connection). For instance, color-changing LED technology with programmable correlated color temperature and/or intensity settings may be employed for these purposes.

The color and/or the brightness of light that exits from one component (e.g., a first light engine) can be controlled independently of the color and/or the brightness of light that exits from another component (e.g., a second light engine or a sidewall).

In some embodiments that comprise one or more sidewall that comprises a light exit surface, light exiting various portions of the sidewall can be adjusted over the course of the day (e.g., with a box-shaped sidewall, one side can be illuminated more strongly in the morning hours and less in the late afternoon hours, and an opposite side can be illuminated less in the morning hours and more in the late afternoon hours to provide or enhance the appearance of movement of the sun during the day.

As discussed above, it is well known that light sources that emit light of respective differing hues (two or more) can be combined to generate mixtures of light that have desired hues. Any light described herein can be provided as a mixture of two or more portions of light that can be of differing color points. For example, the first light engine (and/or the second light engine, and/or any other light engine) can comprise a plurality of LEDs that emit light of two or more respective color points. A light engine that comprises two or more light emitters that emit light of two or more respective color points can be tuned over a range of color points by changing the contribution from each of the two or more light emitters that emit light of respective different color points.

Some embodiments of light fixtures in accordance with the present inventive subject matter comprise a control element (or control elements), which (or each of which) can control one or more of:

a brightness of light emitted from at least a first portion of a sidewall (if included), a brightness of light emitted from at least a second portion of a sidewall (if included), a brightness of light emitted from a first light engine, a brightness of light emitted from a second light engine (if included), a color point of light emitted from at least a first portion of a sidewall (if included), a color point of light emitted from at least a second portion of a sidewall (if included), a color point of light emitted from a first light engine, and a color point of light emitted from a second light engine (if included).

As a first representative embodiment of a light source that comprises plural light emitters, a first light engine can comprise a first LED and a second LED, in which the first LED emits light of a first color point, the second LED emits light of a second color point (different from the first color point), and the light output from the first light engine, which is a mixture of light emitted by the first LED and light emitted by the second LED, can be adjusted (to any point along a tie line extending from the first color point to the second color point) by changing the contribution from the first LED relative to the contribution from the second LED.

As a second representative embodiment of a light source that comprises plural light emitters, a first light engine can comprise a first LED, a second LED and a third LED, in which the first LED emits light of a first color point, the second LED emits light of a second color point (different from the first color point), the third LED emits light of a third color point (different from the first and second color points), and the light output from the first light engine, which is a mixture of light emitted by the first LED, light 108araed by the second LED and light emitted by the third LED, can be adjusted (to any point within an area having the first, second and third color points as its vertices) by changing the contribution from the first LED, the second LED and the third LED relative to each other.

Light from two or more respective light sources can be mixed in any suitable way, e.g., light from one or more of the respective light sources can travel optionally through the same or different light transporting elements, light transmitting elements, etc.

Representative examples of light sources that comprise light emitters that emit light of two or more respective color points, and in which the respective contributions of light of the respective color points can be adjusted, include True-White technology products available from Cree, Inc., Durham, N.C.

By providing light engines that comprise light emitters that emit light of two or more respective color points, it is possible for such a light engine to emit mixtures of light of different color points, e.g., multiple points within the respective regions depicted in FIG. 1, FIG. 2 and FIG. 3, for example, some of all of the points within the respective regions depicted in FIG. 1, FIG. 2 and FIG. 3, by changing the contribution from each of the multiple light emitters in such a light engine.

A representative example of a light fixture in accordance with the first aspect or the second aspect of the present inventive subject matter comprises:

an edge-lit flat panel (e.g., an Essentia flat panel available from Cree, Inc., Durham, N.C.) with blue light-emitting LEDs (e.g., blue LEDs that emit light having a dominant wavelength of 475 nm) and white light-emitting LEDs (e.g., LEDs that emit light having a correlated color temperature of about 5000 K) as the first light engine; and four sidewalls comprising back-lit light boxes according to FIG. 18 with cool-white light-emitting LEDs (e.g., LEDs that emit light having a correlated color temperature of about 6500 K) and warm-white light-emitting LEDs (e.g., LEDs that emit light having a correlated color temperature of about 3000 K) as the second light engine.

FIG. 28 shows the color points of light emitted by representative examples of the two types of LEDs used in the fabrication of the first light engine (the "sky"), and light emitted by the two types of LEDs used in the fabrication of the second light engine (the "sun") plotted on a portion of the CIE 1931 Chromaticity Diagram. For each LED type, multiple data points are shown in FIG. 28, each point corresponding to a different power supplied to the LEDs. Also shown in FIG. 28 are the color points for four settings of the skylight overall, wherein the power to each of the four LED types has been adjusted so that the skylight as a unit delivers a desirable brightness, color, and visual appearance. These four settings correspond to CCT values from approximately 3200 K to 5200 K, which are intended to provide, and do provide, the visual impression of a skylight at different times of day.

Table 1 summarizes relevant characteristics for the four skylight settings, including the electrical power supplied to each of the four LED types.

TABLE 1

| | LED string power in watts | | | | Select characteristics of light delivered by skylight | | | | | | |
|---|---|---|---|---|---|---|---|---|---|---|---|
| Preset | Sun cool white | Sun warm white | Sky blue | Sky white | Lumens | x | Y | CCT/K | duv | CRI | R9 |
| Mid-day | 16.4 | 26.8 | 10.0 | 6.7 | 5642 | 0.3394 | 0.3318 | 5173 | −0.0080 | 85 | 80 |
| Morning | 3.1 | 34.0 | 10.0 | 6.7 | 4745 | 0.3631 | 0.3431 | 4281 | −0.0113 | 82 | 81 |
| Afternoon | 3.1 | 34.0 | 6.3 | 2.6 | 4252 | 0.3826 | 0.3586 | 3792 | −0.0094 | 86 | 91 |
| Evening | 1.8 | 19.7 | 0.0 | 2.6 | 2538 | 0,4209 | 0.3900 | 3171 | −0.0034 | 94 | 68 |

Results in Table 1 and FIG. 28 were measured in an integrating sphere.

As shown in FIG. 28, in this case the light delivered by the skylight has been adjusted to have a white color point slightly below the BBL (blackbody locus). In some embodiments, the color of light delivered may be above, on, or below the BBL.

Since four LED types have been used in this case, in general there are multiple solutions (i.e., sets of supplied power) that can be used to deliver light having a given color point. Thus, the powers listed in Table 1 are one set of many possible sets—others may be desirable (e.g., to maximize CRI, efficiency, or blueness of the sky).

The number of presets is not limited to four. With suitable controls, the number of possible color points within the color gamut defined by the four LED types is virtually unlimited.

In other embodiments, the number of LED types may be greater than four.

In a preferred embodiment, the sun light engine can comprise three (or more) LED types such that the light emitted by the sun light engine may be precisely controlled a in two-dimensional color space (e.g. to stay on the BBL at any achievable CCT value.)

In other embodiments, the color gamut of the selected LED types may be larger than shown in FIG. 28 so that the achievable CCT/color range is correspondingly larger. In particular, the choice of warm white LEDs in the sun light engine, including but not limited to BSY+BSY+RDO combinations such as are found in Cree True White fixtures ("BSY" and "RDO" are defined below). For example, it may be desirable for a skylight fixture to be able to deliver light having a similar color point to natural light around sunset, which can have a very low CCT (<2700 K).

"BSY" is defined as light that has x, y color coordinates (on a 1931 CIE Chromaticity Diagram) which define a point that is within either or both of:

a first area on the 1931 CIE Chromaticity Diagram enclosed by first, second, third, fourth and fifth line segments, the first line segment connecting a first point to a second point, the second line segment connecting the second point to a third point, the third line segment connecting the third point to a fourth point, the fourth line segment connecting the fourth point to a fifth point, and the fifth line segment connecting the fifth point to the first point, the first point having x, y coordinates of 0.32, 0.40, the second point having x, y coordinates of 0.36, 0.48, the third point having x, y coordinates of 0.43, 0.45, the fourth point having x, y coordinates of 0.42, 0.42, and the fifth point having x, y coordinates of 0.36, 0.38; and a second area on the 1931 CIE Chromaticity Diagram enclosed by sixth, seventh, eighth, ninth and tenth line segments, the fifth line segment connecting a fifth point to a sixth point, the seventh line segment connecting the seventh point to an eighth point, the eighth line segment connecting the eighth point to a ninth point, the ninth line segment connecting the ninth point to a tenth point, and the tenth line segment connecting the tenth point to the sixth point, the sixth point having x, y coordinates of 0.29, 0.36, the seventh point having x, y coordinates of 0.32, 0.35, the eighth point having x, y coordinates of 0.41, 0.43, the ninth point having x, y coordinates of 0.44, 0.49, and the tenth point having x, y coordinates of 0.38, 0.53 (in the 1976 CIE Chromaticity Diagram, the sixth point has u', v' coordinates of 0.17, 0.48, the seventh point has u', v' coordinates of 0.20, 0.48, the eighth point has u', v' coordinates of 0.22, 0.53, the ninth point has u', v' coordinates of 0.22, 0.55, and the tenth point has u', v' coordinates of 0.18, 0.55.

"RDO" is defined as red-orange, corresponding to light emitted with a dominant wavelength between 600 nm and 630 nm.

As noted above, FIG. 29 is a photo of an embodiment of an artificial skylight in accordance with the present inventive subject matter, where the sky ("first light engine") has color point (0.3135, 0.3237), and the sun ("second light engine") has color point (0.3451, 0.3516), and FIG. 30 is a photo of an embodiment of an artificial skylight in accordance with the present inventive subject matter, where the sky ("first light engine") has color point (0.2383, 0.2472), and the sun ("second light engine") has color point (0.3451, 0.3516). FIGS. 29 and 30 show embodiments in accordance with the present inventive subject matter that are artificial skylights (i.e., they appear to be skylights) that avoid problems with conventional skylights and that provide benefits that are provided by conventional skylights.

In each of the embodiments shown in FIGS. 29 and 30, a first light engine resembles a sky (i.e., a surface of the first light engine looks like the sky to a viewer), and light exiting from a second light engine has characteristics that resemble those of light emitted by (and received from) the sun. The artificial skylights shown in FIGS. 29 and 30 can thus provide the ability to supply light (in residential buildings, commercial buildings, other buildings and other structures) while avoiding or reducing (in comparison to other devices, such as conventional skylights) water leakage, providing lower heat loss, providing light on overcast or stormy days, simplifying installation, providing the ability for installation (e.g., in locations where installation of a skylight would be problematic or impossible, e.g., in the first story of a multi-story structure, or in a building in which the roof is spaced a large distance from a ceiling), providing the ability to control light exiting from the device into an office, a room or any other space (e.g., controlling the brightness and/or the color of light exiting from the light fixture). In addition, the artificial skylights shown in FIGS. 29 and 30 can simplify cleaning (e.g., in comparison to conventional skylights, the skylights shown in FIGS. 29 and 30 can be more easily accessed, and/or can be removed from a structure on which they are mounted).

Any light fixture disclosed herein can, if desired, comprise one or more luminescent materials. A luminescent material is a material that emits a responsive radiation (e.g., visible light) when excited by a source of exciting radiation. In many instances, the responsive radiation has a wavelength (or hue) that is different from the wavelength (or hue) of the exciting radiation. Persons of skill in the art are familiar with, and have ready access to, a variety of luminescent materials that emit light having a desired peak emission wavelength and/or dominant emission wavelength, or a desired hue, and any of such luminescent materials, or any combinations of such luminescent materials, can be employed, if desired.

One type of luminescent material is phosphors, which are readily available and well known to persons of skill in the art. Other examples of luminescent materials include scintillators, day glow tapes and inks that glow in the visible spectrum upon illumination with ultraviolet light.

Persons of skill in the art are familiar with, and have ready access to, a variety of luminescent materials that emit light having emission wavelengths (dominant or peak) in well-known ranges, and any of such luminescent materials, and any desired combinations of such luminescent materials, can be employed in accordance with the present inventive subject matter.

Several non-limiting representative examples of luminescent materials that can be employed in the present inventive subject matter include cerium-doped yttrium aluminum garnet (aka "YAG:Ce" or "YAG"), $CaAlSiN:Eu^{2+}$ (aka "CASN" or "BR01"), BOSE, quantum dots, nitride phosphors (such as $(Sr, Ca)SiAlN_3:Eu^{2+}$) and narrow band phosphors (such as $K_2SiF_6:Mn^{4+}$).

Luminescent materials, if included, can be in any suitable form. For example, the luminescent element can be embedded in a resin (i.e., a polymeric matrix), such as a silicone material, an epoxy material, a glass material or a metal oxide material, and/or can be applied to one or more surfaces of a resin.

As noted above, in accordance with a first aspect of the present inventive subject matter, there are provided light fixtures (artificial skylights), in which at least a portion of a first light engine resembles a sky (e.g., a surface of the first light engine looks like the sky to a viewer), and light exiting from a second light engine has one or more characteristics that resemble that (or those) of at least a portion of light emitted by (and received from) the sun.

Characteristics of light fixtures in accordance with the present inventive subject matter can be evaluated in a wide variety of ways. One example of a way to evaluate the light fixtures in accordance with the present inventive subject matter is to allow a number of test subjects ("observers", i.e., persons, e.g., ten persons, one at a time) to observe a light fixture in accordance with the present inventive subject matter (and optionally also, simultaneously or in sequence) to observe another light fixture and/or a conventional skylight, and to obtain from each test subject a score (on the respective scales identified below) for each of a number of characteristics, e.g., the following characteristics [A] to [F]:

[A] Shadows: appearance of shadows on the wall (i) directly and (ii) cast from the test subject's hand near the wall; direct sunlight causes sharp shadows, which are a visual cue of the sun's presence; skylights with a diffuser produce a softer, more even shadow—Scale: 1 (clearly artificial); 4 (just like a skylight); 2 and 3 (between 1 and 4, with 2 more toward artificial).

[B] Sun Intensity: impression of light directionality created by brightness contrast between where the sun is hitting vs. overall ambient light, particularly when looking at the wall; direct sunlight is intense and directional, creating contrast when coming through a skylight or a window—Scale: 1 (clearly artificial); 4 (looks just like a real skylight); 2 and 3 (between 1 and 4, with 2 more toward artificial).

[C] Color Uniformity on Wall: when the skylight has two colors with different directionality, some color non-uniformity of the lit space is unavoidable; is it noticeable? Objectionable? Natural light typically—but not always—provides good color uniformity—Scale: 1 (clearly artificial); 4 (looks just like a real skylight); 2 and 3 (between 1 and 4, with 2 more toward artificial).

[D] Glare: gauge comfort level when looking directly at the skylight from different positions; although direct sunlight is inherently glary, a hypothesis is that less glare from the fixture is preferable and would make the skylight more widely deployable—Scale: 1 (acceptable); −1 (not acceptable).

[E] Sky Blue Depth: blue color appearance and perception of remote origin of the sky component when looking directly at the skylight; in skylights that use light from the actual sky, a vertical open space is often used and the sky color can be seen from below, even with a diffuser—Scale: 1 (not detectable); 4 (just like the natural sky); 2 and 3 (between 1 and 4, with 2 more toward not detectable).

[F] Skylight Impression 1.sup.st/delayed: first impression is important; it does not take long for someone to tell if there is a skylight in the room; however, these perceptions can change as people adapt to lighting conditions over about 30 seconds to a few minutes—Scale: 1 (clearly artificial); 4 (just like a skylight); 2 and 3 (between 1 and 4, with 2 more toward artificial).

In another test model, each observer can rate comparatively each of a number of light fixtures, for example, one light fixture per day on three separate days (to rate three different configurations, with the brightnesses for each light engine in each configuration set to a particular value, and the correlated color temperature for each light engine set to a particular value. For each test, each observer can be in the room, by herself or himself, for about ten minutes, and after that time period, the observer can rank each of a number of characteristics of that configuration, and on the third day, each observer can review his or her rankings for all three configurations and make any desired adjustments. As a representative comparison test, for each light fixture configuration, an observer can be asked to give a rating, on a scale of 1 to 4 (1 being "clearly an artificial light, definitely not a skylight"; 2 being "looks more like an parallel light than a skylight"; 3 being "looks more like a skylight than an artificial light"; and 4 being "looks just like a real skylight"), for each of the following characteristics:

[A] How do you feel about the lighting in this room?
[B] At near the entrance, rate if the lighting resembles a skylight?
[C] Sitting on the chair and not looking up, rate whether the lighting resembles a skylight.
[D] Free to move, and look up to the light, rate if the lighting resembles a skylight.
[E] Do shadows (cast on wall or on objects) resemble those from a skylight?
[F] Does the light include light that resembles light having the sun's intensity?
[G] Does the color uniformity on walls resemble that of light from a skylight?
[H] Does the first light engine of the light fixture resemble the blue sky in its color and intensity?

For each characteristic ([A]-[H]), an average can be calculated among the observers (and/or any other statistical analysis can be performed, e.g., removing one or more high and low scores, standard deviation, etc.).

In addition, the observers can be asked to characterize the glare from the light fixtures as "acceptable" or "not acceptable".

In addition, each observer can be asked whether he or she would use the light fixture in his or her office ("Yes", "No" or "indifferent").

In addition, each observer can be asked whether he or she would use the light fixture in his or her home ("Yes", "No" or "indifferent").

In addition, each observer can be asked to state how he or she feels about the lighting in the room in comparison to other lighting in the room (e.g., whether there is any difference, whether the light is better, worse, lighter than a skylight, more glare, etc.).

The relationship between values recorded from such tests can be of interest. For example, a value from [D] which is much lower (e.g., 1 or more, for example 1.2 or 1.3) than the value from [C] might indicate that the blue sky from the first light engine is favorable, but directly viewing the second light engine detracts significantly from such favorable viewpoint.

Below is a table showing various combinations that each comprise a first light engine ("$1^{st}$") and a second light engine ($2^{nd}$), along with respective lux values for vertical illuminance ("v") and horizontal illuminance ("h"), in which brightnesses are adjusted so that the horizontal and vertical illuminances are approximately constant. Illuminance measurements were performed with Konica-Minolta T10 illuminance meter. Horizontal illuminances were measured directly below the light fixture on surface parallel to the ceiling at approximately tabletop height of 2.5 ft from ground. Vertical illuminances were measured on a surface perpendicular to the ceiling at height of about 5 ft from the ground. The configuration of the first and second light engines was similar to the embodiment shown in FIG. 7, mounted in an 8' high ceiling. The power supplied to the multiple LED strings in the first light engine is selected such that the first light engine emits (1) light having a correlated color temperature of 3000 K (and with a vertical illuminance of 101 lux and a horizontal illuminance of 220 lux) exits, (2) light having a correlated color temperature of 4000 K (and with a vertical illuminance of 98 lux and a horizontal illuminance of 210 lux) exits, (3) light having a correlated color temperature of 5000 K (and with a vertical illuminance of 102 lux and a horizontal illuminance of 219 lux) exits, (4) light having a correlated color temperature of 6000 K (and with a vertical illuminance of 102 lux and a horizontal illuminance of 220 lux) exits, (5) light having a correlated color temperature of 9300 K (and with a vertical illuminance of 102 lux and a horizontal illuminance of 221 lux) exits, (6) light having a correlated color temperature of 17,000 K (and with a vertical illuminance of 103 lux and a horizontal illuminance of 223 lux). The power supplied to the two LED strings in the second light engine is selected such that the second light engine emits (1) light having a correlated color temperature of 5000 K (and with a vertical illuminance of 901 lux and a horizontal illuminance of 234 lux) exits, (2) light having a correlated color temperature of 4000 K (and with a vertical illuminance of 929 lux and a horizontal illuminance of 237 lux) exits, and (3) light having a correlated color temperature of 3000 K (and with a vertical illuminance of 955 lux and a horizontal illuminance of 235 lux) exits.

TABLE 2

|  | $1^{st}$ 3000K | $1^{st}$ 4000K | $1^{st}$ 5000K | $1^{st}$ 6000K | $1^{st}$ 9000K | $1^{st}$ 17,000K |
|---|---|---|---|---|---|---|
| $2^{nd}$ 5000K | v 1002 h 454 | v 999 h 444 | v 1003 h 453 | v 1003 h 454 | v 1003 h 455 | *v 1004 *h 457 |
| $2^{nd}$ 4000K | v 1030 h 457 | v 1027 h 447 | v 1031 h 456 | v 1031 h 457 | *v 1031 *h 458 | *v 1032 *h 460 |
| $2^{nd}$ 3000K | v 1056 h 455 | v 1053 h 445 | *v 1057 *h 454 | *v 1057 *h 455 | *v 1057 *h 456 | *v 1058 *h 458 |

As seen above, the favorable results, indicated in Table 2 by "*v" and "*h", tend to the lower right portion of the table, indicating that in some embodiments it is advantageous for the sky color (CCT) to be bluer (higher) than the sun color (CCT).

Representative combinations from Table 2 that provide particularly favorable results include: 17,000 K first light engine and 5000 K second light engine; 9000 K first light engine and 3000 K second light engine; 6000 K first light engine and 3000 K second light engine; 9000 K first light engine and 4000 K second light engine; 17,000 K first light engine and 4000 K second light engine; 5000 K first light engine and 3000 K second light engine; and 17,000 K first light engine and 3000 K second light engine.

Light fixtures in accordance with the present inventive subject matter are scalable (i.e., the size of the light fixtures, or any portion or portions thereof, can be modified by being magnified or shrunk to any degree). For example, a large (or immense) light fixture can be made by increasing the size of one or more components and/or by increasing the number of components (e.g., providing an array of direct-lit panels and an array of downlights, etc.). In view of the scalability of the present inventive subject matter, the brightness (e.g., quantity of lux and/or lumens delivered) is similarly scalable, and accordingly there are effectively no limits.

In some embodiments in accordance with the present inventive subject matter, including some embodiments that include or do not include any of the features described herein, a second light engine is movable relative to a first light engine and/or a sidewall. In some of such embodiments, the light fixture further comprises a motor that is configured to move a second light engine, and/or to change the orientation of the second light engine, relative to the first light engine and/or a sidewall (e.g., by moving and/or altering the orientation of a support that is configured to hold the second light engine), e.g., in devices in accordance with the first aspect of the present inventive subject matter to mimic changes in sunlight over the course of a day and/or seasons of the year (e.g., to alter the angle of at least some of the light that exits from the second light engine to resemble changes that occur to sunlight over the course of a day). In embodiments in which the second light engine is movable relative to the first light engine and the sidewall, such movement can be automatic and/or input manually (e.g., by a user).

In some embodiments in accordance with the present inventive subject matter, including some embodiments that include or do not include any of the features described herein, the light fixture further comprises at least a first waveguide and/or a first light guide, and a second light engine is positioned relative to the first waveguide and/or the first light guide such that light that exits from the second light engine enters the first waveguide (and/or the first light guide). In some of such embodiments, the first waveguide (and/or the first light guide) is/are movable relative to the second light engine to change the orientation and/or the position of the first waveguide (and/or the first light guide) relative to the second light engine. For example, in some embodiments, the light fixture further comprises a waveguide bracket (which is configured to hold the first waveguide) and/or a light guide bracket (which is configured to hold the first light guide) and a motor which is configured to change the orientation and/or position of the first waveguide (and/or the first light guide) relative to the second light engine.

In some embodiments in which the light fixture comprises at least a first waveguide and/or a first light guide, the first waveguide (and/or the first light guide) is configured to change the direction(s) that at least some light that exits from the second light engine travels upon changing the orientation and/or position of the first waveguide (and/or the first light guide) relative to the second light engine.

In some embodiments in which the light fixture comprises at least a first waveguide and/or a first light guide, movement (changing the orientation and/or position) of the first waveguide (and/or the first light guide) relative to the second light engine corresponds to passage of time, e.g., the direction(s) of travel (e.g., the axis of emission) of at least some light that exits from the second light engine after passing through the first waveguide (and/or the first light guide) changes over the course of the day to correlate with (or emulate) the movement of the sun over the course of the day.

In embodiments in which the light fixture comprises at least a first waveguide and/or a first light guide and the first waveguide (and/or the first light guide) is movable relative to the second light engine, such movement can be automatic and/or input manually (e.g., by a user).

Light fixtures in accordance with the present inventive subject matter can be used as skylights, and/or as wall wash lighting (e.g., light fixtures that are configured and/or oriented such that a large portion of light that exits the light fixtures illuminates one or more walls) or as accent lighting (e.g., light fixtures that are configured and/or oriented such that they throw a large amount of light on a particular area or object(s)).

Light sources in the light fixtures in accordance with the present inventive subject matter can be supplied with electricity in any suitable manner. Skilled artisans are familiar with a wide variety of apparatuses and/or components for supplying electricity to light sources, and any such apparatuses and/or components can be employed in connection with the present inventive subject matter. Light fixtures in accordance with the present inventive subject matter can be electrically connected (or selectively connected) to any suitable power source, persons of skill in the art being familiar with a variety of such power sources.

Light fixtures according to the present inventive subject matter can, as desired, include any suitable circuitry components, e.g., drive electronics for supplying and controlling current passed through any light sources in the light fixture. Persons of skill in the art are familiar with a wide variety of ways to supply and control the current passed through light sources, and any such ways can be employed in light fixtures in accordance with the present inventive subject matter. For example, such circuitry can include at least one contact, at least one leadframe, at least one current regulator, at least one power control, at least one voltage control, at least one boost, at least one capacitor and/or at least one bridge rectifier, persons of skill in the art being familiar with such components and being readily able to design appropriate circuitry to meet whatever current flow characteristics are desired.

The light fixtures according to the present inventive subject matter can further comprise any suitable electrical connector, a wide variety of which are familiar to those of skill in the art, e.g., an Edison connector (for insertion in an Edison socket), a GU24 connector, etc., or light fixtures may be directly wired to an electrical branch circuit.

Compensation circuits can be provided to help to ensure that the perceived color (including correlated color temperature) of light exiting a light engine (e.g., a first light engine or a second light engine) is accurate (e.g., within a specific tolerance). Such compensation circuits, if included, can (for example) adjust the current supplied to light sources that emit light of one color and/or separately adjust the current supplied to light sources that emit light of a different color, so as to adjust the color of mixed light, and such adjustment(s) can be (1) based on temperature sensed by one or more temperature sensors (if included), and/or (2) based on light sensed by one or more light sensors (if included) (e.g., based on one or more sensors that detect (i) the color of the light that exits from a light engine and/or a light source, and/or (ii) the brightness of the light being emitted from one or more light sources, and/or (iii) the brightness of light of one or more specific hues of color), and/or based on any other sensors (if included), factors, phenomena, etc.

A wide variety of compensation circuits are known, and any can be employed in the light fixtures according to the present inventive subject matter. For example, a compensation circuit may comprise a digital controller, an analog controller or a combination of digital and analog. For example, a compensation circuit may comprise an application specific integrated circuit (ASIC), a microprocessor, a microcontroller, a collection of discrete components or combinations thereof. In some embodiments, a compensation circuit may be programmed to control one or more light sources. In some embodiments, control of one or more light sources may be provided by the circuit design of the compensation circuit and is, therefore, fixed at the time of manufacture. In still further embodiments, aspects of the compensation circuit, such as reference voltages, resistance values or the like, may be set at the time of manufacture so as to allow adjustment of the control of the one or more light sources without the need for programming or control code.

Energy can be supplied to the at least one light source from any source or combination of sources, for example, the grid (e.g., line voltage), one or more batteries, one or more photovoltaic energy collection devices (i.e., a device that includes one or more photovoltaic cells that convert energy from the sun into electrical energy), one or more windmills, etc.

The light fixtures in accordance with the present inventive subject matter can comprise any suitable heat transfer or dissipation elements, structures, components and/or materials, and/or cooling elements, as desired or needed to comply with regulations and/or to assist in providing a long useful life for the light fixtures and the components therein (e.g., light emitting diodes). Persons of skill in the art are familiar with a wide variety of heat transfer or dissipation elements, structures, components and materials, and schemes for their deployments, and a wide variety of cooling elements, and schemes for their Deployment, and any such heat transfer or dissipation elements, structures, components and/or materials, and/or cooling elements, and schemes, combinations and arrangements thereof can be employed in accordance with the present inventive subject matter.

Many alterations and modifications may be made by those having ordinary skill in the art, given the benefit of the present disclosure, without departing from the spirit and scope of the inventive subject matter. Therefore, it must be understood that the illustrated embodiments have been set forth only for the purposes of example, and that it should not be taken as limiting the inventive subject matter as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the inventive subject matter.

Any two or more structural parts of the light fixtures described herein can be integrated. Any structural part of the light fixtures described herein can be provided in two or more parts (which may be held together in any known way, e.g., with adhesive, screws, bolts, rivets, staples, etc.). Similarly, any two or more functions can be conducted simultaneously, and/or any function can be conducted in a series of steps.

Additionally disclosed is a lighting fixture that appears as a skylight and is referred to as a skylight fixture. The skylight fixture has a sky-resembling assembly and a plurality of sun-resembling assemblies. The sky-resembling assembly has a sky-resembling optical assembly and a sky-specific light source, wherein light from the sky-specific light source exits a planar interior surface of the skylight optical assembly as skylight light. The sun-resembling assemblies are arranged adjacent one another and extend downward from a periphery of the sky-resembling assembly. Each of the plurality of sun-resembling assemblies has a sun-resembling optical assembly and a sun-specific light source, wherein light from the sun-specific light source exits a planar interior surface of the sunlight optical assembly as sunlight light. The planar interior surfaces of the skylight optical assembly and the plurality of sunlight optical assemblies define a cavity. It is understood that the planar surfaces of the various optical assemblies could have other shapes like curved or circular, such as in a dome shaped lighting fixture or the like. One or more control modules alone or in a collective are configured to, in a first mode, drive the sky-specific light source and each sun-specific light source such that the sky-specific light emission has a first color point and the sun-specific light emission of at least one of the plurality of sun-resembling assemblies has a second color point that is different from the first color point. The sky-resembling assembly may be configured to emulate a window of a traditional skylight. Each of the plurality of sun-resembling assemblies may be configured to emulate sunlight passing through and/or reflecting off of sidewalls of a traditional skylight.

An exemplary skylight fixture 310 is illustrated in FIG. 31. The skylight fixture 310 is mounted in a ceiling structure 312, which in the illustrated embodiment is a drop ceiling, such as that used in many commercial buildings. However, those skilled in the art will recognize that the skylight fixture 310 may be installed in any type of ceiling structure 312, such as drywall, wood, masonry, and the like. In essence, the skylight fixture 310 has the general appearance of and emulates a traditional skylight. The skylight fixture 310 takes the general shape of an inverted box that has multiple sidewalls and a bottom wall. For purposes that will become clearer below, the bottom wall is referred to as a sky-resembling assembly 314, and the sidewalls are referred to as sun-resembling assemblies 316. The sky-resembling and sun-resembling assemblies 314, 316 are formed from light engines, the details of which are described further below.

In general, the sky-resembling assembly 314 is configured to emit light and provide the appearance of the sky to a viewer. In essence, the sky-resembling assembly 314 emulates the window portion of a traditional skylight. The sun-resembling assemblies 316 are configured to emulate the sidewalls of a traditional skylight. Generally, the sidewalls of a traditional skylight reflect the more directional sunlight emanating from the sun. For the concepts described herein, the sun-resembling assemblies 316 are configured to emulate sunlight coming through the skylight directly at a particular angle or being reflected off of a sidewall. Accordingly, the sky-resembling assembly 314 is configured to provide the generally non-directional light associated with the sky, whereas the sun-resembling assembly 316 emulates the direct sunlight or a reflection thereof from the sun. Depending on the time of day or night, the intensity, color temperature, color of light emitted from the sky-resembling and sun-resembling assemblies 314, 316 will vary in an effort to emulate the light provided by a traditional skylight at different times of the day or night and any transitions therebetween.

FIGS. 32A and 32B provide cross-sectional views of two different embodiments of the skylight fixture 310. In the embodiment of FIG. 32A, the sun-resembling assemblies 316 are essentially orthogonal to the sky-resembling assembly 314. Opposing sun-resembling assemblies 316 are effectively parallel with one another. In other words, the exposed surfaces of the sun-resembling assembly 316 form a 90 degree angle with the exposed surface of the sky-resembling assembly 314.

For the embodiment of FIG. 32B, the exposed surfaces of the sun-resembling assembly 316 form an obtuse angle α with the exposed surface of the sky-resembling assembly 314. As described further below, increasing the angle between the exposed surfaces of the sun-resembling assemblies 316 and the sky-resembling assembly 314 may improve emulation of sunlight passing through the skylight fixture 310. While there is no specific limitation on the value of the obtuse angle α, experiments have shown particularly effective performance when the obtuse angle α is:

90 degrees <α≤135;
95 degrees ≤α≤130; or
100 degrees ≤α≤125.

Also illustrated in FIGS. 32A and 32B are an electronics module 318 and a general housing 320. The electronics module 318 provides the requisite electronics for the skylight fixture 310. The electronics module 318 may include power supply electronics, control electronics, communication electronics, and/or the requisite driver circuitry for the sky-resembling and sun-resembling assemblies 314, 316. In FIGS. 32A and 32B and select figures to follow, dashed line arrows represent the "sunlight" emanating from the sky-resembling assembly 314, and the solid line arrows represent the "sunlight" emanating directly from or being reflected from the sunlight assembly 316.

FIG. 33 illustrates two skylight fixtures 310 mounted in a ceiling structure 312 in a room with walls 322. While light may not be completely controlled, FIG. 33 illustrates "sunlight" from the sky-resembling assembly 314 projecting predominantly downward into the room, wherein the "sunlight" (solid line arrows) from the sun-resembling assemblies 316 is projected into the room in a more angular fashion, such that the light emanated from the sun-resembling assemblies 316 illuminates and reflects off of the walls 322 in an effort to emulate sunlight coming through a traditional skylight at an angle and directly lighting up the walls 322 or being reflected off of a sidewall of a traditional lighting fixture and being reflected into the room at an angle.

As indicated above, both the sky-resembling and sun-resembling assemblies 314, 316 may be provided by various types of light engines. The sky-resembling and sun-resembling assemblies 314, 316 in a particular skylight fixture 310 may incorporate the same or different types of light engines. If the same light engines are used for both the sky-resembling and sun-resembling assemblies 314, 316, these light engines may be configured the same or differently depending on the spectral capabilities of the light engines.

FIGS. 34-37 illustrate four different types of light engines. The illustrated light engines are provided merely as examples, and do not represent an exclusive or exhaustive list. With reference to FIG. 34, the first type of illustrated light engine may take the form of a display device, such as a light emitting diode (LED) display, a liquid crystal display (LCD), an organic LED (OLED) display, or the like. A typical display assembly 324 will include a display panel 326 on which images are displayed, and appropriate driver electronics 328 to drive the display panel 326. Based on the input of the driver electronics 328, the display panel 326 will display images in the desired manner.

The display assembly 324 is particularly beneficial as a sky-resembling assembly 314 due to the tremendous flexibility in scenes that can be displayed in an effort to emulate the appearance of the sky during any time of the day or night. The display can simply provide a uniform color across the display to emulate the blue sky of day, the sunset in the evening, or the black at night. In more sophisticated embodiments, the display can vary to indicate clouds, stars scattered in the night sky, the reddish orange light illuminating clouds during a sunrise or sunset, and the like. In essence, incorporation of a display assembly 324 provides the flexibility of presenting anything from a specifically colored panel to specific still or moving images, which may be coordinated among multiple skylight fixtures 310.

The embodiments of FIGS. 35, 36, and 37 will generally not be capable of displaying particular images, but may project light of a varying intensity, color, and color temperature while appearing a particular color and brightness. Notably, the light emanating from one of these light engines may be different from a color of the panel the light engine actually appears. For example, one may want the light engine to appear blue, but project white light. In these embodiments, the light projected from the light engines and the appearance of the light engines will be substantially uniform.

With particular reference to FIG. 35, an edge lit-type light engine is provided, wherein an optical assembly 332 is edge lit with one or more light sources 334. In particular, the optical assembly 33332 may be a single or multi-layer optical waveguide, diffuser, lens, or any combination thereof. The light sources 334, which are illustrated as LEDs but are not limited thereto, illuminate the edges of the optical assembly 332, and light is emitted from a front surface of the optical assembly 332. Typically, the light source 334 will extend along all of at least one side of the optical assembly 332, if not multiple or all sides of the optical assembly 332. The light engine 330 will include a light engine housing 336 to maintain the optical assembly 332 and the light source 334 in a proper orientation with respect to one another, as well as to allow the overall light engine 330 to be mounted in the skylight fixture 310. Notably, the LEDs of the light source 334 may be the same or different colors, depending on the application. If LEDs of different colors are provided, the optical assembly 332 will facilitate the mixing of light from the various LEDs, such that light emanates from the front surface of the optical assembly 332 in a uniform manner.

Turning now to FIG. 36, a back lit-type light engine 340 is illustrated. An optical assembly 342 that has a front side and an opposing back side is provided. A light source 344, such as an array of LEDs, is positioned to illuminate the back surface of the optical assembly 342, such that light emitting from the light source 344 passes through the optical assembly 342 and emanates from the front surface of the optical assembly 342. Typically, the LEDs of the LED array of the light source 344 are spaced apart from the back surface of the optical assembly 342, wherein a mixing chamber 346 is provided between the light source and the back surface of the optical assembly 342. This allows LEDs of different colors of light to be used in the light source 344. The different colors of light will mix in the mixing chamber and be passed through the optical assembly 342, which may provide further mixing and diffusion, depending on the particular application. As with the above embodiments, a light engine housing 348 may be provided to hold the optical assembly 342 and the light source 344 in a proper orientation to one another and allow mounting to the skylight fixture 310.

FIG. 37 illustrates a side lit-type light engine 350, which is configured in a similar fashion to that of FIG. 36. The exception is that the LEDs of the light source 354 are provided on the sides of the mixing chamber 356 and perpendicular to the rear surface of the optical assembly 352. Light from the LEDs from the light source 354 will emanate into the mixing chamber 356, and ultimately through the optical assembly 352 such that mixed light emanates from the front surface of the optical assembly 352. A light engine housing 358 may be provided to maintain the proper orientation of the optical assembly 352 and the light source 354, as well as provide the mixing chamber 356. Again, the LEDs of the light source 354 may provide different colors of light, wherein the mixing chamber 356 and the optical assembly 352 are configured such that light emanating from the front surface of the optical assembly 352 is of a desired color. The light sources 334, 344, and 354 need not be LEDs; however, LED-based light sources provide energy efficient and high quality light, as will be described further below. The optical assemblies 332, 342, and 352 may comprise one or more light/waveguides, diffusion films, lens films, diffusers, lenses, and the like.

FIG. 38 illustrates a partial cross-section of a skylight fixture 310, wherein each of the sun-resembling assemblies 316 employs back lit light engines 340. Further, the optical assembly 342 is angled such that the exposed surface of the optical assembly 342 forms an obtuse angle with the exposed surface of the sky-resembling assembly 314, which may employ a display assembly 324, light engine 330, light engine 340, or light engine 350, as described above. As illustrated, the light source 344 is an array of LEDs, wherein each LED of the array of LEDs is distributed along a vertical surface, which is orthogonal to the exposed surface of the sky-resembling assembly 314. A mixing chamber is provided between the LED array and the back surface of the optical assembly 342. While the LEDs of the LED array of the light source 344 are arranged on a vertical plane of the light engine housing 348, the plane on which the LEDs reside may also be angled, wherein the plane on which the LEDs are arranged is parallel to the optical assembly 342. In other embodiments, the plane on which the LEDs reside is not vertical, yet need not be parallel with the optical assembly 342.

In one embodiment, the appearance of the exposed surfaces of the sky-resembling and sun-resembling assemblies 314, 316 are configured to appear as a traditional skylight, which typically has painted, vertical side walls and a window. As such, the sun-resembling assemblies 316 may have optical assemblies 332, 342, 352, that have low gloss interior surfaces that are flat white in color. The interior surfaces are those that are visible once installed. The low gloss, flat white interior surfaces provide the appearance of the vertical side walls, which are typically painted flat white. The sun-resembling assemblies 316 will be of high efficacy and provide a CRI equal to or greater than 85 or 90 in addition to providing an R9 equal to or greater than 50. Ultra-uniform color mixing and uniform luminance across the interior surfaces of the optical assemblies 332, 342, 352 enhance the emulation effect.

The interior surfaces of the optical assembly 332, 342, 352 of the skylight fixture 310 may be a matte diffuser. For a waveguide embodiment, the optical assembly 332 will include a highly reflective backing on the back surface, which is opposite the interior surface. The sky-resembling assembly 314 should provide a CRI of or greater than 85 or 90 in addition to being color changeable. In one embodiment, the color can range from a sky blue to a very high correlated color temperature, such as white light within three, five, seven, or ten MacAdam ellipses of +/−5% of 5000 K or 5500 K, depending on the embodiment.

FIG. 39 illustrates an embodiment wherein multiple (six) skylight fixtures 310 are installed in a ceiling structure 312 in close proximity to one another to form an appealing matrix of virtual skylights. Through appropriate electronics, the light and/or images provided/displayed by each of the skylight fixtures 310 may be the same or coordinated as desired. For example, the movement of the sun, the passing of clouds, movement of shadows and the like may transition from one skylight fixture 310 to another to form a composite display and/or lighting effect from the overall group of skylight fixtures 310. Such operation may be tied to various sensors, information sensors, and the like, such that the light and/or information displayed by the skylight fixtures 310 corresponds to an associated outdoor environment.

As noted, each of the sky-resembling assembly 314 and the sun-resembling assemblies 316 may be configured the same or differently with respect to their lighting capabilities and characteristics. While different ones of the sun-resembling assemblies 316 may be configured differently on a given skylight fixture 310, they are generally configured the same on a given skylight fixture 310. Given the different objectives for the respective sky-resembling and sun-resembling assemblies 314, 316, the sky-resembling and sun-resembling assemblies 314, 316 may be designed to operate at different intensity levels, color spaces, color temperatures, distribution patterns, and the like as well as provide light at different efficacy levels or with different color rendering index values. Further, the different sky-resembling and sun-resembling assemblies 314, 316 may be designed and/or controlled such that each panel provides light with different characteristics, yet the light from the overall skylight fixture 310 combines to provide light with certain characteristics, which are different from that of either of the sky-resembling and sun-resembling assemblies 314, 316.

With certain embodiments, the sun-resembling assemblies 316 are designed to emulate the directional nature of sunlight passing through a traditional skylight. The sky-resembling assemblies 314 are designed to emulate the appearance of the sky and the non-directional nature of sunlight passing through a traditional skylight. The sky-resembling and sun-resembling assemblies 314, 316 may be further configured to emulate the appearance of light passing through or being reflected from window and side walls of the traditional skylight. One of the more significant lighting characteristics in achieving these goals is the color space, and in particular, the color point at which the respective sky-resembling and sun-resembling assemblies 314, 316 operate.

In certain embodiments, the light exiting the sky-resembling assembly 314 is relatively shifted toward blue in the light spectrum to better emulate the appearance of a blue sky. The light exiting the sun-resembling assembly 36 is relatively shifted toward the red in the light spectrum to better emulate the appearance of sunlight. In a first embodiment, the light exiting the sky-resembling assembly 314 has a color point within a first skylight color space A. As shown in FIG. 40A and listed in the table of FIG. 40B, the first skylight color space 11 is represented by a polygon defined by the following x, y coordinates on the 1931 CIE Chromaticity Diagram: (0.37, 0.34), (0.35, 0.38), (0.15, 0.20), and (0.20, 0.14). The light exiting the sun-resembling assembly 316 has one or more color points within a first sunlight color space A. As shown in FIG. 41A and listed in the table of FIG. 41B, the first sunlight color space A is defined by the following x, y coordinates on the 1931 CIE Chromaticity Diagram: (0.29, 0.32), (0.32, 0.29), (0.41, 0.36), (0.48, 0.39), (0.48, 0.43), (0.40, 0.41), and (0.35, 0.38). Both the sky-resembling assembly 314 and the sun-resembling assemblies 316 may be configured to vary the color points during operation to emulate and/or track changing conditions of outside environments throughout the day and night.

In a second embodiment, the light exiting the sky-resembling assembly 314 has a color point within a second skylight color space B. As shown in FIG. 42A and listed in the table of FIG. 42B, the second skylight color space B is defined by the following x, y coordinates on the 1931 CIE Chromaticity Diagram: (0.32, 0.31), (0.30, 0.33), (0.15, 0.17), and (0.17, 0.14). The light exiting the sun-resembling assembly 16 has one or more color points within a second sunlight color space B. As shown in FIG. 43A and listed in the table of FIG. 43B, the second sunlight color space B is defined by the following x, y coordinates on the 1931 CIE Chromaticity Diagram: (0.30, 0.34), (0.30, 0.30), (0.39, 0.36), (0.45, 0.39), (0.47, 0.43), (0.40, 0.41), and (0.35, 0.38). Both the sky-resembling assembly 314 and the sun-resembling assemblies 316 may be configured to vary the color points during operation to emulate and/or track changing conditions of outside environments throughout the day and night.

The first and second embodiments defined above provide relatively limited color spaces for the respective sky-resembling and sun-resembling assemblies 314, 316 to operate. These embodiments are geared toward emulating a traditional skylight during predominately daylight hours between, but not necessarily including, the sunrise and sunset where the sky may appear less blue and more reddish orange. To expand the functionality of the skylight fixture 310 to better emulate the appearance of a traditional skylight outside of daylight hours, operation in expanded color spaces is beneficial. For example, the color spaces may need to be shifted or expanded to address the deeper blues associated with dusk, dawn, and nighttime as well as the more reddish orange and red hues associated with sunrise and sunset. Exemplary enhanced color spaces for the sky-resembling and sun-resembling assemblies 314, 316 are provided in a third embodiment.

In the third embodiment, the light exiting the sky-resembling assembly 314 has a color point within a third skylight color space C. As shown in FIG. 44A and listed in the table of FIG. 44B, the third skylight color space C is defined by the following x, y coordinates on the 1931 CIE Chromaticity Diagram: (0.39, 0.31), (0.34, 0.40), (0.10, 0.20), and (0.16, 0.06). The light exiting the sun-resembling assembly 316 has one or more color points within a third sunlight color space C. As shown in FIG. 45A and listed in the table of FIG. 45B, the third sunlight color space C is defined by the following x, y coordinates on the 1931 CIE Chromaticity Diagram: (0.28, 0.36), (0.35, 0.26), (0.44, 0.33), (0.62, 0.34), (0.50, 0.46), (0.43, 0.45), (0.36, 0.43). Both the sky-resembling assembly 314 and the sun-resembling assemblies 316 may be configured to vary the color points during operation to emulate and/or track changing conditions of outside environments throughout the day and night. The highlighted points in the graphs are exemplary color points for the respective sky-resembling and sun-resembling assemblies 314, 316.

In a fourth embodiment, the color spaces for both the sky-resembling and sun-resembling assemblies 314, 316 are greatly expanded and/or the same or substantially the same. As shown in FIG. 46A and listed in the table of FIG. 46B, the skylight and sunlight color spaces are defined by the following x, y coordinates on the 1931 CIE Chromaticity Diagram: (0.10, 0.20), (0.36, 0.43), (0.43, 0.45), (0.50, 0.46), (0.62, 0.34), (0.44, 0.33), (0.16, 0.06). Both the sky-resembling assembly 314 and the sun-resembling assemblies 316 may be configured to vary the color points during operation to emulate and/or track changing conditions of outside environments throughout the day and night. The highlighted points in the graphs are exemplary color points for the respective sky-resembling (square points) and sun-resembling (triangular points) assemblies 314, 316.

In any of the above or alternative embodiments, the ccx value on the 1931 CIE Chromaticity Diagram of the color point of light exiting the sky-resembling assembly 314 may be less or about equal than the ccx value on the 1931 CIE Chromaticity Diagram of the color point of light exiting the sun-resembling assembly 316. Alternatively, the ccy value on the 1931 CIE Chromaticity Diagram of the color point of light exiting the sky-resembling assembly 314 can be less or about equal than the ccy value on the 1931 CIE Chromaticity Diagram of the color point of light exiting the sun-resembling assembly 316. In other embodiments, both the ccx value on the 1931 CIE Chromaticity Diagram of the color point of light exiting the sky-resembling assembly 314 is less than or about equal the ccx value on the 1931 CIE Chromaticity Diagram of the color point of light exiting the sun-resembling assembly 316, and the ccy value on the 1931 CIE Chromaticity Diagram of the color point of light exiting the sky-resembling assembly 314 is less than or about equal the ccy value on the 1931 CIE Chromaticity Diagram of the color point of light exiting the sun-resembling assembly 316.

In LED-based embodiments, the arrays of LEDs are used for one or both of the sky-resembling and sun-resembling assemblies 314, 316. In the following embodiments, assume that LED arrays are used for both the sky-resembling and sun-resembling assemblies 314, 316. In the first embodiment, which is described in association with the 1931 CIE Chromaticity Diagram of FIG. 47, a two-color LED array is employed as the light source for the sky-resembling assembly 314. A two-color LED array will have multiple LEDs of a first color and multiple LEDs of a second color.

For this embodiment, the first LEDs are bluish LEDs that emit bluish light with a color point CP1 in the lower left of the 1931 CIE Chromaticity Diagram. The bluish LEDs have a 475 nm dominant wavelength and an overall spectrum that is illustrated in FIG. 48, which is a graph of output intensity versus wavelength. The second LEDs are a white LEDs that emit white light at a color point CP2 on or within three or five MacAdam Ellipses (a/k/a MacAdam step ellipses) of the Black Body Curve. In this example, the white LEDs have a color temperature of approximately 5000 K (+/−0.5, 1, 2, or 5%) and a color rendering index (CRI) of at least 85 or 90 (i.e. CRI 85, CRI 90). The white LEDs have an overall spectrum that is illustrated in FIG. 49, which is a graph of output intensity versus wavelength.

For a two-color LED array, the color point of light exiting the sky-resembling assembly 314 can vary along a tie line that extends between the color points associated with the bluish and white LEDs depending on the extent to which the respective LEDs are driven. In this embodiment, the color point of the light exiting the sky-resembling assembly 314 can vary in color along the tie line from white light with a color temperature of approximately 5000 K to a sky blue. Three exemplary color points for sky targets are shown as circles on the tie line. While a two-color LED array is cost effective and provides variable color points along a defined tie line, the overall spectrum associated with the light emitted from a two-color LEDs array is somewhat limited.

One way to increase the overall spectral gamut of the emitted light from the sky-resembling assembly 314 is two use three or more LEDs in the LED array. Using three or more colors in the LED array is beneficial, even if the design dictates varying color along a single, linear tie line. An example of a three color-LED array is illustrated in the 1931 CIE Chromaticity Diagram of FIG. 50. In this example, deeper bluish LEDs, greenish LEDs, and white LEDs are employed. The deeper bluish LEDs emit bluish light with a color point CP3 in the lower left of the 1931 CIE Chromaticity Diagram. The bluish LEDs have a 460 nm dominant wavelength, but can range from about 450 nm to about 465 nm in dominant wavelength as illustrated in FIG. 51, which is a graph of output intensity versus wavelength.

The greenish LEDs emit greenish light with a color point CP5 in the upper left of the 1931 CIE Chromaticity Diagram. The greenish LEDs have a 520 nm dominant wavelength but can range from about 505 nm to about 530 nm in dominant wavelength as illustrated in FIG. 52, which is a graph of output intensity versus wavelength. The white LEDs emit white light at a color point CP5 on or within three or five MacAdam Ellipses of the Black Body Curve. In this example, the white LEDs have a color temperature of approximately 5000 K (+/−0.5, 1, 2, or 5%) and a color rendering index (CRI) of at least 85 or 90 (i.e. CRI 85, CRI 90). The white LEDs have an overall spectrum that is illustrated in FIG. 53, which is a graph of output intensity versus wavelength. While certain colors of LEDs are used in the described embodiments, LEDs of various colors and combinations thereof are considered within the scope of the disclosure.

Similar concepts are used to design the sun-resembling assemblies 316. For example, the 1931 CIE Chromaticity Diagram of FIG. 54 shows three exemplary color spaces for each of three colors of LEDs. Color space CS1 resides in the upper left part of the diagram and corresponds to a greenish yellow LED that emits greenish yellow light. Color space CS2 resides in the lower left part of the diagram and corresponds to a greenish blue LED that emits greenish blue light. Color space CS3 resides in the lower right part of the diagram and corresponds to a reddish LED that emits reddish blue light. The combination of these three different colors of LEDs allows great flexibility in controlling the color and color temperature of the light exiting the sun-resembling assemblies 316. In a more focused application where the sun-resembling assemblies 316 are emulating solely or primarily sunlight and reflections thereof during sunrise, sunset, and daylight times, a target range for the color space resides along the Black Body curve and extends from about 5600 K to 2700 K, inclusive, within three, five, seven, or ten MacAdam ellipses.

For reference, color space CS1 is defined by the following x, y coordinates on the 1931 CIE Chromaticity Diagram: (0.337421, 0.498235), (0.361389, 0.547099), (0.345207, 0.557853), and (0.320079, 0.506653). Color space CS2 is defined by the following x, y coordinates on the 1931 CIE Chromaticity Diagram: (0.253872, 0.284229), (0.281968, 0.363411), (0.269385, 0.367235), and (0239191, 0.282521). Color space CS3 is defined by the following x, y coordinates on the 1931 CIE Chromaticity Diagram: (0.547946, 0.298632), (0.532764, 0.307913), (0.586923, 0.341618), and (0.602105, 0.332400). Again, these are non-limiting examples that are provided for the purposes aiding those skilled in the art in understanding the concepts described herein.

With reference to FIGS. 55 and 56, the skylight fixture 310 provides both vertical and horizontal lighting components. The vertical component is provided by the sky-resembling assembly 314, and the horizontal component is provided by the sun-resembling assemblies 316. Even though the sun-resembling assemblies 316 are not exactly vertical for the embodiment of FIG. 56, for the purposes herein, the sun-resembling assemblies 316 are considered to provide a horizontal lighting component. These vertical and horizontal lighting components ultimately combine to provide a composite lighting component that exits the skylight fixture 310 at an exit plane, which is a plane corresponding to the opening of the skylight fixture 310 opposite the sky-resembling assembly 314.

The vertical and horizontal lighting components are independently controllable with respect to one or more of intensity, color, color temperature, CRI, and the like. As such, the emission profile associated with the composite lighting component, which is effectively the output of the overall skylight fixture 310, can be tailored by controlling the vertical lighting component provided by the sky-resembling assembly 314 and the horizontal lighting components provide by the multiple sun-resembling assemblies 316. Notably, the horizontal lighting components provided by the different sun-resembling assemblies 316 may be the same or different to provide both symmetrical and asymmetrical emission profiles. For example, the skylight fixture 310 may be designed to provide the functionality described above and still have the composite lighting component provide a desired emission profile with a desired color, color temperature, CRI, or any combination thereof. The emission profile of the composite lighting component may have a normalized intensity distribution (i.e. substantially Lambertian Emission profile) to one that is substantially ellipsoidal, symmetrical, or asymmetrical.

Further, by employing three or more colors of LEDs for either or both of the sky-resembling and sun-resembling assemblies 314, 316, the white light color quality of the composite light output of the overall skylight fixture 310 can be significantly improved. In particular, the CRI of the composite light output of the overall skylight fixture 310 can be improved.

With regard to CRI, an LED-based fixture's CRI is calculated by measuring its CRI ratings for various individual colors, which are referred to as R1 through R8, and then taking an average of the results. Interestingly, R9 (red) and R13 (skin tone/beige) are generally not taken into consideration when calculating CRI. These red and skin tone colors have a significant impact on rendering skin colors in a healthy and natural way as well as making people feel at ease and more alert. As such, lighting may have a high CRI and still lack the red and skin tone color content necessary to properly render skin tones and/or enhance mood and alertness. The expanded spectrum provided by using LEDs of three or more colors for a given one of the sky-resembling and sun-resembling assemblies 314, 316 can improve the CRI rating as well as the perceived quality of the composite lighting component. The expanded spectrum may also significantly improve the quality of the vertical and horizontal lighting components.

FIGS. 57 and 58 illustrate the improvement in both CRI and R9 of the composite lighting component when employing LEDs of three or more colors. FIG. 57 is a graph of CRI and R9 over distance from center Nadir (that is six feet from the fixture) for the two-color LED embodiment of FIG. 47. Center Nadir in this test is approximately six feet from the center of the exit plane of the skylight fixture 310. FIG. 58 is a graph of CRI and R9 over distance from center Nadir for the three-color LED embodiment of FIG. 50. The CRI across the entire range significantly improved, and the CRI curve flattened, which indicates tremendous CRI improvement at lower distances. The R9 also improved on average.

FIGS. 59 and 60 illustrate techniques for improving efficacy associated with the overall skylight fixture 310, the sun-resembling assemblies 316, or both. FIG. 59 illustrates the benefit of having an angle of greater than 90 degrees between the interior face of the sun-resembling assemblies 316 and the sky-resembling assembly 314. In essence, the light output distribution of the sun-resembling assemblies 316 favors toward the exit plane, or in other words, is angled downward toward the exit plane. Angling the light output distribution of the sun-resembling assemblies 316 downward reduces the losses associated with the light being passed through and reflected by the light emitting surfaces of the other sun-resembling assemblies 316 and the sky-resembling assembly 314. Again, experiments have shown particularly effective performance when the obtuse angle α is:

90 degrees $<\alpha \leq 135$;
95 degrees $<\alpha \leq 130$; or
100 degrees $<\alpha \leq 125$.

FIG. 60 illustrates another embodiment wherein the interior surfaces of the sun-resembling assemblies 316 are substantially vertical, but the optical configuration of the sun-resembling assemblies 316 are such that the light output distribution of the sun-resembling assemblies 316 is directed or redirected to favor toward the exit plane, or in other words, is angled downward toward the exit plane. This can be provided by angling the plane on which the LED array is provided, employing a diffusor or waveguide structure to redirect the light from the LED array, or the like. Allowing more of the light from the sun-resembling assemblies 316 to escape the skylight fixture 310 without impediment may also increase the emulation of sunlight passing through a traditional skylight at lower angles and more directly illuminating walls, such as during the morning or evening as well as during those fall, winter, and spring months of the year when the earth remains off axis relative to the sun (i.e. the sun is lower on the horizon through the day).

As described above, the respective sky-resembling and sun-resembling assemblies 314, 316 can be individually controlled such that light provided by the sky-resembling and sun-resembling assemblies 314, 316 can emit light at different color points at any given time. The particular color points for the light from the sky-resembling and sun-resembling assemblies 314, 316 may be permanently fixed or dynamically controlled such that the color points for the emitted light can change based on user input, a predefined program, or as a function of any number or combination of variables. The variables may range from date, day, and time of day to any number of sensor outputs, such as indoor and/or outdoor temperature sensors, light sensors, motion sensors, humidity sensors, rain sensors, and the like.

The sky-resembling and sun-resembling assemblies 314, 316 may be further controlled such that the composite lighting output of the skylight fixture 310 achieves a certain color, color temperature, CRI, and/or the like while achieving other lighting goals, such as emulating a traditional skylight in a fixed or dynamic manner. While emulating a traditional skylight has been the subject of much of the discussion thus far, the sky-resembling and sun-resembling assemblies 314, 316 may be controlled to enhance moods, support general and mental health, and/or provide other physiological benefits.

For example, the skylight fixture 310 may be configured to deliver an enhanced circadian stimulus, with reference to Rea, M. S. et al; A model of phototransduction by the human circadian system; Brain Research Reviews 50 (2005) 213-228, which is incorporated herein by reference in its entirety. This is done by controlling the ratio between the horizontal and vertical illuminance provided by the sky-resembling and sun-resembling assemblies 314, 316. The circadian stimulus is controlled by the spectral power distribution, the color temperature and the amount of light of the respective characteristics delivered to the human eye. Vertical illuminance, such as that provided by the sun-resembling assemblies 316, appears to have the greatest efficiency in delivering an impact on circadian rhythms. The skylight fixture 310, by virtue of its vertical and horizontal light emitting surfaces along with independent spectral and brightness control, can provide effective control of this stimulus. Controlling the sky-resembling and sun-resembling assemblies 314, 316 to provide a zonal luminance distribution of 35% or more in a region of 60-90 degrees of nadir will provide a higher vertical illuminance. This could be provided by increasing the brightness of the sun-resembling assemblies 316 and decreasing or maintaining the brightness of the sky-resembling assembly 314. Further, light with a higher amount of red spectral content may be emitted from the sun-resembling assemblies 316, further modulating the circadian or other alertness stimulation, as desired.

The skylight fixtures 310 may control the characteristics of light throughout the day based on when and how much circadian stimulus is desired. In the morning or during a certain time period in the morning, the skylight fixture will increase its 60-90 degree illuminance to 35% or more and change the spectral power distribution and/or system vertical illuminance to provides a circadian stimulus of >0.3, which is a preferred circadian entrainment for humans according to Rea M S, Figueiro M G, Bierman A, Bullough J D.; J Circadian Rhythms; 2010 Feb. 13; 8(1): 2, which is incorporated herein by reference in its entirety. Later in the day, the skylight fixture 10 could reduce its circadian stimulus by providing a spectral power distribution and system vertical illuminance that results in a circadian stimulus of <0.1. One element of this reduction could be a change of the 60-90 degree zonal illuminance distribution 35% or less by modifying the sky-resembling and sun-resembling assembly 314, 316 emission (brightness and/or spectral content) ratios.

In another embodiment, the red spectral content provided by the sun-resembling assemblies 316 can be temporarily increased to increase the red vertical illuminance provided by the skylight fixture 310 during post lunch hours and/or at night to counter the so called "post-lunch dip" and/or to improve nighttime alertness of shift workers. For the potential of increasing the alertness of shift workers by exposing them to a vertical illuminance of red light, reference is made to Figueiro M. G. et al., Biological Research for Nursing 2016, Vol. 18(1) 90, which is incorporated by reference herein in its entirety. For the potential of increasing the alertness during the "post-lunch dip" in humans by providing increased red light exposure, reference is made to Sahin L., Figueiro M. G.; Physiology & Behavior, Vol. 116-117, 2013, 1, which is incorporated by reference herein in its entirety. Again, all of the above embodiments may be provided while or without maintaining desired characteristics of the composite lighting output for the skylight fixture 310.

Multiple skylight fixtures 310 may be controlled collectively by a remote source, by a master fixture, or in a distributed fashion to operate in concert to present a static or dynamic scene. Each of the skylight fixtures 310 may have different or the same light output of the respective sky-resembling and sun-resembling assemblies 314, 316, depending on the nature of the scene. In one scenario, each of the skylight fixtures 310 may provide the same light output for a scene, such that each of the skylight fixtures 310 has the same appearance for a uniform scene. In another scenario, two or more of the skylight fixtures 310 will have different light output configurations, wherein each skylight fixture 310 represents a portion of an overall scene. The skylight fixtures 310 may also be controlled to provide virtually any type of mood, theme, holiday, or like lighting as well wherein the color, color temperature, brightness, and spectral content of the light emitted from the sky-resembling and sun-resembling assemblies 314, 316 is only limited by the nature and capabilities of the light sources and the control thereof. The skylight fixtures 310 may be controlled or configured to operate in different modes at different times or in response to sensor input or outside control input.

For example, the skylight fixtures 310 may function to emulate a traditional skylight with a changing scene that tracks outside conditions during business hours and transitions to decorative accent lighting mode during non-business hours. Alternatively, the skylight fixtures 310 may transition to a mode that enhances alertness or provides some other type of circadian stimuli after normal business hours. Again, such control may be provided by a programming of the skylight fixture or remote control in isolation or based on various input from other sensors and the like. The independent control and the potential for different capabilities and configurations of the respective sky-resembling and sun-resembling assemblies 314, 316 provide tremendous flexibility for a skylight-shaped lighting fixture.

FIG. 61 shows a block diagram of a skylight fixture 310 that is capable of providing wired or wireless communications with a remote device 351. The remote device 351 may be another lighting fixture or skylight fixture 310, a remote control system provided on a server, personal computer, or the like, as well as a mobile computing device, such as a smart phone, commissioning tool, dedicated control module, and the like. Communications between the electronics module 318 and the remote device 351 may be wired or wireless and may work on any type of networking technology. The remote device 351 will include a central processing unit (CPU) 353 or the like, and associated memory 355, which will include the requisite software for controlling operation of the remote device 351 and communications with the electronics module 318. The CPU 353 may be associated with a communication interface 357, which will provide the requisite communication capability for the remote device 351.

FIG. 62 illustrates an exemplary electronics module 318 in association with a sky-resembling assembly 314 and one or more sun-resembling assemblies 316 for a skylight fixture 310. In the illustrated embodiment, the sky-resembling assembly 314 is expanded to illustrate an LED array, which includes a mixture of LEDs 359 of different colors. While those skilled in the art will recognize various color combinations, the following example employs white LEDs 359 that emit white light at a first wavelength, bluish LEDs 359 that emit bluish light at a second wavelength, and greenish LEDs 359 that emit greenish light at a third wavelength. The LED array may be divided into multiple strings of series-connected LEDs 359. In this embodiment, LED string LS1 includes the white LEDs 359 and forms a first group of LEDs. LED string LS2 includes the bluish LEDs 359 and forms a second group of LEDs. LED string LS3 includes the greenish LEDs 359 and forms a third group of LEDs.

The electronics module 318 controls the drive currents $i_1$, $i_2$, and $i_3$, which are used to drive the respective LED strings LS1, LS2, and LS3 of the sky-resembling assembly 314. The sun-resembling assemblies 316 may be similarly configured and driven by the same or different electronics modules 318 in similar fashion. The ratio of drive currents $i_1$, $i_2$, and $i_3$ that are provided through respective LED strings LS1, LS2, and LS3 may be adjusted to effectively control the relative intensities of the white light emitted from the white LEDs 359 of LED string LS1, the bluish light emitted from the bluish LEDs 359 of LED string LS2, and the greenish light emitted from the green LEDs 359 of LED string LS3. The resultant light from each LED string LS1, LS2, and LS3 mixes to generate an overall light output that has a desired color, correlated color temperature (CCT), and intensity, the latter of which may also be referred to as dimming level. As noted, the overall light output may take on any desired color or CCT.

When emulating a traditional skylight, the overall light output of the sky-resembling assembly 314 may range from a deep blue of an evening sky, to a medium blue of a daytime sky, to white light that falls on or within a desired proximity of the Black Body Locus (BBL) and has a desired CCT. The sun-resembling assemblies 316 are controlled in the same fashion to emulate direct and reflected sunlight as well as any of the other colors and CCTs described above for effects ranging from decorative to physiological.

The number of LED strings LSx may vary from one to many and different combinations of LED colors may be used in the different strings. Each LED string LSx may have LEDs of the same color, variations of the same color, or substantially different colors. In the illustrated embodiment, each LED string LS1, LS2, and LS3 is configured such that all of the LEDs 359 that are in the string are all essentially identical in color. However, the LEDs 359 in each string may vary substantially in color or be completely different colors in certain embodiments. A single string embodiment is also envisioned, wherein currents may be individually adjusted for the LEDs of the different colors using bypass circuits or the like.

The electronics module 318 includes AC-DC conversion circuitry 361, control circuitry 360, a communication interface (I/F) 62, and a number of current sources, such as the illustrated DC-DC converters 364. The AC-DC conversion circuitry 361 is configured to receive an AC signal (AC), rectify the AC signal, correct the power factor of the AC signal, and provide a DC power signal (PWR). The DC power signal may be used to directly or indirectly power the control circuitry 360 and any other circuitry provided in the electronics module 318, including the DC-DC converters 364 and the communication interface 362.

The three respective DC-DC converters 364 of the electronics module 318 provide drive currents $i_1$, $i_2$, and $i_3$ for the three LED strings LS1, LS2, and LS3 of the sky-resembling assembly 314 in response to control signals CS1, CS2, and CS3. As noted, additional drive circuitry may be provided for each of the sun-resembling assemblies 316 in similar fashion. The drive currents $i_1$, $i_2$, and $i_3$ may be pulse width modulated (PWM) signals or variable DC signals. If the drive currents $i_1$, $i_2$, and $i_3$ are PWM signals, the control signals CS1, CS2, and CS3 may be PWM signals that effectively turn the respective DC-DC converters 64 on during a logic high state and off during a logic low state of each period of the PWM signal. As a result, the drive currents $i_1$, $i_2$, and $i_3$ for the three LED strings LS1, LS2, and LS3 may also be PWM signals. The intensity of light emitted from each of the three LED strings LS1, LS2, and LS3 will vary based on the duty cycle of the respective PWM signals.

The control circuitry 360 will adjust the duty cycle of the drive currents $i_2$, and $i_3$ provided to each of the LED strings LS1, LS2, and LS3 to effectively adjust the intensity of the resultant light emitted from the LED strings LS1, LS2, and LS3 while maintaining the desired intensity, color and/or CCT based on instructions from the control circuitry 360. If the drive currents $i_1$, $i_2$, and $i_3$ for the three LED strings LS1, LS2, and LS3 are variable DC currents, the control circuitry 360 generates control signals CS1, CS2, and CS3 that result in the DC-DC converters 364 outputting the drive currents $i_1$, $i_2$, and $i_3$ at the appropriate DC levels.

The control circuitry 360 may include a central processing unit (CPU) 366, such as microprocessor or microcontroller, and sufficient memory 368 to store the requisite data and software instructions to enable the control circuitry 360 to function as described herein. The control circuitry 360 may interact with the communication interface 362 to facilitate wired or wireless communications with other skylight fixtures 310 or remote devices, as described above.

When the terms "control system" or "control circuitry" are used in the claims or generically in the specification, the term should be construed broadly to include the hardware and any additional software or firmware that is needed to provide the stated functionality. These terms should not be construed as only software, as electronics are needed to implement control systems described herein. For example, a control system may, but does not necessarily, include the control circuitry 360, the DC-DC converters 364, the AC-DC conversion circuitry 358, and the like.

The expression "correlated color temperature" ("CCT") is used according to its well-known meaning to refer to the temperature of a blackbody that is nearest in color, in a well-defined sense (i.e., can be readily and precisely determined by those skilled in the art). Persons of skill in the art are familiar with correlated color temperatures, and with Chromaticity diagrams that show color points to correspond to specific correlated color temperatures and areas on the diagrams that correspond to specific ranges of correlated color temperatures. Light can be referred to as having a correlated color temperature even if the color point of the light is on the blackbody locus (i.e., its correlated color temperature would be equal to its color temperature); that is, reference herein to light as having a correlated color temperature does not exclude light having a color point on the blackbody locus.

"Light engine" or "light source" can be any structure (or combination of structures) from which light exits. In many cases, a light engine consists of one or more light sources plus one or more mechanical elements, one or more optical elements and/or one or more electrical elements. In many cases, a light engine is a component of a light fixture, i.e., it is not a complete light fixture, but it can be a discrete group or set of LEDs that is spatially segregated and controlled as a unit. In some embodiments, for instance, a light engine in a light fixture can be a discrete set of LEDs (e.g., an array of LEDs) mounted to a board (e.g., a printed circuit board) that is separate from one or more other light engines in the light fixture. In some embodiments, a larger board can comprise different sets or groups of LEDs occupying different portions of the board, and thereby comprise multiple light engines. A light engine can, for example, comprise chip-on-board, packaged LEDs, secondary optics and/or control/drive circuitry. In some embodiments, a light fixture can comprise a first light engine comprising multiple LEDs on a first board, and a second light engine comprising multiple LEDs on a second board. In some embodiments, a light engine can comprise multiple LEDs spaced from each other (in the aggregate) in one dimension, in two dimensions or in three dimensions.

For example, a first light engine can be mounted adjacent to or spaced laterally from but on the same plane with a second light engine and thereby spaced in one dimension. A first light engine can be positioned adjacent to or spaced from a second light engine but positioned at an angle or on a second plane from the second light engine and thereby in two dimensions. A first light engine can be offset from a second light engine in two or three dimensions. A first light engine can be offset or positioned relative to two, three or more dimensions of one or more other light engines. In some embodiments, a light engine can comprise a single light source (e.g., a single LED), or an array of light sources (e.g., a plurality of LEDs, a plurality of other light sources, or a combination of one or more LEDs and/or one or more other light sources). In some embodiments, a plurality of light sources (e.g., a plurality of LEDs) can be on a board and controlled together, for example, a control device (that controls the color point of a mixture of light from the plurality of light sources, and/or that controls brightness of light emitted from one or more of the plurality of light sources, etc.) can control a plurality of light sources on a board (and/or can control all of the light sources on a board).

The expression "light exit region," "light exit surface," or "exit plane" (e.g., "at least a first light exit region is at a boundary of the space"), means any region through which light passes (e.g., as it travels from a space which is to one side of the light exit region to the other side of the light exit region, i.e., as it exits the space through the light exit region). For example, if a light fixture has a cylindrical surface that defines an internal space (closed at the top and open at the bottom), light can exit the space by traveling through the circular light exit region at the bottom of the cylindrical surface (i.e., such circular light exit region is defined by the lower edge of the cylindrical surface). Such a light exit region can be open, or it can be partially or completely occupied by a structure that is at least partially light-transmitting (e.g., transparent or translucent). For example, a light exit region can be an opening in an opaque structure (through which light can exit), a light exit region can be a transparent region in an otherwise opaque structure, a light exit region can be an opening in an opaque structure that is covered by a lens or a diffuser, etc.

Unless otherwise defined, all terms (including technical and scientific terms) used herein have the same meaning as commonly understood by one of ordinary skill in the art to which this inventive subject matter belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein. It will also be appreciated by those of skill in the art that references to a structure or feature that is disposed "adjacent" another feature may have portions that overlap or underlie the adjacent feature.

The color of visible light emitted by a light source, and/or the color of a mixture visible light emitted by a plurality of light sources can be represented on either the 1931 CIE (Commission International de l'Eclairage) Chromaticity Diagram or the 1976 CIE Chromaticity Diagram. Persons of skill in the art are familiar with these diagrams, and these diagrams are readily available.

The CIE Chromaticity Diagrams map out the human color perception in terms of two CIE parameters, namely, x (or ccx) and y (or ccy) (in the case of the 1931 diagram) or u' and v' (in the case of the 1976 diagram). Each color point on the respective diagrams corresponds to a particular hue. For a technical description of CIE chromaticity diagrams, see, for example, "Encyclopedia of Physical Science and Technology", vol. 7, 230-231 (Robert A Meyers ed., 1987). The spectral colors are distributed around the boundary of the outlined space, which includes all of the hues perceived by the human eye. The boundary represents maximum saturation for the spectral colors.

The 1931 CIE Chromaticity Diagram can be used to define colors as weighted sums of different hues. The 1976 CIE Chromaticity Diagram is similar to the 1931 Diagram, except that similar distances on the 1976 Diagram represent similar perceived differences in color.

The expression "hue", as used herein, means light that has a color shade and saturation that correspond to a specific point on a CIE Chromaticity Diagram, i.e., a color point that can be characterized with x, y coordinates on the 1931 CIE Chromaticity Diagram or with u', v' coordinates on the 1976 CIE Chromaticity Diagram.

In the 1931 CIE Chromaticity Diagram, deviation from a color point on the diagram can be expressed either in terms of the x, y coordinates or, alternatively, in order to give an indication as to the extent of the perceived difference in color, in terms of MacAdam ellipses (or plural-step MacAdam ellipses). For example, a locus of color points defined as being ten MacAdam ellipses (also known as "a ten-step MacAdam ellipse) from a specified hue defined by a particular set of coordinates on the 1931 CIE Chromaticity Diagram consists of hues that would each be perceived as differing from the specified hue to a common extent (and likewise for loci of points defined as being spaced from a particular hue by other quantities of MacAdam ellipses).

A typical human eye is able to differentiate between hues that are spaced from each other by more than seven MacAdam ellipses (and is not able to differentiate between hues that are spaced from each other by seven or fewer MacAdam ellipses).

Since similar distances on the 1976 Diagram represent similar perceived differences in color, deviation from a point on the 1976 Diagram can be expressed in terms of the coordinates, u' and v', e.g., distance from the point=$(\Delta u'^2 + \Delta v'^2)^{1/2}$. This formula gives a value, in the scale of the u' v' coordinates, corresponding to the distance between points. The hues defined by a locus of points that are each a common distance from a specified color point consist of hues that would each be perceived as differing from the specified hue to a common extent.

A series of points that is commonly represented on the CIE Diagrams is referred to as the blackbody locus. The chromaticity coordinates (i.e., color points) that lie along the blackbody locus correspond to spectral power distributions that obey Planck's equation: $E(\lambda)=A\lambda^{-5}/(e^{(B/T)}-1)$, where E is the emission intensity, A is the emission wavelength, T is the temperature of the blackbody and A and B are constants. The 1976 CIE Diagram includes temperature listings along the blackbody locus. These temperature listings show the color path of a blackbody radiator that is caused to increase to such temperatures. As a heated object becomes incandescent, it first glows reddish, then yellowish, then white, and finally bluish. This occurs because the wavelength associated with the peak radiation of the blackbody radiator becomes progressively shorter with increased temperature, consistent with the Wien Displacement Law. Illuminants that produce light that is on or near the blackbody locus can thus be described in terms of their color temperature.

The expression "dominant wavelength" is used herein according to its well-known and accepted meaning to refer to the perceived color of a spectrum, i.e., the single wavelength of light which produces a color sensation most similar to the color sensation perceived from viewing light emitted by the light source, as opposed to "peak wavelength", which is well known to refer to the spectral line with the greatest power in the spectral power distribution of the light source. Because the human eye does not perceive all wavelengths equally (it perceives yellow and green better than red and blue), and because the light emitted by many solid state light emitters (e.g., light emitting diodes) is actually a range of wavelengths, the color perceived (i.e., the dominant wavelength) is not necessarily equal to (and often differs from) the wavelength with the highest power (peak wavelength). A truly monochromatic light such as a laser has a dominant wavelength that is the same as its peak wavelength.

It is well known that light sources that emit light of respective differing hues (two or more) can be combined to generate mixtures of light that have desired hues (e.g., non-white light corresponding to desired color points or white light of desired color temperature, etc.). It is also well known that the color point produced by mixtures of colors can readily be predicted and/or designed using simple geometry on a CIE Chromaticity Diagram. It is further well known that starting with the notion of a desired mixed light color point, persons of skill in the art can readily select light sources of different hues that will, when mixed, provide the desired mixed light color point.

For example, persons of skill in the art can select a first light engine (e.g., comprising a light emitting diode and phosphor), plot the color point of the light exiting from the first light engine (i.e., a first color point) on a CIE Chromaticity Diagram, plot a desired range of color points (or a single desired color point) for mixed light, and draw one or more line segments through the desired range of color points (or the single color point) for the mixed light such that the line segment(s) extend beyond the desired color point(s). Each line segment drawn in this way will have one end at the first color point, will pass through the range for the desired mixed light color point (or the desired single color point), and will have its other end at a second color point.

A second light engine can be provided from which light of the second color point exits, and when the first light engine and the second light engine are energized so that light exits from them, the color point of the mixed light will necessarily lie along a line segment connecting the first color point and the second color point, and the location of the color point of the mixed light along the line segment will be dictated by (namely, proportional to) the relative brightness of the respective light that exits from the first and second light engines. That is, the greater the proportion of the mixed light that is from the second light engine, the closer the color point of the mixed light is to the second color point; this relationship is geometrically proportional, i.e., the fraction of the length of the line segment that the color point of the mixed light is spaced from the first color point is equal to the fraction of the mixed light that is from the second light engine (and vice-versa). In geometric terms, the ratio of (1) the distance from the first color point to the color point of the mixed light, divided by (2) the distance from the first color point to the second color point will be equal to the ratio of the brightness (in lumens) of the first light engine divided by the brightness (in lumens) of the combination of light in the mixed light. Accordingly, once one identifies light sources (or light engines) that provide the endpoints of a line segment that extends through the desired mixed light color point, the desired mixed light color point can be obtained by calculating the relative brightness of the first and second light sources (or light engines) necessary to arrive at the desired mixed light color point.

Where more than two light sources (and/or light engines) are used (e.g., where there is mixed light of a first color point from a first light source, light of a second color point from a second light source, and light of a third color point from a third light source), the geometrical relationships can be used to ensure that the desired mixed light color point is obtained (e.g., conceptually, the color point of a sub-mixture of light from the first light source (or the first light engine) and the second light source (or the second light engine) can be determined, and then the color point of a mixture or sub-mixture (having a brightness of the combined brightness of the first light source (or the first light engine) and the second light source (or the second light engine) and the third light source (or the third light engine) can be determined, and the range of mixed light color points that can be reached is defined by the perimeter obtained from drawing lines connecting the respective color points of the light sources (and/or light engines).

As shown in the following figures, disclosed herein are embodiments of luminaires and/or light fixtures for general lighting, task lighting, or the like; more particularly, for illumination of spaces of varying size and floor plan such as a warehouse, office space, hallway, dwelling, or other space. Preferably, the illuminated space comprises an indoor space, although the luminaires disclosed herein may be used in other applications, such as an outdoor space or in a covered spaced exposed to the weather.

Referring now to FIG. 63, an example embodiment of a luminaire/lighting system 400 according to the present disclosure is illustrated. The luminaire 400 is configured as a skylight and disposed within a ceiling 102 of a space to be illuminated. Example embodiments of the luminaire 400 may be disposed within a wall 406. Also in embodiments, the luminaire/lighting system 400 may be disposed in a ceiling and/or wall of a hallway. The luminaire/lighting system 400 may provide, among other things, the aesthetic, design, and functional properties of an equivalent conventional skylight that allows natural light into a space to be illuminated. The luminaire/lighting system 400 may mimic the appearance and/or effects of a conventional skylight, and/or give an "outdoor" feeling to an indoor space, in some cases even with no exterior light supplied by any windows or doors, and instead using the principles of total internal reflection (TIR) and one or more optical waveguides 412. Still further, the waveguide bodies contemplated herein are made of any suitable optically transmissive material, such as an acrylic material, a silicone, a polycarbonate, a glass material, a cyclic olefin copolymer, air, or other suitable material(s), or combinations thereof to achieve a desired effect and/or appearance.

The present disclosure contemplates that the luminaire/lighting system 400 may provide an appearance effect 408 (FIG. 74) such as the illusion of depth, perspective, optical illusions, patterns, skylight imitation, and/or another desired optical effect. Still further, the luminaire/lighting system 400 may provide patterns complementary to the illuminated space. In example embodiments, the appearance of the luminaire/lighting system 400 supplies one or more of the aforementioned desirable effects. Also in example embodiments, the luminaire/lighting system 400 may produce one or more desirable illumination effects such as one or more light distribution and/or illumination patterns in the space to be illuminated. Still further in example embodiments, the desirable appearance effect 408 of the luminaire/lighting system 400 may be directly or indirectly associated with one of the desirable illumination effects.

The present disclosure further contemplates the luminaire/lighting system 400 comprising one or more luminaires 400*a*, 400*b*, . . . 400*n*. Each of the luminaires 400*n* may produce one or more of the appearance effects 408 and/or the illumination effects. Each of the luminaires 400*n*, in operation together to form a coordinated and/or networked lighting system 404, may provide one or more appearance effects 408 and/or illumination effects to develop overall appearance and/or illumination effects 408, desirable for the lighting system 404 as a whole. The luminaire 400 detailed throughout the present disclosure may be referred to interchangeably as the luminaire 400, the skylight 400, the fixture 400, the lighting apparatus 400, and/or the lighting device 400; and further may comprise one or more light emitting diodes (LEDs) 430 and/or another suitable light source (such as a fluorescent bulb, incandescent bulb, and/or excimer lamp).

In FIG. 64, an example construction of the luminaire 400 is depicted. In this embodiment, the luminaire 400 comprises a first optical waveguide 412*a* and a second optical waveguide 412*b*. The first waveguide 412*a* has respective upper and lower surfaces 416, 418 while the second waveguide 412*b* also has respective upper and lower surfaces 420, 422. The lower surface 418 of the first waveguide 412*a* and the upper surface 420 of the lower waveguide 412*b* are disposed adjacent one another, as illustrated in FIG. 65, and aligned along a plane. The edge coupled optical waveguides 412 of the luminaire 400 may be about 1 cm apart. Through this disclosure, waveguides having light directed into an edge thereof may be referred to as edge coupled and/or edge lit optical waveguide interchangeably.

In the example embodiment of FIG. 64, the first and second waveguides 412*a*, 412*b* are square/rectangular in shape. Therefore, the waveguides 412 comprise first, second, third, and fourth edge surfaces 424*a*, 424*b*, 424*c*, 424*d*. Similarly, the second waveguide 412*b* comprises first, second, third, and fourth edge surfaces 424*e*, 424*f*, 424*g*, 424*h*. Extraction features 428 are disposed on one or more planar surfaces 416, 418, 420, 422 of the first and second 412*a*, 412*b* waveguides. In this embodiment, the first and second waveguides 412*a*, 412*b* may comprise other shapes (from a plan view) such as triangles, circles, ovals, asymmetric shapes, and/or other suitable shapes.

Referring still to FIGS. 64 and 65, one or more LED elements or modules 430 illuminate the first and second waveguides 412*a*, 412*b*. The LEDs 430 may be arranged as first and second pluralities of LEDs 432, 434 disposed along one or more edge surfaces 424 of the first and second waveguides 412*a*, 412*b*, respectively. In FIG. 65, the luminaire 400 comprises first and second pluralities of LEDs 432, 434 configured as one or more strings of LEDs 430. The first plurality of LEDs 432 is disposed along the edge surface 424*a* of the first waveguide 412*a* while the second plurality of LEDs 434 is disposed along the edge surface 424*g* of the second waveguide 412*b*.

Light developed by the first plurality of LEDs 432 is directed into the waveguide body 410 of first waveguide 412*a* through the edge surface 424*a*. Similarly, light developed by the second plurality of LEDs 434 is directed into the second waveguide 412*b* through the edge surface 424*g*. In example embodiments, the pluralities of LEDs 432, 434 may extend along more than one of the edge surfaces 424 of the first and second waveguides 412*a*, 412*b*, thereby directing light into the waveguides 412*a*, 412*b* from more than one direction. The quantity, arrangement, and relative locations of the LEDs 430 may be selected to introduce light into the first and second waveguides 412a, 412b in an amount and from a direction suitable for producing one or more of the above-noted appearance effects 408 and/or desired illumination effects.

Also, in example embodiments, the LEDs may be coupled to the first and/or second waveguides 412a, 412b at locations other than the edges 424 thereof. One or more coupling cavities may be disposed on the planar surfaces 416, 418, 420, 422 of the first and/or second waveguides 412a, 412b. Also, in embodiments, the LEDs 430 may be aligned with one or more interior coupling cavities 470 (see FIG. 71B) spaced apart from the edges 424 of the waveguide(s) 412a, 412b. Embodiments described herein as edge coupled or edge lit may comprise, alternatively or additionally, one or more interior coupling cavities and/or other suitable LED coupling configurations for introducing light into the one or more waveguides 412a, 412b.

Light is directed out and away from the first and second waveguides 412a, 412b by the extraction features 428. Referring to FIGS. 64 and 65, in example embodiments, extraction features 428a of the first, upper waveguide 412a are disposed on the upper surface 416 thereof. These extraction features 428a direct light, produced by the first plurality of LEDs 432 and entering the first waveguide 412a through one of the edge surfaces 424a, 424b, 424c, 424d, out of and away from the lower surface 418 thereof. Light directed out of the lower surface 418 of the upper waveguide 412a may enter the lower waveguide 412b through the upper surface 420 thereof.

The upper surface 422 of the lower waveguide 412b may also have extraction features 428b disposed thereon. The extraction features 428b of the lower waveguide 412b also direct light, produced by the second plurality of LEDs 434 and entering the second waveguide 412b through one of the edge surfaces 424e, 424f, 424g, 424h, out of and away from the second waveguide 412b through the lower surface 422 thereof. To produce the appearance effects 408 and illumination effects contemplated herein, the extraction features 428a, 428b are disposed in different patterns 442 (see FIGS. 67-71B) respectively disposed on the first and second waveguides 412a, 412b.

Referring now to FIGS. 66-68, the extraction features 428 and examples of the extraction feature patterns 442 are shown and described. The number, geometry, and spatial array of the extraction features 428 across a waveguide body affects the uniformity and distribution of emitted light. As shown in the example waveguide 412 in FIGS. 66-68, the discrete extraction features 428 may be formed in one or more schemes/arrays. In example embodiments variable extraction feature size is utilized to obtain a uniform or nearly uniform distribution of light. Specifically, the extraction features 428 may be arranged in rows and columns wherein the features in each row extend left to right and the features in each column extend top to bottom as seen in FIGS. 64, 67, and 68. The extraction features 428 closest to the LEDs 430 may be generally smaller and/or more widely spaced apart so that along the length dimension of the waveguide 412 the majority of light travels past such features to be extracted at subsequent parts of the waveguide 412. This results in a gradual extraction of light over the length of the waveguide 412. The center-to-center spacing of extraction features 428 in each row may be preferably constant, although such spacing may be variable, if desired. The extraction features 428 contemplated herein may be formed by injection molding, embossing, laser cutting, calendar rolling, or the extraction features may be added to the waveguide 412 by a film. In further example embodiments, this progression and arrangement of extraction features 428 may be reversed or otherwise ordered to achieve the desired appearance or illumination effect 408. Still further, in embodiments, the extraction features and/or extraction surfaces may be fabricated by texturing, roughening, sanding, and/or other suitable methods of producing surface features for directing light out of and/or away from a waveguide 412.

The luminaire 400 may include a housing 440 (FIG. 63) comprising, among other things, one or more of driver circuitry, the LEDs 430, control circuitry, sensor(s), power circuitry, circuit board(s), or other components. Furthermore, luminaires described herein may be networked with other luminaires, to form a lighting system or lighting network, using wired connections or wireless technology and the operation thereof (on/off and/or color and/or color temperature) may be controlled as desired, for example in coordinated or stand-alone fashion. The LEDs 430 herein may be substantially the same or modified in size, shape, color, number, and/or other characteristics to fit housing and illumination specifications of particular luminaire applications/configurations described herein. The housing 440 further provides structural support to the optical waveguides 412a, 412b whereabouts said housing 440 meets one or more of the edge surfaces 424 of the respective waveguides 412a, 412b.

Each of the LED elements or modules 430 (FIGS. 64-66 and 72) may be a single white or other color LED chip or other bare component, or each may comprise multiple LEDs either mounted separately or together on a single substrate or package to form a module including, for example, at least one phosphor-coated LED either alone or in combination with at least one color LED, such as a green LED, a yellow LED, a red LED, etc. In those cases where a soft white illumination with improved color rendering is to be produced, each LED element or module 430 or a plurality of such elements or modules may include one or more blue shifted yellow LEDs and one or more red LEDs. The LEDs 430 may be disposed in different configurations and/or layouts as desired. Different color temperatures and appearances may be produced using other LED combinations, as is known in the art. In one embodiment, the light source comprises any LED, for example, an MT-G LED incorporating TrueWhite® LED technology or as disclosed in U.S. Pat. No. 9,818,919, the disclosure of which is hereby incorporated by reference herein, as developed and manufactured by Cree, Inc., the assignee of the present application. If desirable, a side emitting LED disclosed in U.S. Pat. No. 8,541,795, the disclosure of which is hereby incorporated by reference herein, may be utilized. In some embodiments, each of the LED elements or modules 430 may comprise one or more LEDs disposed within a coupling cavity with an air gap being disposed between the LED element or module 430 and a light input surface, such as the edge surfaces 424. In any of the embodiments disclosed herein each of the LED element(s) or module(s) 430 preferably have a Lambertian or near-Lambertian light distribution, although each may have a directional emission distribution (e.g., a side emitting distribution), as necessary or desirable. More generally, any Lambertian, symmetric, wide angle, preferential-sided, or asymmetric beam pattern LED element(s) or module(s) may be used as the light source. Still further, any of the LED arrangements and optical elements disclosed in U.S. Pat. No. 9,869,432, which is hereby incorporated by reference herein, may be used.

The waveguides 412 contemplated herein may be tapered depending on application. Tapering a waveguide body causes light to reflect internally along the length of the waveguide body while increasing the angle of incidence. Eventually, this light strikes one side at an angle that allows the light to escape. The opposite example, i.e., a gradually thickening waveguide body over the length thereof, causes light to collimate along the length with fewer and fewer interactions with the waveguide body surfaces. These interactions can be used to extract and control light within the waveguide. When combined with dedicated extraction features, tapering allows one to change the incident angular distribution across an array of features. This, in turn, controls how much, and in what direction light is extracted. Thus, a select combination of tapered surfaces and extraction features may achieve a desired illumination and appearance. Any combination of these features may be employed by the waveguides 412 of the presently described luminaire/lighting system 400, 404.

According to one aspect, a waveguide directs light into at least one, up to an infinite number, of beams or ray groups, wherein the rays of each group travel through the waveguide within a range of angles relative to one another. Each range may be narrow or broad within the TIR limits of the waveguide material. According to another aspect, a waveguide arranges light into a plurality of groups that bounce at least once inside the waveguide by TIR off one or more surfaces of the waveguide. Each group comprises a plurality of light rays that travel at angles that are disposed within a narrow or broad range of angles relative to one another. In any embodiment, the range may be so narrow that the light rays of ray group may be considered to be fully collimated, or nearly so, or the range may be so broad that the light rays of a ray group may be considered to be anti-collimated, or nearly so. Controlling the ray angles in this manner can lead to increased light control, reduced waveguide size and weight, and reduced luminaire costs.

Referring now to FIGS. 69-71B, optical waveguides 412 that may comprise the first and second waveguides 412a, 412b of the luminaire 400 are depicted such that the extraction features 428 disposed thereon form one or more of the extraction feature patterns 442. An extraction feature pattern 442a shown in FIG. 69 is concentrated at an interior portion 444 of the waveguide 412 while a peripheral portion 446 does not have extraction features disposed thereon. Accordingly, light introduced through one or more of the edge surfaces 424 traverses the peripheral portion 446 such that substantially all of said light is totally internally reflected. Once this edge coupled TIR light reaches the interior portion 444 it is directed out of and/or away from the waveguide by the extraction features 428 of the interior-concentrated extraction feature pattern 442a. Therefore, the waveguide 412 of FIG. 69 primarily emits light from the interior portion 444 thereof. FIG. 72 is a photograph depicting the waveguide 112, having the extraction feature pattern 442a of FIG. 69, with blue and/or violet light (such as light comprising a color temperature of about or greater than 10,000 K and preferably about 16,000 K) being introduced into the edge surface 424 of said waveguide 412 by LEDs. The illuminated waveguide 412 of this photograph does not emit light from the peripheral portion 446 but does emit light from the interior portion 444 whereon the extraction features 428 are disposed.

FIG. 70 illustrates an embodiment of the optical waveguide(s) 412 comprising another extraction feature pattern 442b. In this extraction feature pattern 442b, the extraction features 428 are concentrated in the peripheral portion 446 of the waveguide 412 while the interior portion 444 of the waveguide 412 does not have extraction features disposed thereon. Therefore, substantially all of the light introduced into the example waveguide 412 of FIG. 70 is directed out of and away from the waveguide by the extraction features 428 in the peripheral portion 446. Edge coupled light that is not extracted before reaching the interior portion 444 may be TIR while traversing the interior portion 444 and subsequently extracted by the extraction features 428 on another side of the waveguide 412 upon reaching same. FIG. 73 is a photograph depicting the waveguide 412, having the extraction features pattern 442b of FIG. 70, with yellow light (such as light comprising a color temperature of about 3000 k) introduced into the edge surface 124 of said waveguide 112 by the LEDs 430. The illuminated waveguide 412 of this photograph emits light from the peripheral portion 446, whereon the extraction features 428 are disposed, but does not emit light from the interior portion 444.

The example embodiment of the optical waveguide 412 shown in FIGS. 71A-71B comprises another embodiment of an extraction feature pattern 442c comprising arrangement of the extraction features 428 in the peripheral portion 446 as well as first and second transition portions 448a-148d, 450a-150d. In the extraction feature pattern 442c, the peripheral portion 446 is separated into four peripheral quadrants 446a, 446b, 446c, 446d by boundary lines 452a-152d. The boundary lines 452 extend from each corner of the generally square/rectangular waveguide 412 to define the peripheral quadrants 446 as generally trapezoidal. Associated with and disposed adjacent to each of the peripheral quadrants 446a-146d are the respective first and second transition portions 448a-148d, 450a-150d. The first, intermediate transition portions 448 are disposed between each of the peripheral quadrants 446a-146d and the second, interior transition portions 450a-150d. In example embodiments, the density of the extraction features 428 (or degree of roughening/texturing) may decrease gradually from the peripheral quadrants 446a-146d to the intermediate transition portions 448a-148d to the interior transition portions 450a-150d. In this embodiment, a relatively larger proportion of light is extracted by the denser extraction feature arrangement of the peripheral quadrants 446a-146d. An intermediate proportion of light, that is relatively less than that extracted by the peripheral quadrants 446a-146d, is extracted by the intermediate transition portions 448a-148d. A still relatively lesser proportion of light, relative the intermediate transition portions 448a-148d, is extracted by the interior transition portions 450a-150d. The interior portion 444 of the waveguide 412 of FIGS. 71A-71B does not have extraction features disposed thereon and totally internally reflects light that has been coupled into the waveguide.

In an example arrangement of the luminaire 400, the first waveguide 412a comprises the extraction feature pattern 442a (FIG. 69) having interior extraction features and the second waveguide 412b comprises one of the extraction feature patterns 442b, 442c with peripheral extraction features (FIGS. 70 and 71A-71B). Example embodiments of the luminaire 400 are depicted in the photographs of FIGS. 74-76. The e of the luminaire 400a shown in FIG. 74 comprises first and second waveguides 412a, 412b having respective extraction feature patterns 442a and 442b. In this embodiment, blue and/or violet light (such as light comprising a color temperature of about or greater than 10,000 K and preferably about 16,000 K) is edge coupled into the first waveguide 412a while yellow light (such as light comprising a color temperature of about 3000 k) is edge coupled into the second waveguide 412b. Light is emitted into an illuminated space, such as a room, through the lower surface 422 of the second waveguide 412b.

The appearance effect 408 produced by this example embodiment is a yellow perimeter, wherefrom light is emitted according to the extraction feature pattern 442b of the second waveguide 412b, disposed about a blue/violet interior, wherefrom light is extracted by the extraction feature pattern 442a of the first waveguide 412a. The blue/violet light emitted from the lower surface 416 (FIG. 65) of the first waveguide 412a enters the upper surface 420 (FIG. 65) of the second waveguide 412b, passes therethrough relatively unobstructed, and is emitted from the lower surface 422 of the second waveguide 412b. The photographed embodiment produces the appearance effect 408 of a skylight such that an occupant of the illuminated space perceives a desirable yellow light emitted from a blue sky illusion/appearance.

In general, the luminaire(s) 400 is configured to emit light and provide the appearance of the sky to a viewer. For the concepts contemplated by the present disclosure, the luminaire(s) 400 are configured to emulate sunlight coming through a skylight directly at a particular angle or being reflected off of a sidewall. Accordingly, the luminaire(s) 400 may be arranged to provide generally non-directional light associated with the sky as well as emulate the direct sunlight or a reflection thereof from the sun. Depending on the time of day or night, the intensity, color temperature, and/or color of light emitted from the luminaire(s) 400 may vary in an effort to emulate the light provided by a conventional skylight at different times of the day or night and any transitions therebetween.

Referring back to FIG. 71B, an example embodiment of a waveguide 112d is depicted. The waveguide 112d comprises both the interior and peripheral extraction feature patterns 442a, 442b. The LEDs 430 may be coupled to the edge 424 as well as disposed in the interior coupling cavity 470. Light from the LED(s) 430 disposed in the interior coupling cavity 470 is directed out of the waveguide 412d by the interior extraction feature pattern 442a. Light from the LED(s) 430 disposed along the edge 424 of the waveguide 412d is directed out of the waveguide 412d by the peripheral extraction feature pattern 442b. The LED(s) 430 at the interior coupling cavity 470 and the waveguide edges 424 may couple into the waveguide 412d light of the same or different spectrums, colors, correlated color temperatures (CCT), and/or other light qualities. Therefore, the light extracted by the interior and peripheral portions 444, 446 may have different spectrum qualities and/or different directional components. Any of the extraction feature patterns 442 described herein may be combined on a single waveguide, such as is shown in FIG. 71B. The luminaire(s) 400 may comprise a single waveguide that emits light similar and/or in accordance with embodiments described herein as comprising two waveguides. Further, in FIG. 71B the extraction features 428 in the respective interior and exterior portions 444, 446 may be the same or different. One or more specular barriers, grooves, and/or other characteristics of the waveguide body 410 may separate extraction feature patterns 442 when disposed on the same waveguide 412. Embodiments described herein may extract light comprising a first spectrum from one portion of a waveguide body and light comprising a second spectrum from another portion of the waveguide body. Light from light sources comprising different spectrums (or other characteristics) may or may not be mixed within the waveguide body 400 before extraction to achieve the desired appearance effect 108.

In the embodiments of the luminaire 400 shown in FIGS. 75 and 76, the first waveguide comprises the extraction feature pattern 442a (FIG. 69) having interior extraction features, and the second waveguide 412b comprises the extraction feature pattern 442c (FIG. 71A) having peripheral quadrants 446a-146d, boundary lines 452a-152d, and first and second transition portions 448a-148d, 450a-150d. With similarity to FIG. 74, the appearance effect 408 of a yellow perimeter disposed about a blue/violet interior is developed. In the photographed embodiment of FIGS. 75 and 76, the first and second transition portions 448a-148d, 450a-150d, which comprise relatively fewer extraction features 428 as compared with the peripheral quadrants 446a-146d, operate to extract some yellow light while also permitting some blue/violet light, emitted from the first waveguide 412a, to pass therethrough. Accordingly, the transition surfaces 448a-148d, 450a-150d, in conjunction with the boundary lines 452a-152d develop a perception of depth when viewed by a user occupying the illuminated space. This may further complement the appearance effect 408 of a skylight. As desired, the luminaire 400 produces the illusion of depth in a relatively thin, flat luminaire construction utilizing two waveguides configured and aligned one atop/behind the other.

In example embodiments, a material may be disposed between the first and second waveguides 412a, 412b. The material may be specular or otherwise suitably reflective and/or absorptive. The material between the waveguides 412a, 412b may prevent light extracted out of the first waveguide 412a from portions of the waveguide 412a comprising an extraction pattern that overlaps with portions of the second waveguide that also comprise an extraction pattern. For example, the extraction feature pattern 442a may overlap with the extraction feature pattern 442b. In this example, the material disposed between the first and second waveguides 412a, 412b may prevent undesirable light/color mixing at the overlapping edges of the first and second extraction feature patterns 442a, 442b.

Referring now to FIGS. 77-85, example embodiments of the luminaire 400 comprise patterns on the waveguide surface that utilize geometrical and/or linear shapes to develop the perception and/or illusion of a vanishing point. The appearance effects 408 shown in the photographs of the luminaire 400 in FIGS. 79-81, 83, and 84 produce the illusion of depth on a substantially flat, light emitting surface of the waveguide 412. FIGS. 77, 78, 82, and 85 depict mask elements 454 that may be used to produce extraction feature patterns 442 on the waveguides 412. The mask element 454a of FIGS. 77 and 78 produces the extraction feature pattern 442d used to develop the appearance effect 408 of FIGS. 79-81. The mask element 454b of FIG. 82 may be used to product the extraction feature pattern 442e that develops the appearance effect 408 of FIGS. 83 and 84. The mask element 454c of FIG. 85 may produce yet another extraction feature pattern that results in the illusion of depth when viewed by an occupant of a space illuminated by the luminaire 400.

In example embodiments, the extraction feature patterns 442 may include extraction features on both sides of the waveguide 412 and/or the extraction features 428 disposed at various portions of the waveguide 412 may direct light out of the waveguide in different directions. In the example embodiment of the luminaire 400 shown in FIGS. 79-81, only one waveguide 412c is used to produce the illusion of depth. The mask element 454a may be used in fabricating the extraction features 428 disposed on upper and/or lower surfaces 456, 458 of the waveguide 412c. The waveguide 412c of this embodiment may have on the upper surface 456 thereof upper surface extraction features 428c that extract/direct proportionally more light out of the lower surface 458 of the waveguide 412c thereby developing bright portions 460 wherefrom relatively more light emanates. The lower surface 458 of this waveguide 412c may have complementary lower surface extraction features 428d that extract relatively less light out of the lower surface 458 of the waveguide 412c as compared to the upper surface extraction features 428c thereby developing dimmer portions 462. The complementary arrangement of the bright portions 460 and the dimmer portions 462 develops the appearance effect 408 of a vanishing point 464 disposed proximal a center of the waveguide 412c shown in FIGS. 79-81. In example embodiments, the upper and lower extraction features 428c, 428d may be arranged such that the vanishing point 464 is disposed elsewhere on the waveguide 412c when viewed by the occupant of an illuminated space. For example, the vanishing point 464 may be nearer a corner of the waveguide 412c. As shown in the photographs of FIGS. 80 and 81, the appearance effect 408 produced by this embodiment allows the bright and dimmer portions 460, 462 to complement and interact with one another in desirable ways when viewed from different angles.

Also in example embodiments, such as are shown in the photographs of FIGS. 83 and 84, the extraction feature patterns 442 disposed on the first and second waveguides 412a, 412b may be arranged to develop bright portions 466 and dimmer portions 468 that are further enhanced by color selection of the edge coupled LEDs 430 respectively associated with the first and second waveguides 412a, 412c. For example, the lower waveguide 412b depicted in FIG. 83 and having an extraction feature pattern 442e fabricated with the mask element 454b may be operatively paired with the upper waveguide 412c depicted in FIGS. 71A-71B. In such an embodiment, the violet light emitted by the upper waveguide 412a may further enhance the illusion of depth and appearance of a vanishing point 464 produced by the bright and dimmer portions 466, 468 of the second waveguide 412b, as shown in FIG. 84.

In example embodiments, a plurality of the luminaires 400 such as those shown in FIGS. 79-81, 83, and 84 with vanishing points 464 at the same or different positions relative the viewer/occupant may line a ceiling or hallway to develop desirable artistic, aesthetic, and/or architectural concepts. The colors and extraction feature patterns disposed on each waveguide of such a configuration of plural luminaires may be customized/selected to highlight or enhance some portion of the illuminated space, interior and/or exterior architecture, and/or otherwise produce desirable overall visual effects or patterns. The luminaire(s) 400 may operate as a primary light source or as a decorative/architectural element complementary to other existing functional and/or decorative luminaries.

As noted, embodiments of the luminaire 400 may be configured the same or differently with respect to the lighting capabilities and characteristics thereof. In order to meet the specifications of particular applications, the luminaire(s) 400 may be designed to operate at different intensity levels, colors, color temperatures, light distributions, illumination patterns, and/or other lighting characteristics. Further, more than one of the luminaire(s) 400 may be designed and/or controlled such that each panel provides light with different characteristics, yet the light from the overall lighting system 404 combines to provide light with characteristics that may be different from the individual luminaire(s) 400 of the system 404.

In example embodiments, the luminaire(s) 400 may emulate the directional nature of sunlight passing through a conventional skylight, such as during different times of day with corresponding sun positions. The luminaire(s) 400 may be arranged to emulate the appearance of the sky and the non-directional nature of sunlight passing through a conventional skylight. The luminaire(s) 400 may be further configured to emulate the appearance of light passing through or being reflected from window and side walls of a conventional skylight.

Also in embodiments contemplated by this disclosure, the light exiting one or more portions of the luminaire(s) 400 may be relatively shifted toward blue in the light spectrum to emulate the appearance of a blue sky. The light exiting one or more other portions of the luminaire(s) 400 may be relatively shifted toward red in the light spectrum to better emulate the appearance of sunlight. The luminaire(s) 400 may be configured to vary the color, illumination pattern, and/or intensity of emitted light during operation emulate, track, and/or react to changing conditions of outside environments throughout the day and night. For example, it may be desirable for the luminaire(s) 400 to emulate the appearance effect 408 of blue sky and sunlight during nighttime and/or during weather events, e.g., cloudiness or fog. Also, embodiments may emulate a conventional skylight during predominately daylight hours between, but not necessarily including, the sunrise and sunset where the sky may appear less blue and more reddish orange. To expand the functionality of the luminaire(s) 400 to better emulate the appearance of a conventional skylight outside of daylight hours, operation in expanded color spaces and/or with more or less color mixing may be desirable. For example, the colors emitted by the luminaire(s) 400 may be shifted or expanded to address the deeper blues associated with dusk, dawn, and nighttime as well as the more reddish orange and red hues associated with sunrise and sunset.

In example embodiments, the LEDs 430 are coupled to one or more portions of the optical waveguide(s) 412. As mentioned hereinabove, the LEDs 430 may be disposed as strings or groups. Each string or group of LEDs 430 may comprise one color or more than one color of LEDs. A two-color LED string may comprise a plurality of LEDs of a first color and a plurality of LEDs of a second color. Therefore, the color and number of the LEDs 430 may be varied to introduce an overall color into the waveguide body 410 that is a combination of the color produced by the individual LEDs 430 of an LED string or group. The overall spectrum of light introduced into the waveguide body 410 may be controlled by the combination of LEDs selected and/or the extent to which the different LEDs are energized.

For example, the LEDs 430 introducing light into a portion of the waveguide body 410 may be bluish LEDs that emit bluish light comprising a 475 nm dominant wavelength and an overall bluish spectrum illustrated in FIG. 24, which is a graph of output intensity versus wavelength. Further, the LEDs 430 may be white LEDs that emit white light comprising a color temperature of approximately 5000 K ?+/− 0.5, 1, 2, or 5%) and a color rendering index (CRI) of at least 85 or 90 (i.e. CRI 85, CRI 90). Example white LEDs may emit an overall spectrum that is illustrated in FIG. 87, which is a graph of output intensity versus wavelength.

In example embodiments, the overall spectrum of the emitted light from the luminaire(s) 400 may be increased by using three or more LEDs comprising different colors. Using three or more colors of the LEDs 430 may be desirable for creating complex light that increases the accuracy with which the luminaire(s) 400 emulate sunlight. An example of a three color-LED combination may comprise deeper bluish LEDs, greenish LEDs, and white LEDs. Example bluish LEDs may comprise a 418 nm dominant wavelength and an overall spectrum (primary spectrum of ~450 nm-465 nm) that is illustrated in FIG. 88, which is a graph of output intensity versus wavelength. Example greenish LEDs may comprise a 458 nm dominant wavelength and an overall spectrum (primary spectrum of 505 nm-530 nm) that is illustrated in FIG. 89, which is a graph of output intensity versus wavelength. Example white LEDs may comprise a color temperature of approximately 5000 K+/−0.5, 1, 2, or 5%) and a color rendering index (CRI) of at least 85 or 90 (i.e. CRI 85, CRI 90). Also, example white LEDs may comprise an overall spectrum that is illustrated in FIG. 90, which is a graph of output intensity versus wavelength. While certain colors of LEDs are used in the described embodiments, LEDs of various colors and combinations thereof are considered within the scope of the disclosure. A three color LED combination of the above-mentioned example LEDs may supply light to the first waveguide 412a and/or the interior portion 444 of a single waveguide embodiment of the luminaire(s) 400.

As noted hereinabove, the respective portions 444, 446 and/or the respective waveguides 412a, 412b of the luminaire(s) 400 may be individually controlled such that light introduced therein and emitted thereby may be of different colors or spectrums at any selected time. The particular spectrums and/or colors for particular portions and/or waveguides may be permanently fixed or dynamically controlled such that the appearance effect(s) 408 produced by the emitted light may change based on user input, a predefined program, and/or as a function of any number or combination of control inputs/variables. The control inputs may include date, day, time of day, sensor outputs (such as indoor and/or outdoor temperature sensors, light sensors, motion sensors, humidity sensors, rain sensors, and/or other suitable sensors), architectural/structural qualities of the building in which the luminaire(s) 400 is disposed, and/or other suitable control inputs.

The luminaire(s) 400 may be further controlled such that the composite lighting output produced thereby supplies a certain color, color temperature, CRI, and/or otherwise suitable light while achieving other lighting goals, such as emulating a conventional skylight, developing a depth effect, creating a vanishing point, enhancing room aesthetics, highlight architectural features, and/or other suitable lighting goals.

A networked plurality of the luminaire(s) 400 may be controlled collectively by a remote source, by a master fixture, or in a distributed fashion to operate in concert to present a static or dynamic scene. Each of the luminaire(s) 400 may have different or the same light output depending on the desired scene lighting. In one scenario, each of the luminaire(s) 400 may provide the same light output for a scene, such that each of the luminaire(s) 400 comprises the same appearance effect 408 for a uniform scene. In another scenario, two or more of the luminaire(s) 400 comprise different light output configurations, wherein each of the luminaire(s) 400 represents a portion of an overall scene. The luminaire(s) 400 may also be controlled to provide virtually any type of mood, theme, holiday, and/or like lighting as well wherein the color, color temperature, brightness, and spectral content of the light emitted from the luminaire(s) 400 is fully customizable through selection of the light sources and the control thereof. The luminaire(s) 400 may be controlled or configured to operate in different modes at different times or in response to sensor input or outside control input.

For example, the luminaire(s) 400 may function to emulate a conventional skylight with a changing scene that tracks outside conditions during business hours and transitions to decorative accent lighting mode during non-business hours. Alternatively, the luminaire(s) 400 may transition to a mode that enhances alertness or provides some other type of circadian stimuli after normal business hours. Again, such control may be provided by a programming of the luminaire(s) 400, remote control, and/or control based on various inputs from other sensors and controls. The independent control and the potential for different capabilities and configurations of the luminaire(s) 400 provides flexibility and customization for a luminaire, waveguide, and/or waveguide assembly emitting different spectrums of light from discrete portions thereof. The luminaire(s) 400 described herein may include the control, functionality, and/or LED/color point combinations disclosed in U.S. Pat. Nos. 10,465,869 and 10,451,229, the disclosures of which are hereby incorporated by reference herein.

In an example embodiment, the light source(s)/LEDs 430 may comprise three (or more) LED types such that the light emitted by the luminaire(s) 400 may be precisely controlled a in two-dimensional color space (e.g. to stay on the black body locus at any achievable CCT value). In other embodiments, the color gamut of the selected LED types may have a range such that the achievable CCT/color range is correspondingly larger. In particular, the choice of warm white LEDs in the luminaire(s) 400, including but not limited to BSY+BSY+RDO combinations such as are found in Cree True White fixtures. "BSY" is a blue-shifted yellow LED; and "RDO" is a red-orange LED corresponding to light emitted with a dominant wavelength between 600 nm and 630 nm). For example, it may be desirable for the luminaire(s) 100 to produce light comprising a color similar to natural light around sunset, which may have a low CCT (<2700 K).

Any of the embodiments disclosed herein may include a power circuit that may further be used with light control circuitry that controls color temperature of any of the embodiments disclosed herein in accordance with viewer/occupant input such as disclosed in U.S. Pat. No. 10,278,250, the disclosure which is hereby incorporated by reference herein.

Further, any of the embodiments disclosed herein may include one or more communication components forming a part of the light control circuitry, such as an RF antenna that senses RF energy. The communication components may be included, for example, to allow the luminaire to communicate with other luminaires and/or with an external wireless controller, such as disclosed in U.S. Pat. No. 8,975,827, entitled "Lighting Fixture for Distributed Control" or U.S. Pat. No. 9,706,617, "entitled "Handheld Device That Is Capable of Interacting with a Lighting Fixture," both owned by the assignee of the present application, wherein the entire contents of the foregoing patents are hereby incorporated by reference herein. More generally, the control circuitry includes at least one of a network component, an RF component, a control component, and a sensor. The sensor may provide an indication of ambient lighting levels thereto and/or occupancy within the illuminated area. Such sensor may be integrated into the light control circuitry and may cause the luminaire to adjust output lighting levels as a function of ambient light levels and/or detected motion.

As noted previously in connection with FIGS. 40A-40B, a sky-resembling assembly (e.g., 314 in various figures herein) is relatively shifted toward blue in the light spectrum to better emulate the appearance of a blue sky according to various sky conditions. A first skylight color space 11 was illustrated in FIG. 40A, represented by a polygon defined by the following x, y coordinates on the 1931 CIE Chromaticity Diagram: (0.37, 0.34), (0.35, 0.38), (0.15, 0.20), and (0.20, 0.14). As will be described in connection with FIGS. 91A-91D. Applicant has found that utility of a sky-resembling assembly may be enhanced with one or more color points in second skylight color space (11B in FIG. 91A) adjacent to the first skylight color space (11A), or with one or more color points in a combined color space that encompasses the foregoing first and second color spaces (11A, 11B), FIG. 91A is a 1931 CIE Chromaticity Diagram on which color spaces 11A, 11B for embodiments of a sky-resembling assembly are provided. FIG. 91B is a table of (x, y) coordinates that define the first color space 11A, with the first color space 11A being represented by a polygon defined by the following x, y coordinates on the 1931 CIE Chromaticity Diagram: (0.37, 0.34), (0.35, 0.38), (0.15, 0.20), and (0.20, 0.14). FIG. 91C is a table of (x, y) coordinates that define the second color space 11B, with the second color space 11B being represented by a polygon defined by the following x, y coordinates on the 1931 CIE Chromaticity Diagram: (0.35, 0.38), (0.105, 0.195), (0.12, 0.135), (0.17, 0.10), (0.20, 0.14), and (0.15, 0.20). FIG. 91D is a table of (x, y) coordinates that define a combined color space (including the first and second color spaces 11A and 11B in FIG. 91A), wherein the combined color space being represented by a polygon defined by the following x, y coordinates on the 1931 CIE Chromaticity Diagram: (0.37, 0.34), (0.35, 0.38), (0.105, 0.195), (0.12, 0.135), (0.17, 0.10), and (0.20, 0.14), As shown in FIG. 91A, upper left and lower right boundary lines of the combined color space point are locally roughly parallel to the blackbody locus, and point generally to about 484 nm and about 470 nm, respectively, on the spectral locus bounding the chromaticity diagram. In certain embodiments, a sky-resembling assembly may be configured to produce color points only in the first color space 11A, or color points only in the second color space 11B, or color points in the combined color space that encompasses both the first and second color spaces 11A, 11B. The second color space 11B may enable color points with saturation, gamut, and/or vividness properties differing from those in the first color space 11A, thereby providing desirable lighting effects such as permitting a more realistic sky emulation.

FIG. 92A is a 1976 CIE Chromaticity Diagram on which color spaces and exemplary color points for a fifth embodiment of a sky-resembling assembly are provided, including sky color spaces 11A and 11B corresponding to those represented in FIG. 91A. The 1976 CIE Chromaticity Diagram is similar to the 1931 CIE Chromaticity Diagram (e.g., shown in FIG. 91A), except that similar distances on the 1976 CIE Diagram represent similar perceived differences in color. Four different linear groupings (lines) of color points include points within the two color sky spaces 11A, 11B. A first linear grouping of color points centrally located within left and right bounds corresponds to a sky-resembling assembly of a skylight test fixture. A second linear grouping ("Min") and third linear grouping ("Max") represent color points obtained by modeling. A fourth linear grouping represents a measured superlative gamut group, including color points closest to the spectral locus, providing enhanced gamut or vividness. FIG. 92B is a table of (u', v') coordinates of a 1976 CIE Chromaticity Diagram (with corresponding (x, y) coordinates of a 1931 CIE Chromaticity Diagram) that define the color space 11B shown in FIG. 92A.

In certain embodiments, a sky-resembling light assembly includes at least one light engine that comprises a first multi-LED array including bluish LEDs, greenish LEDs, and white LEDs that are arranged in multiple strings of connected LEDs, wherein such strings are separately controllable. One example of a sky-resembling light assembly as outlined above was described previously herein in connection with FIG. 62, including first to third strings of connected LEDs, such a string of white LEDs, a string of bluish LEDs, and a string of greenish LEDs.

FIG. 93A is a 1976 CIE Chromaticity Diagram on which color spaces (regions) for bluish LEDs, greenish LEDs, and white LEDs, as well as exemplary color points for aggregated emissions of the foregoing LEDs, for certain embodiments of a sky-resembling assembly are provided. In certain embodiments, a sky-resembling light assembly includes at least one light engine that comprises at least one first multi-LED array including bluish LEDs, greenish LEDs, and white LEDs. In certain embodiments, the bluish LEDs are configured to produce light emissions having a bluish color point within a polygonal area with vertices having x, y coordinates of (0.05, 0.58), (0.06, 0.65), (0.14, 0.65), (0.14, 0.55), (0.13, 0.48), and (0.05, 0.48) on a 1931 CIE Chromaticity Diagram, while the greenish LEDs are configured to produce light emissions having a greenish color point within a polygonal area with vertices having x, y coordinates of (0.05, 0.58), (0.06, 0.65), (0.14, 0.65), (0.14, 0.55), (0.13, 0.48), and (0.05, 0.48) on a 1931 CIE Chromaticity Diagram, and the white LEDs are configured to produce light emissions having a white color point within a polygonal area with vertices having x, y coordinates of (0.3028, 0.3304), (0.3213, 0.3371), (0.3221, 0.3261), and (0.3048, 0.3209) on a 1931 CIE Chromaticity Diagram. FIG. 93A further shows a linear grouping of color points (proximate to the white LED region) that corresponds to aggregated light emissions (i.e., exiting a light exit surface) pf a sky-resembling assembly of a skylight test fixture.

FIGS. 93B, 93C, and 93D provide tables of (u', v') coordinates of a 1976 CIE Chromaticity Diagram (with corresponding (x, y) coordinates of a 1931 CIE Chromaticity Diagram) that define the polygonal color spaces containing color points producible by the greenish LEDs, the bluish LEDs, and the white LEDs, respectively, in FIG. 93A.

As an alternative to providing a sky-resembling assembly having a string of white LEDs, a string of bluish LEDs, and a string of greenish LEDs that are separately controllable (as shown in FIG. 62), in certain embodiments a sky-resembling assembly may include a mixed-color string including both greenish and bluish LEDs, and a white string including white LEDs, with the first and second strings are separately controllable. Despite the reduced tunability afforded by providing two separately controllable strings according to this arrangement (versus three separately controllable strings as shown in FIG. 62) Applicant has found that careful selection of the number and type of the bluish and greenish LEDs, and controlling a ratio of currents between the two strings in a specified way, permit highly realistic simulation of sky conditions to be attained.

FIG. 94 is a schematic diagram of an exemplary electronics module 318 in association with a sky-resembling assembly 314 and one or more (preferably multiple) sun-resembling assemblies 316 for a skylight fixture 310. In the illustrated embodiment, the sky-resembling assembly 314 is expanded to illustrate an LED array, which includes a mixture of LEDs 359 of different colors (e.g., white LEDs 359 that emit white light at a first color point, bluish LEDs 359 that emit bluish light at a second color point, and greenish LEDs 359 that emit greenish light at a third color point). The LED array is divided into first and second strings of connected LEDs 359. In this embodiment, LED string LS1 includes a group of green LEDs 359 arranged in series with a group of blue LEDs 359—more specifically, a parallel-connected group of greenish LEDs 359 is arranged in series with a series-parallel connected group of bluish LEDs 359 of LED string LS1. LED string LS2 includes a connected group of white LEDs 359. Although a series connected group of white LEDs 359 is shown, it is to be appreciated that the white LEDs 359 may be connected in series-parallel in certain embodiments. Any suitable number of white, greenish, and bluish LEDs 359 may be provided in the respective strings LS2, LS1.

The electronics module 318 controls the drive currents $i_1$ and $i_2$, which are used to drive the respective LED strings LS1 and LS2 of the sky-resembling assembly 314. The sun-resembling assemblies 316 may be similarly configured and driven by the same or different electronics modules 318 in similar fashion. The ratio of drive currents $i_1$ and $i_2$ that are provided through respective LED strings LS1 and LS2 may be adjusted to effectively control the relative intensities of the bluish/greenish light emitted from the greenish and bluish LEDs 359 of LED string LS1, and the white light emitted from the white LEDs 359 of LED string LS2. The resultant light from each LED string LS1 and LS2 mixes to generate an overall light output that has a desired color, correlated color temperature (CCT), and intensity, the latter of which may also be referred to as dimming level. As noted previously herein, the overall light output may take on any desired color or CCT.

When emulating a traditional skylight, the overall light output of the sky-resembling assembly 314 may range from a deep blue of an evening sky, to a medium blue of a daytime sky, to white light that falls on or within a desired proximity of the Black Body Locus (BBL) and has a desired CCT. Additional effects (e.g., an overcast sky, a partly cloudy sky, a dawn sky, a dusk sky, and a nighttime sky) may also be provided. The sun-resembling assemblies 316 are controlled in the same fashion to emulate direct and reflected sunlight as well as any of the other colors and CCTs described above for effects ranging from decorative to physiological.

The electronics module 318 includes AC-DC conversion circuitry 361, control circuitry 360, a communication interface (I/F) 62, and a number of current sources, such as the illustrated DC-DC converters 364. The AC-DC conversion circuitry 361 is configured to receive an AC signal (AC), rectify the AC signal, correct the power factor of the AC signal, and provide a DC power signal (PWR). The DC power signal may be used to directly or indirectly power the control circuitry 360 and any other circuitry provided in the electronics module 318, including the DC-DC converters 364 and the communication interface 362.

The respective DC-DC converters 364 of the electronics module 318 provide drive currents $i_1$ and $i_2$ for the LED strings LS1 and LS2 of the sky-resembling assembly 314 in response to control signals CS1 and CS2. Additional drive circuitry may be provided for each of the sun-resembling assemblies 316 in similar fashion. The drive currents $i_1$ and $i_2$ may be pulse width modulated (PWM) signals or variable DC signals. If the drive currents $i_1$ and $i_2$ are PWM signals, the control signals CS1 and CS2 may be PWM signals that effectively turn the respective DC-DC converters 64 on during a logic high state and off during a logic low state of each period of the PWM signal. As a result, the drive currents $i_1$ and $i_2$ for the two LED strings LS1 and LS2 may also be PWM signals. The intensity of light emitted from each of the two LED strings LS1 and LS2 will vary based on the duty cycle of the respective PWM signals.

The control circuitry 360 will adjust the duty cycle of the drive currents and $i_2$ provided to each of the LED strings LS1 and LS2 to effectively adjust the intensity of the resultant light emitted from the LED strings LS1 and LS2 while maintaining the desired intensity, color and/or CCT based on instructions from the control circuitry 360. If the drive currents $i_1$ and $i_2$ for the two LED strings LS1 and LS2 are variable DC currents, the control circuitry 360 generates control signals CS1 and CS2 that result in the DC-DC converters 364 outputting the drive currents $i_1$ and $i_2$ at the appropriate DC levels.

The control circuitry 360 may include a central processing unit (CPU) 366, such as microprocessor or microcontroller, and sufficient memory 368 to store the requisite data and software instructions to enable the control circuitry 360 to function as described herein. The control circuitry 360 may interact with the communication interface 362 to facilitate wired or wireless communications with other skylight fixtures 310 or remote devices, as described hereinabove (including but not limited to a remote device 351 shown and described in connection with FIG. 61).

Although only a small number of LEDs 359 were shown in the LED strings LS1 and LS2 of FIG. 94, any suitable number of LEDs may be provided. FIG. 95 is a schematic diagram of a first (bluish/greenish) string and a second (white) string useable in place of LED strings LS1 and LS2 of the electronics module of FIG. 94 according to an exemplary embodiment. The bluish/greenish (first) string, which receives drive current $i_1$, includes a group of thirty greenish LEDs G1-G30 arranged in parallel, with such group being arranged in series with a series-parallel connected group of sixty bluish LEDs B1-1360 (i.e., including five subgroups of series connected bluish LEDs B1-1312, B13-B24, B25-B36, B37-B48, and B49-B60 arranged in parallel with one another). The white (second) string, which receives drive current $i_2$, includes a first subgroup of fifteen series connected white LEDs W1-W15 arranged in parallel with a second subgroup of fifteen series connected white LEDs W16-W30. In certain embodiments, the white LEDs W1-W30 are arranged to produce white light having a color point in a range of 5000 K to 7000 K, or in a range of 6000 K to 6800 K, or about 6500 K. As shown, a ratio of number of bluish LEDs B1-1360 to greenish LEDs G1-G30 is 2:1, and a ratio of number of bluish LEDs B1-1360 to white LEDs W1-W30 is 2:1. However, other numerical ratios of bluish LEDs to greenish LEDs and/or to white LEDs may be provided. In certain embodiments, a ratio of quantity of bluish LEDs to quantity of greenish LEDs is at least 1.5:1, at least 2:1, at least 2.5:1, or at least 3:1, or in a range of 1.5:1 to 5:1. In certain embodiments, a ratio of quantity of bluish LEDs to quantity of white LEDs is at least 1.5:1, at least 2:1, at least 2.5:1, or at least 3:1, or in a range of 1.5:1 to 5:1. Additionally, other interconnection types within or between groups of LEDs beyond those shown in FIG. 95 may be employed.

Although FIGS. 94 and 95 separately illustrate LED strings that are separately controllable, this does not require LEDs of different color points to be physically segregated from one another, or LEDs of one string to be physically segregated from LEDs of another string, within a light engine of a sky-resembling assembly. Instead, to promote color mixing, it is advantageous in certain embodiments to intersperse LEDs of different color points and of different LED strings among one another. FIG. 96 illustrates a portion of a light engine as part of a sky-resembling assembly according to one embodiment, showing greenish LEDs (G1-G5) and bluish LEDs (B52-B60) of a first multi-LED string physically interspersed among white LEDs (W1-W4)

of a second multi-LED string, with alternating color point between adjacent LEDs mounted on a circuit board.

Although a linear arrangement of LEDs is shown in FIG. 96, any suitable geometric arrangement may be employed.

In certain embodiments, a current ratio of white string to bluish/greenish string of a two-string sky-resembling light engine is varied between a minimum brightness setting and a maximum brightness setting. In certain embodiments, the current ratio of blue to white string governed by Equation 1 at maximum brightness, and is governed by Equation 2 at minimum brightness, with such equations set out below.

$$\beta = 7.1 \cdot 10^{-3} \cdot \psi^2 - 0.1138 \cdot \psi - 0.0978 \quad \text{(Equation 1)}$$

$$\beta = 14.8 \cdot 10^{-3} \cdot \psi + 0.055 \cdot \psi + 0.0437 \quad \text{(Equation 2)}$$

where, $\beta$=Ratio of blue string current to white string current, and $\psi$=Blueness factor. In certain embodiments, Blueness factor ranges from 1 to 19. In certain embodiments, the Blueness factor is represented on a scale termed herein "pseudo CCT," corresponding to a control input labeled as "CCT" (but not necessarily corresponding to correlated color temperature, hence the use herein of the term "pseudo CCT" to avoid confusion) employed by a Lutron® App (electronic lighting control application) commercially available from Lutron Electronics Co., Inc. (Coopersburg, Penn., USA) that may be operated on a wired or wireless computing device and used to control a first (e.g., bluish/greenish) LED string and second (e.g., white) LED string as disclosed in connection with FIGS. 94-95. In the Lutron® App, a blueness level 1=white and is represented by a pseudo CCT value of 2700 K, while a blueness level 19=blue and is represented by a pseudo CCT value of 4500 K. It is noted that different "13" points reside on SKY gamut across different scenes.

FIG. 97 is a plot of blue/green string to white string current ratio for different Blueness factors (with factors ranging from 1 to 19) for a white LED string and a mixed color LED string according to one embodiment. As shown, the ratio of "blue" (specifically bluish/greenish) to "white" current varies at different brightness levels, with the ratio increasing with selected Blueness factor.

Current ratios between a bluish/greenish LED string and a white LED string may be varied to represent different sky scenes on a sky-resembling assembly of a skylight fixture according to certain embodiments. FIG. 98 is a plot of blue/green LED string to white LED string current ratio for an exemplary group of different scenes achievable by a sky-resembling assembly of skylight fixture according to one embodiment, with the scenes including night, dawn, morning, noon/midday, and bright sunrise in level of increasing blue/green LED string to white LED string current ratio, including a ratio of under 0.5 to represent a dawn scene to a ratio greater than 4.75 to represent a bright sunrise scene.

FIG. 99 is a plot of current versus sky pseudo correlated color temperature for nineteen pseudo CCT values ranging from 2700 K to 4500 K for a sky-resembling assembly of a skylight fixture including first and second LED strings according to one embodiment, the first LED string including greenish and bluish LEDs and the second LED string including white LEDs. As shown, in certain embodiments, a plot of currents supplied to a blue/green LED string and to a white LED string may be asymmetric or unbalanced (e.g., exhibiting slope shapes that differ from mere inversion of one relative to the other) over a range of blueness factors or pseudo CCT values. Merely inverting the shape of plotted current for the bluish/greenish LED string 1 would not yield the same shape of the plotted current for the white LED string 2. The white string receives its maximum current (about 105 mA) at a relatively low pseudo CCT value of 2900 K, while the bluish/greenish string receives its maximum current at a relatively high pseudo CCT value of 4500 K.

FIG. 99 provides relatively high resolution over a relatively narrow range of pseudo CCT (from 2700 K to 4500 K), whereas less resolution over a broader range of pseudo CCT (from 2700 K to 7000 K) is provided in FIG. 100. Such figure is a plot of current versus sky pseudo correlated color temperature for five pseudo CCT values ranging from 2700 K to 7000 K for a sky-resembling assembly including first and second LED strings of a skylight fixture according to one embodiment, the first LED string including greenish and bluish LEDs and the second LED string including white LEDs. Similar trends in current for the two LED strings are shown in FIGS. 99 and 100.

As noted previously herein, emulation of a skylight by a skylight fixture according to embodiments herein is rendered not be a sky-resembling assembly alone, but by a combination of a sky-resembling assembly and one or more (preferably multiple) sun-resembling assemblies. In certain embodiments, a sky-resembling assembly may comprise two independent sky-resembling light engines each comprising two main LED strings (i.e., a bluish-greenish string and a white string), used in combination with first and second (e.g., east and west) sun-resembling assemblies. In certain embodiments, white light from the sun-resembling assemblies washes the blueness factor provide by the sky-resembling assemblies based on the scene. Controlling currents to independent sky- and sun-resembling assemblies at different ratios permits generation of emissions that emulate the appearance of a natural sky.

FIG. 101 is a plot of warm white versus cool white string currents for five CCT values ranging from 3000 K to 5000 K for a single sun-resembling assembly (e.g., "East" sun-resembling assembly) including first and second LED strings of one sun-resembling assembly of a skylight fixture according to one embodiment. As shown, cool white LED string current increases with increasing CCT, while warm white LED string current decreases with increasing CCT, in a generally symmetric fashion. It is to be appreciated that a first "East" sun-resembling assembly may be combined with a second "West" sun-resembling assembly and a sky-resembling assembly as part of a single skylight fixture according to certain embodiments.

In certain embodiments, various preset scenes of a light fixture may be displayed, employing in combination the control of a sky-resembling assembly's blueness factor (or pseudo CCT as described herein) in combination with a sky resembling assembly's brightness, a sun-resembling assembly's correlated color temperature, and a sun-resembling assembly's brightness. In certain embodiments, time-dependent daily transitions (including light level/brightness, CCT, light distribution, and/or fading) may be automatically implemented and/or accessed by a user via presets.

FIG. 102A is a table identifying preset names as well as time-dependent varying color point (e.g., CCT or pseudo CCT/blueness factor) and light level percentage values over a 24 hour period for east and west sun-resembling assemblies and a sky-resembling assembly of a skylight fixture according to one embodiment. Various preset names are identified in the rightmost column as "night," "dawn," "morning," "noon/midday," "afternoon," and "dusk." As shown, CCT levels and brightness for individual assemblies of the east sun-resembling assembly, the west sun-resembling assembly, and the sky-resembling assembly vary with time of day (or preset mode). During "fading" periods, brightness (or light level) may transition from one value to another, either with or without changes in CCT for individual assemblies. In certain embodiments, fading is performed continuously from one defined point in time to the next defined point in time. Although a specific sequence is shown in FIG. 102A, in certain embodiments the times and actions to be taken by the respective assemblies of the east sun-resembling assembly, the west sun-resembling assembly, and the sky-resembling assembly may be pre-configured by a manufacturer or configured (and/or re-configured) by a user.

In certain embodiments, additional static presets that are not part of a daily time-driven control sequence may be provided to control an east sun-resembling assembly, the west sun-resembling assembly, and the sky-resembling assembly. FIG. 102B is a table identifying additional static presets (e.g., "bright sunrise," "cloudy day," and "moonlight") with corresponding CCT and light level percentage values for east and west sun-resembling assemblies and a sky-resembling assembly of a skylight fixture according to one embodiment. Additional or different static presets may be pre-programmed or programmed by a user.

In summary, various luminaires contemplated hereinabove may be relatively thin and conducive to surface mounting and/or mounting within ceilings and/or walls with very thin plenums, e.g., 4-6 inches, by using one or more flat, planar waveguides to deliver light. Skylights comprising waveguides may improve the ease of manufacture, power efficiency, and decrease material and manufacturing costs associated with producing other skylights and/or skylight replacement-type fixtures. A dual waveguide luminaire comprises one waveguide that is edge coupled with LEDs to produce a predominantly blue light emulating a blue sky and a second separate waveguide edge coupled with LEDs to create a predominantly white light emulating sunlight derived from a blue sky. The first and second light emitting surfaces do not substantially overlap in physical alignment/orientation so that light from the different waveguides does not color mix, as such mixing may produce an undesirable third color perception. To accomplish this, the first waveguide may comprise extraction features that are populated proximal a central portion of the waveguide, and the second waveguide may comprise extraction features that are disposed about a peripheral region of the second waveguide. When the first waveguide is illuminated with blue light the center/interior glows blue. Likewise, when the second waveguide is illuminated with white light the periphery thereof glows white. This arrangement creates the illusion of a skylight housed within a thin and flat construction. The light sources do not need to be blue and/or white, but instead may be any other color, such as a different CCT white light, to differently develop the illusion of depth. Further, the light sources may produce light of different brightness/lumen levels.

When one uses a relatively small light source which emits into a broad (e.g., Lambertian) angular distribution (common for LED-based light sources), the conservation of etendue, as generally understood in the art, requires an optical system having a large emission area to achieve a narrow (collimated) angular light distribution. In the case of parabolic reflectors, a large optic is thus generally required to achieve high levels of collimation. In order to achieve a large emission area in a more compact design, the prior art has relied on the use of Fresnel lenses, which utilize refractive optical surfaces to direct and collimate the light. Fresnel lenses, however, are generally planar in nature, and are therefore not well suited to re-directing high-angle light emitted by the source, leading to a loss in optical efficiency. In contrast, in the present disclosure, light is coupled into the optic, where primarily TIR is used for re direction and collimation. This coupling allows the full range of angular emission from the source, including high-angle light, to be re-directed and collimated, resulting in higher optical efficiency in a more compact form factor.

In at least some of the present embodiments, the distribution and direction of light within the waveguide is better known, and hence, light is controlled and extracted in a more controlled fashion. In standard optical waveguides, light bounces back and forth through the waveguide. In the present embodiments, light is extracted as much as possible over one pass through the waveguide to minimize losses.

In some embodiments, one may wish to control the light rays such that at least some of the rays are collimated, but in the same or other embodiments, one may also wish to control other or all of the light rays to increase the angular dispersion thereof so that such light is not collimated. In some embodiments, one might wish to collimate to narrow ranges, while in other cases, one might wish to undertake the opposite.

As in the present embodiments, a waveguide may include various combinations of mixing features, extraction features, and redirection features necessary to produce a desired light distribution. A lighting system may be designed without constraint due to color mixing requirements, the need for uniformity of color and brightness, and other limits that might otherwise result from the use of a specific light source. Further, the light transport aspect of a waveguide allows for the use of various form factors, sizes, materials, and other design choices. The design options for a lighting system utilizing a waveguide as described herein are not limited to any specific application and/or a specific light source.

All references, including publications, patent applications, and patents, cited herein are hereby incorporated by reference to the same extent as if each reference were individually and specifically indicated to be incorporated by reference and were set forth in its entirety herein.

The word "exemplary" is used to mean serving as an example or illustration. To the extent that the term "include", "have", or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The disclosed systems and methods are well adapted to attain the ends and advantages mentioned as well as those that are inherent therein. The particular implementations disclosed above are illustrative only, as the teachings of the present disclosure may be modified and practiced in different but equivalent manners apparent to those skilled in the art having the benefit of the teachings herein. It is therefore evident that the particular illustrative implementations disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Those skilled in the art will recognize improvements and modifications to the preferred embodiments of the present disclosure. All such improvements and modifications are considered within the scope of the concepts disclosed herein and the claims that follow.

What is claimed is:

1. A light fixture comprising:
    a sky-resembling light assembly comprising a first light exit surface and at least one first light engine that comprises a first multi-LED array including bluish LEDs, greenish LEDs, and white LEDs, wherein LEDs of the first multi-LED array are arranged in multiple separately-controllable strings of connected LEDs;
    a sun-resembling light assembly comprising a plurality of second light engines that each comprises a second multi-LED array;
    wherein, upon supplying electricity to the light fixture:
        light having x, y color coordinates defining a first color point on a 1931 CIE Chromaticity Diagram exits the at least one first light engine through the first light exit surface, and
        light having a second x, y color coordinates defining a second color point on a 1931 CIE Chromaticity Diagram point exits at least one second light engine of the plurality of second light engines, the second color point being more yellow-ish white than the first color point;
    wherein the first light engine and the plurality of second light engines are positioned and oriented such that at least some light that exits the first light exit surface travels to a region to which at least some light that exits the plurality of second light engines travels; and
    wherein the light fixture is configured to be mounted within or against a building surface, and is configured to produce emissions providing an appearance of a skylight or window without transmission of exterior light through any portion of the light fixture.

2. The light fixture of claim 1, wherein the building surface comprises a ceiling surface, a vertical wall, or a slanted structure.

3. The light fixture of claim 2, wherein when the light fixture is mounted horizontally within or against a ceiling surface, light exiting the light fixture at high angles relative to vertical is more yellow-ish white compared to the light exiting the light fixture directly below the fixture, which is more blue-ish white.

4. The light fixture of claim 1, wherein the x coordinate value of the first color point and the x coordinate value of the second color point on the 1931 CIE Chromaticity Diagram differ by at least 0.1.

5. The light fixture of claim 1, wherein for the at least one first light engine, the multiple separately-controllable strings of connected LEDs comprise a first string incorporating the bluish LEDs, a second string incorporating the greenish LEDs, and a third string incorporating the white LEDs.

6. The light fixture of claim 1, wherein for the at least one first light engine, the multiple separately-controllable strings of connected LEDs comprise a first string incorporating the bluish LEDs and the greenish LEDs, and a second string incorporating the white LEDs.

7. The light fixture of claim 6, wherein the first string comprises a parallel connected group of greenish LEDs arranged in series with a series-parallel connected group of bluish LED.

8. The light fixture of claim 7, wherein the second string comprises a series-parallel connected group of white LEDs.

9. The light fixture of claim 6, wherein a ratio of quantity of bluish LEDs to quantity of greenish LEDs is at least 2:1 and a ratio of quantity of bluish LEDs to quantity of white LEDs is at least 2:1.

10. The light fixture of claim 1, wherein the second color point is within a polygonal area with vertices having x, y coordinates of (0.29, 0.32), (0.32, 0.29), (0.41, 0.36), (0.48, 0.39), (0.48, 0.43), (0.40, 0.41), and (0.35, 0.38) on a 1931 CIE Chromaticity Diagram.

11. The light fixture of claim 10, wherein the first color point is within a polygonal area with vertices having x, y coordinates of (0.37, 0.34), (0.35, 0.38), (0.105, 0.195), (0.12, 0.135), (0.17, 0.10), and (0.20, 0.14) on a 1931 CIE Chromaticity Diagram.

12. The light fixture of claim 10, wherein the first color point is within a polygonal area with vertices having x, y coordinates of (0.35, 0.38), (0.105, 0.195), (0.12, 0.135), (0.17, 0.10), (0.20, 0.14), and (0.15, 0.20) on a 1931 CIE Chromaticity Diagram.

13. The light fixture of claim 10, wherein the first color point is within a polygonal area with vertices having x, y coordinates of (0.37, 0.34), (0.35, 0.38), (0.15, 0.20), and (0.20, 0.14) on a 1931 CIE Chromaticity Diagram.

14. The light fixture of claim 1, wherein the bluish LEDs have a peak wavelength in a range of from about 450 nm to about 465 nm, and the greenish LEDs have a peak wavelength in a range of from about 505 nm to about 530 nm.

15. The light fixture of claim 1, wherein:
    the bluish LEDs are configured to produce light emissions having a bluish color point within a polygonal area with vertices having x, y coordinates of (0.05, 0.58), (0.06, 0.65), (0.14, 0.65), (0.14, 0.55), (0.13, 0.48), and (0.05, 0.48) on a 1931 CIE Chromaticity Diagram;

the greenish LEDs are configured to produce light emissions having a greenish color point within a polygonal area with vertices having x, y coordinates of (0.05, 0.58), (0.06, 0.65), (0.14, 0.65), (0.14, 0.55), (0.13, 0.48), and (0.05, 0.48) on a 1931 CIE Chromaticity Diagram; and the white LEDs are configured to produce light emissions having a white color point within a polygonal area with vertices having x, y coordinates of (0.3028, 0.3304), (0.3213, 0.3371), (0.3221, 0.3261), and (0.3048, 0.3209) on a 1931 CIE Chromaticity Diagram.

16. The light fixture of claim 1, further comprising a control module configured to automatically adjust the first color point, the second color point, and wavelength distribution of the plurality of second light engines over the course of a day, based on at least one of the following: (A) time of day; (B) wired or wireless user input, (C) input from one or more sensors, (D) input from a camera; and (E) reports of outdoor lighting and/or weather conditions.

17. The light fixture of claim 1, wherein the sky-resembling light assembly is configured to cause the light exit surface to selectively resemble the following: a light blue sky, a deep blue sky, an overcast sky, a partly cloudy sky, a dawn sky, a dusk sky, and a nighttime sky.

18. The light fixture of claim 1, further comprising a control module configured to perform at least one of the following: (A) vary a circadian stimulus value of light exiting the light fixture at different times of a calendar day; and (B) vary an alertness stimulation value of light exiting the light fixture at different times of a calendar day.

19. The light fixture of claim 1, wherein second light engines of the plurality of second light engines comprise independently controllable brightness and color point, with the plurality of second light engines being configured to emulate sunlight at different times of a calendar day transiting through a skylight or reflected through a skylight.

20. The light fixture of claim 1, wherein the sun-resembling light assembly comprises at least one light-transmissive interior surface, and the at least one light-transmissive interior surface in combination with the first light exit surface of the sky-resembling light assembly define a cavity.

21. The light fixture of claim 1, wherein:
light exiting the at least one first light engine has a first far-field light distribution; and
light exiting at least one second light engine of the plurality of second light engines has a second far-field light distribution that differs from the first far-field light distribution.

22. The light fixture of claim 1, wherein further comprising at least one control element configured to control a brightness of light exiting from the at least one first light engine independently from controlling a brightness of light exiting from at least one second light engine of the plurality of second light engines.

23. The light fixture of claim 1, further comprising at least one control element configured to control a brightness of light exiting from the first light engine and at least one second light engine of the plurality of second light engines based on at least one parameter selected from the group consisting of: (1) a color point of a mixture of light exiting from the light fixture, (2) a brightness of light exiting from the light fixture, (3) a time of day, and (4) a melatonin suppression setting.

24. The light fixture of claim 1, further comprising at least one control element configured to vary a circadian stimulus value of light exiting the light fixture based on a time of day.

25. The light fixture of claim 1, further comprising at least one light extraction element that affects light distribution characteristics of light exiting from at least one of the at least one first light engine and the plurality of second light engines.

26. The light fixture of claim 1, further comprising at least one light diffusing element that affects light distribution characteristics of light exiting from at least one of the at least one first light engine and the plurality of second light engines.

* * * * *

UNITED STATES PATENT AND TRADEMARK OFFICE
CERTIFICATE OF CORRECTION

PATENT NO.         : 12,225,643 B2                                    Page 1 of 1
APPLICATION NO.    : 18/449228
DATED              : February 11, 2025
INVENTOR(S)        : Bernd P. Keller et al.

It is certified that error appears in the above-identified patent and that said Letters Patent is hereby corrected as shown below:

In the Specification

Column 16, Line 3, replace "non-Lam bertian" with --non-Lambertian--.
Column 43, Line 12, replace "defines an angle between 0 degrees and degrees" with --defines an angle between 0 degrees and 45 degrees--.
Column 43, Line 23, replace "defines an angle between 0 degrees and degrees" with --defines an angle between 0 degrees and 25 degrees--.
Column 46, Line 10, replace "FIG. depicts a light fixture 250 that" with --FIG. 25 depicts a light fixture 250 that--.
Column 89, Line 55, replace "A is the emission wavelength" with --$\lambda$ is the emission wavelength--.
Column 106, Lines 31, 42, and 43, replace "blueish LEDs B1-1360" with --blueish LEDs B1-B60--.
Column 106, Line 32, replace "five subgroups of series connected bluish LEDs B1-1312" with --five subgroups of series connected bluish LEDs B1-B12--.
Column 107, Line 33, replace "different "13" points" with --different "$\beta$" points--.

Signed and Sealed this
Twenty-ninth Day of April, 2025

Coke Morgan Stewart
*Acting Director of the United States Patent and Trademark Office*